United States Patent
Lee et al.

(10) Patent No.: US 10,968,188 B2
(45) Date of Patent: Apr. 6, 2021

(54) BENZOTHIAZOL COMPOUNDS AND METHODS USING THE SAME FOR TREATING NEURODEGENERATIVE DISORDERS

(71) Applicant: 1ST Biotherapeutics, Inc., Gyeonggi-do (KR)

(72) Inventors: Jinhwa Lee, Gyeonggi-do (KR); Suyeon Jo, Gyeonggi-do (KR); A Yeong Park, Gyeonggi-do (KR); Gwibin Lee, Gyeonggi-do (KR); Jae Eun Kim, Seoul (KR); Misoon Kim, Gyeonggi-do (KR); Gyooseung Jung, Gyeonggi-do (KR); Seung Mook Lim, Gyeonggi-do (KR); Keonseung Lim, Gyeonggi-do (KR); Minwoo Lee, Gyeonggi-do (KR); Heekyoung Yang, Gyeonggi-do (KR); Hyonam Kim, Gyeonggi-do (KR); Hyeongjun Kim, Seoul (KR); Wanjun Li, Hubei (CN); Mingzhu Fan, Hubei (CN)

(73) Assignee: 1st Biotherapeutics, Inc., Gyeongg-do (KR)

( * ) Notice: Subject to any disclaimer, the term of this patent is extended or adjusted under 35 U.S.C. 154(b) by 0 days.

(21) Appl. No.: 15/931,827

(22) Filed: May 14, 2020

(65) Prior Publication Data
US 2020/0270222 A1    Aug. 27, 2020

Related U.S. Application Data

(62) Division of application No. 16/148,265, filed on Oct. 1, 2018, now Pat. No. 10,669,246.

(60) Provisional application No. 62/696,432, filed on Jul. 11, 2018, provisional application No. 62/666,800, filed on May 4, 2018, provisional application No. 62/566,649, filed on Oct. 2, 2017.

(51) Int. Cl.

| | |
|---|---|
| A61K 31/428 | (2006.01) |
| C07D 277/82 | (2006.01) |
| A61P 25/28 | (2006.01) |
| A61P 25/16 | (2006.01) |
| C07D 513/04 | (2006.01) |
| C07D 471/04 | (2006.01) |
| A61K 31/506 | (2006.01) |
| A61K 31/4439 | (2006.01) |
| A61K 31/437 | (2006.01) |
| C07F 7/08 | (2006.01) |
| A61K 31/695 | (2006.01) |
| C07F 5/02 | (2006.01) |
| A61K 31/69 | (2006.01) |
| C07D 417/10 | (2006.01) |
| C07D 417/04 | (2006.01) |

(52) U.S. Cl.
CPC .......... *C07D 277/82* (2013.01); *A61K 31/428* (2013.01); *A61K 31/437* (2013.01); *A61K 31/4439* (2013.01); *A61K 31/506* (2013.01); *A61K 31/69* (2013.01); *A61K 31/695* (2013.01); *A61P 25/16* (2018.01); *A61P 25/28* (2018.01); *C07D 417/04* (2013.01); *C07D 417/10* (2013.01); *C07D 471/04* (2013.01); *C07D 513/04* (2013.01); *C07F 5/025* (2013.01); *C07F 7/0812* (2013.01)

(58) Field of Classification Search
CPC .................................................. A61K 31/428
See application file for complete search history.

(56) References Cited

U.S. PATENT DOCUMENTS

| | | |
|---|---|---|
| 7,928,140 B2 | 4/2011 | Booker et al. |
| 8,053,574 B2 | 11/2011 | Bruce et al. |
| 8,993,580 B2 | 3/2015 | Ren et al. |
| 9,505,784 B2 | 11/2016 | Choi et al. |
| 2011/0172228 A1 | 7/2011 | Ren et al. |
| 2019/0100500 A1 | 4/2019 | Lee et al. |

FOREIGN PATENT DOCUMENTS

| | | |
|---|---|---|
| WO | WO-01/57008 A1 | 8/2001 |
| WO | WO-2007/095588 A1 | 8/2007 |
| WO | WO-2008/016131 A1 | 2/2008 |
| WO | WO-2009/017822 A2 | 2/2009 |

(Continued)

OTHER PUBLICATIONS

Hantschel, O., et al.; "Regulation of the C-ABL and BCR-ABL Tyrosine Kinases", Nature Reviews, Molecular Cell Biology, vol. 5, Jan. 2004, pp. 33-44.

(Continued)

*Primary Examiner* — Brian E McDowell
(74) *Attorney, Agent, or Firm* — Harness, Dickey & Pierce, P.L.C.

(57) ABSTRACT

The present disclosure provides a compound of general Formula (I) having c-abl kinase inhibitory activity or pharmaceutically acceptable salt thereof, a pharmaceutical composition comprising the compound, and a method useful to treat or prevent neurodegenerative diseases using the compound.

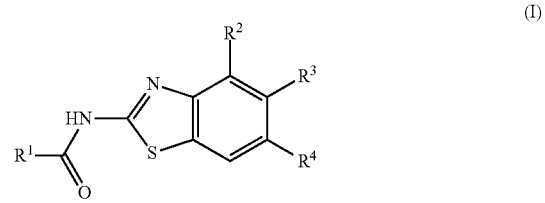

(I)

20 Claims, 7 Drawing Sheets

(56) References Cited

FOREIGN PATENT DOCUMENTS

| WO | WO-2009/133127 A1 | 11/2009 |
|---|---|---|
| WO | WO-10/008847 A2 | 1/2010 |
| WO | WO-10/100144 A1 | 9/2010 |

OTHER PUBLICATIONS

Hebron, M. L., et al.; "Nilotinib reverses loss of dopamine neurons and improves motor behavior via autophagic degradation of a-synuclein in Parkinson's disease models", Human Molecular Genetics, 2013, vol. 22, No. 16, pp. 3315-3328.

Imamura, K., et al.; "The Src/c-Abl pathway is a potential therapeutic target in amyotrophic lateral sclerosis", Science Translational Medicine, vol. 9, May 24, 2017, pp. 1-10.

Jellinger, K. A., et al., "Multiple system atrophy: pathogenic mechanisms and biomarkers", High Impact Review in Neuroscience, Neurology or Psychiatry Review Article, J Neural Transm., 2016, pp. 1-18.

Mahul-Mellier, A., et al.; "c-Abl phosphorylates a-synuclein and regulates its degradation: implication for a-synuclein clearance and contribution to the pathogenesis of Parkinson's disease", Human Molecular Genetics, 2014, vol. 23, No. 11, pp. 2858-2879.

International Search Report from corresponding PCT Application No. PCT/KR2018/011660, dated Jan. 29, 2019.

Imidazo[1,2-a]pyridin-6-yl-benzamide analogs as potent RAF inhibitors, Bioorganic & Medicinal Chemistry Letters (2017), 27(23), 5221-5224.

ASK1 pharmacophore model derived from diverse classes of inhibitors, Bioorganic & Medicinal Chemistry Letters (2014), 24(18), 4418-4423.

Design and biological evaluation of imidazo[1,2-a]pyridinesas novel and potent ASK1 inhibitors, Bioorganic & Medicinal Chemistry Letters (2012), 22(24), 7326-7329.

Salovich, et al.; Bioorganic & Medicinal Chemistry Letters, 2012, 22, 5084-5088.

RN 1187453-71-9 in CALPUS, 2010.

RN 2258671-51-9 in CALPUS, 2018.

Office Action (Restriction Requirement) dated Feb. 27, 2019 issued in U.S. Appl. No. 16/148,265.

Office Action (Non-final) dated Jun. 3, 2019 issued in U.S. Appl. No. 16/148,265.

Office Action (Final) dated Aug. 23, 2019 issued in U.S. Appl. No. 16/148,265.

Office Action (Non-final) dated Dec. 18, 2019 issued in U.S. Appl. No. 16/148,265.

Office Action (Final) dated Mar. 20, 2020 issued in U.S. Appl. No. 16/148,265.

BENZOTHIAZOL COMPOUNDS AND METHODS USING THE SAME FOR TREATING NEURODEGENERATIVE DISORDERS

CROSS-REFERENCE TO RELATED APPLICATIONS

This application is a divisional application of U.S. patent application Ser. No. 16/148,265, filed on Oct. 1, 2018, which claims the benefits of, and priority to, U.S. provisional application Ser. No. 62/566,649 filed 2 Oct. 2017, 62/666,800 filed 4 May 2018, and 62/696,432 filed 11 Jul. 2018. The entire disclosures of the applications identified in this paragraph are incorporated herein by references.

FIELD

The present disclosure generally relates to compounds having enzyme inhibitory activity, pharmaceutical compositions comprising the compound, and methods of using the compounds for treating diseases.

BACKGROUND

α-synuclein is part of a large family of proteins including β- and γ-synuclein and synoretin. α-synuclein is expressed in the normal state associated with synapses and is believed to play a role in neural plasticity, learning and memory. Several studies have implicated α-synuclein with a central role in Parkinson disease pathogenesis. Molecular changes in the α-synuclein protein that increase protein misfolding and aggregation have a direct role in disease pathogenesis. Aggregation of α-synuclein contributes to the formation of Lewy bodies and neutrites, the pathologic hallmarks of Parkinson disease and α-synucleinopathies. Activation of tyrosine kinase c-abl contributes to α-synuclein-induced neurodegeneration.

The tyrosine kinase c-abl is tightly regulated non-receptor protein tyrosine kinase involved in a wide range of cellular processes, including growth, survival and stress response (*Nat Rev Mol Cell Biol,* 2004, 5:33-44) and c-abl involved in regulation several cellular processes and has implicated in the development of the central nervous system by controlling neurogenesis. More recently, increasing evidence from various experimental model systems has also revealed that c-abl is activated in neurodegenerative disease such as Alzheimer's disease, Parkinson's disease, Neiman-Pick type C diseases and tauopathies. (*Human Molecular Genetics,* 2014, Vol. 23, No. 11)

The stress-signaling non-receptor tyrosine kinase c-abl links parkin to sporadic forms of Parkinson's disease via tyrosine phosphorylation. Tyrosine phosphorylation of parkin by c-abl is a major post-translational modification that leads to loss of parkin function and disease progression in sporadic Parkinson disease. Inhibition of c-abl offers new therapeutic opportunities for blocking Parkinson disease progression. (*The Journal of Neuroscience,* 2011, 31(1):157-163) Amyotrophic lateral sclerosis (ALS) is a fatal neurodegenerative disease characterized by progressive death of motor neurons. Knockdown of c-abl with small interfering RNAs (siRNAs) also rescued ALS motor neuron degeneration. (*Imamura et al., Sci. Transl. Med.* 9, 2017) Multiple System Atrophy (MSA) is a rare, rapidly progressive neurodegenerative disease without any current treatment. In MSA there is accumulation of α-synuclein in the neurons and oligodendrocytes of the substantia nigra, striatum, olivopontocerebellar structures and spinal cord. (*J Neural Transm Vienna Austria* 1996. 2016; 123 (6))

Administration of the tyrosine kinase inhibitor nilotinib decreases c-abl activity and ameliorates autophagic clearance of α-synuclein in transgenic and lentiviral gene transfer models. Activation of c-abl in the mouse forebrain induces neurodegeneration in the hippocampus and striatum. Therefore, an increase in c-abl activity via phosphorylation may be associated with the α-synuclein pathology detected in Parkinson disease and other neurodegenerative disease. (*Hum Mol Genet.* 2013 Aug. 15).

c-abl is a potential therapeutic target for α-synucleinopathy, Parkinson disease, Alzheimer disease, ALS, Dementia with Lewy body and MSA.

WO 2010/008847 describes compounds having a heterobicyclic core, such as benzothiazol, substituted with an amid containing moiety, such as acetamido, for treating cancer.

SUMMARY

The present disclosure provides a compound having c-abl kinase inhibitory activity, a composition comprising the compound and a method useful to treat a neurodegenerative disease. In an embodiment, the compound is a compound of Formula (I):

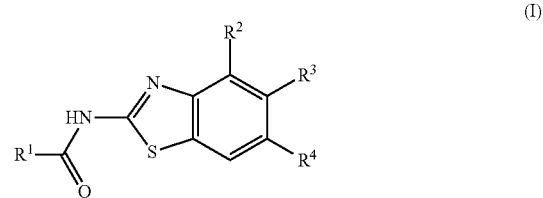

or a pharmaceutically acceptable salt thereof, wherein:
$R^1$ is cyclopropyl, cyclobutyl, or 3- or 4-membered heterocyclyl, wherein $R^1$ is optionally substituted with one or more groups selected from the group consisting of halo, alkyl, hydroxyalkyl and haloalkyl,
$R^2$ and $R^3$ are independently —H, halo, alkyl, alkoxy, —$CF_3$, or —$OCF_3$,
$R^4$ is aryl, heteroaryl, cycloalkyl, heterocyclyl, or heteroalkyl, wherein $R^4$ is optionally substituted with one or more groups selected from the group consisting of halo, hydroxyl, alkyl, alkenyl, alkynyl, haloalkyl, hydroxyalkyl, trimethylsilylethoxymethyl, —$NO_2$, —$NR_aR_b$, —$NR_aC(=O)R_b$, —$NR_aC(=O)NR_aR_b$, —$NR_aC(=O)OR_b$, —$OR_a$, —CN, —$C(=O)R_a$, —$C(=O)OR_a$, —$C(=O)NR_aR_b$, —$OC(=O)R_a$, —$OC(=O)OR_a$, —$OC(=O)NR_aR_b$, —$SR_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl, and
$R_a$ and $R_b$ are independently —H, halo, amino, alkyl, or haloalkyl.

In another embodiment, the present disclosure provides pharmaceutical compositions comprising a therapeutically effective amount of a compound described herein and a pharmaceutically-acceptable carrier.

In yet another embodiment, the present disclosure provides methods of inhibiting or treating a neurodegenerative disease comprising administering to a subject in need thereof a therapeutically effective amount of one or more compounds described herein.

DETAILED DESCRIPTION

The following description is merely exemplary in nature and is not intended to limit the present disclosure, application, or uses.

Definitions

The generic terms used in the present disclosure are herein defined for clarity.

This specification uses the terms "substituent", "radical", "group", "moiety", and "fragment" interchangeably.

As used herein, the term "alkenyl" refers to a straight or branched hydrocarbonyl group with at least one site of unsaturation, i.e., a carbon-carbon, sp2 double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

As used herein, the term "alkoxy" is RO— where R is alkyl. Non-limiting examples of alkoxy groups include methoxy, ethoxy and propoxy.

As used herein, the term "alkoxyalkyl" refers to an alkyl moiety substituted with an alkoxy group. Examples of alkoxyalkyl groups include methoxymethyl, methoxyethyl, methoxypropyl and ethoxyethyl.

As used herein, the term "alkoxycarbonyl" is ROC(O)—, where R is an alkyl group as defined herein. In various embodiments, R is a $C_1$-$C_{10}$ alkyl group or a $C_1$-$C_6$ alkyl group.

As used herein, the term "alkyl" refers to a straight or branched chain hydrocarbonyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl. "lower alkyl" means alkyl having from 1 to 4 carbon atoms.

As used herein, if the term "$C_1$-$C_6$" is used, it means the number of carbon atoms is from 1 to 6. For example, $C_1$-$C_6$ alkyl means an alkyl which carbon number is any integer of from 1 to 6.

As used herein, the term "alkylamino" refers to an amino group substituted with one or more alkyl groups. "N-(alkyl) amino" is RNH— and "N,N-(alkyl)$_2$amino" is R$_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, dimethylamino, diethylamino, and methylethylamno.

As used herein, the term "alkylaminoalkyl" refers to an alkyl moiety substituted with an alkylamino group, wherein alkylamino is as defined herein. Examples of alkylaminoakyl groups include methylaminomethyl and ethylaminomethyl.

As used herein, the term "alkynyl" refers to a straight or branched carbon-chain group with at least one site of unsaturation, i.e., a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—CH$_2$C≡CH).

As used herein, the term "aryl" refers to any monocyclic or bicyclic carbon ring of up to 7 atoms in each ring, wherein at least one ring is aromatic, or an aromatic ring system of 5 to 14 carbon atoms which includes a carbocyclic aromatic group fused with a 5- or 6-membered cycloalkyl group. Representative examples of aryl groups include, but are not limited to, phenyl, tolyl, xylyl, naphthyl, tetrahydronaphthyl, anthracenyl, fluorenyl, indenyl, azulenyl and indanyl. A carbocyclic aromatic group can be unsubstituted or optionally substituted.

As used herein, the term "cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl. "Cycloalkyloxy" is RO—, where R is cycloalkyl.

As used herein, the terms "halogen" and "halo" refers to chloro (—Cl), bromo (—Br), fluoro (—F) or iodo (—I). "Haloalkoxy" refers to an alkoxy group substituted with one or more halo groups and examples of haloalkoxy groups include, but are not limited to, —OCF$_3$, —OCHF$_2$ and —OCH$_2$F. "Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl. "Haloalkyl" refers to an alkyl moiety substituted with one or more halo groups. Examples of haloalkyl groups include —CF$_3$ and —CHF$_2$.

As used herein, the term "heteroalkyl" refers to a straight- or branched-chain alkyl group having from 2 to 14 carbons (in some embodiments, 2 to 10 carbons) in the chain, one or more of which has been replaced by a heteroatom selected from S, O, P and N. Exemplary heteroalkyls include alkyl ethers, secondary and tertiary alkyl amines, amides, alkyl sulfides, and the like.

As used herein, the term "heterocyclyl" includes the heteroaryls defined below and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. "Heterocyclyloxy" is RO—, where R is heterocyclyl. "Heterocyclylthio" is RS—, where R is heterocyclyl.

As used herein, the term "3- or 4-membered heterocyclyl" refers to a monocyclic ring having 3 or 4 ring atoms wherein at least one ring atom is heteroatom selected from the group consisting of N, O and S. Non-limiting examples of 3- or 4-membered heterocyclyl include aziridinyl, 2H-azirinyl, oxiranyl, thiiranyl, azetidinyl, 2,3-dihyroazetyl, azetyl, 1,3-diazetidinyl, oxetanyl, 2H-oxetyl, thietanyl, and 2H-thietyl.

As used herein, the term "heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl. "Heteroaryloxy" is RO—, where R is heteroaryl.

As used herein, the term "hydroxyalkoxy" refers to an alkoxy group substituted with a hydroxyl group (—OH), wherein alkoxy is as defined herein. An example of hydroxyalkoxy is hydroxyethoxy.

As used herein, the term "hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

As used herein, the term "pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

As used herein, the term "pharmaceutically acceptable carrier" refers to a diluent, adjuvant, excipient, or carrier, or other ingredient which is pharmaceutically-acceptable and with which a compound of the invention is administered.

As used herein, the term "pharmaceutically acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo [2.2.2]oct-2-enel-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

As used herein, the term "substituted" means any of above groups (i.e., alkyl, aryl, heteroaryl, heterocycle or cycloalkyl) wherein at least one hydrogen atom of the moiety being substituted is replaced with a substituent. In one embodiment, each carbon atom of the group being substituted is substituted with no more than two substituents. In another embodiment, each carbon atom of the group being substituted is substituted with no more than one substituent. In the case of a keto substituent, two hydrogen atoms are replaced with an oxygen which is attached to the carbon via a double bond. Unless specifically defined, substituents include halogen, hydroxyl, (lower) alkyl, haloalkyl, mono- or di-alkylamino, aryl, heterocycle, —$NO_2$, $B(OH)_2$, BPin, —$NR_aR_b$, —$NR_aC(=O)R_b$, —$NR_aC(=O)NR_aR_b$, —$NR_aC(=O)OR_b$, —$NR_aSO_2R_b$, —$OR_a$, —CN, —$C(=O)R_a$, —$C(=O)OR_a$, —$C(=O)NR_aR_b$, —$OC(=O)R_a$, —$OC(=O)OR_a$, —$OC(=O)NR_aR_b$, —$NR_aSO_2R_b$, —$PO_3R_a$, —$PO(OR_a)(OR_b)$, —$SO_2R_a$, —$S(O)R_a$, —$SO(N)R_a$ (e.g., sulfoximine), —$(R_a)S=NR_b$ (e.g., sulfilimine) and —$SR_a$, wherein $R_a$ and $R_b$ are the same or different and independently hydrogen, halogen, amino, alkyl, haloalkyl, aryl or heterocycle, or wherein $R_a$ and $R_b$ taken together with the nitrogen atom to which they are attached form a heterocycle. $R_a$ and $R_b$ may be in the plural based on atoms which those are attached to.

As used herein, the term "therapeutically effective amount" means when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "therapeutically effective amount" is the amount of a compound of the present invention in the combination sufficient to cause the intended biological effect.

As used herein, the term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

In another embodiment, the compounds of Formula (I) are used for modulating the activity of a protein kinase c-abl.

As used herein, the term "modulating" or "modulation" refers to the alteration of the catalytic activity of a protein kinase. In particular, modulating refers to the activation or inhibition of the catalytic activity of a protein kinase, depending on the concentration of the compound or salt to which the protein kinase is exposed or, more preferably, the inhibition of the catalytic activity of a protein kinase. The term "catalytic activity" as used herein refers to the rate of phosphorylation of tyrosine, serine or threonine under the influence, direct or indirect, of a protein kinase.

The three main classes that pharmacological inhibitors of kinase activity are categorized by are (1) Type I, or "DFG-in" ATP competitive inhibitors, which directly compete with ATP in the ATP binding site (i.e., dual SRrc ABL inhibitor dasatinib, (2) Type II, or "DFG-out" ATP competitive inhibitors, which, in addition to binding the ATP binding site also engage an adjacent hydrophobic binding site that is only accessible when the kinase is in an inactivated configuration (i.e., the activation loop is oriented in a conformation that would block substrate binding) (i.e., imatinib, nilotinib), and (3) non-ATP competitive inhibitors that bind at sites outside the ATP binding site that affect the activity of the kinase (i.e. GNF-2).

As used herein, the phrase "compound(s) of this/the disclosure" includes any compound(s) of Formula (I), as well as clathrates, hydrates, solvates, or polymorphs thereof. And, even if the term "compound(s) of the disclosure" does not mention its pharmaceutically acceptable sat, the term includes salts thereof. In one embodiment, the compounds of this disclosure include stereochemically pure compounds, e.g., those substantially free (e.g., greater than 85% ee, greater than 90% ee, greater than 95% ee, greater than 97% ee, or greater than 99% ee) of other stereoisomers. That is, if the compounds of Formula (I) according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

Compounds of the Present Disclosure

The present disclosure provides a compound of Formula (I):

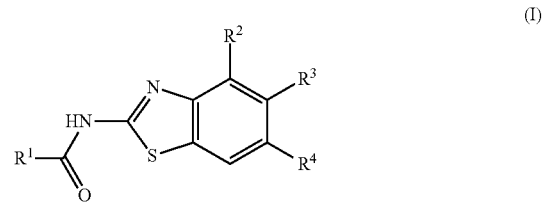

or a pharmaceutically acceptable salt thereof, wherein:
$R^1$ is cyclopropyl, cyclobutyl, or 3- or 4-membered heterocyclyl, wherein $R^1$ is optionally substituted with one or more groups selected from the group consisting of halo, alkyl, hydroxyalkyl, haloalkyl, and monoalkylaminoalkyl,
$R^2$ and $R^3$ are independently —H, halo, alkyl, alkoxy, —CF$_3$, or —OCF$_3$,
$R^4$ is aryl, heteroaryl, cycloalkyl, heterocyclyl, or heteroalkyl, wherein $R^4$ is optionally substituted with one or more groups selected from the group consisting of halo, hydroxyl, alkyl, alkenyl, alkynyl, haloalkyl, hydroxyalkyl, trimethylsilylethoxymethyl, —NO$_2$, —NR$_a$R$_b$, —NR$_a$C(=O)R$_b$, —NR$_a$C(=O)NR$_a$R$_b$, —NR$_a$C(=O)OR$_b$, —OR$_a$, —CN, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —SR$_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl, and
$R_a$ and $R_b$ are independently —H, halo, amino, alkyl, or haloalkyl.

In some embodiments, $R^1$ is cyclopropyl, cyclobutyl, or 3- or 4-membered heterocyclyl, wherein $R^1$ is optionally substituted with one or more groups selected from the group consisting of halo, $C_1$-$C_3$ alkyl, $C_1$-$C_3$ hydroxyalkyl and $C_1$-$C_3$ haloalkyl; $R^2$ and $R^3$ are independently —H, halo, $C_1$-$C_3$ alkyl, $C_1$-$C_3$ alkoxy, —CF$_3$, or —OCF$_3$; $R^4$ is aryl, heteroaryl, cycloalkyl, or heterocyclyl, wherein $R^4$ is optionally substituted with one or more groups selected from the group consisting of halo, hydroxyl, $C_1$-$C_3$ alkyl, $C_2$-$C_3$ alkenyl, $C_2$-$C_3$ alkynyl, $C_1$-$C_3$ haloalkyl, mono-$C_1$-$C_3$ alkylamino, di-$C_1$-$C_3$ alkylamino, —NO$_2$, —NR$_a$R$_b$, —NR$_a$C(=O)R$_b$, —NR$_a$C(=O)NR$_a$R$_b$, —NR$_a$C(=O)OR$_b$, —OR$_a$, —CN, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —SR$_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl, and $R_a$ and $R_b$ are independently —H, halo, amino, $C_1$-$C_3$ alkyl, or $C_1$-$C_3$ haloalkyl.

In various embodiments, $R^1$ is cyclopropyl or cyclobutyl, wherein $R^1$ is optionally substituted with one or more groups selected from the group consisting of halo, $C_1$-$C_3$ alkyl, $C_1$-$C_3$ hydroxyalkyl and $C_1$-$C_3$ haloalkyl. In particular embodiments, $R^1$ is cyclopropyl, fluorocyclopropyl, hydroxycyclopropyl, hydroxymethylcyclopropyl, difluorocyclopropyl, methylaminomethylcyclopropyl, cyclobutyl, fluorocyclobutyl, or difluorocyclobutyl. In other particular embodiments, $R^1$ is cyclopropyl, fluorocyclopropyl, cyclobutyl, or fluorocyclobutyl.

In some other embodiments, $R^1$ is 3- or 4-membered heterocyclyl, wherein $R^1$ is optionally substituted with one or more groups selected from the group consisting of halo, $C_1$-$C_3$ alkyl, $C_1$-$C_3$ hydroxyalkyl and $C_1$-$C_3$ haloalkyl. In particular embodiments, the 3- or 4-membered heterocyclyl is selected from the group consisting of aziridinyl, 2H-aziridinyl, oxiranyl, thiiranyl, azetidinyl, 2,3-dihyroazetyl, azetyl, 1,3-diazetidinyl, oxetanyl, 2H-oxetyl, thietanyl, and 2H-thietyl.

In some embodiments, $R^2$ and $R^3$ are independently —H, methyl, or fluoro.

In some embodiments, $R^4$ is phenyl, pyridinyl, pyrimidinyl, indolinyl, pyrazolyl, thiazolyl, oxoindolinyl, pyrrolopyridinyl, pyrazolyl, pyrazolopyridinyl, oxodihydropyrrolopyridinyl, thiophenyl, or isothiazolyl, wherein $R^4$ is optionally substituted with one or more groups selected from the group consisting of halo, alkyl, alkenyl, alkynyl, hydroxyalkyl, amino, cyano, acetyl, hydroxy, and haloalkyl. In particular embodiments, $R^4$ is fluoro-methylphenyl, chloro-methylphenyl, dimethylphenyl, acetamido-methylphenyl, hydroxy-methylphenyl, hydroxypropanyl-methylphenyl, methyl-propenylphenyl, methyl-pyridinylethynylphenyl, methyl-pyrrolylphenyl, methyl-thiazolylphenyl, imidazolyl-methylphenyl, cyano-methylphenyl, methyl-pyrazolylphenyl, ethynyl-methylphenyl, methylpyridinyl, fluoro-methyl-methylaminophenyl, dimethylpyridinyl, fluoro-methylpyridinyl, fluoromethyl-methylpyridinyl, cyanopyridinyl, trifluoromethyl-methylpyridinyl, hydroxymethylpyridinyl, hydroxymethyl-methylpyridinyl, hydroxyethyl-methylpyridinyl, chloro-methylpyridinyl, aminopyridinyl, acetyl-methylpyridinyl, amino-dimethylpyridinyl, hydroxyethyl-methylprydinyl, methylindolyl, trimethylsilylethoxymethylindolyl, acetyl-methylindolinyl, methylpyrimidinyl, dimethylpyrimidinyl, trifluoromethylpyrimidinyl, pyrazolyl, methylthiazolyl, methyloxoindolinyl, pyrrolopyridinyl, methylpyrrolopyridinyl, methyl-tetrahydropyranyl, methylpyrazolyl, methyl-oxodihydrobibenzothiazolyl, pyrazolopyridinyl, oxodihydropyrrolopyridinyl, methylisothiazolyl, chloromethylisothiazolyl, dimethylisothiazolyl, or fluoro-methylindolyl. In particular embodiments, $R^4$ is fluoro-methylphenyl, chloro-methylphenyl, bimethylphenyl, acetamido-methylphenyl, hydroxyl-methylphenyl, methyl-propenylphenyl, ethynyl-methylphenyl, fluoro-methyl-methylaminophenyl, methyl-pyrrolylphenyl, methyl-thiazolylphenyl, cyano-methylphenyl, imidazolyl-methylphenyl, methylpyridinyl, chloro-methylpyridinyl, fluoro-methylpyridinyl, fluoromethyl-methylpyridinyl, bimethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethylmethylpyridinyl, cyanopyridinyl, trifluoromethylpyridinyl, methylthiophenyl, methylindolinyl, methylpyrimidinyl, dimethylpyrimidinyl, pyrazolyl, methylpyrazolyl, methylindolinyl, methyloxoindolinyl, pyrrolopyridinyl, methylpyrrolopyridinyl, methylpyrrolyl, pyrazolopyridinyl, dihydropyrrolopyridinyl, methylisothiazolyl, dimethylisothiazolyl, methylindazolyl, or methyl-bibenzothiazolyl. In particular embodiments, $R^4$ is pyridinyl or phenyl that has one or more substitutions selected from the group consisting of alkyl, alkenyl, alkynyl, halo, hydroxyl, hydroxyalkyl, haloalkyl, cyano, amino, alkoxy, and haloalkoxy. In some particular embodiments, $R^4$ is selected from the group consisting of:

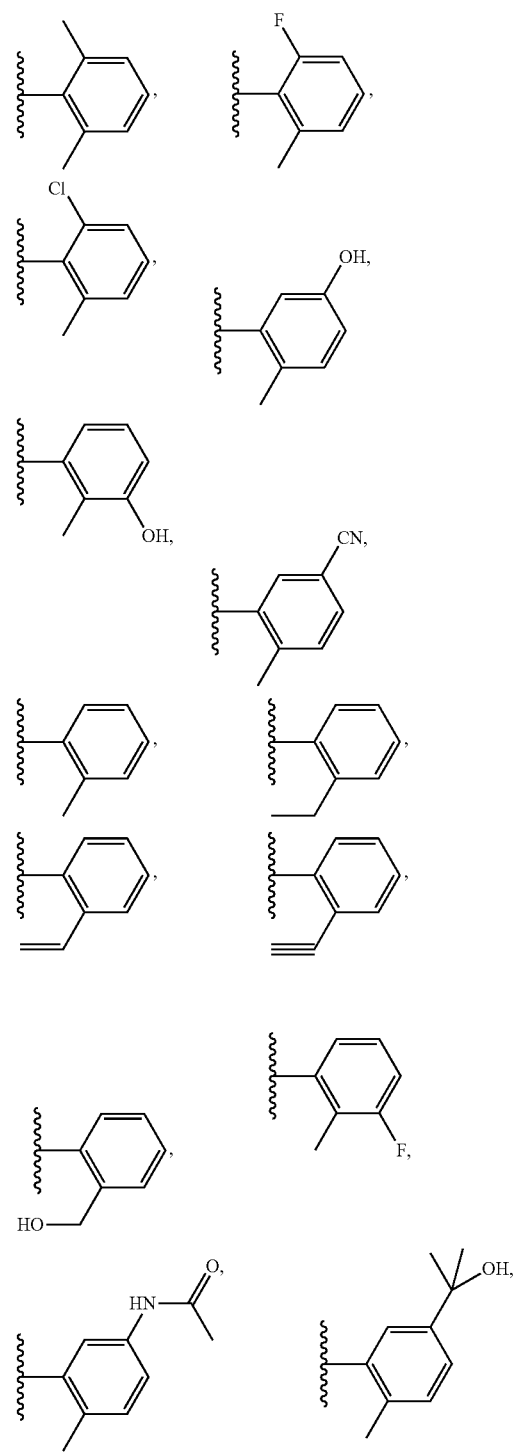

-continued

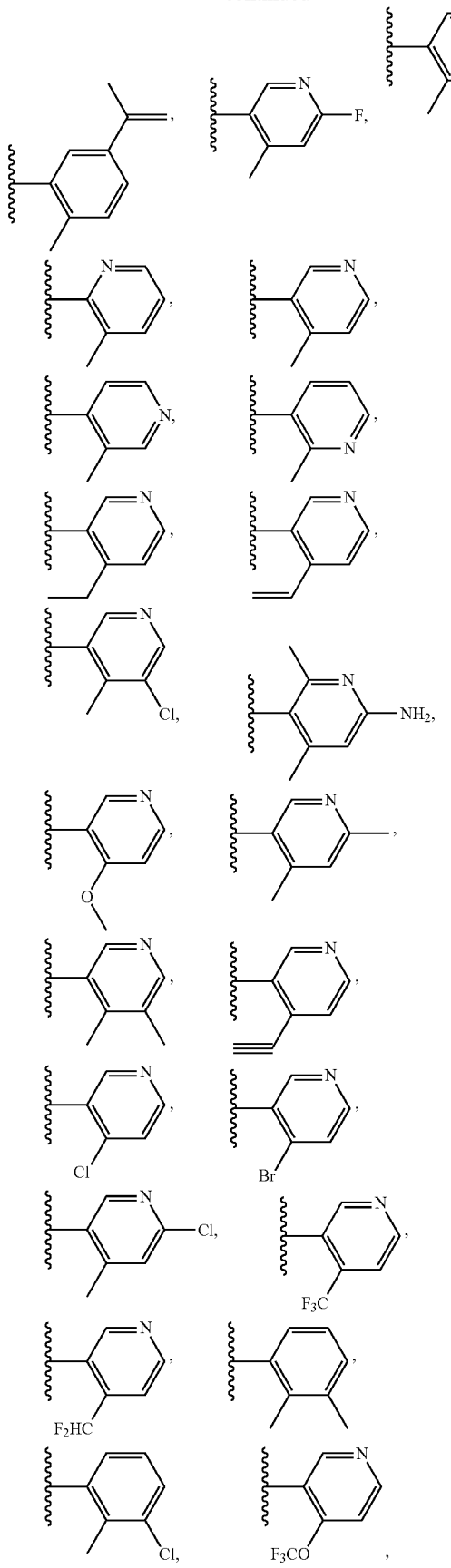
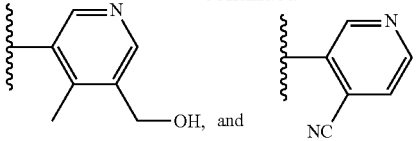

In some embodiments, $R^1$ is cyclopropyl, fluorocyclopropyl, difluorocyclopropyl, cyclobutyl, fluorocyclobutyl, or difluorocyclobutyl; $R^2$ and $R^3$ are independently —H, methyl, or fluoro; and $R^4$ is fluoro-methylphenyl, chloro-methylphenyl, bimethylphenyl, acetamido-methylphenyl, hydroxyl-methylphenyl, methyl-propenylphenyl, ethynyl-methylphenyl, fluoro-methyl-methylaminophenyl, methyl-pyrrolylphenyl, methyl-thiazolylphenyl, cyano-methylphenyl, imidazolyl-methylphenyl, methylpyridinyl, chloro-methylpyridinyl, fluoro-methylpyridinyl, fluoromethyl-methylpyridinyl, bimethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethyl-methylpyridinyl, cyanopyridinyl, trifluoromethylpyridinyl, methylthiophenyl, methylindolinyl, methylpyrimidinyl, dimethylpyrimidinyl, pyrazolyl, methylpyrazolyl, methylindolinyl, methyloxoindolinyl, pyrrolopyridinyl, methylpyrrolopyridinyl, methylpyrrolyl, pyrazolopyridinyl, dihydropyrrolopyridinyl, methylisothiazolyl, dimethylisothiazolyl, methylindazolyl, or methyl-bibenzothiazolyl.

The inventors had synthesized and evaluated lots of compounds to find out compounds having good c-abl inhibition activity and high selectivity against c-abl, thereby having good effect against neurodegenerative disease.

In some embodiments, $R^1$ is unsubstituted cyclopropyl and non-limiting examples include the following compounds and pharmaceutically acceptable salts thereof:
N-(6-(4-methylpyridin-3-yl)benzo[d]thiazol-2-yl)cyclopropanecarboxamide;
N-(6-(5-acetamido-2-methylphenyl)benzo[d]thiazol-2-yl) cyclopropanecarboxamide;
N-(6-(6-aminopyridin-3-yl)benzo[d]thiazol-2-yl)cyclopropanecarboxamide;
N-(6-(2-fluoro-6-methylphenyl)benzo[d]thiazol-2-yl)cyclopropanecarboxamide;
N-(6-(1H-pyrrolo[2,3-b]pyridin-5-yl)benzo[d]thiazol-2-yl) cyclopropanecarboxamide;
N-(6-(3-methyl-1H-pyrrolo[2,3-b]pyridin-5-yl)benzo[d]thiazol-2-yl)cyclopropane carboxamide;
N-(6-(1H-pyrazolo[3,4-b]pyridin-5-yl)benzo[d]thiazol-2-yl)cyclopropanecarboxamide;
N-(6-(2-oxo-2,3-dihydro-1H-pyrrolo[2,3-b]pyridin-5-yl) benzo[d]thiazol-2-yl) cyclopropanecarboxamide;
N-(6-(2,3-dihydro-1H-pyrrolo[2,3-b]pyridin-5-yl)benzo[d]thiazol-2-yl)cyclopropane carboxamide;
N-(6-(6-fluoro-5-methyl-1H-indol-4-yl)benzo[d]thiazol-2-yl)cyclopropanecarboxamide; and
N-(6-(5-fluoro-4-methylpyridin-3-yl)benzo[d]thiazol-2-yl) cyclopropanecarboxamide.

In some embodiments, $R^1$ is fluorocyclopropyl and non-limiting examples include the following compounds and pharmaceutically acceptable salts thereof:
2-fluoro-N-(6-(2-fluoro-6-methylphenyl)benzo[d]thiazol-2-yl)cyclopropane-1-carboxamide;
N-(6-(2-chloro-6-methylphenyl)benzo[d]thiazol-2-yl)-2-fluorocyclopropane-1-carboxamide;
N-(6-(2,6-dimethylphenyl)benzo[d]thiazol-2-yl)-2-fluorocyclopropane-1-carboxamide;

2-fluoro-N-(6-(4-methylpyridin-3-yl)benzo[d]thiazol-2-yl)cyclopropane-1-carboxamide;
2-fluoro-N-(6-(5-fluoro-4-methylpyridin-3-yl)benzo[d]thiazol-2-yl)cyclopropane-1-carboxamide;
2-fluoro-N-(6-(2-methyl-5-(prop-1-en-2-yl)phenyl)benzo[d]thiazol-2-yl)cyclopropane-1-carboxamide;
N-(6-(2-chloro-4-methylpyridin-3-yl)benzo[d]thiazol-2-yl)-2-fluorocyclopropane-1-carboxamide;
N-(6-(2,4-dimethylpyridin-3-yl)benzo[d]thiazol-2-yl)-2-fluorocyclopropane-1-carboxamide;
2-fluoro-N-(6-(5-hydroxy-2-methylphenyl)benzo[d]thiazol-2-yl)cyclopropane-1-carboxamide;
2-fluoro-N-(6-(5-(2-hydroxypropan-2-yl)-2-methylphenyl)benzo[d]thiazol-2-yl) cyclopropane-1-carboxamide;
2-fluoro-N-(6-(3-hydroxy-2-methylphenyl)benzo[d]thiazol-2-yl)cyclopropane-1-carboxamide;
N-(6-(6-amino-2,4-dimethylpyridin-3-yl)benzo[d]thiazol-2-yl)-2-fluorocyclopropane-1-carboxamide;
2-fluoro-N-(6-(5-methylindolin-4-yl)benzo[d]thiazol-2-yl)cyclopropane-1-carboxamide;
2-fluoro-N-(6-(2-fluoro-6-methylphenyl)thiazolo[4,5-c]pyridin-2-yl)cyclopropane-1-carboxamide;
N-(6-(1-acetyl-5-methylindolin-4-yl)benzo[d]thiazol-2-yl)-2-fluorocyclopropane-1-carboxamide;
2-fluoro-N-(6-(2-fluoro-6-methyl-3-(methylamino)phenyl)benzo[d]thiazol-2-yl) cyclopropane-1-carboxamide;
2-fluoro-N-(6-(4-methoxypyridin-3-yl)benzo[d]thiazol-2-yl)cyclopropane-1-carboxamide;
2-fluoro-N-(6-(3-methylthiophen-2-yl)benzo[d]thiazol-2-yl)cyclopropane-1-carboxamide;
3-(2-(2-fluorocyclopropane-1-carboxamido)benzo[d]thiazol-6-yl)-4-methylpyridine 1-oxide;
(2-(2-fluorocyclopropane-1-carboxamido)benzo[d]thiazol-6-yl)boronic acid;
2-fluoro-N-(6-(4-methylpyrimidin-5-yl)benzo[d]thiazol-2-yl)cyclopropane-1-carboxamide;
N-(6-(6-acetyl-4-methylpyridin-3-yl)benzo[d]thiazol-2-yl)-2-fluorocyclopropane-1-carboxamide;
N-(6-(4,6-dimethylpyridin-3-yl)benzo[d]thiazol-2-yl)-2-fluorocyclopropane-1-carboxamide;
N-(6-(6-chloro-4-methylpyridin-3-yl)benzo[d]thiazol-2-yl)-2-fluorocyclopropane-1-carboxamide;
2-fluoro-N-(6-(4-methyl-6-(trifluoromethyl)pyridin-3-yl)benzo[d]thiazol-2-yl)cyclopropane-1-carboxamide;
2-fluoro-N-(6-(4-(hydroxymethyl)pyridin-3-yl)benzo[d]thiazol-2-yl)cyclopropane-1-carboxamide;
2-fluoro-N-(6-(6-(hydroxymethyl)-4-methylpyridin-3-yl)benzo[d]thiazol-2-yl)cyclopropane-1-carboxamide;
2-fluoro-N-(6-(6-(1-hydroxyethyl)-4-methylpyridin-3-yl)benzo[d]thiazol-2-yl)cyclopropane-1-carboxamide;
2-fluoro-N-(6-(4-(trifluoromethyl)pyridin-3-yl)benzo[d]thiazol-2-yl)cyclopropane-1-carboxamide;
N-(6-(1H-pyrazol-3-yl)benzo[d]thiazol-2-yl)-2-fluorocyclopropane-1-carboxamide;
2-fluoro-N-(6-(2-methyl-5-(pyridin-2-ylethynyl)phenyl)benzo[d]thiazol-2-yl)cyclopropane-1-carboxamide;
2-fluoro-N-(6-(2-methyl-5-(1H-pyrazol-1-yl)phenyl)benzo[d]thiazol-2-yl)cyclopropane-1-carboxamide;
2-fluoro-N-(6-(5-methyl-1H-indol-4-yl)benzo[d]thiazol-2-yl)cyclopropane-1-carboxamide;
2-fluoro-N-(6-(5-(hydroxymethyl)-4-methylpyridin-3-yl)benzo[d]thiazol-2-yl)cyclopropane-1-carboxamide;
2-fluoro-N-(4-fluoro-6-(4-methylpyridin-3-yl)benzo[d]thiazol-2-yl)cyclopropane-1-carboxamide;
2-fluoro-N-(4-fluoro-6-(2-fluoro-6-methylphenyl)benzo[d]thiazol-2-yl)cyclopropane-1-carboxamide;
2-fluoro-N-(6-(5-methylthiazol-4-yl)benzo[d]thiazol-2-yl)cyclopropane-1-carboxamide;
N-(6-(4,6-dimethylpyrimidin-5-yl)benzo[d]thiazol-2-yl)-2-fluorocyclopropane-1-carboxamide;
2-fluoro-N-(6-(7-methyl-2-oxoindolin-6-yl)benzo[d]thiazol-2-yl)cyclopropane-1-carboxamide;
N-(6-(5-ethynyl-2-methylphenyl)benzo[d]thiazol-2-yl)-2-fluorocyclopropane-1-carboxamide;
N-(6-(4-chloropyridin-3-yl)benzo[d]thiazol-2-yl)-2-fluorocyclopropane-1-carboxamide;
N-(6-(4-cyanopyridin-3-yl)benzo[d]thiazol-2-yl)-2-fluorocyclopropane-1-carboxamide;
2-fluoro-N-(6-(2-fluoro-4-methylpyridin-3-yl)benzo[d]thiazol-2-yl)cyclopropane-1-carboxamide;
2-fluoro-N-(6-(4-(trifluoromethyl)pyrimidin-5-yl)benzo[d]thiazol-2-yl)cyclopropane-1-carboxamide;
2-fluoro-N-(6-(2-methyl-5-(1H-pyrrol-3-yl)phenyl)benzo[d]thiazol-2-yl)cyclopropane-1-carboxamide;
2-fluoro-N-(6-(2-methyl-5-(thiazol-2-yl)phenyl)benzo[d]thiazol-2-yl)cyclopropane-1-carboxamide;
N-(6-(5-cyano-2-methylphenyl)benzo[d]thiazol-2-yl)-2-fluorocyclopropane-1-carboxamide;
2-fluoro-N-(6-(4-methyl-1-(tetrahydro-2H-pyran-2-yl)-1H-pyrazol-3-yl)benzo[d]thiazol-2-yl)cyclopropane-1-carboxamide;
2-fluoro-N-(6-(4-methyl-1H-pyrazol-3-yl)benzo[d]thiazol-2-yl)cyclopropane-1-carboxamide;
2-fluoro-N-(6-(2-methyl-5-(1H-pyrrol-2-yl)phenyl)benzo[d]thiazol-2-yl)cyclopropane-1-carboxamide;
2-fluoro-N-(6-(2-methyl-5-(1H-pyrazol-3-yl)phenyl)benzo[d]thiazol-2-yl)cyclopropane-1-carboxamide;
2-fluoro-N-(6-(5-methyl-2-oxoindolin-4-yl)benzo[d]thiazol-2-yl)cyclopropane-1-carboxamide;
2-fluoro-N-(4-methyl-2-oxo-2,3-dihydro-[5,6'-bibenzo[d]thiazol]-2'-yl)cyclopropane-1-carboxamide;
N-(6-(1H-pyrrolo[2,3-b]pyridin-5-yl)benzo[d]thiazol-2-yl)-2-fluorocyclopropane-1-carboxamide;
2-fluoro-N-(6-(3-methylisothiazol-5-yl)benzo[d]thiazol-2-yl)cyclopropane-1-carboxamide;
N-(6-(4-chloro-3-methylisothiazol-5-yl)benzo[d]thiazol-2-yl)-2-fluorocyclopropane-1-carboxamide;
2-fluoro-N-(6-(7-methyl-1H-indazol-4-yl)benzo[d]thiazol-2-yl)cyclopropane-1-carboxamide;
2-fluoro-N-(6-(7-methyl-1H-indazol-6-yl)benzo[d]thiazol-2-yl)cyclopropane-1-carboxamide;
N-(6-(3,4-dimethylisothiazol-5-yl)benzo[d]thiazol-2-yl)-2-fluorocyclopropane-1-carboxamide;
N-(6-(5-(1H-imidazol-2-yl)-2-methylphenyl)benzo[d]thiazol-2-yl)-2-fluorocyclopropane-1-carboxamide;
2-fluoro-N-(6'-methyl[6,7'-bibenzo[d]thiazol]-2-yl)cyclopropane-1-carboxamide;
2-fluoro-N-(6-(6-(fluoromethyl)-4-methylpyridin-3-yl)benzo[d]thiazol-2-yl)cyclopropane-1-carboxamide;
2-fluoro-N-(6-(6-fluoro-5-methyl-1H-indol-4-yl)benzo[d]thiazol-2-yl)cyclopropane-1-carboxamide;
2-fluoro-N-(5-fluoro-6-(4-methylpyridin-3-yl)benzo[d]thiazol-2-yl)cyclopropane-1-carboxamide;
2-fluoro-N-(6-(6-fluoro-4-methylpyridin-3-yl)benzo[d]thiazol-2-yl)cyclopropane-1-carboxamide;
2-fluoro-N-(6-(4-methylpyridin-3-yl)benzo[d]thiazol-2-yl)cyclopropane-1-carboxamide;
2-fluoro-N-(6-(4-methylpyridin-3-yl)benzo[d]thiazol-2-yl)cyclopropane-1-carboxamide;
2-fluoro-N-(6-(4-methylpyridin-3-yl)benzo[d]thiazol-2-yl)cyclopropane-1-carboxamide;
2-fluoro-N-(6-(2-methylpyridin-3-yl)benzo[d]thiazol-2-yl)cyclopropane-1-carboxamide;

2-fluoro-N-(6-(3-methylpyridin-4-yl)benzo[d]thiazol-2-yl) cyclopropane-1-carboxamide;
2-fluoro-N-(6-(3-methylpyridin-2-yl)benzo[d]thiazol-2-yl) cyclopropane-1-carboxamide;
N-(6-(4-ethylpyridin-3-yl)benzo[d]thiazol-2-yl)-2-fluorocyclopropane-1-carboxamide;
2-fluoro-N-(6-(4-vinylpyridin-3-yl)benzo[d]thiazol-2-yl) cyclopropane-1-carboxamide;
N-(6-(4-ethynylpyridin-3-yl)benzo[d]thiazol-2-yl)-2-fluorocyclopropane-1-carboxamide;
N-(6-(4-bromopyridin-3-yl)benzo[d]thiazol-2-yl)-2-fluorocyclopropane-1-carboxamide;
2-fluoro-N-(6-(4-(trifluoromethoxy)pyridin-3-yl)benzo[d]thiazol-2-yl)cyclopropane-1-carboxamide;
N-(6-(4-(difluoromethyl)pyridin-3-yl)benzo[d]thiazol-2-yl)-2-fluorocyclopropane-1-carboxamide;
N-(6-(5-chloro-4-methylpyridin-3-yl)benzo[d]thiazol-2-yl)-2-fluorocyclopropane-1-carboxamide;
N-(6-(4,5-dimethylpyridin-3-yl)benzo[d]thiazol-2-yl)-2-fluorocyclopropane-1-carboxamide;
2-fluoro-N-(6-(6-fluoro-5-methylindolin-4-yl)benzo[d]thiazol-2-yl)cyclopropane-1-carboxamide;
2-fluoro-N-(6-(o-tolyl)benzo[d]thiazol-2-yl)cyclopropane-1-carboxamide;
N-(6-(2-ethylphenyl)benzo[d]thiazol-2-yl)-2-fluorocyclopropane-1-carboxamide;
2-fluoro-N-(6-(2-vinylphenyl)benzo[d]thiazol-2-yl)cyclopropane-1-carboxamide;
N-(6-(2-ethynylphenyl)benzo[d]thiazol-2-yl)-2-fluorocyclopropane-1-carboxamide;
N-(6-(2-bromophenyl)benzo[d]thiazol-2-yl)-2-fluorocyclopropane-1-carboxamide;
2-fluoro-N-(6-(2-methoxyphenyl)benzo[d]thiazol-2-yl)cyclopropane-1-carboxamide;
2-fluoro-N-(6-(2-(trifluoromethoxy)phenyl)benzo[d]thiazol-2-yl)cyclopropane-1-carboxamide;
2-fluoro-N-(6-(2-(trifluoromethyl)phenyl)benzo[d]thiazol-2-yl)cyclopropane-1-carboxamide;
N-(6-(2-(difluoromethyl)phenyl)benzo[d]thiazol-2-yl)-2-fluorocyclopropane-1-carboxamide;
2-fluoro-N-(6-(2-(hydroxymethyl)phenyl)benzo[d]thiazol-2-yl)cyclopropane-1-carboxamide;
2-fluoro-N-(6-(3-fluoro-2-methylphenyl)benzo[d]thiazol-2-yl)cyclopropane-1-carboxamide;
N-(6-(3-chloro-2-methylphenyl)benzo[d]thiazol-2-yl)-2-fluorocyclopropane-1-carboxamide;
N-(6-(2,3-dimethylphenyl)benzo[d]thiazol-2-yl)-2-fluorocyclopropane-1-carboxamide;
N-(4-chloro-6-(4-methylpyridin-3-yl)benzo[d]thiazol-2-yl)-2-fluorocyclopropane-1-carboxamide;
2-fluoro-N-(6-(4-methylpyridin-3-yl)-4-(trifluoromethyl)benzo[d]thiazol-2-yl)cyclopropane-1-carboxamide;
2-fluoro-N-(4-methoxy-6-(4-methylpyridin-3-yl)benzo[d]thiazol-2-yl)cyclopropane-1-carboxamide;
2-fluoro-N-(4-methyl-6-(4-methylpyridin-3-yl)benzo[d]thiazol-2-yl)cyclopropane-1-carboxamide;
N-(5-chloro-6-(4-methylpyridin-3-yl)benzo[d]thiazol-2-yl)-2-fluorocyclopropane-1-carboxamide;
2-fluoro-N-(6-(4-methylpyridin-3-yl)-5-(trifluoromethyl) benzo[d]thiazol-2-yl)cyclopropane-1-carboxamide;
2-fluoro-N-(5-methoxy-6-(4-methylpyridin-3-yl)benzo[d]thiazol-2-yl)cyclopropane-1-carboxamide;
2-fluoro-N-(5-methyl-6-(4-methylpyridin-3-yl)benzo[d]thiazol-2-yl)cyclopropane-1-carboxamide;
N-(6-(1H-imidazol-2-yl)benzo[d]thiazol-2-yl)-2-fluorocyclopropane-1-carboxamide;
2-fluoro-N-(6-(4-methyl-1H-imidazol-2-yl)benzo[d]thiazol-2-yl)cyclopropane-1-carboxamide;
N-(6-(1H-imidazol-4-yl)benzo[d]thiazol-2-yl)-2-fluorocyclopropane-1-carboxamide;
2-fluoro-N-(6-(2-methyl-1H-imidazol-4-yl)benzo[d]thiazol-2-yl)cyclopropane-1-carboxamide;
2-fluoro-N-(6-(3-methylpyrazin-2-yl)benzo[d]thiazol-2-yl) cyclopropane-1-carboxamide;
2-fluoro-N-(6-(4-methyloxazol-5-yl)benzo[d]thiazol-2-yl) cyclopropane-1-carboxamide;
2-fluoro-N-(6-(3-methyl-1H-pyrrol-2-yl)benzo[d]thiazol-2-yl)cyclopropane-1-carboxamide;
N-(6-(1H-benzo[d]imidazol-4-yl)benzo[d]thiazol-2-yl)-2-fluorocyclopropane-1-carboxamide;
2-fluoro-N-(6-(5-methyl-1H-benzo[d]imidazol-4-yl)benzo[d]thiazol-2-yl)cyclopropane-1-carboxamide;
N-(6-(1H-pyrrolo[2,3-b]pyridin-4-yl)benzo[d]thiazol-2-yl)-2-fluorocyclopropane-1-carboxamide;
2-fluoro-N-(6-(5-methyl-1H-pyrrolo[2,3-b]pyridin-4-yl) benzo[d]thiazol-2-yl)cyclopropane-1-carboxamide;
2-fluoro-N-(6-(4-methylpyridazin-3-yl)benzo[d]thiazol-2-yl)cyclopropane-1-carboxamide;
2-fluoro-N-(6-(5-methylpyridazin-4-yl)benzo[d]thiazol-2-yl)cyclopropane-1-carboxamide; and
2-fluoro-N-(6-(5-methyl-2,3-dihydro-1H-pyrrolo[2,3-b] pyridin-4-yl)benzo[d]thiazol-2-yl)cyclopropane-1-carboxamide.

In some embodiments, $R^1$ is hydroxymethylcyclopropyl and non-limiting examples include the following compounds and pharmaceutically acceptable salts thereof:
2-(hydroxymethyl)-N-(6-(4-methylpyridin-3-yl)benzo[d] thiazol-2-yl)cyclopropane-1-carboxamide;
2-(hydroxymethyl)-N-(6-(5-methyl-1H-indol-4-yl)benzo[d] thiazol-2-yl)cyclopropane-1-carboxamide;
N-(6-(2-fluoro-6-methylphenyl)benzo[d]thiazol-2-yl)-2-(hydroxymethyl)cyclopropane-1-carboxamide;
N-(6-(2-fluoro-6-methylphenyl)benzo[d]thiazol-2-yl)-2-(hydroxymethyl)cyclopropane-1-carboxamide;
N-(6-(2-fluoro-6-methylphenyl)benzo[d]thiazol-2-yl)-2-(hydroxymethyl)cyclopropane-1-carboxamide;
N-(6-(5-fluoro-4-methylpyridin-3-yl)benzo[d]thiazol-2-yl)-2-(hydroxymethyl)cyclopropane-1-carboxamide; and
N-(6-(6-fluoro-5-methyl-1H-indol-4-yl)benzo[d]thiazol-2-yl)-2-(hydroxymethyl) cyclopropane-1-carboxamide.

In some embodiments, $R^1$ is hydroxycyclopropyl or difluorocyclopropyl and non-limiting examples include the following compounds and pharmaceutically acceptable salts thereof:
2-hydroxy-N-(6-(4-methylpyridin-3-yl)benzo[d]thiazol-2-yl)cyclopropane-1-carboxamide;
2-hydroxy-N-(6-(4-methylpyridin-3-yl)benzo[d]thiazol-2-yl)cyclopropane-1-carboxamide;
2,2-difluoro-N-(6-(4-methylpyridin-3-yl)benzo[d]thiazol-2-yl)cyclopropane-1-carboxamide;
2,2-difluoro-N-(6-(2-fluoro-6-methylphenyl)benzo[d]thiazol-2-yl)cyclopropane-1-carboxamide; and
2,2-difluoro-N-(6-(5-fluoro-4-methylpyridin-3-yl)benzo[d] thiazol-2-yl)cyclopropane-1-carboxamide.

In some embodiments, $R^1$ is unsubstituted cyclobutyl and non-limiting examples include the following compounds and pharmaceutically acceptable salts thereof:
N-(6-(2-fluoro-6-methylphenyl)benzo[d]thiazol-2-yl)cyclobutanecarboxamide;
N-(6-(4-methylpyridin-3-yl)benzo[d]thiazol-2-yl)cyclobutanecarboxamide; and
N-(6-(5-fluoro-4-methylpyridin-3-yl)benzo[d]thiazol-2-yl) cyclobutanecarboxamide.

In some embodiments, $R^1$ is fluorocyclobutyl and non-limiting examples include the following compounds and pharmaceutically acceptable salts thereof:

3-fluoro-N-(6-(4-methylpyridin-3-yl)benzo[d]thiazol-2-yl)cyclobutane-1-carboxamide;
3-fluoro-N-(6-(4-methylpyridin-3-yl)benzo[d]thiazol-2-yl)cyclobutane-1-carboxamide;
3-fluoro-N-(6-(2-fluoro-6-methylphenyl)benzo[d]thiazol-2-yl)cyclobutane-1-carboxamide;
3-fluoro-N-(6-(2-fluoro-6-methylphenyl)benzo[d]thiazol-2-yl)cyclobutane-1-carboxamide;
3-fluoro-N-(6-(5-fluoro-4-methylpyridin-3-yl)benzo[d]thiazol-2-yl)cyclobutane-1-carboxamide;
3,3-difluoro-N-(6-(4-methylpyridin-3-yl)benzo[d]thiazol-2-yl)cyclobutane-1-carboxamide;
3,3-difluoro-N-(6-(2-fluoro-6-methylphenyl)benzo[d]thiazol-2-yl)cyclobutane-1-carboxamide; and
3,3-difluoro-N-(6-(5-fluoro-4-methylpyridin-3-yl)benzo[d]thiazol-2-yl)cyclobutane-1-carboxamide.

In particular embodiment, the compound of this discloser is selected from the group consisting of:
2-fluoro-N-(6-(2-fluoro-6-methylphenyl)benzo[d]thiazol-2-yl)cyclopropane-1-carboxamide;
N-(6-(2-chloro-6-methylphenyl)benzo[d]thiazol-2-yl)-2-fluorocyclopropane-1-carboxamide;
N-(6-(2,6-dimethylphenyl)benzo[d]thiazol-2-yl)-2-fluorocyclopropane-1-carboxamide;
2-fluoro-N-(6-(4-methylpyridin-3-yl)benzo[d]thiazol-2-yl)cyclopropane-1-carboxamide;
N-(6-(4-methylpyridin-3-yl)benzo[d]thiazol-2-yl)cyclopropanecarboxamide;
2-fluoro-N-(6-(5-fluoro-4-methylpyridin-3-yl)benzo[d]thiazol-2-yl)cyclopropane-1-carboxamide;
2-(hydroxymethyl)-N-(6-(4-methylpyridin-3-yl)benzo[d]thiazol-2-yl)cyclopropane-1-carboxamide;
N-(6-(5-acetamido-2-methylphenyl)benzo[d]thiazol-2-yl)cyclopropanecarboxamide;
N-(6-(2-chloro-4-methylpyridin-3-yl)benzo[d]thiazol-2-yl)-2-fluorocyclopropane-1-carboxamide;
N-(6-(2,4-dimethylpyridin-3-yl)benzo[d]thiazol-2-yl)-2-fluorocyclopropane-1-carboxamide;
2-fluoro-N-(6-(5-hydroxy-2-methylphenyl)benzo[d]thiazol-2-yl)cyclopropane-1-carboxamide;
2-fluoro-N-(6-(2-methyl-5-(prop-1-en-2-yl)phenyl)benzo[d]thiazol-2-yl)cyclopropane-1-carboxamide;
N-(6-(6-aminopyridin-3-yl)benzo[d]thiazol-2-yl)cyclopropanecarboxamide;
2-fluoro-N-(6-(3-hydroxy-2-methylphenyl)benzo[d]thiazol-2-yl)cyclopropane-1-carboxamide;
N-(6-(6-amino-2,4-dimethylpyridin-3-yl)benzo[d]thiazol-2-yl)-2-fluorocyclopropane-1-carboxamide;
2-fluoro-N-(6-(5-methylindolin-4-yl)benzo[d]thiazol-2-yl)cyclopropane-1-carboxamide;
N-(6-(1-acetyl-5-methylindolin-4-yl)benzo[d]thiazol-2-yl)-2-fluorocyclopropane-1-carboxamide;
2,2-difluoro-N-(6-(4-methylpyridin-3-yl)benzo[d]thiazol-2-yl)cyclopropane-1-carboxamide;
3-fluoro-N-(6-(4-methylpyridin-3-yl)benzo[d]thiazol-2-yl)cyclobutane-1-carboxamide;
2,2-difluoro-N-(6-(2-fluoro-6-methylphenyl)benzo[d]thiazol-2-yl)cyclopropane-1-carboxamide;
N-(6-(4-methylpyridin-3-yl)benzo[d]thiazol-2-yl)cyclobutanecarboxamide;
2-fluoro-N-(6-(2-fluoro-6-methyl-3-(methylamino)phenyl)benzo[d]thiazol-2-yl)cyclopropane-1-carboxamide;
N-(6-(5-fluoro-4-methylpyridin-3-yl)benzo[d]thiazol-2-yl)cyclopropanecarboxamide;
2,2-difluoro-N-(6-(5-fluoro-4-methylpyridin-3-yl)benzo[d]thiazol-2-yl)cyclopropane-1-carboxamide;
N-(6-(5-fluoro-4-methylpyridin-3-yl)benzo[d]thiazol-2-yl)cyclobutanecarboxamide;
3-fluoro-N-(6-(5-fluoro-4-methylpyridin-3-yl)benzo[d]thiazol-2-yl)cyclobutane-1-carboxamide;
3,3-difluoro-N-(6-(5-fluoro-4-methylpyridin-3-yl)benzo[d]thiazol-2-yl)cyclobutane-1-carboxamide;
2-fluoro-N-(6-(4-methoxypyridin-3-yl)benzo[d]thiazol-2-yl)cyclopropane-1-carboxamide;
2-fluoro-N-(6-(3-methylthiophen-2-yl)benzo[d]thiazol-2-yl)cyclopropane-1-carboxamide;
3-(2-(2-fluorocyclopropane-1-carboxamido)benzo[d]thiazol-6-yl)-4-methylpyridine 1-oxide;
N-(6-(2-fluoro-6-methylphenyl)benzo[d]thiazol-2-yl)-2-(hydroxymethyl)cyclopropane-1-carboxamide;
2-fluoro-N-(6-(4-methylpyrimidin-5-yl)benzo[d]thiazol-2-yl)cyclopropane-1-carboxamide;
N-(6-(6-acetyl-4-methylpyridin-3-yl)benzo[d]thiazol-2-yl)-2-fluorocyclopropane-1-carboxamide;
N-(6-(2-fluoro-6-methylphenyl)benzo[d]thiazol-2-yl)-2-(hydroxymethyl)cyclopropane-1-carboxamide;
N-(6-(5-fluoro-4-methylpyridin-3-yl)benzo[d]thiazol-2-yl)-2-(hydroxymethyl)cyclopropane-1-carboxamide;
N-(6-(4,6-dimethylpyridin-3-yl)benzo[d]thiazol-2-yl)-2-fluorocyclopropane-1-carboxamide;
N-(6-(6-chloro-4-methylpyridin-3-yl)benzo[d]thiazol-2-yl)-2-fluorocyclopropane-1-carboxamide;
2-fluoro-N-(6-(4-(hydroxymethyl)pyridin-3-yl)benzo[d]thiazol-2-yl)cyclopropane-1-carboxamide;
2-fluoro-N-(6-(6-(hydroxymethyl)-4-methylpyridin-3-yl)benzo[d]thiazol-2-yl)cyclopropane-1-carboxamide;
2-fluoro-N-(6-(6-(1-hydroxyethyl)-4-methylpyridin-3-yl)benzo[d]thiazol-2-yl)cyclopropane-1-carboxamide;
2-fluoro-N-(6-(4-(trifluoromethyl)pyridin-3-yl)benzo[d]thiazol-2-yl)cyclopropane-1-carboxamide;
N-(6-(1H-pyrazol-3-yl)benzo[d]thiazol-2-yl)-2-fluorocyclopropane-1-carboxamide;
2-fluoro-N-(6-(2-methyl-5-(1H-pyrazol-1-yl)phenyl)benzo[d]thiazol-2-yl)cyclopropane-1-carboxamide;
2-fluoro-N-(6-(5-methyl-1H-indol-4-yl)benzo[d]thiazol-2-yl)cyclopropane-1-carboxamide;
N-(6-(2-fluoro-6-methylphenyl)benzo[d]thiazol-2-yl)cyclopropanecarboxamide;
2-fluoro-N-(6-(5-(hydroxymethyl)-4-methylpyridin-3-yl)benzo[d]thiazol-2-yl)cyclopropane-1-carboxamide;
2-fluoro-N-(4-fluoro-6-(4-methylpyridin-3-yl)benzo[d]thiazol-2-yl)cyclopropane-1-carboxamide;
2-fluoro-N-(6-(5-methylthiazol-4-yl)benzo[d]thiazol-2-yl)cyclopropane-1-carboxamide;
2-fluoro-N-(6-(7-methyl-2-oxoindolin-6-yl)benzo[d]thiazol-2-yl)cyclopropane-1-carboxamide;
N-(6-(5-ethynyl-2-methylphenyl)benzo[d]thiazol-2-yl)-2-fluorocyclopropane-1-carboxamide;
N-(6-(4-chloropyridin-3-yl)benzo[d]thiazol-2-yl)-2-fluorocyclopropane-1-carboxamide;
N-(6-(4-cyanopyridin-3-yl)benzo[d]thiazol-2-yl)-2-fluorocyclopropane-1-carboxamide;
2-fluoro-N-(6-(2-fluoro-4-methylpyridin-3-yl)benzo[d]thiazol-2-yl)cyclopropane-1-carboxamide;
N-(6-(1H-pyrrolo[2,3-b]pyridin-5-yl)benzo[d]thiazol-2-yl)cyclopropanecarboxamide;
2-fluoro-N-(6-(2-methyl-5-(1H-pyrrol-3-yl)phenyl)benzo[d]thiazol-2-yl)cyclopropane-1-carboxamide;
2-fluoro-N-(6-(2-methyl-5-(thiazol-2-yl)phenyl)benzo[d]thiazol-2-yl)cyclopropane-1-carboxamide;

N-(6-(5-cyano-2-methylphenyl)benzo[d]thiazol-2-yl)-2-fluorocyclopropane-1-carboxamide;
2-fluoro-N-(6-(4-methyl-1H-pyrazol-3-yl)benzo[d]thiazol-2-yl)cyclopropane-1-carboxamide;
2-fluoro-N-(6-(2-methyl-5-(1H-pyrrol-2-yl)phenyl)benzo[d]thiazol-2-yl)cyclopropane-1-carboxamide;
2-fluoro-N-(6-(2-methyl-5-(1H-pyrazol-3-yl)phenyl)benzo[d]thiazol-2-yl)cyclopropane-1-carboxamide;
2-fluoro-N-(6-(5-methyl-2-oxoindolin-4-yl)benzo[d]thiazol-2-yl)cyclopropane-1-carboxamide;
N-(6-(3-methyl-1H-pyrrolo[2,3-b]pyridin-5-yl)benzo[d]thiazol-2-yl)cyclopropanecarboxamide;
N-(6-(1H-pyrrolo[2,3-b]pyridin-5-yl)benzo[d]thiazol-2-yl)-2-fluorocyclopropane-1-carboxamide;
N-(6-(1H-pyrazolo[3,4-b]pyridin-5-yl)benzo[d]thiazol-2-yl)cyclopropanecarboxamide;
N-(6-(2-oxo-2,3-dihydro-1H-pyrrolo[2,3-b]pyridin-5-yl)benzo[d]thiazol-2-yl)cyclopropanecarboxamide;
N-(6-(2,3-dihydro-1H-pyrrolo[2,3-b]pyridin-5-yl)benzo[d]thiazol-2-yl)cyclopropanecarboxamide;
2-fluoro-N-(6-(3-methylisothiazol-5-yl)benzo[d]thiazol-2-yl)cyclopropane-1-carboxamide;
2-fluoro-N-(6-(7-methyl-1H-indazol-4-yl)benzo[d]thiazol-2-yl)cyclopropane-1-carboxamide;
2-fluoro-N-(6-(7-methyl-1H-indazol-6-yl)benzo[d]thiazol-2-yl)cyclopropane-1-carboxamide;
N-(6-(3,4-dimethylisothiazol-5-yl)benzo[d]thiazol-2-yl)-2-fluorocyclopropane-1-carboxamide;
N-(6-(5-(1H-imidazol-2-yl)-2-methylphenyl)benzo[d]thiazol-2-yl)-2-fluorocyclopropane-1-carboxamide;
2-fluoro-N-(6'-methyl-[6,7'-bibenzo[d]thiazol]-2-yl)cyclopropane-1-carboxamide;
2-fluoro-N-(6-(6-(fluoromethyl)-4-methylpyridin-3-yl)benzo[d]thiazol-2-yl)cyclopropane-1-carboxamide;
2-fluoro-N-(6-(6-fluoro-4-methylpyridin-3-yl)benzo[d]thiazol-2-yl)cyclopropane-1-carboxamide; and
2-fluoro-N-(6-(4-methylpyridin-3-yl)benzo[d]thiazol-2-yl)cyclopropane-1-carboxamide.

In some particular embodiments, the compound is selected from the group consisting of:
(1S,2S)-2-fluoro-N-(6-(2-fluoro-6-methylphenyl)benzo[d]thiazol-2-yl)cyclopropane-1-carboxamide;
(1S,2S)-2-fluoro-N-(6-(4-methylpyridin-3-yl)benzo[d]thiazol-2-yl)cyclopropane-1-carboxamide;
N-(6-(4-methylpyridin-3-yl)benzo[d]thiazol-2-yl)cyclopropanecarboxamide; and
(1S,2S)-2-fluoro-N-(6-(5-fluoro-4-methylpyridin-3-yl)benzo[d]thiazol-2-yl)cyclopropane-1-carboxamide.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants. In various embodiments, the compound is a compound of Formula (II):

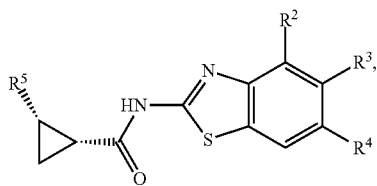

(II)

wherein $R^2$, $R^3$, and $R^4$ are as defined above, and $R^5$ is selected from the group consisting of halo, $C_1$-$C_3$ alkyl, $C_1$-$C_3$ hydroxyalkyl and $C_1$-$C_3$ haloalkyl. In particular embodiments, $R^4$ is fluoro-methylphenyl, chloro-methylphenyl, bimethylphenyl, acetamido-methylphenyl, hydroxyl-methylphenyl, methyl-propenylphenyl, ethynyl-methylphenyl, fluoro-methyl-methylaminophenyl, methyl-pyrrolylphenyl, methyl-thiazolylphenyl, cyano-methylphenyl, imidazolyl-methylphenyl, methylpyridinyl, chloro-methylpyridinyl, fluoro-methylpyridinyl, fluoromethyl-methylpyridinyl, bimethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethyl-methylpyridinyl, cyanopyridinyl, trifluoromethylpyridinyl, methylthiophenyl, methylindolinyl, methylpyrimidinyl, dimethylpyrimidinyl, pyrazolyl, methylpyrazolyl, methylindolinyl, methyloxoindolinyl, pyrrolopyridinyl, methylpyrrolopyridinyl, methylpyrrolyl, pyrazolopyridinyl, dihydropyrrolopyridinyl, methylisothiazolyl, dimethylisothiazolyl, methylindazolyl, or methylbibenzothiazolyl.

Non-limiting examples of the compounds of the present disclosure include the following compounds and pharmaceutically acceptable salts thereof:
(1S,2S)-2-fluoro-N-(6-(2-fluoro-6-methylphenyl)benzo[d]thiazol-2-yl)cyclopropane-1-carboxamide;
(1S,2S)-N-(6-(2-chloro-6-methylphenyl)benzo[d]thiazol-2-yl)-2-fluorocyclopropane-1-carboxamide;
(1S,2S)-N-(6-(2,6-dimethylphenyl)benzo[d]thiazol-2-yl)-2-fluorocyclopropane-1-carboxamide;
(1S,2S)-2-fluoro-N-(6-(4-methylpyridin-3-yl)benzo[d]thiazol-2-yl)cyclopropane-1-carboxamide;
(1S,2S)-2-fluoro-N-(6-(5-fluoro-4-methylpyridin-3-yl)benzo[d]thiazol-2-yl)cyclopropane-1-carboxamide;
(1S,2S)-2-fluoro-N-(6-(2-methyl-5-(prop-1-en-2-yl)phenyl)benzo[d]thiazol-2-yl)cyclopropane-1-carboxamide;
(1S,2S)-N-(6-(2-chloro-4-methylpyridin-3-yl)benzo[d]thiazol-2-yl)-2-fluorocyclopropane-1-carboxamide;
(1S,2S)-N-(6-(2,4-dimethylpyridin-3-yl)benzo[d]thiazol-2-yl)-2-fluorocyclopropane-1-carboxamide;
(1S,2S)-2-fluoro-N-(6-(5-hydroxy-2-methylphenyl)benzo[d]thiazol-2-yl)cyclopropane-1-carboxamide;
(1S,2S)-2-fluoro-N-(6-(5-(2-hydroxypropan-2-yl)-2-methylphenyl)benzo[d]thiazol-2-yl)cyclopropane-1-carboxamide;
(1S,2S)-2-fluoro-N-(6-(3-hydroxy-2-methylphenyl)benzo[d]thiazol-2-yl)cyclopropane-1-carboxamide;
(1S,2S)-N-(6-(6-amino-2,4-dimethylpyridin-3-yl)benzo[d]thiazol-2-yl)-2-fluorocyclopropane-1-carboxamide;
(1S,2S)-2-fluoro-N-(6-(5-methylindolin-4-yl)benzo[d]thiazol-2-yl)cyclopropane-1-carboxamide;
(1S,2S)-2-fluoro-N-(6-(2-fluoro-6-methylphenyl)thiazolo[4,5-c]pyridin-2-yl)cyclopropane-1-carboxamide;
(1S,2S)-N-(6-(1-acetyl-5-methylindolin-4-yl)benzo[d]thiazol-2-yl)-2-fluorocyclopropane-1-carboxamide;
(1S,2S)-2-fluoro-N-(6-(2-fluoro-6-methyl-3-(methylamino)phenyl)benzo[d]thiazol-2-yl)cyclopropane-1-carboxamide;
(1S,2S)-2-fluoro-N-(6-(4-methoxypyridin-3-yl)benzo[d]thiazol-2-yl)cyclopropane-1-carboxamide;
(1S,2S)-2-fluoro-N-(6-(3-methylthiophen-2-yl)benzo[d]thiazol-2-yl)cyclopropane-1-carboxamide;
3-(2-((1S,2S)-2-fluorocyclopropane-1-carboxamido)benzo[d]thiazol-6-yl)-4-methylpyridine 1-oxide;
(2-((1S,2S)-2-fluorocyclopropane-1-carboxamido)benzo[d]thiazol-6-yl)boronic acid;

(1S,2S)-2-fluoro-N-(6-(4-methylpyrimidin-5-yl)benzo[d]
thiazol-2-yl)cyclopropane-1-carboxamide;
(1S,2S)-N-(6-(6-acetyl-4-methylpyridin-3-yl)benzo[d]thi-
azol-2-yl)-2-fluorocyclopropane-1-carboxamide;
(1S,2S)-N-(6-(4,6-dimethylpyridin-3-yl)benzo[d]thiazol-2-
yl)-2-fluorocyclopropane-1-carboxamide;
(1S,2S)-N-(6-(6-chloro-4-methylpyridin-3-yl)benzo[d]thi-
azol-2-yl)-2-fluorocyclopropane-1-carboxamide;
(1S,2S)-2-fluoro-N-(6-(4-methyl-6-(trifluoromethyl)pyri-
din-3-yl)benzo[d]thiazol-2-yl)cyclopropane-1-carboxam-
ide;
(1S,2S)-2-fluoro-N-(6-(4-(hydroxymethyl)pyridin-3-yl)
benzo[d]thiazol-2-yl)cyclopropane-1-carboxamide;
(1S,2S)-2-fluoro-N-(6-(6-(hydroxymethyl)-4-methylpyri-
din-3-yl)benzo[d]thiazol-2-yl)cyclopropane-1-carboxam-
ide;
(1S,2S)-2-fluoro-N-(6-(6-(1-hydroxyethyl)-4-methylpyri-
din-3-yl)benzo[d]thiazol-2-yl)cyclopropane-1-carboxam-
ide;
(1S,2S)-2-fluoro-N-(6-(4-(trifluoromethyl)pyridin-3-yl)
benzo[d]thiazol-2-yl)cyclopropane-1-carboxamide;
(1S,2S)-N-(6-(1H-pyrazol-3-yl)benzo[d]thiazol-2-yl)-2-
fluorocyclopropane-1-carboxamide;
(1S,2S)-2-fluoro-N-(6-(2-methyl-5-(pyridin-2-ylethynyl)
phenyl)benzo[d]thiazol-2-yl)cyclopropane-1-carboxam-
ide;
(1S,2S)-2-fluoro-N-(6-(2-methyl-5-(1H-pyrazol-1-yl)phe-
nyl)benzo[d]thiazol-2-yl)cyclopropane-1-carboxamide;
(1S,2S)-2-fluoro-N-(6-(5-methyl-1H-indol-4-yl)benzo[d]
thiazol-2-yl)cyclopropane-1-carboxamide;
(1S,2S)-2-fluoro-N-(6-(5-(hydroxymethyl)-4-methylpyri-
din-3-yl)benzo[d]thiazol-2-yl)cyclopropane-1-carboxam-
ide;
(1S,2S)-2-fluoro-N-(4-fluoro-6-(4-methylpyridin-3-yl)
benzo[d]thiazol-2-yl)cyclopropane-1-carboxamide;
(1S,2S)-2-fluoro-N-(4-fluoro-6-(2-fluoro-6-methylphenyl)
benzo[d]thiazol-2-yl)cyclopropane-1-carboxamide;
(1S,2S)-2-fluoro-N-(6-(5-methylthiazol-4-yl)benzo[d]thi-
azol-2-yl)cyclopropane-1-carboxamide;
(1S,2S)-N-(6-(4,6-dimethylpyrimidin-5-yl)benzo[d]thiazol-
2-yl)-2-fluorocyclopropane-1-carboxamide;
(1S,2S)-2-fluoro-N-(6-(7-methyl-2-oxoindolin-6-yl)benzo
[d]thiazol-2-yl)cyclopropane-1-carboxamide;
(1S,2S)-N-(6-(5-ethynyl-2-methylphenyl)benzo[d]thiazol-
2-yl)-2-fluorocyclopropane-1-carboxamide;
(1S,2S)-N-(6-(4-chloropyridin-3-yl)benzo[d]thiazol-2-yl)-
2-fluorocyclopropane-1-carboxamide;
(1S,2S)-N-(6-(4-cyanopyridin-3-yl)benzo[d]thiazol-2-yl)-
2-fluorocyclopropane-1-carboxamide;
(1S,2S)-2-fluoro-N-(6-(2-fluoro-4-methylpyridin-3-yl)
benzo[d]thiazol-2-yl)cyclopropane-1-carboxamide;
(1S,2S)-2-fluoro-N-(6-(4-(trifluoromethyl)pyrimidin-5-yl)
benzo[d]thiazol-2-yl)cyclopropane-1-carboxamide;
(1S,2S)-2-fluoro-N-(6-(2-methyl-5-(1H-pyrrol-3-yl)phenyl)
benzo[d]thiazol-2-yl)cyclopropane-1-carboxamide;
(1S,2S)-2-fluoro-N-(6-(2-methyl-5-(thiazol-2-yl)phenyl)
benzo[d]thiazol-2-yl)cyclopropane-1-carboxamide;
(1S,2S)-N-(6-(5-cyano-2-methylphenyl)benzo[d]thiazol-2-
yl)-2-fluorocyclopropane-1-carboxamide;
(1S,2S)-2-fluoro-N-(6-(4-methyl-1-(tetrahydro-2H-pyran-
2-yl)-1H-pyrazol-3-yl)benzo[d]thiazol-2-yl)cyclopro-
pane-1-carboxamide;
(1S,2S)-2-fluoro-N-(6-(4-methyl-1H-pyrazol-3-yl)benzo[d]
thiazol-2-yl)cyclopropane-1-carboxamide;
(1S,2S)-2-fluoro-N-(6-(2-methyl-5-(1H-pyrrol-2-yl)phenyl)
benzo[d]thiazol-2-yl)cyclopropane-1-carboxamide;
(1S,2S)-2-fluoro-N-(6-(2-methyl-5-(1H-pyrazol-3-yl)phe-
nyl)benzo[d]thiazol-2-yl)cyclopropane-1-carboxamide;
(1S,2S)-2-fluoro-N-(6-(5-methyl-2-oxoindolin-4-yl)benzo
[d]thiazol-2-yl)cyclopropane-1-carboxamide;
(1S,2S)-2-fluoro-N-(4-methyl-2-oxo-2,3-dihydro-[5,6'-
bibenzo[d]thiazol]-2'-yl)cyclopropane-1-carboxamide;
(1S,2S)-N-(6-(1H-pyrrolo[2,3-b]pyridin-5-yl)benzo[d]thi-
azol-2-yl)-2-fluorocyclopropane-1-carboxamide;
(1S,2S)-2-fluoro-N-(6-(3-methylisothiazol-5-yl)benzo[d]
thiazol-2-yl)cyclopropane-1-carboxamide;
(1S,2S)-N-(6-(4-chloro-3-methylisothiazol-5-yl)benzo[d]
thiazol-2-yl)-2-fluorocyclopropane-1-carboxamide;
(1S,2S)-2-fluoro-N-(6-(7-methyl-1H-indazol-4-yl)benzo[d]
thiazol-2-yl)cyclopropane-1-carboxamide;
(1S,2S)-2-fluoro-N-(6-(7-methyl-1H-indazol-6-yl)benzo[d]
thiazol-2-yl)cyclopropane-1-carboxamide;
(1S,2S)-N-(6-(3,4-dimethylisothiazol-5-yl)benzo[d]thiazol-
2-yl)-2-fluorocyclopropane-1-carboxamide;
(1S,2S)-N-(6-(5-(1H-imidazol-2-yl)-2-methylphenyl)benzo
[d]thiazol-2-yl)-2-fluorocyclopropane-1-carboxamide;
(1S,2S)-2-fluoro-N-(6'-methyl-[6,7'-bibenzo[d]thiazol]-2-
yl)cyclopropane-1-carboxamide;
(1S,2S)-2-fluoro-N-(6-(6-(fluoromethyl)-4-methylpyridin-
3-yl)benzo[d]thiazol-2-yl)cyclopropane-1-carboxamide;
(1S,2S)-2-fluoro-N-(6-(6-fluoro-5-methyl-1H-indol-4-yl)
benzo[d]thiazol-2-yl)cyclopropane-1-carboxamide;
(1S,2S)-2-fluoro-N-(5-fluoro-6-(4-methylpyridin-3-yl)
benzo[d]thiazol-2-yl)cyclopropane-1-carboxamide; and
(1S,2S)-2-fluoro-N-(6-(6-fluoro-4-methylpyridin-3-yl)
benzo[d]thiazol-2-yl)cyclopropane-1-carboxamide.

In yet another embodiment, there is provided a pharmaceutical composition comprising a therapeutically effective amount of a compound of Formula (I) or a pharmaceutically acceptable salt thereof, and a pharmaceutically acceptable carrier.

In another embodiment, there is provided a method for treating a neurodegenerative disease or disorder comprising administering to a subject in need thereof a therapeutically effective amount of a compound of Formula (I) or pharmaceutically acceptable salt thereof. That is, there is provided a medical use of Formula (I) or pharmaceutically acceptable salt thereof, wherein Formula (I) or pharmaceutically acceptable salt thereof is used as an effective agent. In one embodiment, the medical-use is for treatment or prevention of the neurodegenerative disease or disorder.

Medical Uses and Methods of Treatment Using the Compounds According to the Present Disclosure The present disclosure further provides methods for treating a neurodegenerative disease or disorder in a subject having or susceptible to having such a disease or disorder, by administering to the subject a therapeutically effective amount of one or more compounds as described above. In one embodiment, the treatment is preventative treatment. In another embodiment, the treatment is palliative treatment. In another embodiment, the treatment is restorative treatment.

1. Diseases or Conditions

The compound of the present disclosure for inhibiting c-abl activity is useful for treatment or prevention of a neurodegenerative disease or disorder. The compound can be used for inhibiting or hindering c-abl kinase activity, and for treating a neurodegenerative disease or disorder, or for preventing aggravation of such disease. Thus, the present disclosure provides a method for inhibiting or hindering c-abl activity in a cell, wherein the cell is contacted with an effective amount of a compound of the present disclosure. In one embodiment, such cell is present in a subject (for example, Alzheimer patients). In another embodiment, there is provided a medical use for treating or preventing a neurodegenerative disease or disorder in a subject, using the compound according to the present disclosure. The method of the present disclosure comprises administering to a subject in need of treatment or prevention a pharmaceutical composition containing a therapeutically or prophylactically effective amount of c-abl inhibitor. The neurodegenerative disease or disorder includes, but is not limited to, α-synucleinopathy, Parkinson's disease, dementia with Lewy body, multiple system atrophy (MSA), Alzheimer's disease or amyotrophic lateral sclerosis (ALS).

2. Subjects

Suitable subjects to be treated according to the present disclosure include mammalian subjects. Mammals according to the present disclosure include, but are not limited to, human, canine, feline, bovine, caprine, equine, ovine, porcine, rodents, lagomorphs, primates, and the like, and encompass mammals in utero. Subjects may be of either gender and at any stage of development. In one embodiment, the suitable subject to be treated according to the present disclosure is human.

3. Administration and Dosing

The compounds of the present disclosure are generally administered in a therapeutically effective amount. The compounds of the present disclosure can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 50 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains. For example, Remington: The Science and Practice of Pharmacy, Mack Publishing Co., 20th ed., 2000 can be used.

Pharmaceutical Compositions, Dosage Forms and Administration Routes

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release. Most parenteral formulations are aqueous solutions containing excipients, including salts, buffering agents and isotonic agents. Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Transdermal Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical or transdermal administration can also be performed by electroporation, iontophoresis, phonophoresis and the like.

Compositions for topical administration may be formulated as immediate or modified release, including delayed or sustained release.

Combination Therapy

A pharmaceutical composition according to the present disclosure may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by c-abl kinase. Examples of such active ingredients are, without limitation, agents to treat a neurodegenerative disease or disorder.

References for Preparing Pharmaceutical Compositions

Methods for preparing pharmaceutical compositions for treating or preventing a disease or condition are well known in the art to which the present disclosure pertains. For example, based on *Handbook of Pharmaceutical Excipients* (7th ed.), *Remington: The Science and Practice of Pharmacy* (20th ed.), *Encyclopedia of Pharmaceutical Technology* (3rd ed.), or *Sustained and Controlled Release Drug Delivery Systems* (1978), pharmaceutically acceptable excipients, carriers, additives and so on can be selected and then mixed with the compounds of the present disclosure for making the pharmaceutical compositions.

The present disclosure provides a compound having various pharmacological effects by inhibiting c-abl activity, a pharmaceutical composition having the compound as an effective agent, a medical use, particularly for treating a neurodegenerative disease or disorder, of the compound, and a method of treatment or prevention comprising administering the compound to a subject in need of such treatment or prevention. The compounds of the present disclosure and pharmaceutically acceptable salts thereof have good safety and high selectivity for c-able, and thus exhibit superior property as a drug.

DETAILED DESCRIPTION

Figure 1:
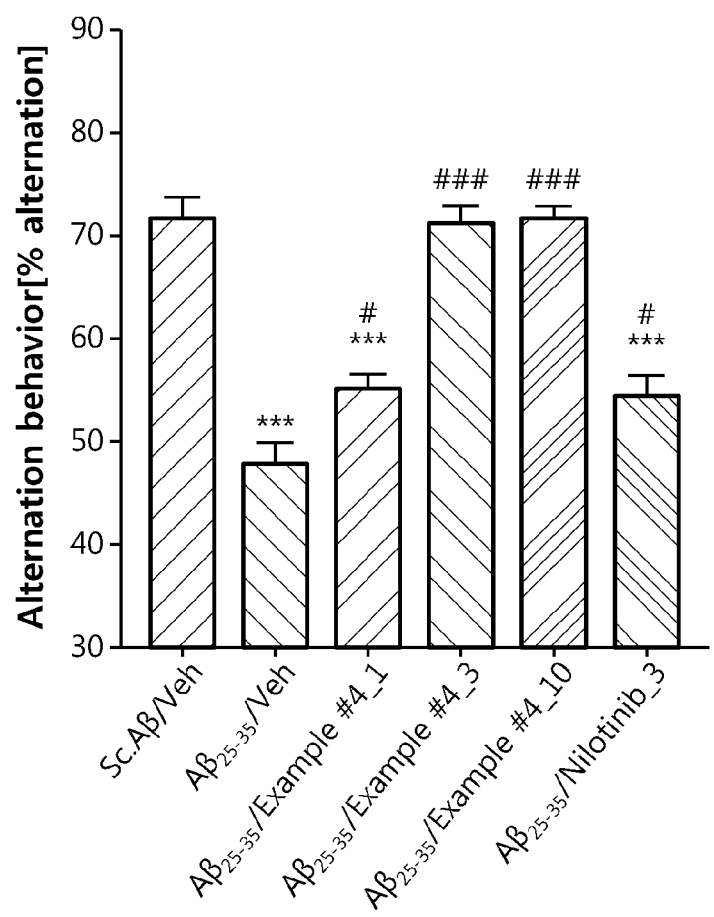
FIGS. 1, 2 and 3 show effects of Example 4 and nilotinib on $A\beta_{25-35}$-induced cognitive deficits in mice. a, spontaneous alternation deficits. b, step-through latency. c, escape latency. * $p<0.05$,  $p<0.01$, *$p<0.001$ vs. the Sc.Aβ/Veh group, #$p<0.05$, ###$p<0.001$ vs. the $A\beta_{25-35}$/Veh group.
Figure 2:
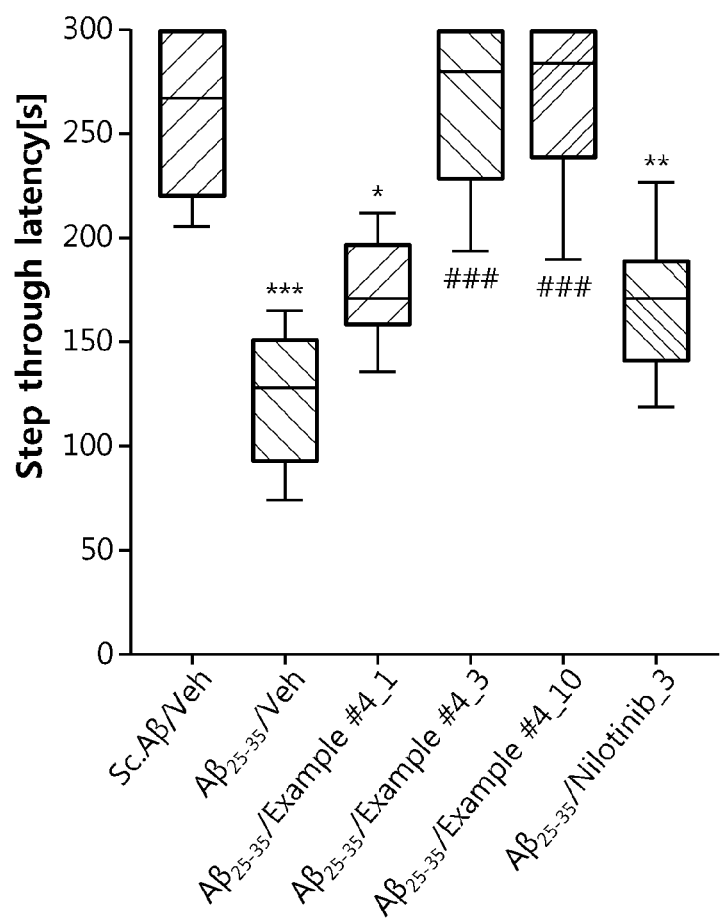
Figure 3:
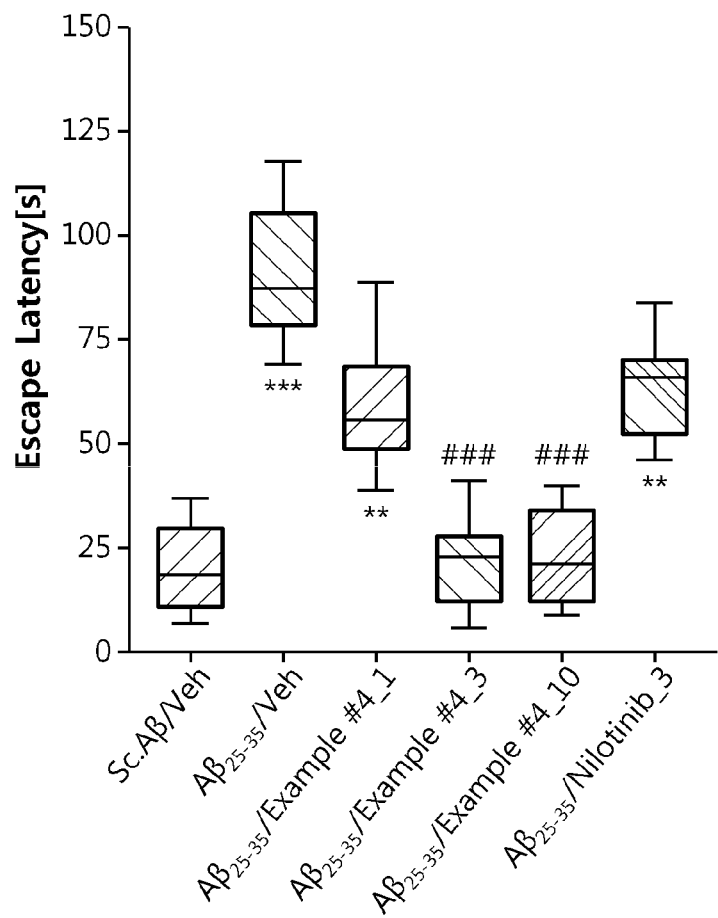
Figure 4:
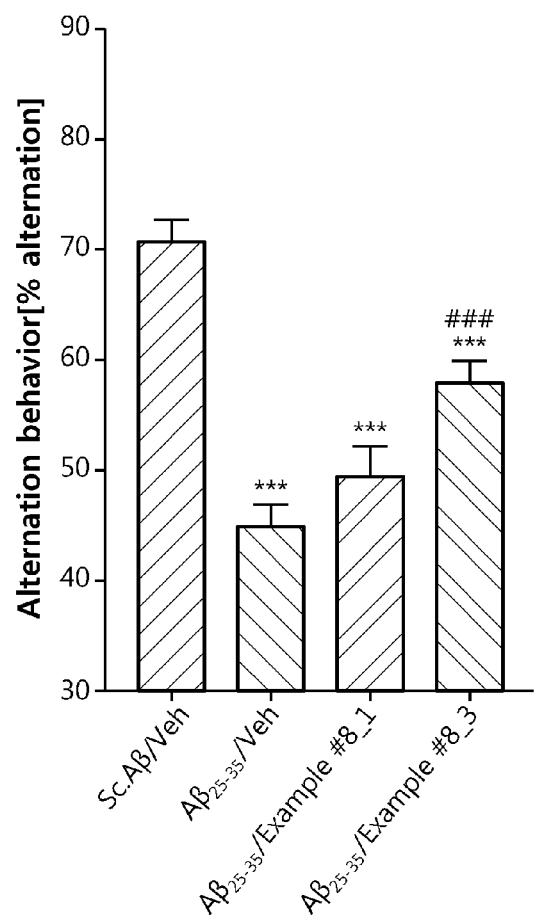
FIGS. 4, 5 and 6 show effects of Example 8 and nilotinib on $A\beta_{25-35}$-induced cognitive deficits in mice. a, spontaneous alternation deficits. b, step-through latency. c, escape latency. *** $p<0.001$ vs. the Sc.Aβ/Veh group, ###$p<0.001$ vs. the $A\beta_{25-35}$/Veh group.
Figure 5:
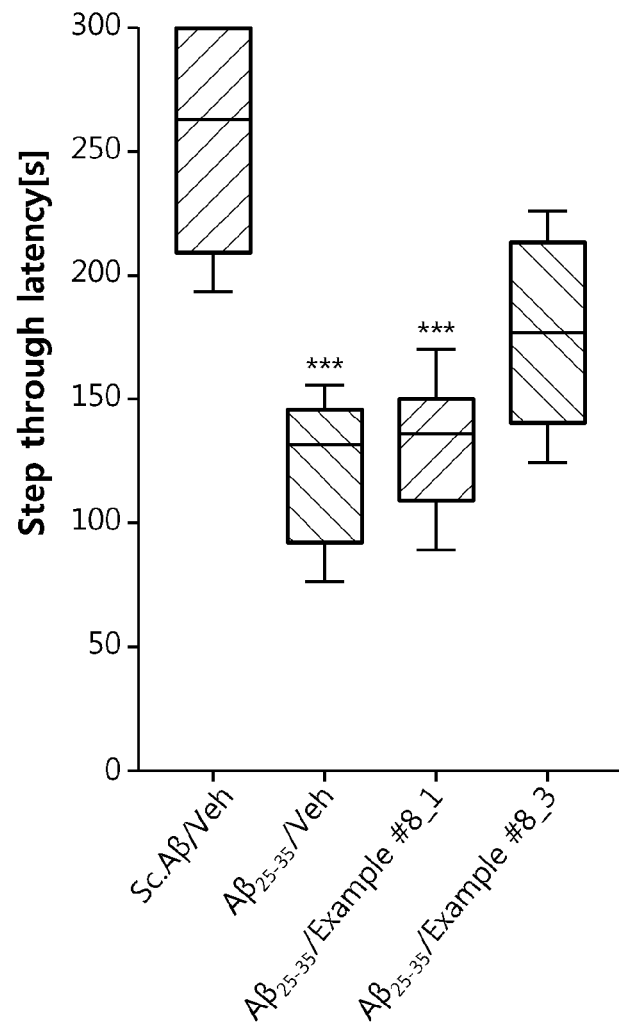
Figure 6:
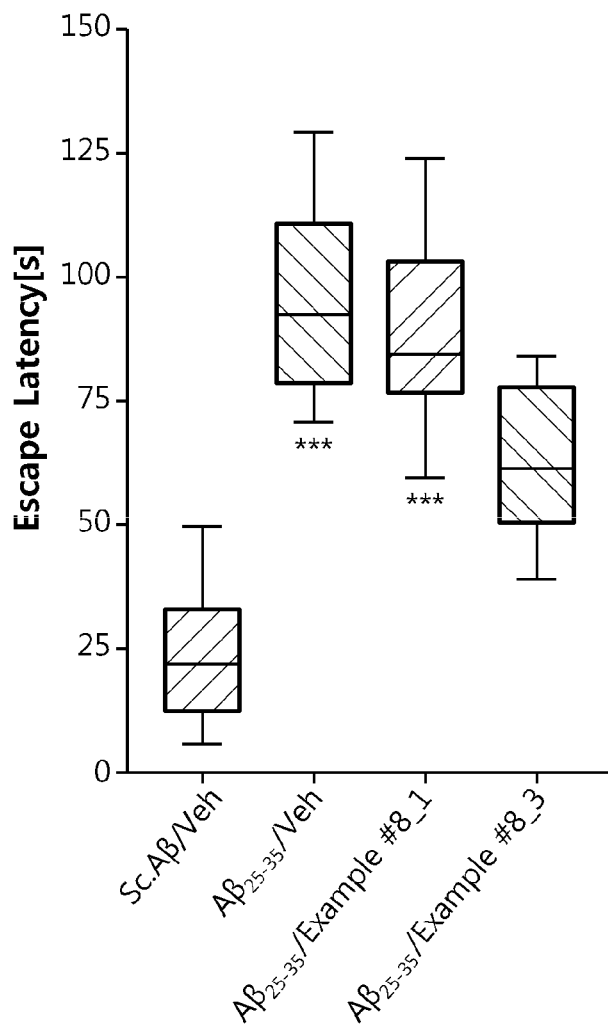

Hereinafter, the present disclosure is described in considerable detail with examples to help those skilled in the art understand the present disclosure. However, the following examples are offered by way of illustration and are not intended to limit the scope of the invention. It is apparent that various changes may be made without departing from the spirit and scope of the invention or sacrificing all of its material advantages.

Synthesis of Formula (I) Compounds

Synthetic methods A to X were used to prepare the compounds of the following. Below, the illustrating synthetic examples of some compounds of the present disclosure are described, and other compounds can be prepared by the similar method to the one described below with different starting or reacting materials.

Synthetic Method A

Example 1. (1S,2S)-2-fluoro-N-(6-(2-fluoro-6-methylphenyl)benzo[d]thiazol-2-yl) cyclopropane-1-carboxamide Step 1) 6-(2-fluoro-6-methylphenyl)benzo[d]thiazol-2-amine To a solution of Compound 1 (300 mg, 1.31 mmol, 1 eq) and Compound 2 (403.18 mg, 2.62 mmol, 2 eq) in dioxane (8 mL) and H$_2$O (2 mL) was added SPhos biphenyl G2 (94.36 mg, 130.95 μmol, 0.1 eq) and K$_3$PO$_4$ (416.95 mg, 1.96 mmol, 1.5 eq). The mixture was stirred at 80° C. for 3 hr. under N$_2$. The reaction mixture was concentrated under reduced pressure to remove solvent. Water (20 mL) was added in the reaction mixture, then the mixture was extracted with EA (20 mL*2), the combined organic layers were dried over Na$_2$SO$_4$, filtered and concentrated under reduced pressure to give a residue. The residue was purified by column chromatography (SiO2, PE:EA=10:1 to 5:1) to Compound 3 (485 mg, crude) as a yellow solid.

$^1$H NMR (400 MHz, CDCl$_3$) δ=7.61 (d, J=8.3 Hz, 1H), 7.51 (d, J=1.4 Hz, 1H), 7.26-7.19 (m, 2H), 7.08 (d, J=7.5 Hz, 1H), 6.99 (t, J=8.7 Hz, 1H), 5.34 (br s, 2H), 2.19 (s, 3H).

Step 2) (1S,2S)-2-fluoro-N-(6-(2-fluoro-6-methylphenyl)benzo[d]thiazol-2-yl)cyclopropane-1-carboxamide To a solution of Compound 3 (200 mg, 774.25 μmol, 1 eq) and Compound 4 (80.58 mg, 774.25 μmol, 1 eq) in DMF (2 mL) was added HATU (588.79 mg, 1.55 mmol, 2 eq) and TEA (235.04 mg, 2.32 mmol, 323.30 μL, 3 eq). The mixture was stirred at 25° C. for 2 h, Then the mixture was stirred at 25° C. for 12 hr. The reaction mixture was concentrated under reduced pressure to remove solvent. The residue was diluted with water 20 mL and extracted with EA (20 mL*2). The combined organic layers were filtered and concentrated under reduced pressure to give a residue. The residue was purified by prep-HPLC (basic condition; column: Phenomenex Gemini 150*25 mm*10 μm; mobile phase: [water (0.05% ammonia hydroxide v/v)-ACN]; B %: 50%-80%, 12 min). Example 1 (50 mg, 136.17 μmol, 17% yield, 93% purity) was obtained as a white solid.

$^1$H NMR (400 MHz, DMSO-$d_6$) δ=12.75 (br s, 1H), 7.92 (s, 1H), 7.81 (d, J=8.3 Hz, 1H), 7.33 (br d, J=8.2 Hz, 2H), 7.20-7.11 (m, 2H), 5.16-4.92 (m, 1H), 2.23 (td, J=6.7, 13.4 Hz, 1H), 2.14 (s, 3H), 1.82-1.68 (m, 1H), 1.37-1.25 (m, 1H).

Synthetic Method B

Example 3. (1S,2S)-N-(6-(2,6-dimethylphenyl)benzo[d]thiazol-2-yl)-2-fluorocyclopropane-1-carboxamide

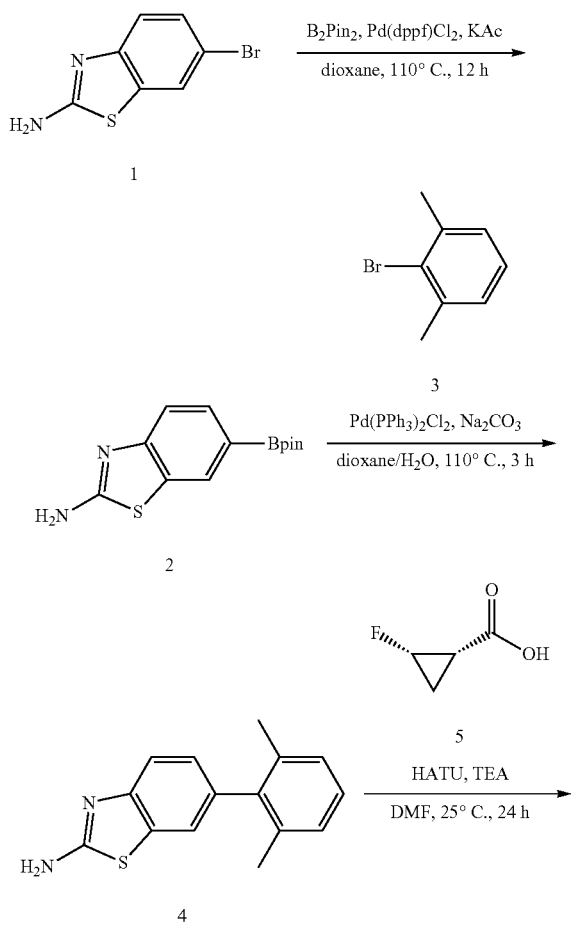

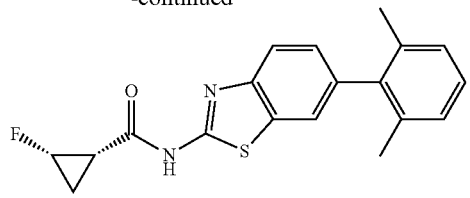

Example 3

Step 1) 6-(4,4,5,5-tetramethyl-1,3,2-dioxaborolan-2-yl)benzo[d]thiazol-2-amine To a solution of Compound 1 (500 mg, 2.18 mmol, 1 eq) and B$_2$Pin$_2$ (665.06 mg, 2.62 mmol, 1.2 eq) in dioxane (8 mL) was added Pd(dppf)Cl$_2$ (159.69 mg, 218.25 μmol, 0.1 eq) and KOAc (321.29 mg, 3.27 mmol, 1.5 eq). The mixture was stirred at 110° C. for 12 hr under N$_2$. The reaction mixture was concentrated under reduced pressure to remove solvent. The residue was diluted with brine 50 mL and extracted with EA 20 mL (20 mL*3). The combined organic layers was filtered and concentrated under reduced pressure to give a residue. The residue was purified by column chromatography (SiO$_2$, Petroleum ether:Ethyl acetate=5:1 to 3:1). Compound 2 (907 mg, 1.55 mmol, 71% yield, 47% purity) was obtained as a light yellow solid.

$^1$H NMR (400 MHz, CDCl$_3$) δ=8.06 (s, 1H), 7.77-7.74 (m, 1H), 7.60 (d, J=7.2 Hz, 1H), 4.13 (q, J=7.2 Hz, 2H), 1.28 (s, 12H).

Step 2) 6-(2,6-dimethylphenyl)benzo[d]thiazol-2-amine

To a solution of Compound 2 (200 mg, 342.12 μmol, 1 eq) and Compound 3 (75.98 mg, 410.54 μmol, 54.66 μL, 1.2 eq) in dioxane (5 mL) and H$_2$O (2 mL) was added Na$_2$CO$_3$ (54.39 mg, 513.18 μmol, 1.5 eq) and Pd(PPh$_3$)$_2$Cl$_2$ (24.01 mg, 34.21 μmol, 0.1 eq). The mixture was stirred at 110° C. for 3 hr under N$_2$. The reaction mixture was concentrated under reduced pressure to remove solvent. The residue was purified by column chromatography (SiO$_2$, Petroleum ether/Ethyl acetate=10:1 to 8:1). Compound 4 (123 mg, 267.57 μmol, 78% yield, 55% purity) was obtained as a red brown oil.

$^1$H NMR (400 MHz, CDCl$_3$) δ=7.63-7.54 (m, 2H), 7.33 (t, J=7.1 Hz, 1H), 7.19-7.14 (m, 1H), 7.14-7.08 (m, 2H), 5.21 (br s, 2H), 2.05 (s, 6H).

Step 3) (1S,2S)-N-(6-(2,6-dimethylphenyl)benzo[d]thiazol-2-yl)-2-fluorocyclopropane-1-carboxamide To a solution of Compound 4 (123 mg, 267.57 μmol, 1 eq) and Compound 5 (27.85 mg, 267.57 μmol, 1 eq) in DMF (3 mL) was added HATU (203.48 mg, 535.14 μmol, 2 eq) and TEA (81.23 mg, 802.71 μmol, 111.73 μL, 3 eq). The mixture was stirred at 25° C. for 12 hr. Then the mixture was stirred at 25° C. for 12 hr. The reaction mixture was diluted with EA 20 mL and extracted with brine 20 mL. The combined organic layers was dried over Na$_2$SO$_4$, filtered and concentrated under reduced pressure to give a residue. The residue was purified by prep-HPLC (FA condition, column: Phenomenex Synergi C18 150*30 mm*4 um; mobile phase: [water (0.225% FA)-ACN]; B %: 50%-80%, 10 min).

Example 3 (15.8 mg, 41.31 μmol, 15% yield, 89% purity) was obtained as a white solid.

$^1$H NMR (400 MHz, CDCl$_3$) δ=7.83 (d, J=8.3 Hz, 1H), 7.60 (d, J=1.0 Hz, 1H), 7.24 (dd, J=1.6, 8.3 Hz, 2H), 7.20-7.17 (m, 1H), 7.15-7.11 (m, 2H), 5.03-4.81 (m, 1H), 2.04 (d, J=2.5 Hz, 6H), 1.97 (d, J=5.4 Hz, 1H), 1.43-1.35 (m, 1H), 1.26 (br s, 1H).

Synthetic Method C

Example 5. N-(6-(4-methylpyridin-3-yl)benzo[d]thiazol-2-yl) cyclopropanecarboxamide

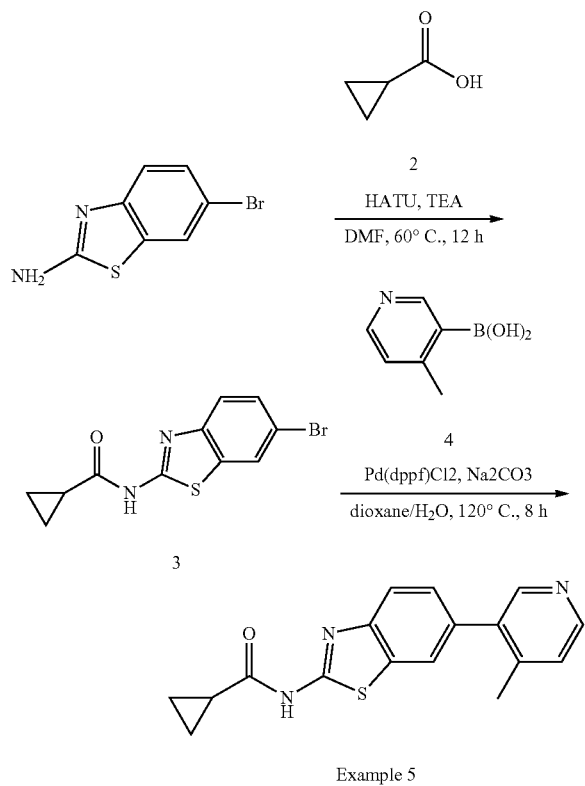

Example 5

Step 1) N-(6-bromobenzo[d]thiazol-2-yl)cyclopropanecarboxamide

To a solution of Compound 1 (200 mg, 872.98 μmol, 1 eq) and Compound 2 (75.15 mg, 872.98 μmol, 1 eq) in DMF (2 mL) was added HATU (497.89 mg, 1.30 mmol, 2 eq) and TEA (265.01 mg, 2.61 mmol, 365 uL, 3 eq). The mixture was stirred at 60° C. for 12 h. Then, the reaction mixture was concentrated under reduced pressure to remove solvent. The residue was diluted with water 20 mL and extracted with EA (20 mL*2). The combined organic layers were filtered and concentrated under reduced pressure to give a residue. The residue was purified by column chromatography (SiO$_2$, Methylene chloride/Methanol=20:1). Compound 3 (194 mg, 654.73 μmol, 75% yield) was obtained as a white solid.

$^1$H NMR (400 MHz, DMSO-d$_6$) δ=12.71 (s, CONH), 8.23 (s, 1H), 7.66 (d, J=8.8 Hz, 1H), 7.56 (d, J=8.8 Hz, 1H), 2.03-2.00 (m, 1H), 0.97-0.94 (m, 4H).

Step 2) N-(6-(4-methylpyridin-3-yl)benzo[d]thiazol-2-yl)cyclopropane carboxamide To a solution of Compound 3 (100 mg, 0.336 mmol, 1 eq) and Compound 4 (92 mg, 0.672 mmol, 2 eq) in dioxane (8 mL) and H$_2$O (2 mL) was added Pd(dppf)Cl$_2$ (24 mg, 0.0336 mmol, 0.1 eq) and Ns$_2$CO$_3$ (71 mg, 0.672 mmol, 2 eq). The mixture was stirred at 120° C. for 8 hr under N$_2$. The reaction mixture was concentrated under reduced pressure to remove solvent. Water (10 mL) was added in the reaction mixture, then the mixture was extracted with EA (10 mL*2), the combined organic layers were dried over Na$_2$SO$_4$, filtered and concentrated under reduced pressure to give a residue. The residue was purified by column chromatography (SiO2, n-Hexane:EA=1:2) to Example 5 (88 mg, 85% yield) as a white solid.

Synthetic Method D

Example 14. (1S,2S)-2-fluoro-N-(6-(5-hydroxy-2-methylphenyl)benzo[d]thiazol-2-yl)cyclopropane-1-carboxamide

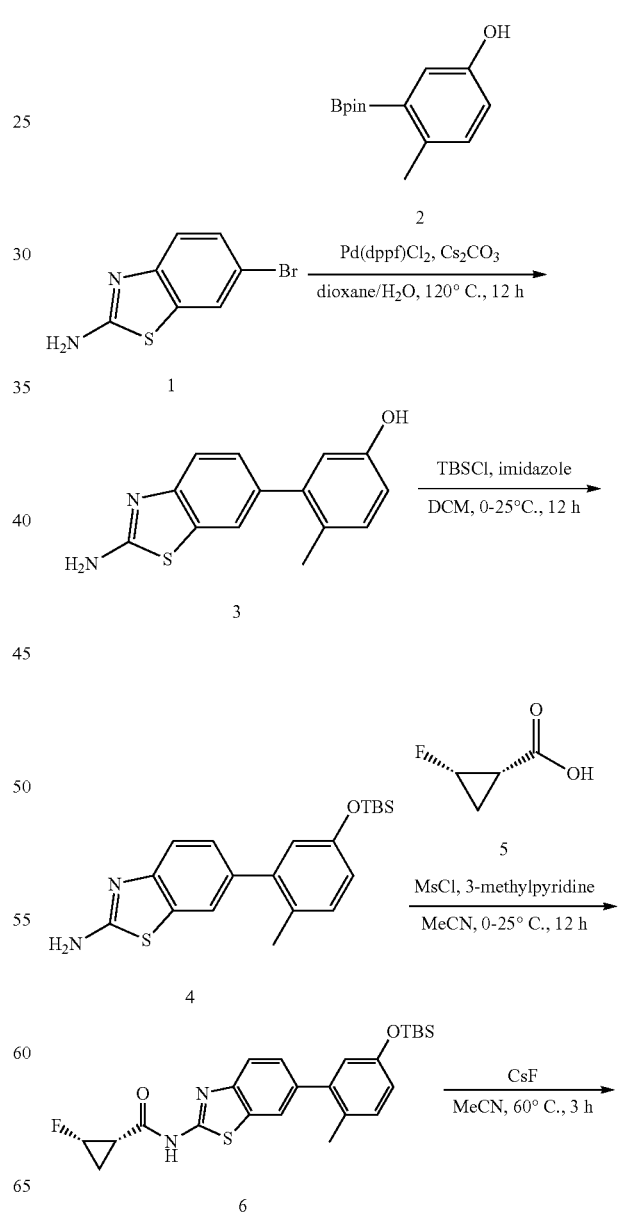

-continued

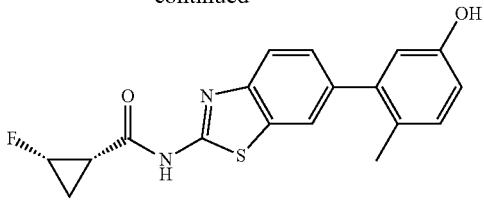

Example 14

Step 1) 3-(2-aminobenzo[d]thiazol-6-yl)-4-methylphenol

To a solution of Compound 1 (306.31 mg, 1.34 mmol, 1 eq) and Compound 2 (313 mg, 1.34 mmol, 1 eq) in dioxane (5 mL) and H2O (1 mL) was added Pd(PPh$_3$)2Cl$_2$ (93.85 mg, 133.70 μmol, 0.1 eq) and Na$_2$CO$_3$ (212.57 mg, 2.01 mmol, 1.5 eq). The mixture was stirred at 110° C. for 3 hr under N$_2$. The reaction mixture was concentrated under reduced pressure to remove solvent. The residue was purified by column chromatography (SiO$_2$, Petroleum ether/Ethyl acetate=10/1 to 1:1). Compound 3 (207 mg, 807.58 μmol, 60% yield) was obtained as a red oil.

$^1$H NMR (400 MHz, CDCl$_3$) δ=7.69-7.66 (m, 1H), 7.57-7.55 (m, 1H), 7.50-7.44 (m, 2H), 7.13 (d, J=7.8 Hz, 1H), 6.75 (s, 1H), 5.26 (br s, 2H), 2.20 (s, 3H).

Step 2) 6-(5-((tert-butyldimethylsilyl)oxy)-2-methylphenyl)benzo[d]thiazol-2-amine To a solution of Compound 3 (157 mg, 612.51 μmol, 1 eq) in DCM (5 mL) was added IMIDAZOLE (125.09 mg, 1.84 mmol, 3 eq) and TBSCl (230.80 mg, 1.53 mmol, 187.64 μL, 2.5 eq) at 0° C. The mixture was stirred at 25° C. for 12 hr. The reaction mixture was concentrated under reduced pressure to remove solvent. The residue was diluted with water 30 mL and extracted with EA (30 mL*2). The combined organic layers were dried over Na$_2$SO$_4$, filtered and concentrated under reduced pressure to give a residue. The residue was purified by column chromatography (SiO$_2$, Petroleum ether/Ethyl acetate=10/1 to 1:1). Compound 4 (211 mg, 546.60 μmol, 89% yield, 96% purity) was obtained as a light yellow oil.

$^1$H NMR (400 MHz, DMSO-d$_6$) δ=7.61 (d, J=1.8 Hz, 1H), 7.49 (s, 2H), 7.36 (d, J=8.3 Hz, 1H), 7.17-7.11 (m, 2H), 6.73 (dd, J=2.6, 8.2 Hz, 1H), 6.67 (d, J=2.6 Hz, 1H), 2.16 (s, 3H), 0.95 (s, 9H), 0.19-0.16 (m, 6H)

Step 3) (1S,2S)-N-(6-(5-((tert-butyldimethylsilyl)oxy)-2-methylphenyl)benzo[d]thiazol-2-yl)-2-fluorocyclopropane-1-carboxamide To a solution of Compound 4 (211 mg, 546.60 μmol, 1 eq) and Compound 5 (68.27 mg, 655.92 μmol, 1.2 eq) in MeCN (5 mL) was added MsCl (125.23 mg, 1.09 mmol, 84.61 uL, 2 eq) and 3-methylpyridine (254.51 mg, 2.73 mmol, 266.12 uL, 5 eq) at 0° C., The mixture was stirred at 25° C. for 12 hr. The reaction mixture was concentrated under reduced pressure to remove solvent. The residue was diluted with water 30 mL and extracted with EA (20 mL*2). The combined organic layers were dried over Na$_2$SO$_4$, filtered and concentrated under reduced pressure to give a residue. The residue was purified by prep-TLC (SiO$_2$, PE:EA=1:1). Compound 6 (185 mg, 392.97 μmol, 71% yield, 97% purity) was obtained as a yellow solid.

$^1$H NMR (400 MHz, DMSO-d$_6$) δ=12.71 (s, 1H), 7.95 (d, J=1.6 Hz, 1H), 7.78 (d, J=8.3 Hz, 1H), 7.38 (dd, J=1.8, 8.3 Hz, 1H), 7.18 (d, J=8.2 Hz, 1H), 6.78 (dd, J=2.6, 8.3 Hz, 1H), 6.72 (d, J=2.5 Hz, 1H), 5.15-4.93 (m, 1H), 2.22 (br d, J=5.5 Hz, 1H), 2.17 (s, 3H), 1.81-1.71 (m, 1H), 1.31 (br dd, J=9.3, 12.9 Hz, 1H), 0.95 (s, 9H), 0.18 (s, 6H).

Step 4) (1S,2S)-2-fluoro-N-(6-(5-hydroxy-2-methylphenyl)benzo[d]thiazol-2-yl) cyclopropane-1-carboxamide To a solution of Compound 6 (165 mg, 350.49 μmol, 1 eq) in MeCN (8 mL) was added CsF (159.72 mg, 1.05 mmol, 38.77 μL, 3 eq). The mixture was stirred at 60° C. for 3 hr. The reaction mixture was concentrated under reduced pressure to remove solvent. The residue was diluted with water 30 mL and extracted with EA (20 mL*2). The combined organic layers were dried over Na$_2$SO$_4$, filtered and concentrated under reduced pressure to give a residue. The residue was purified by prep-HPLC (TFA condition; column: Boston pH-lex 150*25 10 um; mobile phase: [water (0.1% TFA)-ACN]; B %: 35%-65%, 10 min). Example 14 (83.6 mg, 183.17 μmol, 52% yield, 100% purity, TFA) was obtained as a white solid.

$^1$H NMR (400 MHz, DMSO-d$_6$) δ=12.73 (br s, 1H), 7.92 (d, J=1.6 Hz, 1H), 7.77 (d, J=8.3 Hz, 1H), 7.36 (dd, J=1.8, 8.3 Hz, 1H), 7.08 (d, J=8.1 Hz, 1H), 6.72-6.64 (m, 2H), 5.17-4.93 (m, 1H), 2.27-2.17 (m, 1H), 2.12 (s, 3H), 1.82-1.68 (m, 1H), 1.31 (tdd, J=6.3, 8.9, 12.8 Hz, 1H); LCMS (electrospray) m/z 343.2 (M+H)+.

Synthetic Method E

Example 15. (1S,2S)-2-fluoro-N-(6-(5-(2-hydroxypropan-2-yl)-2-methylphenyl)benzo[d]thiazol-2-yl) cyclopropane-1-carboxamide

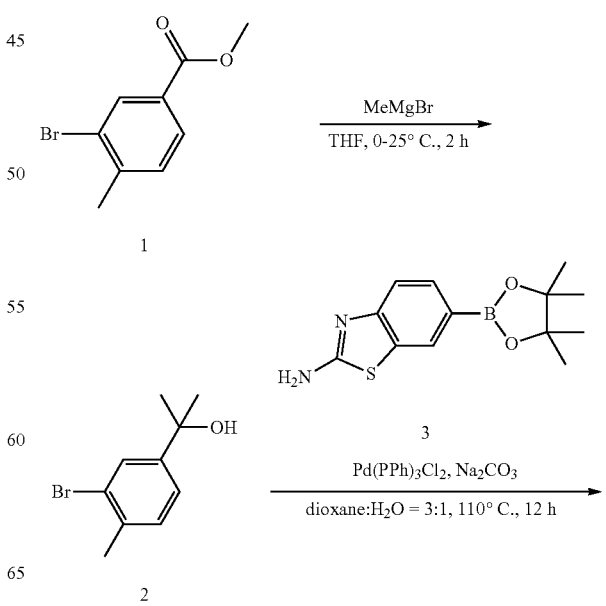

-continued

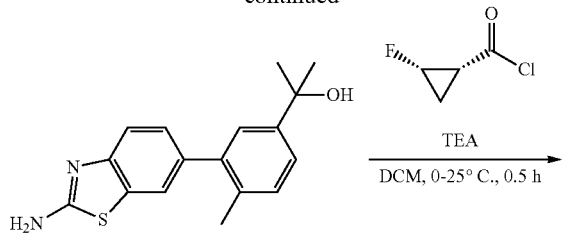

Example 15

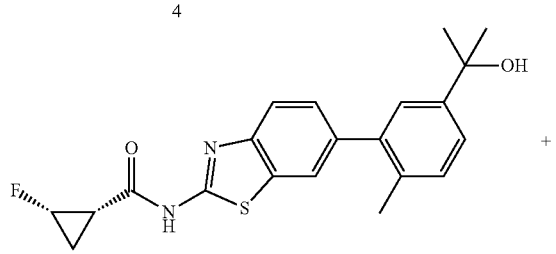

Example 16

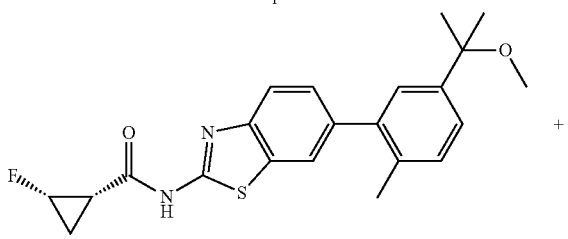

Example 17

Step 1) 2-(3-bromo-4-methylphenyl)propan-2-ol

A mixture of Compound 1 (500 mg, 2.18 mmol, 1 eq) in THF (10 mL) was degassed and purged with $N_2$ for 3 times, and then the mixture was stirred at 0° C. for 0.5 hr under $N_2$ atmosphere, then added MeMgBr (3 M, 2.91 mL, 4 eq) in the solution slowly. The solution was then allowed to stir and warm slowly at 25° C. for 1.5 hr. The residue was purified by prep-TLC (SiO$_2$, PE:EA=7:1). Compound 2 (400 mg, 1.75 mmol, 80% yield) was obtained as a light yellow oil.

$^1$H NMR (400 MHz, CDCl$_3$) δ=1.58 (s, 6H), 2.40 (s, 3H), 7.22 (d, J=8.03 Hz, 1H), 7.33 (dd, J=7.97, 1.95 Hz, 1H), 7.69 (d, J=2.01 Hz, 1H).

Step 2) 2-(3-(2-aminobenzo[d]thiazol-6-yl)-4-methylphenyl)propan-2-ol

To a solution of Compound 3 (506.25 mg, 1.83 mmol, 1.5 eq) and Compound 2 (280 mg, 1.22 mmol, 1 eq) in dioxane (5 mL) and H$_2$O (2 mL) was added Pd(PPh$_3$)$_2$Cl$_2$ (85.78 mg, 122.21 μmol, 0.1 eq) and Na$_2$CO$_3$ (194.29 mg, 1.83 mmol, 1.5 eq). The mixture was stirred at 110° C. for 12 hr under $N_2$. The residue was purified by prep-TLC (SiO$_2$, PE:EA=1:1). Compound 4 (210 mg, 703.75 μmol, 57% yield) was obtained as a light yellow oil.

Step 3) (1S,2S)-2-fluoro-N-(6-(5-(2-hydroxypropan-2-yl)-2-methylphenyl)benzo[d]thiazol-2-yl)cyclopropane-1-carboxamide A mixture of Compound 4 (300 mg, 1.01 mmol, 1 eq) in DCM (10 mL) was added TEA (203.46 mg, 2.01 mmol, 279.87 μL, 2 eq) at 0° C. under N$_2$ atmosphere, then added (1R,2S)-2-fluorocyclopropanecarbonyl chloride (147.82 mg, 1.21 mmol, 1.2 eq) into the mixture, then stirred at 25° C. for 0.5 hr. The residue was purified by pre-HPLC (column: Phenomenex Synergi C18 150*25*10 um; mobile phase: [water (0.05% HCl)-ACN]; B %: 40%-60%, 7.8 min). Then purified by pre-HPLC (column: Phenomenex Gemini 150*25 mm*10 um; mobile phase: [water (10 mM NH$_4$HCO$_3$)-ACN]; B %: 45%-75%, 10 min)

Example 15 (23 mg, 59.82 μmol, 6% Yield, 100% Purity) was Obtained as a Light Yellow Solid $^1$H NMR (400 MHz, DMSO-d$_6$) δ=1.29 (dq, J=15.12, 6.42 Hz, 1H), 1.43 (s, 6H), 1.66-1.84 (m, 1H), 2.16-2.22 (m, 1H), 2.23 (s, 3H), 4.91-5.14 (m, 1H), 4.98 (s, 1H), 7.22 (d, J=8.53 Hz, 1H), 7.32-7.36 (m, 2H), 7.38 (dd, J=8.28, 1.51 Hz, 1H), 7.76 (d, J=8.28 Hz, 1H), 7.92 (s, 1H), 12.61 (br s, 1H); LCMS (electrospray) m/z 385.3 (M+H)+.

Example 16 (52 mg, 126.58 μmol, 12% Yield, 97% Purity) was Obtained as a Light Yellow Solid $^1$H NMR (400 MHz, DMSO-d$_6$) δ=1.23-1.36 (m, 1H), 1.46 (s, 6H), 1.67-1.82 (m, 1H), 2.16-2.23 (m, 1H), 2.25 (s, 3H), 3.00 (s, 3H), 4.91-5.16 (m, 1H), 7.24 (s, 1H), 7.28 (s, 2H), 7.40 (br d, J=8.28 Hz, 1H), 7.77 (d, J=8.28 Hz, 1H), 7.95 (s, 1H), 11.92-13.28 (m, 1H); LCMS (electrospray) m/z 399.4 (M+H)+.

Example 17 (9.5 mg, 24.37 μmol, 2% Yield, 94% Purity) was Obtained as a Light Yellow Solid $^1$H NMR (400 MHz, DMSO-d$_6$) δ=1.29 (br s, 1H), 1.64-1.80 (m, 1H), 2.11 (s, 3H), 2.18 (br s, 1H), 2.24 (s, 3H), 4.93-5.12 (m, 1H), 5.07 (s, 1H), 5.44 (s, 1H), 7.29 (d, J=7.91 Hz, 1H), 7.35 (s, 1H), 7.38 (br d, J=8.53 Hz, 1H), 7.42 (br d, J=7.91 Hz, 1H), 7.74 (br d, J=8.16 Hz, 1H), 7.93 (s, 1H), 11.65-13.53 (m, 1H); LCMS (electrospray) m/z 367.3 (M+H)+.

Synthetic Method F

Example 18. (1S,2S)-2-fluoro-N-(6-(4-methylpyridin-3-yl)thiazolo[4,5-b]pyridin-2-yl)cyclopropane-1-carboxamide

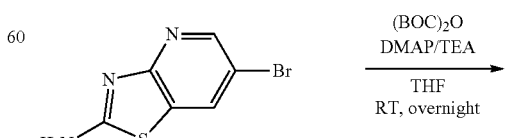

-continued

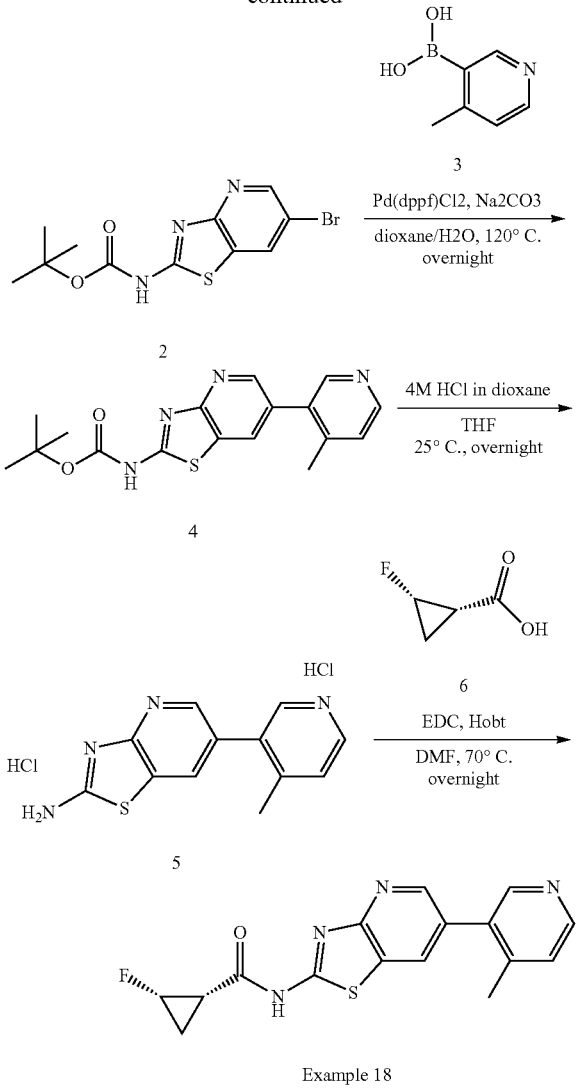

Example 18

Step 1) tert-butyl(6-bromothiazolo[4,5-b]pyridin-2-yl)carbamate

To a solution of Compound 1 (500 mg, 2.17 mmol, 1 eq) and Di-tert-butyl Dicarbonate (711 mg, 3.26 mmol, 1.5 eq) in THF (10 mL) was added 4-Dimethylaminopyridine (398 mg, 3.25 mmol, 1.5 eq) and triethylamine (0.6 mL, 4.34 mmol, 2.0 eq). The mixture was stirred at 25° C. for 12 h. The reaction mixture was concentrated under reduced pressure to remove solvent. Water (20 mL) was added in the reaction mixture, then the mixture was extracted with EA, the combined organic layers were dried over Na₂SO₄, filtered and concentrated under reduced pressure to give a residue. The residue was purified by column chromatography (SiO₂, MC:MeOH=95:5) to give Compound 2 (454 mg, 63% yield) as a white solid.

Step 2) tert-butyl(6-(4-methylpyridin-3-yl)thiazolo[4,5-b]pyridin-2-yl)carbamate To a solution of Compound 2 (65 mg, 0.20 μmol, 1 eq) and Compound 3 (40 mg, 0.30 μmol, 1.5 eq) in 1,4-dioxane (2 mL) was added Pd(dppf)Cl₂ (7 mg, 0.01 mmol, 0.05 eq) and Na₂CO₃ (42 mg, 0.40 mmol, 2 eq) in H₂O (0.2 mL). The mixture was stirred at 120° C. for 1 hr. The reaction mixture was concentrated under reduced pressure to remove solvent. The residue was purified by MPLC (EA:Hex=1:1 to MC:MeOH=95:5) to give Compound 4 (46 mg, 67% yield) as a white solid. LCMS (electrospray) m/z=343.1 (M+H)+

Step 3) 6-(4-methylpyridin-3-yl)thiazolo[4,5-b]pyridin-2-amine. 2HCl salt

A solution of Compound 4 (41 mg, 0.12 mmol) in tetrahydrofuran (0.6 mL) was added 4M HCl in dioxane. The mixture was stirred at the room temperature for 12 hr. Then, the residue was concentrated in vacuo. Compound 5 (45 mg, clean crude, Red brown oil) was used without further purification. LCMS (electrospray) m/z 343.1 (M+H)+

Step 4) (1S,2S)-2-fluoro-N-(6-(4-methylpyridin-3-yl)thiazolo[4,5-b]pyridin-2-yl)cyclopropane-1-carboxamide A mixture of Compound 5 (45 mg, 0.14 mmol, 1 eq), Compound 6 (30 mg, 0.28 mmol, 2.0 eq), HATU (109 mg, 0.28 mmol, 2 eq) and DIPEA (93 mg, 0.72 mmol, 5 eq) in DMF (1 mL) was stirred at 70° C. for 12 hr. Solvent was removed by evaporation, diluted with H2O, extracted with DCM and MeOH, the combined organic phase was washed with brine (15 mL), dried with Na₂SO₄, filtered, concentrated to give a residue. The residue was purified by silica gel column chromatograph (MC:MeOH=95:5~9:1). Example 18 (12 mg, 24% yield, 97% purity) was obtained as a white solid.

¹H NMR (400 MHz, DMSO-d₆) δ=13.06 (s, 1H), 8.57-8.55 (m, 2H), 8.49-8.47 (m, 2H), 7.40-7.38 (m, 1H), 5.16-4.99 (m, 1H), 2.23 (s, 3H), 2.28-2.25 (m, 1H), 1.80-1.74 (m, 1H), 1.37-1.32 (m, 1H); LCMS (electrospray) m/z 329.0 (M+H)+.

Synthetic Method G

Example 28. (1S,2S)-2-fluoro-N-(5-(6-(1-hydroxyethyl)-4-methylpyridin-3-yl)benzo[d]thiazol-2-yl)cyclopropane-1-carboxamide

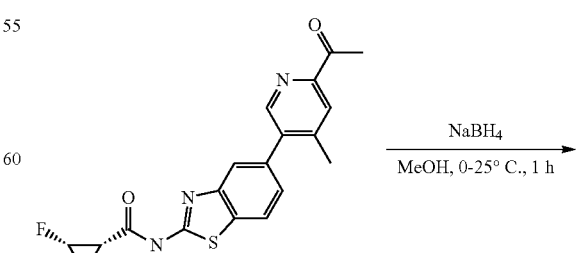

Example 21

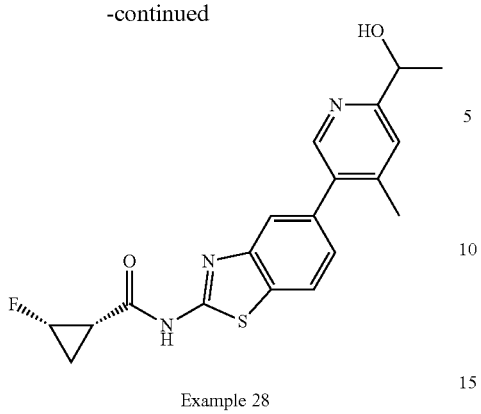

Example 28

To a solution of Example 21 (100 mg, 270.70 μmol, 1 eq) in MeOH (5 mL) was added NaBH₄ (30.72 mg, 812.10 μmol, 3 eq) at 0° C., then stirred at 25° C. for 1 hr. The reaction mixture was concentrated under reduced pressure to remove solvent. Then the reaction mixture was diluted with H₂O (20 mL), then the mixture was extracted with EA (50 mL*3). The combined organic layers were washed with brine (50 mL*2), dried over Na₂SO₄, filtered and concentrated under reduced pressure to give a residue. The residue was purified by prep-HPLC (column: Phenomenex Gemini 150*25 mm*10 um; mobile phase: [water (10 mM NH₄HCO₃)-ACN]; B %: 22%-52%, 10 min). Example 28 (51 mg, 137.31 μmol, 50% yield, 100% purity) was obtained as a light yellow solid.

$^1$H NMR (400 MHz, CDCl₃) δ=1.29-1.39 (m, 1H), 1.58 (d, J=6.60 Hz, 3H), 1.94-2.10 (m, 2H), 2.32 (s, 3H), 4.33 (br s, 1H), 4.71-4.92 (m, 1H), 4.93-5.00 (m, 1H), 7.24 (s, 1H), 7.26-7.28 (m, 1H), 7.72 (d, J=1.34 Hz, 1H), 7.90 (d, J=8.07 Hz, 1H), 8.41 (s, 1H), 10.63 (br s, 1H); LCMS (electrospray) m/z 372.2 (M+H)+.

Synthetic Method H

Example 29. (1S,2S)-2-fluoro-N-(5-(6-(hydroxymethyl)-4-methylpyridin-3-yl)benzo[d]thiazol-2-yl)cyclopropane-1-carboxamide

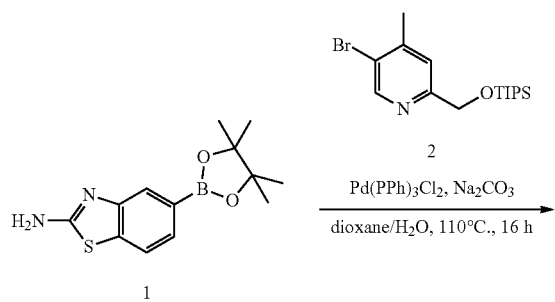

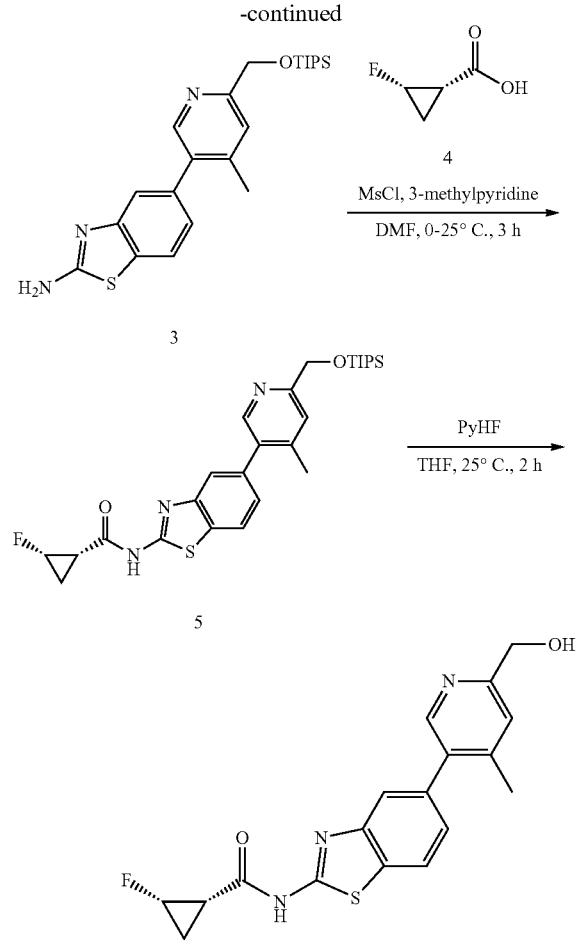

Example 29

Step 1) 5-(4-methyl-6-(((triisopropylsilyl)oxy)methyl)pyridin-3-yl)benzo[d]thiazol-2-amine A mixture of Compound 2 (600 mg, 1.67 mmol, 1 eq), Compound 1 (461.19 mg, 1.67 mmol, 1 eq), Pd(PPh₃)₂Cl₂ (117.22 mg, 167.00 μmol, 0.1 eq), Na₂CO₃ (265.50 mg, 2.51 mmol, 1.5 eq) in DIOXANE (20 mL) H₂O (5 mL) was degassed and purged with N₂ for 3 times, and then the mixture was stirred at 110° C. for 16 hr under N₂ atmosphere. The reaction mixture was diluted with H2O (20 mL), then the mixture was extracted with ethyl acetate (30 mL*3). The combined organic layers were washed with brine (20 mL*2), dried over Na2SO4, filtered and concentrated under reduced pressure to give a residue. The residue was purified by column chromatography (SiO₂, Petroleum ether/Ethyl acetate=2:1). Compound 3 (380 mg, 888.52 μmol, 53% yield) was obtained as a light yellow solid.

Step 2) (1S,2S)-2-fluoro-N-(5-(4-methyl-6-(((triisopropylsilyl)oxy)methyl)pyridin-3-yl)benzo[d]thiazol-2-yl)cyclopropane-1-carboxamide To a solution of Compound 3 (180.00 mg, 420.88 μmol, 1 eq) in DMF (10 mL) was added Compound 4 (52.57 mg, 505.05 μmol, 1.2 eq), 3-methylpyridine (195.98 mg, 2.10 mmol, 204.92 μL, 5 eq), MsCl (96.42 mg, 841.76 μmol, 65.15 μL, 2 eq) at 0° C. under N₂. The mixture was stirred at 25° C. for 3 hr. The reaction mixture was diluted with H$_2$O (20 mL), then the mixture was extracted with EA (50 mL*3). The combined organic layers were washed with brine (50 mL*2), dried over Na$_2$SO$_4$, filtered and concentrated under reduced pressure to give a residue. The residue was purified by column chromatography (silica gel, Petroleum ether/Ethyl acetate=1:1). Compound 5 (200 mg, 389.30 μmol, 92% yield) was obtained as a light yellow liquid.

$^1$H NMR (400 MHz, CDCl$_3$) δ=1.06 (s, 1H), 1.11-1.15 (m, 18H), 1.18-1.22 (m, 3H), 1.30-1.37 (m, 1H), 1.78-1.81 (m, 1H), 2.35 (s, 3H), 4.71-4.74 (m, 1H), 4.98 (s, 2H), 7.29 (br d, J=1.22 Hz, 1H), 7.53 (s, 1H), 7.64 (s, 1H), 7.87 (d, J=8.07 Hz, 1H), 8.40 (s, 1H).

Step 3) (1S,2S)-2-fluoro-N-(5-(6-(hydroxymethyl)-4-methylpyridin-3-yl)benzo[d]thiazol-2-yl)cyclopropane-1-carboxamide To a solution of Compound 5 (180.00 mg, 350.37 μmol, 1 eq) in THF (6 mL) was added pyridine; hydrofluoride (3.30 g, 23.31 mmol, 3 mL, 70% purity, 66.52 eq). The mixture was stirred at 25° C. for 2 hr. The reaction mixture was diluted with H$_2$O (20 mL), then the mixture was extracted with EA (20 mL*3). The combined organic layers were washed with brine (20 mL*2), dried over Na$_2$SO$_4$, filtered and concentrated under reduced pressure to give a residue. The residue was purified by prep-HPLC (column: Phenomenex Gemini 150*25 mm*10 um; mobile phase: [water (10 mM NH$_4$HCO$_3$)-ACN]; B %: 20%-50%, 12 min).

Example 29 (12 mg, 29.55 μmol, 8% Yield, 88% Purity) was Obtained as a Light Yellow Solid $^1$H NMR (400 MHz, DMSO-d$_6$) δ=1.31 (dq, J=15.10, 6.46 Hz, 1H), 1.69-1.82 (m, 1H), 2.18-2.26 (m, 1H), 2.31 (s, 3H), 4.58 (br d, J=3.79 Hz, 2H), 4.91-5.17 (m, 1H), 5.42 (br s, 1H), 7.31 (d, J=8.07 Hz, 1H), 7.42 (s, 1H), 7.72 (s, 1H), 8.06 (d, J=8.07 Hz, 1H), 8.33 (s, 1H), 12.70 (br s, 1H); LCMS (electrospray) m/z 358.3 (M+H)+.

Synthetic Method I

Example 31. (1S,2S)-2-fluoro-N-(5-(5-methyl-1H-indol-4-yl)benzo[d]thiazol-2-yl)cyclopropane-1-carboxamide

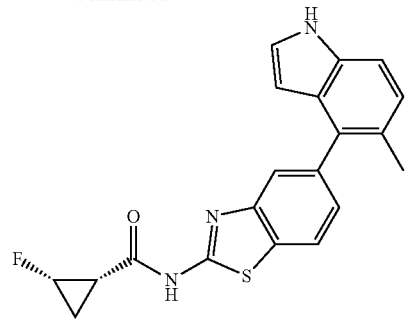

Example 31

To a solution of Example 25 (170 mg, 342.96 μmol, 1 eq) in THF (3 mL) was added TBAF (269.01 mg, 1.03 mmol, 3 eq) and ethane-1,2-diamine (103.06 mg, 1.71 mmol, 114.76 μL, 5 eq) The mixture was stirred at 80° C. for 24 hr. The reaction mixture was concentrated under reduced pressure to remove solvent. The residue was diluted with water (20 mL) and extracted with ethyl acetate (20 mL*2). The combined organic layers were dried over Na$_2$SO$_4$, filtered and concentrated under reduced pressure to give a residue. The residue was purified by prep-TLC (Silica gel, Petroleum ether:Ethyl acatate=1:1). The residue was purified by prep-HPLC (basic condition; column: Waters Xbridge 150*25 5 u; mobile phase: [water (0.05% ammonia hydroxide v/v)-ACN]; B %: 35%-65%, 10 min).

Example 31 (52.2 mg, 142.85 μmol, 41% Yield, 100% Purity) was Obtained as a White Solid $^1$H NMR (400 MHz, DMSO-d$_6$) δ=12.73 (br s, 1H), 11.06 (br s, 1H), 8.05 (d, J=8.2 Hz, 1H), 7.67 (d, J=1.1 Hz, 1H), 7.35-7.22 (m, 3H), 7.05 (d, J=8.3 Hz, 1H), 6.00 (br s, 1H), 5.18-4.89 (m, 1H), 2.28-2.18 (m, 4H), 1.83-1.70 (m, 1H), 1.31 (tdd, J=6.3, 9.0, 12.8 Hz, 1H); LCMS (electrospray) m/z 366.2 (M+H)+.

Synthetic Method J

Example 32. (1S,2S)-N-(6-(1-acetyl-5-methylindolin-4-yl)benzo[d]thiazol-2-yl)-2-fluorocyclopropane-1-carboxamide

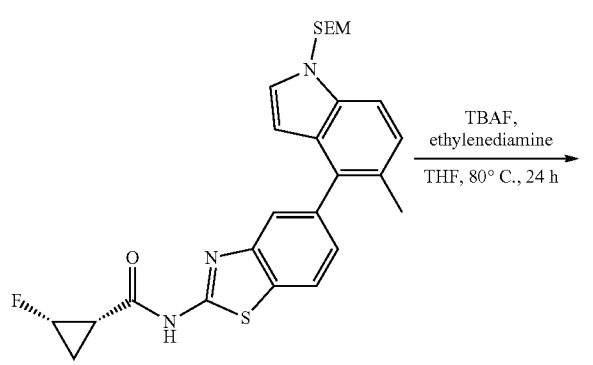

Example 25

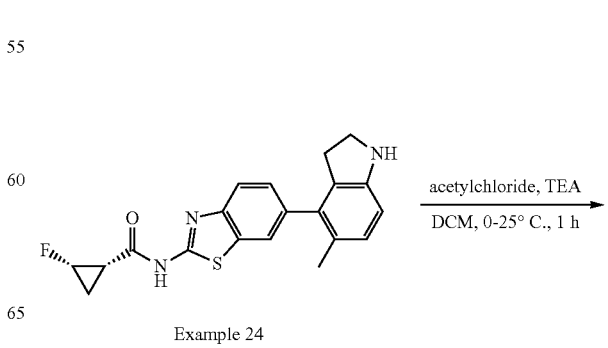

Example 24

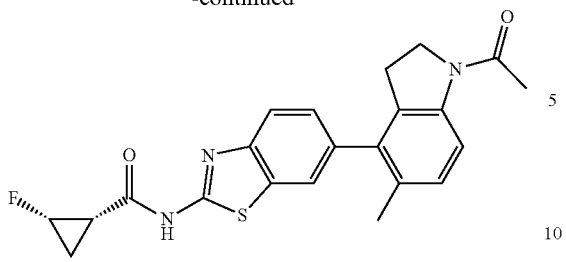

Example 32

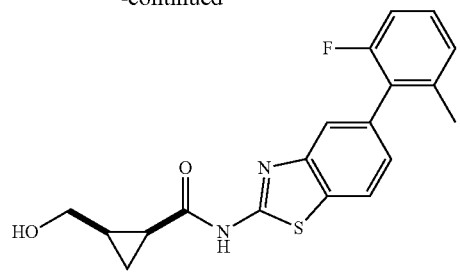

Example 33

To a solution of Example 24 (59 mg, 149.33 μmol, 1 eq) in DCM (3 mL) was added TEA (15.11 mg, 149.33 μmol, 20.79 μL, 1 eq). The mixture was cooled to 0° C. and was dropwise added acetyl chloride (11.72 mg, 149.33 μmol, 10.66 μL, 1 eq). The mixture was stirred at 25° C. for 1 hr. The reaction mixture was concentrated under reduced pressure to remove solvent. The residue was diluted with water 20 mL and extracted with DCM (20 mL*2). The combined organic layers were dried over $Na_2SO_4$, filtered and concentrated under reduced pressure to give a residue. The residue was purified by prep-HPLC (TFA condition; column: Boston pH-lex 150*25 10 um; mobile phase: [water (0.1% TFA)-ACN]; B %: 40%-70%, 10 min). Example 32 (8.9 mg, 16.15 μmol, 10% yield, 95% purity, TFA) was obtained as a white solid.

$^1$H NMR (400 MHz, DMSO-$d_6$) δ=12.74 (s, 1H), 7.95 (d, J=8.3 Hz, 1H), 7.88 (d, J=1.4 Hz, 1H), 7.80 (d, J=8.3 Hz, 1H), 7.29 (dd, J=1.7, 8.2 Hz, 1H), 7.10 (d, J=8.5 Hz, 1H), 5.18-4.91 (m, 1H), 4.02 (br t, J=8.4 Hz, 2H), 2.85 (br s, 2H), 2.27-2.19 (m, 1H), 2.13 (s, 3H), 2.05 (s, 3H), 1.82-1.67 (m, 1H), 1.37-1.21 (m, 1H); LCMS (electrospray) m/z 410.1 (M+H)+.

Synthetic Method K

Example 33. (1S,2R)-N-(5-(2-fluoro-6-methylphenyl)benzo[d]thiazol-2-yl)-2-(hydroxymethyl)cyclopropane-1-carboxamide Step 1) methyl(1R,2S)-2-((5-(2-fluoro-6-methylphenyl)benzo[d]thiazol-2-yl)carbamoyl)cyclopropane-1-carboxylate To a solution of Compound 1 (200 mg, 774.25 μmol, 1 eq) and Compound 2 (cis) (111.59 mg, 774.25 μmol, 1 eq) in MeCN (5 mL) was added MsCl (177.38 mg, 1.55 mmol, 119.85 μL, 2 eq) and 3-methylpyridine (360.52 mg, 3.87 mmol, 376.95 μL, 5 eq) at 0° C. The mixture was stirred at 25° C. for 2 hr. The reaction mixture was concentrated under reduced pressure to remove solvent. The residue was diluted with water 30 mL and extracted with ethyl acetate (20 mL*2). The combined organic layers were dried over $Na_2SO_4$, filtered and concentrated under reduced pressure to give a residue. The residue was purified by column chromatography (Silica gel, Petroleum ether/Ethyl acetate=10/1 to 1:1). Compound 3 (cis) (222 mg, 577.49 μmol, 74% yield) was obtained as a light yellow solid.

$^1$H NMR (400 MHz, CDCl$_3$) δ=7.86 (d, J=8.1 Hz, 1H), 7.61 (d, J=0.6 Hz, 1H), 7.24 (dt, J=1.8, 8.0 Hz, 2H), 7.09 (d, J=7.7 Hz, 1H), 7.00 (t, J=8.6 Hz, 1H), 3.70 (s, 3H), 2.32-2.21 (m, 2H), 2.17 (s, 3H), 1.94-1.87 (m, 1H), 1.48-1.41 (m, 1H).

Step 2) (1S,2R)-N-(5-(2-fluoro-6-methylphenyl)benzo[d]thiazol-2-yl)-2-(hydroxymethyl)cyclopropane-1-carboxamide To a solution of Compound 3 (cis) (100 mg, 260.13 μmol, 1 eq) in THF (5 mL) was added LiBHEt3 (1 M, 1.04 mL, 4 eq). The mixture was stirred at −40° C. for 0.5 hr. The reaction mixture was quenched by addition water 1 mL at −40° C. The mixture was purified by column chromatography (Silica gel, Petroleum ether/Ethyl acetate=1:1). The combined organic layers was filtered and concentrated under reduced pressure to give a residue. The residue was purified by prep-HPLC (column: Gemini 150*25 5 u; mobile phase: [water (0.05% ammonia hydroxide v/v)-ACN]; B %: 37%-67%, 12 min). Example 33 (cis) (6 mg, 16.83 μmol, 6% yield) was obtained as a white solid.

$^1$H NMR (400 MHz, DMSO-$d_6$) δ=7.95 (br d, J=7.9 Hz, 1H), 7.54 (s, 1H), 7.36-7.27 (m, 1H), 7.17 (d, J=7.6 Hz, 1H), 7.15-7.09 (m, 2H), 3.69 (dd, J=5.6, 11.3 Hz, 1H), 3.54-3.45 (m, 1H), 2.14 (s, 3H), 2.05-1.95 (m, 1H), 1.60-1.48 (m, 1H), 1.12-0.98 (m, 2H); LCMS (electrospray) m/z 357.1 (M+H)+.

Synthetic Method L

Example 46. (1S,2S)-2-fluoro-N-(6-(2-fluoro-6-methyl-3-(methylamino)phenyl)benzo[d]thiazol-2-yl)cyclopropane-1-carboxamide

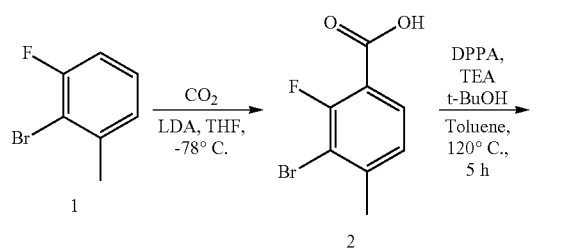

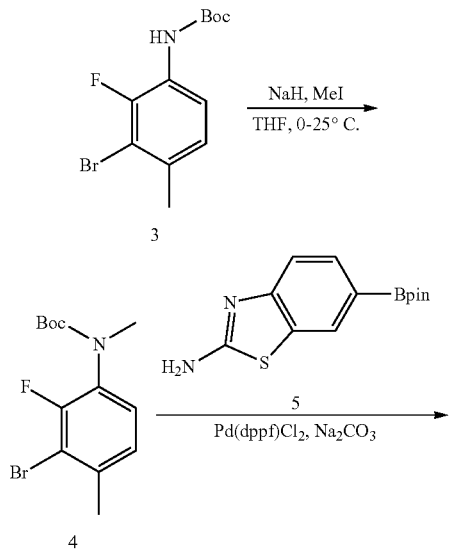

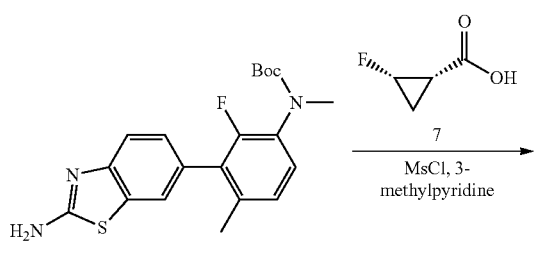

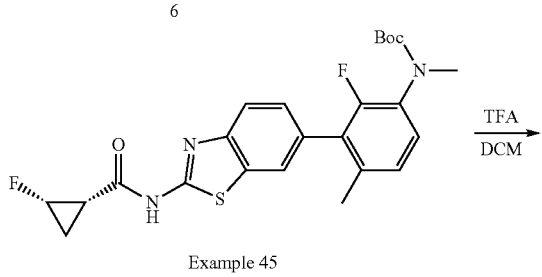

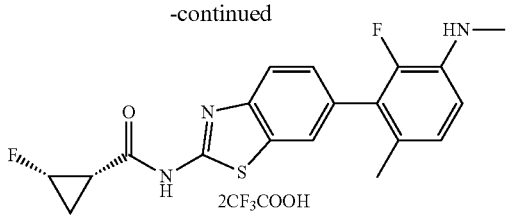

Example 46

Step 1) 3-bromo-2-fluoro-4-methylbenzoic acid

To a solution of Compound 1 (10 g, 52.90 mmol, 1 eq) in THF (200 mL) was added LDA (2 M, 27.77 mL, 1.05 eq) at −78° C. under $N_2$. The reaction mixture was stirred at −78° C. for 0.5 hr. The $CO_2$ (6.98 g, 158.71 mmol, 3 eq) (solid) was added. The mixture was stirred at 20° C. for 1.5 hr. TLC (PE:EA=1:1) showed the starting material disappeared and a new main spot was detected. Water (100 mL) was added and the aqueous phase was extracted with EA (50 mL*2). The aqueous phase was treated with 1M HCl until PH=3~4, then the mixture was filtered and the filter cake was concentrated in vacuum to give product. Compound 2 (12 g, 51.49 mmol, 97% yield) as a white solid which was used in next step directly.

$^1$H NMR (400 MHz, METHANOL-d4) δ=7.80 (t, J=7.6 Hz, 1H), 7.22 (d, J=8.1 Hz, 1H), 2.62-2.41 (m, 3H).

Step 2) tert-butyl(3-bromo-2-fluoro-4-methylphenyl)carbamate

To a solution of Compound 2 (1 g, 4.29 mmol, 1 eq) in toluene (20 mL) was added TEA (477.65 mg, 4.72 mmol, 657.02 µL, 1.1 eq) and DPPA (1.30 g, 4.72 mmol, 1.02 mL, 1.1 eq). The reaction mixture was stirred at 120° C. for 1.5 hr. Then the t-BuOH (477.11 mg, 6.44 mmol, 615.62 µL, 1.5 eq) was added. The mixture was stirred at 120° C. for 3.5 hr. TLC (PE:EA=3:1) showed the starting material disappeared and anew main spot was detected. LCMS showed 44% desired mass and no starting material. The reaction was concentrated in vacuum. Water (50 mL) was added and the aqueous phase was extracted with DCM (50 mL*2). The combined organic phase was washed with saturated brine (10 mL*2) and the organic layer was dried over anhydrous $Na_2SO_4$. The mixture was concentrated in vacuum. The crude product was purified by prep-TLC (PE:EA=3:1) to give product. Compound 5 (520 mg, 1.66 mmol, 38% yield, 97% purity) as a white solid which was used in next step directly.

$^1$H NMR (400 MHz, CDCl$_3$) δ=8.08-7.76 (m, 1H), 7.00 (d, J=8.3 Hz, 1H), 6.68-6.46 (m, 1H), 2.41-2.33 (m, 3H), 1.53 (s, 9H).

Step 3) tert-butyl(3-bromo-2-fluoro-4-methylphenyl)(methyl)carbamate

To a solution of Compound 3 (0.42 g, 1.34 mmol, 1 eq) in THF (15 mL) was added NaH (64.29 mg, 1.61 mmol, 60% purity, 1.2 eq). The reaction mixture was stirred at 0° C. for 0.5 hr. Then the MeI (228.14 mg, 1.61 mmol, 100.06 µL, 1.2 eq) was added. The mixture was stirred at 20° C. for 1.5 hr. TLC (PE:EA=3:1) showed the starting material disappeared and a new main spot was detected. LCMS showed 88% desired mass and no starting material. The reaction was concentrated in vacuum. Water (50 mL) was added and the aqueous phase was extracted with EA (30 mL*2). The combined organic phase was washed with saturated brine (30 mL*2) and the organic layer was dried over anhydrous Na₂SO₄. The mixture was concentrated in vacuum. The crude product was purified by prep-TLC (PE:EA=3:1) to give product. Compound 4 (350 mg, 1.10 mmol, 82% yield) as a light yellow liquid which was used in next step directly.

$^1$H NMR (400 MHz, CDCl₃) δ=7.16-6.95 (m, 2H), 3.26-3.16 (m, 3H), 2.49-2.31 (m, 3H), 1.39-1.10 (m, 9H).

Step 4) tert-butyl(3-(2-aminobenzo[d]thiazol-6-yl)-2-fluoro-4-methylphenyl)(methyl)carbamate To a solution of Compound 5 (343.70 mg, 1.24 mmol, 1.2 eq) in dioxane/H₂O (10 mL) was added Pd(PPh₃)₂Cl₂ (72.80 mg, 103.71 μmol, 0.1 eq), Compound 4 (330 mg, 1.04 mmol, 1 eq) and Na₂CO₃ (219.85 mg, 2.07 mmol, 2 eq) under N₂. The mixture was stirred at 80° C. for 16 hr. LCMS showed 36% desired mass and 26% starting material 2. Water (10 mL) was added and the aqueous phase was extracted with EA (10 mL*2). The combined organic phase was washed with saturated brine (10 mL*2), and concentrated in vacuum. The crude product was purified by prep-TLC (PE:EA=2:1) to give product. Compound 6 (280 mg, 375.77 μmol, 36% yield, 52% purity) as a light yellow liquid.

Step 5) tert-butyl(2-fluoro-3-(2-((1S,2S)-2-fluorocyclopropane-1-carboxamido)benzo[d]thiazol-6-yl)-4-methylphenyl)(methyl)carbamate To a solution of Compound 6 (260 mg, 348.93 μmol, 1 eq) in MeCN (10 mL) was added MsCl (79.94 mg, 697.86 μmol, 54.01 μL, 2 eq), Compound 7 (79.90 mg, 767.65 μmol, 2.2 eq) and 3-methylpyridine (64.99 mg, 697.86 μmol, 67.95 μL, 2 eq) under N₂. The mixture was stirred at 20° C. for 2 hr. LCMS showed 34% desired mass and no starting material. Water (10 mL) was added and the aqueous phase was extracted with EA (10 mL*2). The combined organic phase was washed with saturated brine (10 mL*2), and concentrated in vacuum. The crude product was purified by prep-TLC (PE:EA=1:1) to give Example 45 (256 mg, 47% purity). The crude product (56 mg) was purified by prep-HPLC (column: Phenomenex Gemini 150*25 mm*10 um; mobile phase: [water (10 mM NH₄HCO₃)-ACN]; B %: 40%-70%, 9 min). Example 45 (5 mg, 86% purity) as a white solid.

$^1$H NMR (400 MHz, METHANOL-d4) δ=7.98-7.66 (m, 2H), 7.47-7.03 (m, 3H), 5.20-4.99 (m, 1H), 3.23-3.09 (m, 3H), 2.25-2.02 (m, 4H), 1.97-1.77 (m, 1H), 1.60-1.24 (m, 10H); LCMS (electrospray) m/z 474.7 (M+H)+.

Step 6) (1S,2S)-2-fluoro-N-(6-(2-fluoro-6-methyl-3-(methylamino)phenyl)benzo[d]thiazol-2-yl)cyclopropane-1-carboxamide To a solution of Example 45 (200 mg, 198.51 μmol, 1 eq) in DCM (10 mL) was added TFA (67.90 mg, 595.52 μmol, 44.09 μL, 3 eq). The mixture was stirred at 20° C. for 1 hr. The reaction mixture was concentrated in vacuum. The crude product was purified by prep-HPLC (column: Phenomenex Synergi C18 150*25*10 um; mobile phase: [water (0.1% TFA)-ACN]; B %: 35%-58%, 7 min) to give product. Example 46 (46.3 mg, 73.90 μmol, 37% yield, 96% purity, 2•TFA) as a white solid.

$^1$H NMR (400 MHz, METHANOL-d4) δ=7.88-7.80 (m, 1H), 7.68-7.62 (m, 1H), 7.58-7.54 (m, 1H), 7.35 (br d, J=7.8 Hz, 1H), 7.27-7.19 (m, 1H), 5.14-5.01 (m, 1H), 3.19-2.83 (m, 3H), 2.43-2.06 (m, 4H), 2.01-1.76 (m, 1H), 1.44-1.09 (m, 1H); LCMS (electrospray) m/z 374.1 (M+H)+.

Synthetic Method M

Example 53. N-methyl-6-(4-methylpyridin-3-yl)benzo[d]thiazol-2-amine

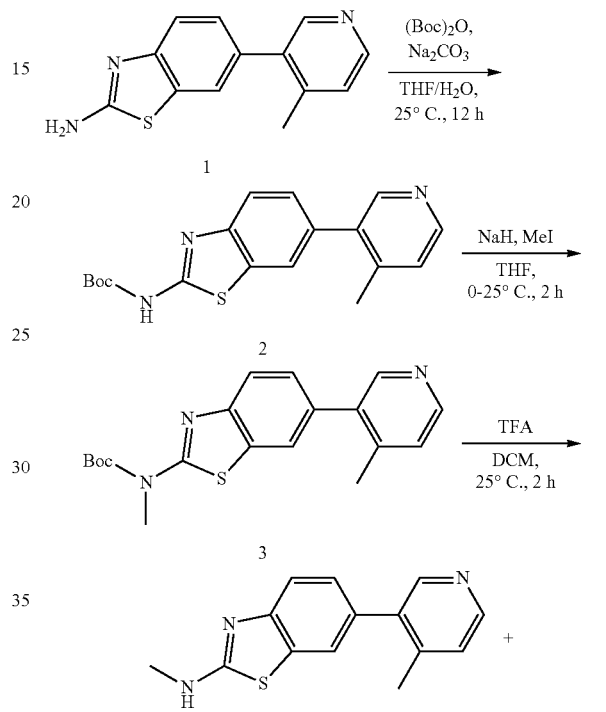

Step 1) tert-butyl(6-(4-methylpyridin-3-yl)benzo[d]thiazol-2-yl)carbamate

To a solution of Compound 1 (100 mg, 414.40 μmol, 1 eq) in THF/H₂O (5 mL) was added Na₂CO₃ (87.84 mg, 828.81 μmol, 2 eq) and tert-butoxycarbonyl tert-butyl carbonate (108.53 mg, 497.28 μmol, 114.24 μL, 1.2 eq). The mixture was stirred at 25° C. for 12 hr. The residue was purified by column chromatography (SiO₂, Petroleum ether/Ethyl acetate=1:1). Compound 2 (120 mg, 351.47 μmol, 84% yield) was obtained as a light yellow solid.

Step 2) tert-butyl methyl(6-(4-methylpyridin-3-yl)benzo[d]thiazol-2-yl)carbamate To a solution of Compound 2 (120 mg, 351.47 μmol, 1 eq) in THF (5 mL) was added NaH (28.11 mg, 702.93 μmol, 60% purity, 2 eq) at 0° C. for 0.5 hr, then added MeI (74.83 mg, 527.20 μmol, 32.82 μL, 1.5 eq) into the mixture, after stirred at 25° C. for 1.5 hr. The residue was purified by column chromatography (SiO₂, Petroleum ether/Ethyl acetate=3:1). Compound 3 (100 mg, 281.33 μmol, 80% yield) was obtained as a light yellow solid.

Step 3) N-methyl-6-(4-methylpyridin-3-yl)benzo[d]thiazol-2-amine

To a solution of Compound 3 (100 mg, 281.33 μmol, 1 eq) in DCM (2 mL) was added TFA (0.4 mL). The mixture was stirred at 25° C. for 1 hr. The residue was purified by pre-HPLC (column: Boston pH-lex 150*25 10 um; mobile phase: [water (0.1% TFA)-ACN]; B %: 1%-30%, 10 min). Example 53 (9.8 mg, 19.46 μmol, 6% yield, 96% purity, 2TFA) was obtained as a light yellow solid.

¹H NMR (400 MHz, METHANOL-d₄) δ=2.62 (s, 3H), 3.19 (s, 3H), 7.51 (dd, J=8.31, 1.71 Hz, 1H), 7.66 (d, J=8.31 Hz, 1H), 7.88 (d, J=1.47 Hz, 1H), 8.03 (d, J=5.87 Hz, 1H), 8.66-8.78 (m, 2H); LCMS (electrospray) m/z 256.2 (M+H)+.

Example 54 (10.3 mg, 25.66 μmol, 9% Yield, 92% Purity, TFA) was Obtained as a Light Yellow Solid ¹H NMR (400 MHz, METHANOL-d₄) δ=2.57 (s, 3H), 3.87 (s, 3H), 7.71 (dd, J=8.56, 1.71 Hz, 1H), 7.82 (d, J=8.56 Hz, 1H), 7.96-8.03 (m, 2H), 8.68-8.76 (m, 2H).

Synthetic Method N

Example 55. (1S,2S)-2-fluoro-N-(6-(4-methoxypyridin-3-yl)benzo[d]thiazol-2-yl)cyclopropane-1-carboxamide

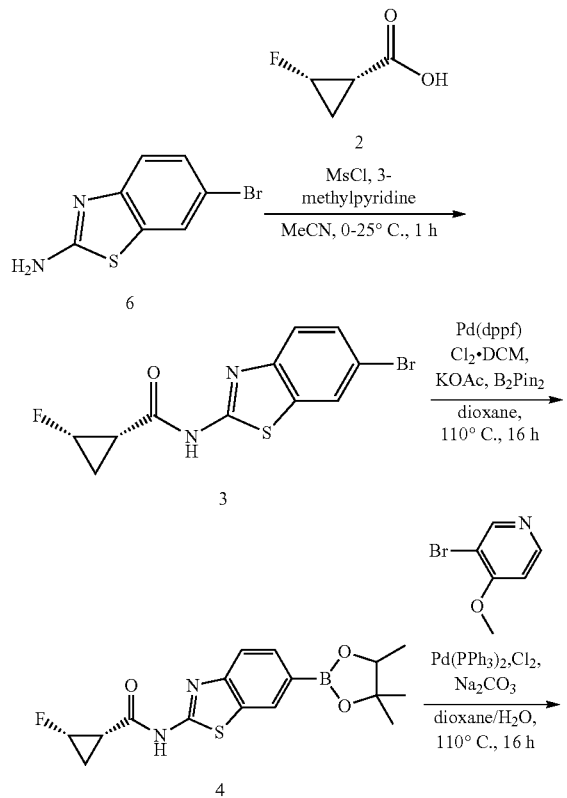

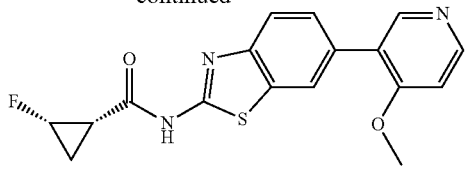

Example 55

Step 1) (1S,2S)-N-(6-bromobenzo[d]thiazol-2-yl)-2-fluorocyclopropane-1-carboxamide To a solution of Compound 1 (1.2 g, 5.24 mmol, 1.2 eq) in MeCN (15 mL) was added Compound 2 (454.30 mg, 4.36 mmol, 1 eq), 3-methylpyridine (2.03 g, 21.82 mmol, 2.13 mL, 5 eq), MsCl (1.00 g, 8.73 mmol, 675.69 μL, 2 eq) at 0° C., then the mixture was stirred at 25° C. for 1 hr. The reaction mixture was concentrated under reduced pressure to remove solvent. The reaction mixture was diluted with H₂O (20 mL), then the mixture was extracted with ethyl acetate (30 mL*3). The combined organic layers were washed with brine (20 mL*2), dried over Na₂SO₄, filtered and concentrated under reduced pressure to give Compound 3 (1.2 g, 3.81 mmol, 87% yield) as a light yellow solid which was used in next step directly.

¹H NMR (400 MHz, DMSO-d₆) δ=1.31 (ddt, J=12.79, 9.00, 6.40, Hz, 1H), 1.65-1.83 (m, 1H), 2.13-2.29 (m, 1H), 4.87-5.18 (m, 1H), 7.51-7.60 (m, 1H), 7.68 (d, J=8.56 Hz, 1H), 8.25 (d, J=1.96 Hz, 1H), 12.78 (s, 1H).

Step 2) (1S,2S)-2-fluoro-N-(6-(4,4,5,5-tetramethyl-1,3,2-dioxaborolan-2-yl)benzo[d]thiazol-2-yl)cyclopropane-1-carboxamide A mixture of Compound 3 (1.1 g, 3.49 mmol, 1 eq), 4,4,5,5-tetramethyl-2-(4,4,5,5-tetramethyl-1,3,2-dioxaborolan-2-yl)-1,3,2-dioxaborolane (1.33 g, 5.24 mmol, 1.5 eq), KOAc (1.03 g, 10.47 mmol, 3 eq), Pd(dppf)Cl₂.CH₂Cl₂ (285.03 mg, 349.03 μmol, 0.1 eq) in dioxane (20 mL) was degassed and purged with N₂ for 3 times, and then the mixture was stirred at 110° C. for 16 hr under N₂ atmosphere. The reaction mixture was diluted with H₂O (20 mL), then the mixture was extracted with ethyl acetate (30 mL*3). The combined organic layers were washed with brine (20 mL*2), dried over Na₂SO₄, filtered and concentrated under reduced pressure to give a residue. The residue was purified by column chromatography (Silica gel, Petroleum ether/Ethyl acetate=2:1). Compound 4 (1.15 g, 3.17 mmol, 90% yield) was obtained as a light yellow solid.

¹H NMR (400 MHz, METHANOL-d₄) δ=1.20 (s, 12H), 1.33-1.27 (m, 1H), 1.93-1.80 (m, 1H), 2.22-2.12 (m, 1H), 4.87-5.18 (m, 1H), 7.69-7.75 (m, 1H), 7.76-7.82 (m, 1H), 8.23 (s, 1H).

Step 3) (1S,2S)-2-fluoro-N-(6-(4-methoxypyridin-3-yl)benzo[d]thiazol-2-yl)cyclopropane-1-carboxamide A mixture of Compound 4 (150 mg, 414.11 μmol, 1 eq), 3-bromo-4-methoxy-pyridine (77.86 mg, 414.11 μmol, 1 eq), Pd(PPh₃)₂Cl₂ (29.07 mg, 41.41 μmol, 0.1 eq), Na₂CO₃ (87.78 mg, 828.21 μmol, 2 eq) in dioxane/H₂O (10 mL) was degassed and purged with N₂ for 3 times, and then the mixture was stirred at 110° C. for 3 hr under N₂ atmosphere. The reaction mixture was diluted with H₂O (20 mL), then the mixture was extracted with EA (20 mL*3). The combined organic layers were washed with brine (20 mL*2), dried over Na₂SO₄, filtered and concentrated under reduced pressure to give a residue. The residue was purified by column chromatography (Silica gel, Petroleum ether/Ethyl acetate=0:1). Then the residue was purified by prep-HPLC (column: Phenomenex Gemini 150*25 mm*10 um; mobile phase: [water (10 mM NH₄HCO₃)-ACN]; B %: 24%-54%, 10 min). Example 55 (23 mg, 63.63 μmol, 15% yield, 95% purity) was obtained as a light yellow solid.

¹H NMR (400 MHz, CDCl₃) δ=1.33-1.44 (m, 1H), 1.91-2.13 (m, 2H), 3.94 (s, 3H), 4.79-5.05 (m, 1H), 6.96 (d, J=5.87 Hz, 1H), 7.63 (dd, J=8.38, 1.65 Hz, 1H), 7.87 (d, J=8.44 Hz, 1H), 8.02 (d, J=1.47 Hz, 1H), 8.51-8.55 (m, 2H), 10.35 (br s, 1H); LCMS (electrospray) m/z 344.3 (M+H)+.

Synthetic Method O

Example 58. (2-((1S,2S)-2-fluorocyclopropane-1-carboxamido)benzo[d]thiazol-6-yl)boronic acid. HCl salt

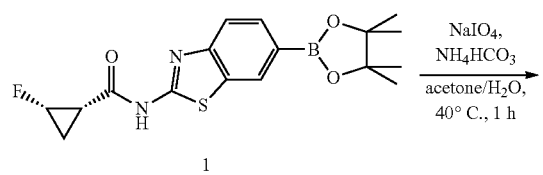

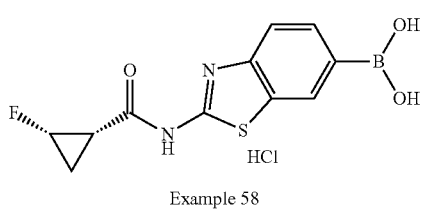

Example 58

To a solution of Compound 1 (200 mg, 552.14 μmol, 1 eq) in ACETONE (5 mL) and H₂O (5 mL) was added NaIO₄ (708.59 mg, 3.31 mmol, 183.57 μL, 6 eq) and NH₄HCO₃ (261.90 mg, 3.31 mmol, 272.81 μL, 6 eq). The mixture was stirred at 40° C. for 1 hr. The reaction mixture was concentrated under reduced pressure to remove solvent. The residue was diluted with H₂O (20 mL), then the mixture was extracted with ethyl acetate (20 mL*3). The combined organic layers were washed with brine (20 mL*2), dried over Na₂SO₄, filtered and concentrated under reduced pressure to give a residue. The residue was purified by pre-HPLC (column: Phenomenex Synergi C18 150*25*10 um; mobile phase: [water (0.05% HCl)-ACN]; B %: 15%-41%, 8 min). Example 58 (58 mg, 172.24 μmol, 31% yield, 94% purity, HCl) was obtained as a light yellow solid.

¹H NMR (400 MHz, METHANOL-d₄) δ=1.26-1.39 (m, 1H), 1.81-1.94 (m, 1H), 2.19 (dtd, J=9.19, 6.87, 6.87, 4.34 Hz, 1H), 4.87-5.18 (m, 1H), 7.69-7.75 (m, 1H), 7.81 (br d, J=7.82 Hz, 1H), 8.22 (s, 1H); LCMS (electrospray) m/z 281.2 (M+H)+.

Synthetic Method P

Example 71. (1S,2R)-N-(6-(2-fluoro-6-methylphenyl)benzo[d]thiazol-2-yl)-2-((methylamino)methyl)cyclopropane-1-carboxamide

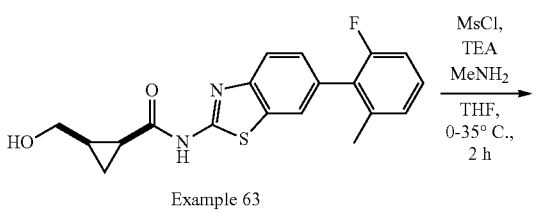

Example 63

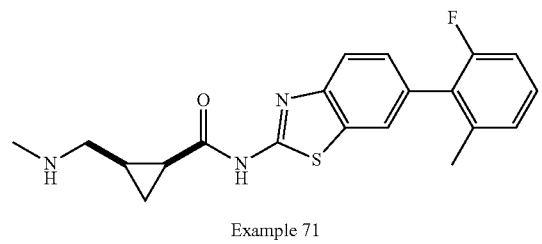

Example 71

To a solution of Example 63 (210 mg, 589.20 μmol, 1 eq) in THF (10 mL) was added TEA (59.62 mg, 589.20 μmol, 82.01 μL, 1 eq) and MsCl (67.49 mg, 589.20 μmol, 45.60 μL, 1 eq) at 0° C. The mixture was stirred at 25° C. for 2 hr. Then the methanamine (2 M, 2.95 mL, 10 eq) was added. The mixture was stirred at 40° C. for 16 hr. LCMS showed 40% desired Mass and 25% starting material. Water (10 mL) was added and the aqueous phase was extracted with EA (10 mL*2). The combined organic phase was washed with saturated brine (20 mL*2), and concentrated in vacuum. The crude product was purified by prep-HPLC (column: Phenomenex Synergi C18 150*25*10 um; mobile phase: [water (0.05% HCl)-ACN]; B %: 20%-40%, 7.8 min) to give product. Example 71 (47 mg, 100.93 μmol, 17% yield, 95% purity, 2 HCl) was obtained as a light yellow solid.

¹H NMR (400 MHz, METHANOL-d4) δ=7.74 (s, 1H), 7.87-7.71 (m, 1H), 7.61 (d, J=8.4 Hz, 1H), 7.49-7.40 (m, 1H), 7.30 (dt, J=5.7, 7.9 Hz, 1H), 7.14 (d, J=7.7 Hz, 1H), 7.02 (t, J=8.9 Hz, 1H), 3.88 (br d, J=6.5 Hz, 2H), 2.74 (s, 3H), 2.16 (s, 3H), 1.87 (dt, J=5.7, 8.2 Hz, 1H), 1.71 (qd, J=7.9, 15.3 Hz, 1H), 1.30-1.06 (m, 2H); LCMS (electrospray) m/z 370.0 (M+H)+.

Synthetic Method Q

Example 80. (1S,2S)-2-fluoro-N-(4-fluoro-6-(4-methylpyridin-3-yl)benzo[d]thiazol-2-yl) cyclopropane-1-carboxamide

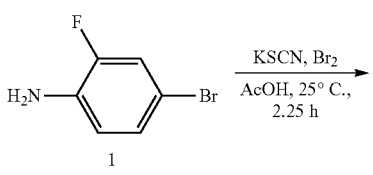

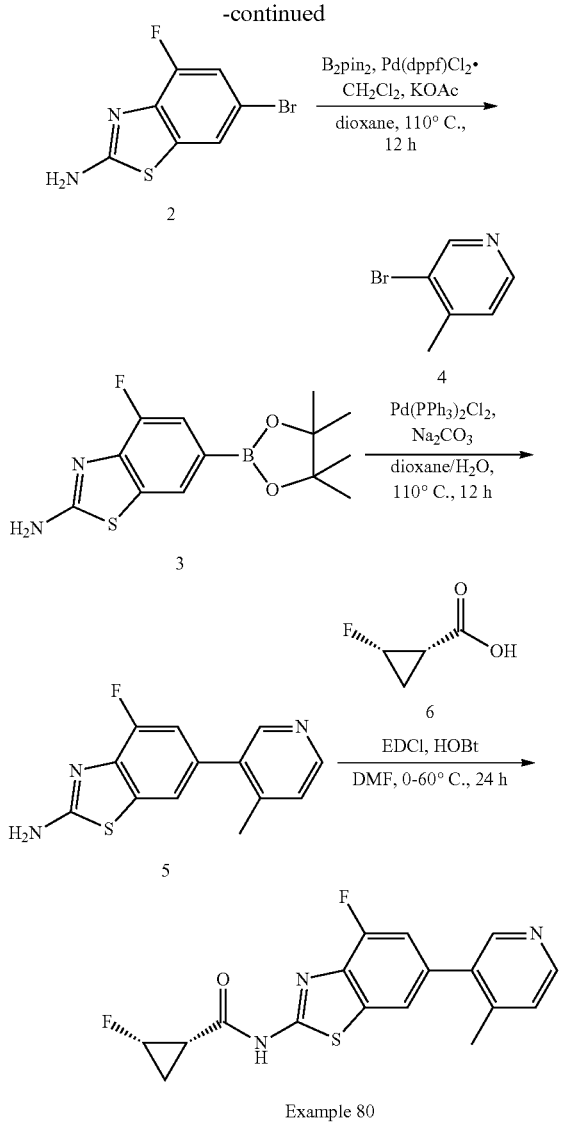

mL) was added Pd(dppf)Cl$_2$·CH$_2$Cl$_2$ (101.47 mg, 124.25 µmol, 0.1 eq) and AcOK (365.82 mg, 3.73 mmol, 3 eq). The mixture was stirred at 110° C. for 12 hr under N$_2$. Then the mixture was stirred at 110° C. for 3 hr. The reaction mixture was concentrated under reduced pressure to remove solvent. The residue was purified by column chromatography (Silica gel, Petroleum ether/Ethyl acetate=10/1 to 1:1). Compound 3 (322 mg, 1.09 mmol, 88% yield) was obtained as a light yellow solid.

$^1$H NMR (400 MHz, DMSO-d$_6$) δ=7.89 (s, 2H), 7.77 (s, 1H), 7.21 (d, J=11.1 Hz, 1H), 1.29 (s, 12H).

Step 3) 4-fluoro-6-(4-methylpyridin-3-yl)benzo[d]thiazol-2-amine

To a solution of Compound 3 (150 mg, 509.94 µmol, 1 eq) and Compound 4 (105.27 mg, 611.93 µmol, 67.91 µL, 1.2 eq) in dioxane (5 mL) and H$_2$O (1 mL) was added Pd(PPh$_3$)$_2$Cl$_2$ (35.79 mg, 50.99 µmol, 0.1 eq) and Na$_2$CO$_3$ (162.14 mg, 1.53 mmol, 3 eq). The mixture was stirred at 110° C. for 12 hr under N$_2$. The reaction mixture was concentrated under reduced pressure to remove solvent. The residue was diluted with 20 mL and extracted with ethyl acetate (20 mL*2). The combined organic layers were dried over Na$_2$SO$_4$, filtered and concentrated under reduced pressure to give a residue. The residue was purified by prep-TLC (Silica gel plate, Petroleum ether:Ethyl acetate=0:1). Compound 5 (50 mg, 160.05 µmol, 31% yield, 83% purity) was obtained as a white solid Step 4) (1S,2S)-2-fluoro-N-(4-fluoro-6-(4-methylpyridin-3-yl)benzo[d]thiazol-2-yl)cyclopropane-1-carboxamide To a solution of Compound 5 (50 mg, 160.05 µmol, 1 eq) and Compound 6 (19.99 mg, 192.05 µmol, 1.2 eq) in DMF (2 mL) was added EDCI (61.36 mg, 320.09 µmol, 2 eq) and HOBt (43.25 mg, 320.09 µmol, 2 eq) at 0° C. The mixture was stirred at 60° C. for 12 hr. The reaction mixture was diluted with water 20 mL and extracted with ethyl acetate (20 mL*2). The combined organic layers were dried over Na$_2$SO$_4$, filtered and concentrated under reduced pressure to give a residue. The residue was purified by prep-HPLC (column: Phenomenex Synergi C18 150*25*10 um; mobile phase: [water (0.1% TFA)-ACN]; B %: 15%-36%, 7 min). Example 80 (8.9 mg, 13.94 µmol, 8% yield, 89% purity, 2TFA) was obtained as a white solid.

$^1$H NMR (400 MHz, DMSO-d$_6$) δ=13.07 (s, 1H), 8.64 (br d, J=7.7 Hz, 2H), 7.95 (br d, J=1.2 Hz, 1H), 7.68 (br s, 1H), 7.47 (br d, J=11.5 Hz, 1H), 5.17-4.96 (m, 1H), 2.43 (br s, 3H), 2.23 (td, J=6.9, 13.5 Hz, 1H), 1.83-1.70 (m, 1H), 1.34 (qd, J=6.4, 15.1 Hz, 1H); LCMS (electrospray) m/z 346.3 (M+H)+.

Step 1) 6-bromo-4-fluorobenzo[d]thiazol-2-amine

To a solution of Compound 1 (1 g, 5.26 mmol, 1 eq) in AcOH (10 mL) was added thiocyanatopotassium (2.05 g, 21.05 mmol, 2.05 mL, 4 eq). To the solution was dropped at 25° C. for 15 minutes bromine (1.68 g, 10.53 mmol, 542.61 µL, 2 eq) in AcOH (3 mL). After the end of dropping, the mixture was stirred at 25° C. for 2 hr. The reaction mixture was concentrated under reduced pressure to remove AcOH. The PH was adjusted to 7 with 1M NaOH, and the mixture extracted with EA (50 mL*2). The combined organic layers were dried over Na$_2$SO$_4$, filtered and concentrated under reduced pressure to give a residue. The residue was purified by column chromatography (Silica gel, Petroleum ether/Ethyl acetate=20/1 to 0:1). Compound 2 (307 mg, 1.24 mmol, 23% yield) was obtained as a white solid.

$^1$H NMR (400 MHz, DMSO-d$_6$) δ=7.86 (s, 2H), 7.77 (d, J=1.2 Hz, 1H), 7.35 (dd, J=1.8, 10.5 Hz, 1H).

Step 2) 4-fluoro-6-(4,4,5,5-tetramethyl-1,3,2-dioxaborolan-2-yl)benzo[d]thiazol-2-amine To a solution of Compound 2 (307 mg, 1.24 mmol, 1 eq) and B$_2$pin$_2$ (473.27 mg, 1.86 mmol, 1.5 eq) in dioxane (5

Example 85. (1S,2S)-N-(6-(5-ethynyl-2-methylphenyl)benzo[d]thiazol-2-yl)-2-fluorocyclopropane-1-carboxamide Using ((3-bromo-4-methylphenyl)ethynyl)trimethylsilane, the title compound was obtained as described for the synthetic method B Synthetic Method R Example 91. 3-(2-((1S,2S)-2-fluorocyclopropane-1-carboxamido)thiazolo[5,4-b]pyridin-5-yl)-N,4-dimethylbenzamide. 2 HCl salt

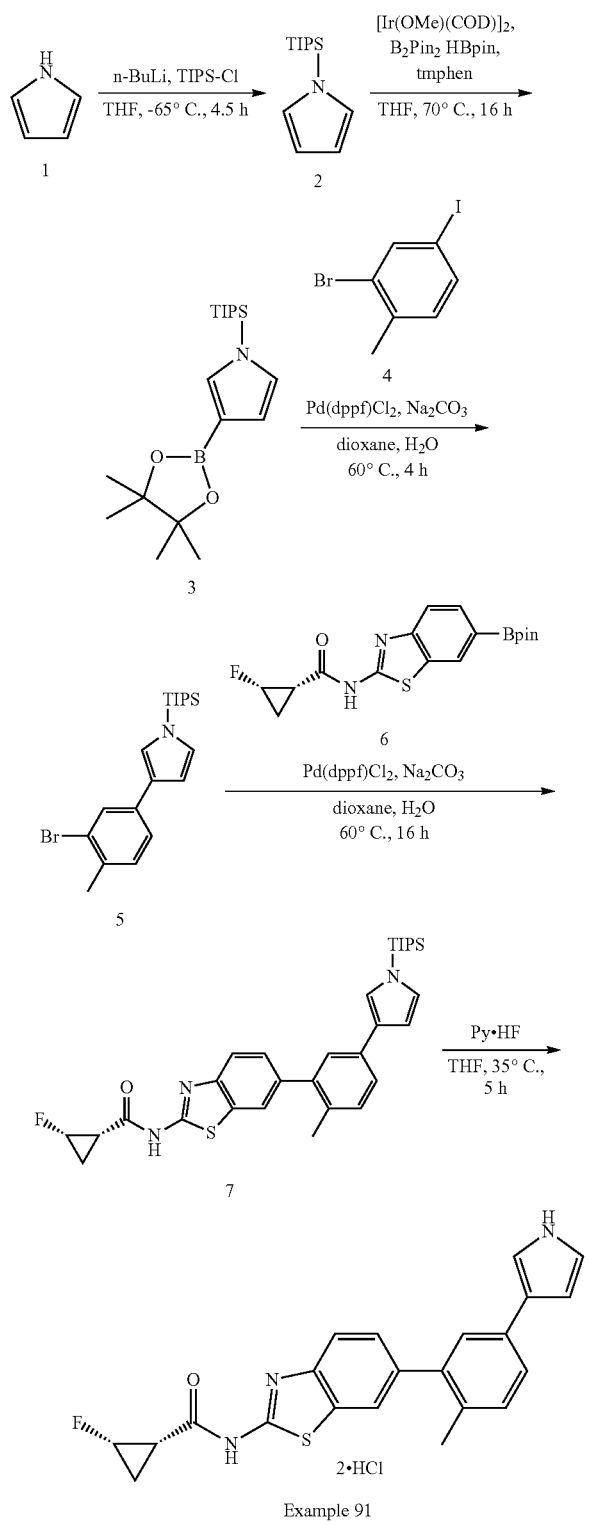

Example 91

Step 1) 1-(triisopropylsilyl)-1H-pyrrole n-BuLi (2.2 M, 16.21 mL, 1.20 eq) was added dropwise to the solution of Compound 1 (2 g, 29.81 mmol, 2.07 mL, 1 eq) in THF (40 mL) at −65° C., and the whole mixture was stirred for 0.5 hr at −65° C. TIPSCl (6.32 g, 32.76 mmol, 7.01 mL, 1.10 eq) was added to the mixture, and the whole mixture was stirred for 4 hr. at −65° C. Saturated ammonium chloride aqueous solution (40 mL) was added to the mixture at 0° C., and the whole mixture was extracted with EtOAc (40 mL*3). The combined organic layers were washed with brine (20 mL), dried over sodium sulfate, filtered and concentrated in vacuum to give a residue. The residue was purified by silica gel chromatography (100-200 mesh silica gel, Petroleum ether) to afford Compound 2 (5.6 g, 25.06 mmol, 84% yield) as colorless oil.

$^1$H NMR (400 MHz, CDCl$_3$) δ=6.81 (t, J=1.8 Hz, 2H), 6.32 (t, J=1.9 Hz, 2H), 1.52-1.39 (m, 3H), 1.10 (d, J=7.5 Hz, 18H).

Step 2) 3-(4,4,5,5-tetramethyl-1,3,2-dioxaborolan-2-yl)-1-(triisopropylsilyl)-1H-pyrrole To a solution of (1,5-Cyclooctadiene)(methoxy)iridium(I) Dimer (47.47 mg, 71.61 μmol, 0.02 eq) in THF (15 mL) were added 3,4,7,8-tetramethyl-1,10-phenanthroline (33.84 mg, 143.22 μmol, 0.04 eq) and 4,4,5,5-tetramethyl-1,3,2-dioxaborolane (45.82 mg, 358.06 μmol, 51.95 μL, 0.1 eq). The mixture was degassed and purged with nitrogen for 3 times, and then the mixture was stirred at 15° C. for 0.5 h under nitrogen atmosphere. Then Compound 2 (800 mg, 3.58 mmol, 884.96 μL, 1 eq) and 4,4,5,5-tetramethyl-2-(4,4,5,5-tetramethyl-1,3,2-dioxaborolan-2-yl)-1,3,2-dioxaborolane (909.24 mg, 3.58 mmol, 1 eq) were added. The mixture was degassed and purged with nitrogen for 3 times, and then the mixture was stirred at 70° C. for 16 h under nitrogen atmosphere. The reaction mixture was quenched by diluting with EtOAc (40 mL), and then filtered through celite. The filtrate were washed with water (10 mL) and brine (10 mL), dried over sodium sulfate, filtered and the filtrate was concentrated in vacuum to give a residue. The residue was purified by flash silica gel chromatography (100~200 mesh silica gel, Petroleum ether/Ethyl acetate=1/0 to 100/1, product came out at Petroleum ether/Ethyl acetate=100/1) to afford Compound 3 (900 mg, 2.58 mmol, 71% yield) as white solid.

$^1$H NMR (400 MHz, CDCl$_3$) δ=7.23 (t, J=1.4 Hz, 1H), 6.81 (t, J=2.2 Hz, 1H), 6.62 (dd, J=1.2, 2.5 Hz, 1H), 1.46 (quin, J=7.5 Hz, 3H), 1.32 (s, 12H), 1.09 (d, J=7.5 Hz, 19H).

Step 3) 3-(3-bromo-4-methylphenyl)-1-(triisopropylsilyl)-1H-pyrrole

To a solution of Compound 3 (180 mg, 515.18 μmol, 1 eq) and Compound 4 (137.68 mg, 463.67 μmol, 0.9 eq) in dioxane (4 mL) and H$_2$O (1 mL) was added Na$_2$CO$_3$ (109.21 mg, 1.03 mmol, 2 eq) and Pd(dppf)Cl$_2$ (37.70 mg, 51.52 μmol, 0.1 eq). The mixture was degassed and purged with nitrogen for 3 times, and then the mixture was stirred at 60° C. for 4 h under nitrogen atmosphere. The reaction mixture was quenched by diluting with EtOAc (40 mL), and then filtered through celite. The filtrate were washed with water (10 mL) and brine (10 mL), dried over sodium sulfate, filtered and concentrated in vacuum to give a residue. The residue was purified by prep-TLC (Petroleum ether/Ethyl acetate=20/1, Rf=0.8) to afford Compound 5 as colorless oil.

¹H NMR (400 MHz, CDCl₃) δ=7.70 (d, J=1.7 Hz, 1H), 7.36 (dd, J=1.7, 7.8 Hz, 1H), 7.17 (d, J=7.9 Hz, 1H), 7.01 (t, J=1.7 Hz, 1H), 6.79 (t, J=2.4 Hz, 1H), 6.56 (dd, J=1.4, 2.6 Hz, 1H), 2.37 (s, 3H), 1.48 (quin, J=7.5 Hz, 3H), 1.12 (d, J=7.5 Hz, 19H).

Step 4) (1S,2S)-2-fluoro-N-(6-(2-methyl-5-(1-(tri-isopropylsilyl)-1H-pyrrol-3-yl)phenyl)benzo[d]thiazol-2-yl)cyclopropane-1-carboxamide To a solution of Compound 5 (130 mg, 311.38 μmol, 1 eq) and Compound 6 (112.79 mg, 311.38 μmol, 1 eq) in dioxane (3 mL) and H₂O (0.6 mL) was added Na₂CO₃ (66.01 mg, 622.76 μmol, 2 eq) and Pd(dppf)Cl₂ (22.78 mg, 31.14 μmol, 0.1 eq). The mixture was degassed and purged with nitrogen for 3 times, and then the mixture was stirred at 60° C. for 16 h under nitrogen atmosphere. The reaction mixture was diluted with EtOAc (40 mL), and then the resulting organic phase was washed with water (10 mL) and brine (10 mL), dried over sodium sulfate, filtered and then the resulting organic phase was concentrated in vacuum to give a residue. The residue was purified by silica gel chromatography (300-400 mesh silica gel, Petroleum ether/Ethyl acetate=10/1 to 1/1, product came out at Petroleum ether/Ethyl acetate=2/1) to afford Compound 7 as brown oil.

Step 5) (1S,2S)-2-fluoro-N-(6-(2-methyl-5-(1H-pyrrol-3-yl)phenyl)benzo[d]thiazol-2-yl)cyclopropane-1-carboxamide. 2 HCl salt To a solution of Compound 7 (110 mg, 190.76 μmol, 1 eq) in THF (4 mL) was added pyridine; hydrofluoride (1.10 g, 11.10 mmol, 1 mL). The mixture was stirred at 35° C. for 3 h. LC-MS showed 2% of Compound 7 remained. The mixture was stirred at 35° C. for 2 h. The reaction mixture was diluted with ethyl acetate (20 mL), and then the resulting organic phase was washed with HCl aqueous solution (4 mL, 0.5 M), brine (4 mL), dried over sodium sulfate, filtered and the filtrate was concentrated in vacuum to give a residue. The residue was purified by prep-HPLC (HCl condition, column: Phenomenex Synergi C18 150*25*10 um; mobile phase: [water (0.05% HCl)-ACN]; B %: 41%-61%, 11 min), followed by lyophilization. But HNMR showed the product was not clean, so it was diluted with water and lyophilizated again to afford Example 91 as off-white solid.

¹H NMR (400 MHz, DMSO-d₆) δ=12.70 (s, 1H), 10.87 (br s, 1H), 7.98 (d, J=1.6 Hz, 1H), 7.79 (d, J=8.3 Hz, 1H), 7.48-7.36 (m, 3H), 7.27-7.18 (m, 2H), 6.77 (q, J=2.3 Hz, 1H), 6.43 (d, J=1.7 Hz, 1H), 5.17-4.91 (m, 1H), 2.27-2.23 (m, 1H), 2.21 (s, 3H), 1.83-1.67 (m, 1H), 1.31 (tdd, J=6.4, 9.0, 12.8 Hz, 1H); LCMS (electrospray) m/z 392.1 (M+H)+.

Synthetic Method S

Example 92. (1S,2S)-2-fluoro-N-(6-(2-methyl-5-(thiazol-2-yl)phenyl)benzo[d]thiazol-2-yl)cyclopropane-1-carboxamide. 2 HCl salt

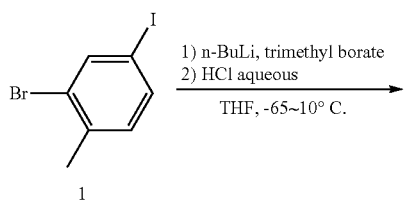

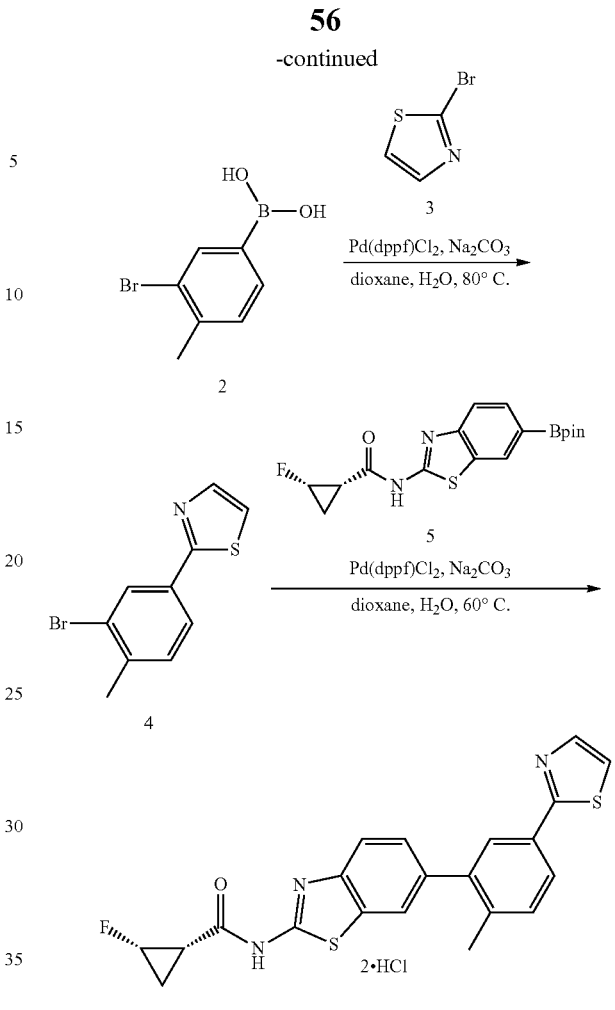

Example 92

Step 1) (3-bromo-4-methylphenyl)boronic acid

Compound 1 (3 g, 10.10 mmol, 1 eq) in THF (30 mL) was placed into 250 ml round bottom flask. The reaction solution was cooled to −65° C. under a nitrogen atmosphere. n-BuLi (2.2 M, 5.05 mL, 1.1 eq) to the cooled solution was slowly added dropwise, the mixture was stirred for 1 h at the same temperature. TRIMETHYL BORATE (1.26 g, 12.12 mmol, 1.37 mL, 1.2 eq) were added dropwise to the above solution at the same temperature. The mixture was stirred at −65° C. for 1 h. Then cool bath was removed and the mixture was stirred at −65~10° C. for 16 h. The mixture was acidified by dropwise addition of HCl solution (2 M, 5 mL) to the reaction solution, which was stirred for 1.5 hour. The mixture were concentrated in vacuum to afford a residue. The residue was purified by reverse-MPLC (FA condition, A:water, B:MeCN, 40% B). The fraction were concentrated to remove solvent, and aqueous phase was extracted with ethyl acetate (50 mL*3). The combined organic layers were washed with brine (50 mL), dried over sodium sulfate, filtered and the filtrate was concentrated in vacuum to give Compound 2 (1.3 g, 6.05 mmol, 59% yield) as white solid.

¹H NMR (400 MHz, DMSO-d₆) δ=8.15 (s, 0.5H), 7.95 (s, 0.3H), 7.93 (s, 1H), 7.73 (d, J=7.5 Hz, 1H), 7.66 (d, J=7.5 Hz, 0.3H), 7.37 (d, J=7.5 Hz, 1H), 7.32 (d, J=7.6 Hz, 0.3H), 2.37 (s, 3H), 2.34 (s, 0.9H).

Step 2) 2-(3-bromo-4-methylphenyl)thiazole

To a solution of Compound 2 (255 mg, 1 eq) and 2-bromothiazole (220 mg, 1.34 mmol, 120.88 μL, 1.13 eq) in dioxane (5 mL) and H$_2$O (1 mL) were added Pd(dppf)Cl$_2$ (86.84 mg, 118.69 μmol, 0.1 eq) and Na$_2$CO$_3$ (251.59 mg, 2.37 mmol, 2 eq). The mixture was degassed and purged with nitrogen for 3 times, and then the mixture was stirred at 80° C. for 6 h under nitrogen atmosphere. The reaction mixture was diluted with ethyl acetate (40 mL), and then the resulting organic phase was filtered through celite. The filtrate were washed with water (10 mL) and brine (10 mL), dried over sodium sulfate, filtered and concentrated in vacuum to give a residue. The residue was purified by silica gel chromatography (300-400 mesh silica gel, Petroleum ether/Ethyl acetate=1/0 to 100/1, product came out at Petroleum ether/Ethyl acetate=100/1) to afford crude product. The crude product was purified by reverse-MPLC (FA condition, A:water, B:MeCN, 55% B) to afford Compound 4 (40 mg, 157.39 μmol, 13% yield) as off-white solid.

$^1$H NMR (400 MHz, CDCl3) δ=8.16 (d, J=1.6 Hz, 1H), 7.86 (d, J=3.2 Hz, 1H), 7.78 (dd, J=1.8, 7.9 Hz, 1H), 7.33 (d, J=3.2 Hz, 1H), 7.30 (d, J=7.9 Hz, 1H), 2.44 (s, 3H).

Step 3) (1S,2S)-2-fluoro-N-(6-(2-methyl-5-(thiazol-2-yl)phenyl)benzo[d]thiazol-2-yl)cyclopropane-1-carboxamide. 2 HCl salt To a solution of (1S,2S)-2-fluoro-N-[6-(4,4,5,5-tetramethyl-1,3,2-dioxaborolan-2-yl)-1,3-benzothiazol-2-yl]cyclopropanecarboxamide (57.01 mg, 157.39 μmol, 1 eq) and Compound 4 (40 mg, 157.39 μmol, 1 eq) in dioxane (1 mL) and H$_2$O (0.2 mL) were added Na$_2$CO$_3$ (33.36 mg, 314.78 μmol, 2 eq) and Pd(dppf)Cl$_2$ (11.52 mg, 15.74 μmol, 0.1 eq). The mixture was degassed and purged with nitrogen for 3 times, and then the mixture was stirred at 60° C. for 16 h under nitrogen atmosphere. The reaction mixture was diluted with EtOAc (40 mL), and then the resulting organic phase was washed with water (10 mL) and brine (10 mL), dried over sodium sulfate, filtered and concentrated in vacuum to give a residue. The residue was purified by silica gel chromatography (200-300 mesh silica gel, Petroleum ether/Ethyl acetate=5/1 to 0/1) to afford product. The product was purified by prep-HPLC (HCl condition, column: Phenomenex Synergi C18 150*25*10 um; mobile phase: [water (0.05% HCl)-ACN]; B %: 48%-65%, 10 min), followed by lyophilization to afford Example 92 (25.8 mg, 53.00 μmol, 33% yield, 99% purity, 2HCl) as light yellow solid.

$^1$H NMR (400 MHz, DMSO-d$_6$) δ=12.88 (br s, 1H), 8.16 (d, J=1.3 Hz, 1H), 8.02 (d, J=3.2 Hz, 1H), 7.98 (dd, J=1.8, 7.9 Hz, 1H), 7.95-7.90 (m, 2H), 7.88 (d, J=3.2 Hz, 1H), 7.63-7.53 (m, 2H), 5.33-5.01 (m, 1H), 2.42 (s, 3H), 2.40-2.33 (m, 1H), 1.96-1.77 (m, 1H), 1.53-1.36 (m, 1H); LCMS (electrospray) m/z 410.2 (M+H)+.

Synthetic Method T

Example 95. (1S,2S)-2-fluoro-N-(6-(4-methyl-1H-pyrazol-3-yl)benzo[d]thiazol-2-yl)cyclopropane-1-carboxamide

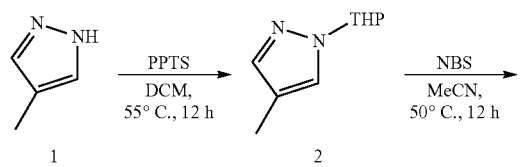

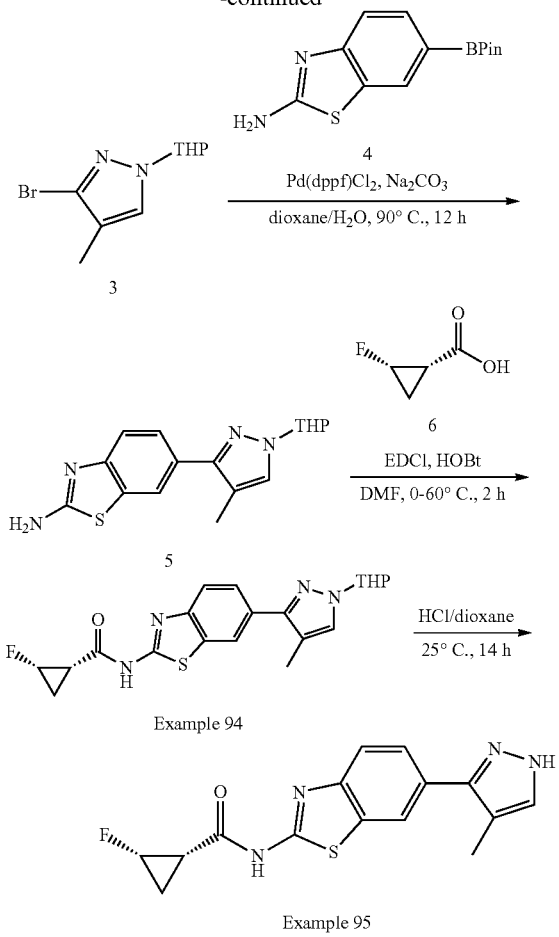

Step 1) 4-methyl-1-(tetrahydro-2H-pyran-2-yl)-1H-pyrazole

To a solution of Compound 1 (2 g, 24.36 mmol, 1.96 mL, 1 eq) in DCM (30 mL) was added PPTS (612.16 mg, 2.44 mmol, 0.1 eq) and 3,4-dihydro-2H-pyran (6.15 g, 73.08 mmol, 6.68 mL, 3 eq). The mixture was stirred at 55° C. for 12 hr. The reaction mixture was concentrated under reduced pressure to remove solvent. The residue was diluted with 80 mL and extracted with ethyl acetate (80 mL*2). The combined organic layers were dried over Na$_2$SO$_4$, filtered and concentrated under reduced pressure to give a residue. The residue was purified by column chromatography (Silica gel, Petroleum ether/Ethyl acetate=50/1 to 5:1). Compound 2 (2.5 g, 15.04 mmol, 61% yield) was obtained as a colorless oil.

$^1$H NMR (400 MHz, CDCl$_3$) δ=7.37 (d, J=6.0 Hz, 2H), 5.32 (dd, J=2.4, 9.7 Hz, 1H), 4.09-3.99 (m, 1H), 3.69 (dt, J=2.8, 11.3 Hz, 1H), 2.08 (s, 3H), 2.07-1.99 (m, 2H), 1.78-1.51 (m, 4H).

Step 2) 3-bromo-4-methyl-1-(tetrahydro-2H-pyran-2-yl)-1H-pyrazole

To a solution of Compound 2 (2.3 g, 13.84 mmol, 1 eq) in MeCN (23 mL) was added NBS (2.46 g, 13.84 mmol, 1 eq). The mixture was stirred at 55° C. for 12 hr. The reaction mixture was concentrated under reduced pressure to remove solvent. The residue was purified by column chromatography (silica gel, Petroleum ether/Ethyl acetate=1:0 to 50:1). Compound 3 (2.4 g, 9.79 mmol, 70% yield) was obtained as a yellow oil.

¹H NMR (400 MHz CDCl₃) δ=7.34 (s, 1H), 5.26 (dd, J=2.4, 9.4 Hz, 1H), 4.09-3.99 (m, 1H), 3.72-3.62 (m, 1H), 2.06-2.03 (m, 2H), 2.02 (d, J=0.7 Hz, 3H), 1.78-1.54 (m, 4H).

Step 3) 6-(4-methyl-1-(tetrahydro-2H-pyran-2-yl)-1H-pyrazol-3-yl)benzo[d]thiazol-2-amine To a solution of Compound 3 (1 g, 4.08 mmol, 1 eq) and Compound 4 (1.13 g, 4.08 mmol, 1 eq) in dioxane (10 mL) and H₂O (3 mL) was added Na₂CO₃ (864.81 mg, 8.16 mmol, 2 eq) and Pd(dppf)Cl₂ (298.51 mg, 407.97 μmol, 0.1 eq). The mixture was stirred at 90° C. for 12 hr under N₂. The reaction mixture was concentrated under reduced pressure to remove solvent. The residue was purified by column chromatography (silica gel, Petroleum ether/Ethyl acetate=20/1 to 1:1). Compound 5 (780 mg, 2.11 mmol, 51% yield, 85% purity) was obtained as a yellow solid.

Step 4) (1S,2S)-2-fluoro-N-(6-(4-methyl-1-(tetrahydro-2H-pyran-2-yl)-1H-pyrazol-3-yl)benzo[d]thiazol-2-yl)cyclopropane-1-carboxamide To a solution of Compound 5 (350 mg, 946.23 μmol, 1 eq) and Compound 6 (136.43 mg, 1.31 mmol, 1.39 eq) in DMF (5 mL) was added EDCI (418.80 mg, 2.18 mmol, 2.31 eq) and HOBt (295.20 mg, 2.18 mmol, 2.31 eq) at 0° C. The mixture was stirred at 60° C. for 2 hr. The reaction mixture was diluted with water 30 mL and extracted with ethyl acetate (30 mL*2). The combined organic layers were washed with brine (30 mL*2), dried over Na₂SO₄, filtered and concentrated under reduced pressure to give a residue. The residue was purified by prep-HPLC (column: Luna C18 150*25 5 u; mobile phase: [water (0.225% FA)-ACN]; B %: 48%-68%, 7.8 min). Example 94 (200 mg, 482.83 μmol, 51% yield, 96% purity) was obtained as a white solid. (50 mg would be delivered).

¹H NMR (400 MHz, DMSO-d₆) δ=12.72 (br s, 1H), 8.22 (s, 1H), 7.81-7.71 (m, 3H), 5.36 (dd, J=2.1, 10.0 Hz, 1H), 5.16-4.92 (m, 1H), 3.94 (br d, J=11.9 Hz, 1H), 3.68-3.58 (m, 1H), 2.28-2.19 (m, 4H), 2.16-2.05 (m, 1H), 2.02-1.89 (m, 2H), 1.81-1.65 (m, 2H), 1.60-1.50 (m, 2H), 1.31 (tdd, J=6.4, 8.9, 12.8 Hz, 1H); LCMS (electrospray) m/z 401.1 (M+H)+.

Step 5) (1S,2S)-2-fluoro-N-(6-(4-methyl-1H-pyrazol-3-yl)benzo[d]thiazol-2-yl)cyclopropane-1-carboxamide Example 94 (140 mg, 338.61 μmol, 1 eq) was added to HCl/dioxane (4 M, 3 mL, 35.44 eq). The mixture was stirred at 25° C. for 2 hr. LCMS showed ~59% of starting material was remained and ~40% of desired mass was detected. Then the mixture was stirred at 40° C. for 12 hr. The reaction mixture was concentrated under reduced pressure to remove solvent. The residue was diluted with water 20 mL and extracted with DCM (20 mL*2). The combined organic layers were dried over Na2SO4, filtered and concentrated under reduced pressure to give a residue. The residue was purified by prep-HPLC (column: Luna C18 150*25 5 u; mobile phase: [water (0.225% FA)-ACN]; B %: 31%-51%, 7.8 min). Example 95 (41.4 mg, 130.87 μmol, 38% yield, 100% purity) was obtained as a white solid.

¹H NMR (400 MHz, DMSO-d₆) δ=12.46 (br s, 2H), 8.15 (s, 1H), 7.80-7.75 (m, 1H), 7.74-7.66 (m, 1H), 7.47 (br s, 1H), 5.12-4.88 (m, 1H), 2.30-2.19 (m, 4H), 1.85-1.70 (m, 1H), 1.36-1.22 (m, 1H); LCMS (electrospray) m/z 317.2 (M+H)+.

Synthetic Method U

Example 99. (1S,2S)-2-fluoro-N-(4-methyl-2-oxo-2,3-dihydro-[5,6'-bibenzo[d]thiazol]-2'-yl)cyclopropane-1-carboxamide

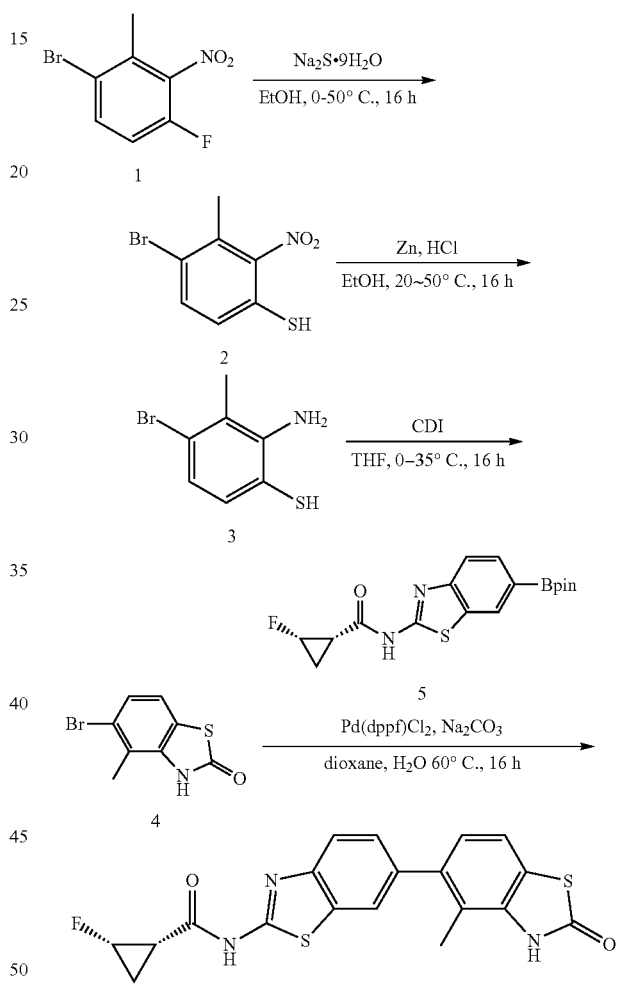

Example 99

Step 1) 4-bromo-3-methyl-2-nitrobenzenethiol

To a solution of Na₂S.9H₂O (16.42 g, 68.37 mmol, 11.48 mL, 2 eq) in EtOH (80 mL) was dropwise added Compound 1 (8 g, 34.18 mmol, 1 eq). The mixture was stirred at 50° C. for 2 hr. The reaction was quenched by HCl to pH=5 slowly and then extracted with Ethyl acetate (80 mL*2). The combined organic phase was washed with water (80 mL*2), dried over anhydrous Na₂SO₄, filtered and concentrated in vacuum. Compound 2 (2.5 g, crude) as a green solid.

¹H NMR (400 MHz, CDCl₃) δ=7.21 (d, J=8.3 Hz, 1H), 6.93 (d, J=8.3 Hz, 1H), 4.53 (br s, 1H), 2.32-2.29 (m, 3H).

Step 2) 2-amino-4-bromo-3-methylbenzenethiol

To a solution of Compound 2 (2.5 g, 10.08 mmol, 1 eq) (crude) in EtOH (25 mL) was added HCl (55.11 g, 151.15 mmol, 54.03 mL, 10% purity, 15 eq) at 0° C. Then Zn (7.06 g, 107.92 mmol, 10.71 eq) was added and the mixture was stirred at 35° C. for 2 hr. The reaction mixture was concentrated under reduced pressure to remove solvent. Then water phase was washed with Petroleum ether (100 mL*2). Then water phase by solid NaHCO$_3$ to pH=5 slowly and filtered, the filter cake was concentrated in vacuum, then filtrate was extracted with Ethyl acetate (100 mL*2). The combined organic phase was washed with brine (50 mL*2), dried over anhydrous Na$_2$SO$_4$, filtered and concentrated in vacuum. Compound 3 (0.99 g, 4.54 mmol, 45% yield) was obtained as a white solid.

$^1$H NMR (400 MHz, DMSO-d$_6$) δ=7.14-7.09 (m, 1H), 6.94-6.86 (m, 1H), 5.59-5.49 (m, 2H), 2.28 (s, 3H).

Step 3) 5-bromo-4-methylbenzo[d]thiazol-2(3H)-one

To a solution of CDI (661.64 mg, 4.08 mmol, 1 eq) in THF (9 mL) was dropwise added Compound 3 (0.89 g, 4.08 mmol, 1 eq) at 0° C. Then reaction mixture was added and the mixture was stirred at 35° C. for 16 hr. The reaction mixture was filtered and the filtrate was concentrated in vacuum. The residue was extracted with Ethyl acetate (100 mL*2). The combined organic phase was washed with water (100 mL*2). The organic layer was dried over anhydrous Na$_2$SO$_4$. The solution was filtered and concentrated in vacuum. Compound 4 (1.05 g, crude) was obtained as a off-white solid.

$^1$H NMR (400 MHz, DMSO-d$_6$) δ=12.28-11.73 (m, 1H), 7.33 (d, J=4.0 Hz, 2H), 2.39 (s, 3H)

Step 4) (1S,2S)-2-fluoro-N-(4-methyl-2-oxo-2,3-dihydro-[5,6'-bibenzo[d]thiazol]-2'-yl)cyclopropane-1-carboxamide A mixture of Compound 4 (500 mg, 2.05 mmol, 1 eq), Compound 5 (506.47 mg, 1.40 mmol, 6.82e-1 eq), Pd(dppf)Cl$_2$ (75.00 mg, 102.50 μmol, 0.05 eq), Na$_2$CO$_3$ (434.55 mg, 4.10 mmol, 2 eq) in dioxane (10 mL) and H$_2$O (2 mL) was degassed and purged with N$_2$ for 3 times, and then the mixture was stirred at 80° C. for 16 hr under N$_2$ atmosphere. The reaction mixture was concentrated in vacuum. The crude product was purified by prep-HPLC (column: Phenomenex Synergi C18 150*25*10 um; mobile phase: [water (0.05% HCl)-ACN]; B %: 35%-55%, 11 min) to give product. Example 99 (53 mg, 117.93 μmol, 5% yield, 97% purity, HCl) as a white solid.

$^1$H NMR (400 MHz, DMSO-d$_6$) δ=12.75-12.70 (m, 1H), 11.78-11.74 (m, 1H), 7.95 (d, J=1.5 Hz, 1H), 7.79 (d, J=8.3 Hz, 1H), 7.47 (d, J=8.1 Hz, 1H), 7.41-7.37 (m, 1H), 7.08 (s, 1H), 5.17-4.94 (m, 1H), 2.29-2.18 (m, 4H), 1.81-1.71 (m, 1H), 1.36-1.28 (m, 1H): LCMS (electrospray) m/z 400.1 (M+H)+.

Synthetic Method V

Example 107. (1S,2S)-2-fluoro-N-(6-(7-methyl-1H-indazol-4-yl)benzo[d]thiazol-2-yl)cyclopropane-1-carboxamide

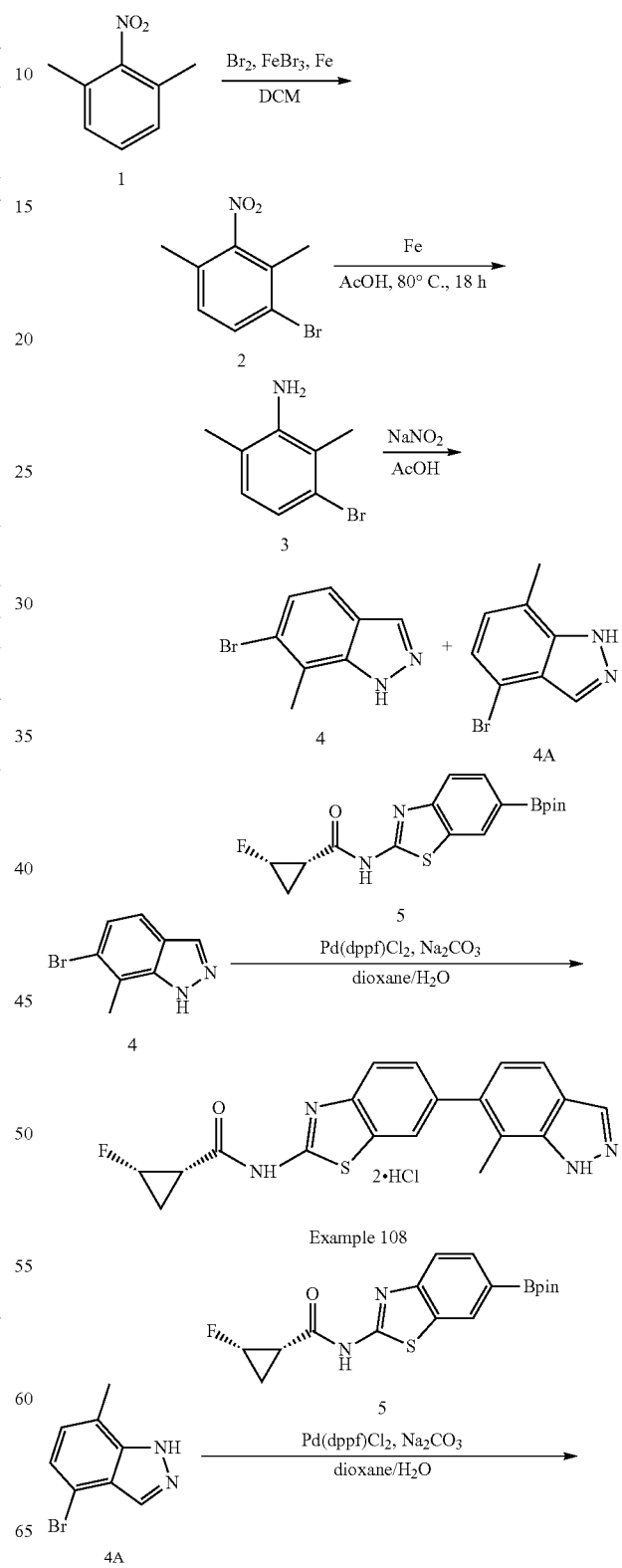

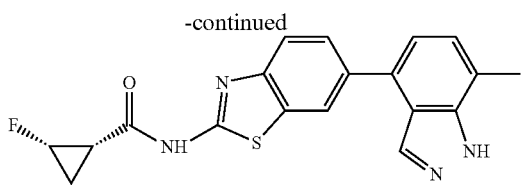

Example 107

Step 1) 1-bromo-2,4-dimethyl-3-nitrobenzene

To a solution of Compound 1 (5 g, 33.08 mmol, 4.50 mL, 1 eq), FeBr$_3$ (195.52 mg, 661.54 μmol, 0.02 eq) and Fe (461.80 mg, 8.27 mmol, 0.25 eq) in DCM (50 mL) was added Br$_2$ (5.81 g, 36.38 mmol, 1.88 mL, 1.1 eq) of DCM (5 mL) dropwise at 15° C. The mixture was stirred at 30° C. for 20 hr. TLC showed the reaction was completed. The mixture was washed by saturated sodium sulfite water solution (100 mL*2), the organic phase was washed with brine (150 mL) and dried with anhydrous sodium sulfate (Na$_2$SO$_4$), filtered and concentrated in vacuum. The residue was used to the next step without any purification. Compound 2 (7.2 g, 31.30 mmol, 94% yield) was obtained as white solid.

$^1$H NMR (400 MHz, CDCl$_3$) δ=7.56 (d, J=8.2 Hz, 1H), 7.02 (d, J=8.2 Hz, 1H), 2.35 (s, 3H), 2.26 (s, 3H).

Step 2) 3-bromo-2,6-dimethylaniline

To a solution of Compound 2 (7.2 g, 31.30 mmol, 1 eq) in AcOH (80 mL) was added Fe (6.99 g, 125.19 mmol, 4 eq) at 10° C. The mixture was stirred at 80° C. for 18 hr. TLC indicated the reaction was completed. The mixture was filtered and the filtrate was neutralized with saturated sodium hydroxide aqueous solution. The aqueous phase was extracted with Ethyl acetate (100 mL*2), the organic phase was washed with brine (150 mL) and dried with anhydrous sodium sulfate (Na$_2$SO$_4$), filtered and concentrated in vacuum. The residue was purified by silica gel chromatography eluted with Petroleum ether/Ethyl acetate=5:1. Compound 3 (4.6 g, 22.99 mmol, 73% yield) was obtained as brown oil.

$^1$H NMR (400 MHz, CDCl$_3$) δ=6.94 (d, J=8.1 Hz, 1H), 6.80 (d, J=8.1 Hz, 1H), 3.84-3.49 (m, 2H), 2.30 (s, 3H), 2.14 (s, 3H).

Step 3) 4-bromo-7-methyl-1H-indazole

To a solution of Compound 3 (4.1 g, 20.49 mmol, 1 eq) in AcOH (50 mL) was added NaNO$_2$ (1.70 g, 24.59 mmol, 1.2 eq) in H$_2$O (10 mL) dropwise at 0° C. for 30 min. The mixture was stirred at 15° C. for 18 hr. LC-MS showed the reaction was completed. The mixture was poured into H2O (100 mL), the aqueous phase was extracted with ethyl acetate (150 mL*2). The combined organic phase was washed with brine (200 mL), dried with anhydrous Na$_2$SO$_4$, filtered and concentrated in vacuum to afford 5 g crude product. 2 g of the crude product was purified by prep-HPLC (column: Phenomenex luna C18 250*50 mm*10 μm; mobile phase: [water (0.05% HCl)-ACN]; B %: 30%-60%, 30 min, 40% min), followed by lyophilization to afford 0.3 g white solid, 0.3 g white solid was purified by prep-HPLC (column: Phenomenex Synergi C18 150*25*10 um; mobile phase: [water (0.05% HCl)-ACN]; B %: 30%-50%, 11 min), followed by lyophilization. Compound 4 (75 mg, 355.35 μmol, 1% yield) was obtained as white solid. Compound 4A (195 mg, 923.92 μmol, 4% yield) was obtained as white solid.

Compound 4 $^1$H NMR (400 MHz, METHANOL-d$_4$) δ=8.02 (s, 1H), 7.50 (d, J=8.6 Hz, 1H), 7.29 (d, J=8.6 Hz, 1H), 2.61 (s, 3H).

Compound 4A $^1$H NMR (400 MHz, METHANOL-d$_4$) δ=7.99 (s, 1H), 7.20 (d, J=7.5 Hz, 1H), 7.04 (dd, J=0.9, 7.5 Hz, 1H), 2.52 (d, J=0.6 Hz, 3H).

Step 4) (1S,2S)-2-fluoro-N-(6-(7-methyl-1H-indazol-4-yl)benzo[d]thiazol-2-yl)cyclopropane-1-carboxamide To a solution of Compound 4A (195 mg, 923.92 μmol, 1 eq) and Compound 5 (401.60 mg, 1.11 mmol, 1.2 eq) in dioxane (3 mL) and H$_2$O (0.5 mL) were added Na$_2$CO$_3$ (293.77 mg, 2.77 mmol, 3 eq) and Pd(dppf)Cl$_2$ (135.21 mg, 184.78 μmol, 0.2 eq) at 10° C. The mixture was stirred at 60° C. for 18 hr. LC-MS showed the reaction was completed. The mixture was poured into H$_2$O (10 mL), a lot of yellow solid formed, filtered and the filter cake was concentrated in vacuum. The filter cake was purified by triturated with Methanol (10 mL), filtered and the filter cake was concentrated. Example 107 (149.2 mg, 385.61 μmol, 41% yield, 94% purity) was obtained as yellow solid.

$^1$H NMR (400 MHz, DMSO-d$_6$) δ=13.30 (br s, 1H), 12.74 (br s, 1H), 8.35-8.20 (m, 2H), 7.90-7.83 (m, 1H), 7.81-7.74 (m, 1H), 7.21 (br s, 2H), 5.17-4.93 (m, 1H), 2.57 (s, 3H), 2.24 (br s, 1H), 1.83-1.69 (m, 1H), 1.31 (br s, 1H): LCMS (electrospray) m/z 367.0 (M+H)+.

Example 108. (1S,2S)-2-fluoro-N-(6-(7-methyl-1H-indazol-6-yl)benzo[d]thiazol-2-yl)cyclopropane-1-carboxamide

Step 1) (1S,2S)-2-fluoro-N-(6-(7-methyl-1H-indazol-6-yl)benzo[d]thiazol-2-yl)cyclopropane-1-carboxamide To a solution of Compound 4 (75 mg, 355.35 μmol, 1 eq) and Compound 5 (154.46 mg, 426.42 μmol, 1.2 eq) in dioxane (2 mL) and H$_2$O (0.5 mL) were added Na$_2$CO$_3$ (112.99 mg, 1.07 mmol, 3 eq) and Pd(dppf)Cl$_2$ (52.00 mg, 71.07 μmol, 0.2 eq) at 10° C. The mixture was stirred at 60° C. for 18 hr. LC-MS showed the reaction was completed. The mixture was poured into Petroleum ether (10 mL), filtered with silica gel and the filtrate was concentrated in vacuum. The residue was purified by prep-HPLC (column: Phenomenex Synergi C18 150*25*10 um; mobile phase: [water (0.05% HCl)-ACN]; B %: 30%-60%, 10 min), followed by lyophilization. Example 108 (26.4 mg, 59.61 μmol, 16% yield, 99% purity, 2HCl) was obtained as white solid, which was checked by 2D NMR.

$^1$H NMR (400 MHz, METHANOL-d$_4$) δ=8.31 (s, 1H), 7.90 (s, 1H), 7.84 (d, J=8.3 Hz, 1H), 7.73 (d, J=8.4 Hz, 1H), 7.48 (d, J=8.3 Hz, 1H), 7.22 (d, J=8.3 Hz, 1H), 5.09-4.97 (m, 1H), 5.09-4.94 (m, 1H), 2.51 (s, 3H), 2.24-2.16 (m, 1H), 1.95-1.82 (m, 1H), 1.39-1.27 (m, 1H): LCMS (electrospray) m/z 367.1 (M+H)+.

Synthetic Method W

Example 111. (1S,2S)-2-fluoro-N-(6'-methyl-[6,7'-bibenzo[d]thiazol]-2-yl)cyclopropane-1-carboxamide

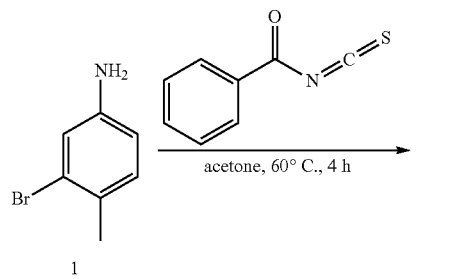

1

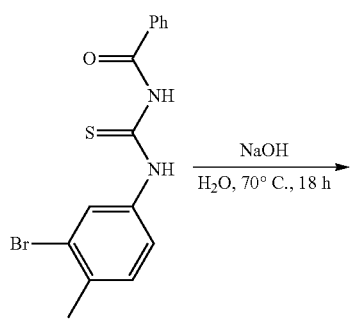

2

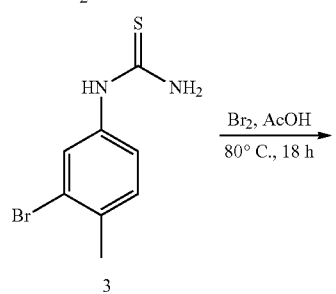

3

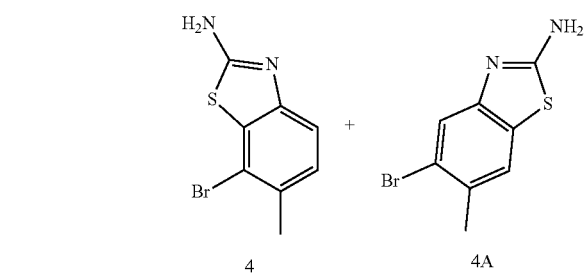

4     4A

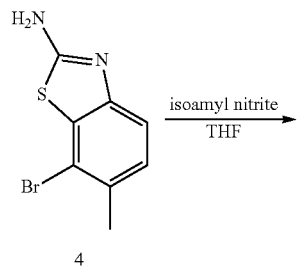

4

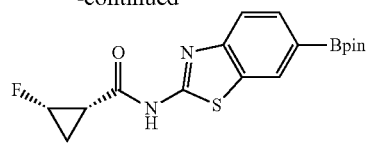

5

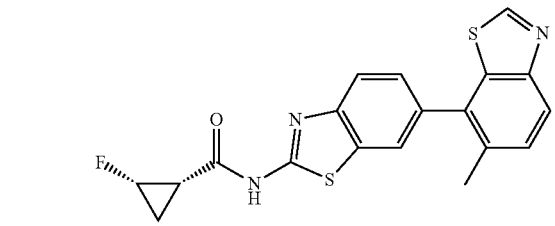

6

Example 111

Step 1) N-((3-bromo-4-methylphenyl)carbamothioyl)benzamide

To a solution of Compound 1 (5 g, 26.87 mmol, 1 eq) in acetone (50 mL) was added benzoyl isothiocyanate (4.39 g, 26.87 mmol, 3.62 mL, 1 eq) in acetone (10 mL) dropwise at 60° C. The mixture was refluxed at 60° C. for 4 hr. TLC (Petroleum ether/Ethyl acetate=5/1) showed Compound 1 was consumed and a main spot. The mixture was concentrated. The residue was purified by triturated with Petroleum ether (60 mL) and Ethyl acetate (6 mL). Compound 2 (8.77 g, 25.11 mmol, 93% yield) was obtained as white solid.

$^1$H NMR (400 MHz, CDCl$_3$) δ=12.58-12.23 (m, 1H), 9.20-9.02 (m, 1H), 8.01-7.85 (m, 3H), 7.72-7.64 (m, 1H), 7.60-7.54 (m, 3H), 7.30 (s, 1H), 2.46-2.40 (m, 3H).

Step 2) 1-(3-bromo-4-methylphenyl)thiourea

To a solution of Compound 2 (8.77 g, 25.11 mmol, 1 eq) in H$_2$O (80 mL) was added NaOH (4.02 g, 100.45 mmol, 4 eq) at 10° C. The mixture was stirred at 70° C. for 18 hr. TLC (Petroleum ether/Ethyl acetate=5/1) showed Compound 2 was consumed and a main spot. T The mixture was acidified with hydrochloric acid solution (2 N) to PH=2-3 and a lot of white solid formed. The reaction mixture was filtered and the filter cake was dried. The residue was purified by triturated with Ethyl acetate (40 mL). Compound 3 (4.65 g, 18.97 mmol, 75% yield) was obtained as white solid.

$^1$H NMR (400 MHz, METHANOL-d$_4$) δ=7.61 (s, 1H), 7.31-7.26 (m, 1H), 7.24-7.19 (m, 1H), 2.37 (s, 3H).

Step 3) 7-bromo-6-methylbenzo[d]thiazol-2-amine

To a solution of Compound 3 (4.65 g, 18.97 mmol, 1 eq) in CH3COOH (80 mL) was added Br$_2$ (3.33 g, 20.87 mmol, 1.08 mL, 1.1 eq) at 10° C. The mixture was stirred at 80° C. for 18 hr. The mixture was poured into H$_2$O (80 mL), the aqueous phase was extracted with ethyl acetate (100 mL*2). The combined organic phase was washed with brine (100 mL), dried with anhydrous Na$_2$SO$_4$, filtered and concentrated in vacuum. The residue was purified by triturated with Petroleum ether (50 mL) and Ethyl acetate (10 mL), filtered and the filter cake was concentrated to afford 7-bromo-6-methyl-1,3-benzothiazol-2-amine. The filter liquor was concentrated, purified by silica gel chromatography eluted with Petroleum ether/Ethyl acetate=1:1 to afford 5-bromo-6-methyl-1,3-benzothiazol-2-amine. Compound 4 (1.3 g, 5.34 mmol, 28% yield, 99% purity) was obtained as white solid. Compound 4A (870 mg, 3.58 mmol, 18% yield) was obtained as white solid.

Compound 4 $^1$H NMR (400 MHz, DMSO-d$_6$) δ=7.55 (s, 2H), 7.24-7.20 (m, 1H), 7.19-7.15 (m, 1H), 2.35 (s, 3H).

Compound 4A $^1$H NMR (400 MHz, CDCl$_3$) δ=7.73 (s, 1H), 7.45 (s, 1H), 5.21 (br s, 2H), 2.45 (s, 3H).

Step 4) 7-bromo-6-methylbenzo[d]thiazole

To a solution of Compound 4 (300 mg, 1.23 mmol, 1 eq) in THF (10 mL) was added ISOAMYL NITRITE (288.81 mg, 2.47 mmol, 331.97 μL, 2 eq) at 10° C. The mixture was stirred at 70° C. for 18 hr. LC-MS showed Compound 4 was consumed and a main peak of desired mass. The mixture was poured into H$_2$O (20 mL), the aqueous solution was extracted with ethyl acetate (30 mL*2). The combined organic phase was washed with brine (50 mL), dried with anhydrous Na$_2$SO$_4$, filtered and concentrated in vacuum. TLC (Petroleum ether/Ethyl acetate=10:1) showed a main spot. The residue was purified by silica gel chromatography eluted with Petroleum ether/Ethyl acetate=10:1. Compound 5 (180 mg, 788.31 μmol, 63% yield, 99% purity) was obtained as yellow solid.

Step 5) (1S,2S)-2-fluoro-N-(6'-methyl-[6,7'-bibenzo[d]thiazol]-2-yl)cyclopropane-1-carboxamide To a solution of Compound 5 (160 mg, 700.72 μmol, 1 eq) and Compound 6 (304.58 mg, 840.86 μmol, 1.2 eq) in dioxane (3 mL) and H$_2$O (0.6 mL) were added Pd(dppf)Cl$_2$ (102.54 mg, 140.14 μmol, 0.2 eq) and Na$_2$CO$_3$ (74.27 mg, 700.72 μmol, 1 eq) at 10° C. The mixture was stirred at 60° C. for 18 hr. The mixture was poured into Petroleum ether (10 mL), filtered with silica gel and the filtrate was concentrated in vacuum. The residue was purified by prep-HPLC (column: Phenomenex Synergi C18 150*25*10 um; mobile phase: [water (0.05% HCl)-ACN]; B %: 44%-64%, 9 min), followed by lyophilization. Example 111 (60 mg, 156.31 μmol, 22% yield, 99% purity) was obtained as yellow solid.

$^1$H NMR (400 MHz, METHANOL-d$_4$) δ=9.60 (s, 1H), 8.02 (d, J=8.4 Hz, 1H), 7.99 (d, J=1.3 Hz, 1H), 7.94 (d, J=8.3 Hz, 1H), 7.69 (d, J=8.4 Hz, 1H), 7.52 (dd, J=1.7, 8.3 Hz, 1H), 5.05 (dt, J=3.9, 6.2 Hz, 1H), 2.39 (s, 3H), 2.22 (dtd, J=4.3, 6.9, 9.1 Hz, 1H), 1.96-1.83 (m, 1H), 1.39-1.28 (m, 1H): LCMS (electrospray) m/z 384.0 (M+H)+.

Synthetic Method X

Example 112. (1S,2S)-2-fluoro-N-methyl-N-(6-(4-methylpyridin-3-yl)benzo[d]thiazol-2-yl)cyclopropane-1-carboxamide

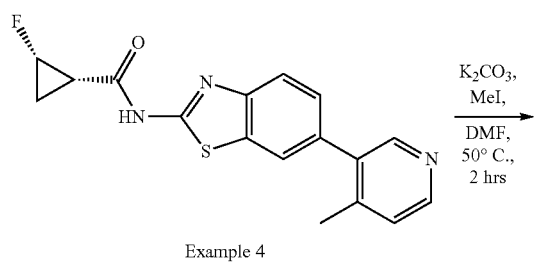

Example 4

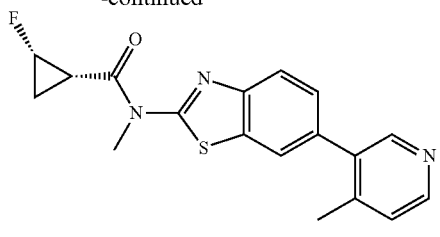

Example 112

MeI (28 μl, 0.45 mmol, 1.5 eq.) was dissolved in N,N-dimethyl formamide (1 ml) and was dropwised to a stirred solution of Example 4 (100 mg, 0.3 mmol, 1 eq.) and K$_2$CO$_3$ (124 mg, 0.9 mmol, 3 eq.) in N,N-dimethyl formamide (2 ml). The mixture was stirred at 50° C. for 2 hrs under N$_2$. After completion of the reaction, the reaction mixture was extracted with Ethyl Acetate (20 ml×2) and Water (20 ml), the combined organic layers were dried over Mg$_2$SO$_4$, filtered and concentrated under reduced pressure to give a crude product. The residue was purified by short path silica gel column chromatography (EA 100% gradient). The resulting precipitations were collected by filtration and washed by Ether and dried to give Example 112 as a white solid. (47 mg, 0.14 mmol, yield 46%).

$^1$H NMR (400 MHz, DMSO-d$_6$) δ=8.44-8.41 (m, 2H), 8.04 (d, J=1.6 Hz, 1H), 7.89 (d, J=8.4 Hz, 1H), 7.47 (dd, J12=1.6 Hz, J13=8.4 Hz, 1H), 7.35 (t, J=7.35 Hz, 1H), 5.21 (J12=2.9 Hz, J13=66.27 Hz, 1H), 3.95 (s, N—CH3, 3H), 2.66-2.62 (m, 1H), 2.29 (s, Me, 3H), 1.83-1.79 (m, 1H), 1.35-1.31 (m, 1H): LCMS (electrospray) m/z 342.1 (M+H)+.

Synthetic Method Y

Example 113. (1S,2S)-2-fluoro-N-(6-(6-(fluoromethyl)-4-methylpyridin-3-yl)benzo[d]thiazol-2-yl)cyclopropane-1-carboxamide. TFA salt

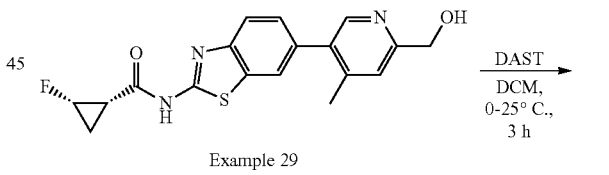

Example 29

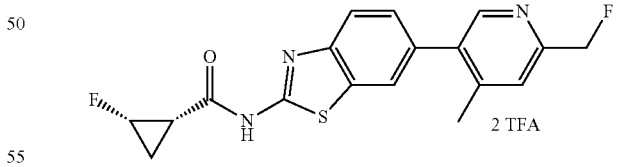

Example 113

To a solution of Example 29 (380 mg, 1.06 mmol, 1 eq) in DCM (5 mL) was added DAST (685.52 mg, 4.25 mmol, 561.90 μL, 4 eq) at 0° C. The mixture was stirred at 30° C. for 3 hr under N2 atmosphere. The reaction mixture was diluted with DCM (5 mL), and then the resulting organic phase was washed with saturated sodium bicarbonate aqueous solution (10 mL) and brine (10 mL), dried over sodium sulfate, filtered and the filtrate was concentrated in vacuum to give a residue. The residue was purified by pre-HPLC (column: Phenomenex Synergi C18 150*25*10 um; mobile phase: [water (0.1% TFA)-ACN]; B %: 20%-50%, 10 min).

Example 113 (62 mg, 102.38 μmol, 9% Yield, 97% Purity, 2TFA) was Obtained as a Light Yellow Solid $^1$H NMR (400 MHz, DMSO-$d_6$) δ=1.32 (ddt, J=12.84, 8.99, 6.33, 6.33 Hz, 1H), 1.69-1.82 (m, 1H), 2.20-2.28 (m, 1H), 2.36 (s, 3H), 4.93-5.17 (m, 1H), 5.46 (s, 1H), 5.57 (s, 1H), 7.48 (dd, J=8.31, 1.83 Hz, 1H), 7.53 (s, 1H), 7.84 (d, J=8.31 Hz, 1H), 8.07 (d, J=1.59 Hz, 1H), 8.48 (s, 1H), 12.77 (br s, 1H); LCMS (electrospray) m/z 360.0 (M+H)+.

Synthetic Method Z

Example 114. (1S,2S)-2-fluoro-N-(6-(6-fluoro-5-methyl-1H-indol-4-yl)benzo[d]thiazol-2-yl)cyclopropane-1-carboxamide. 2HCl salt

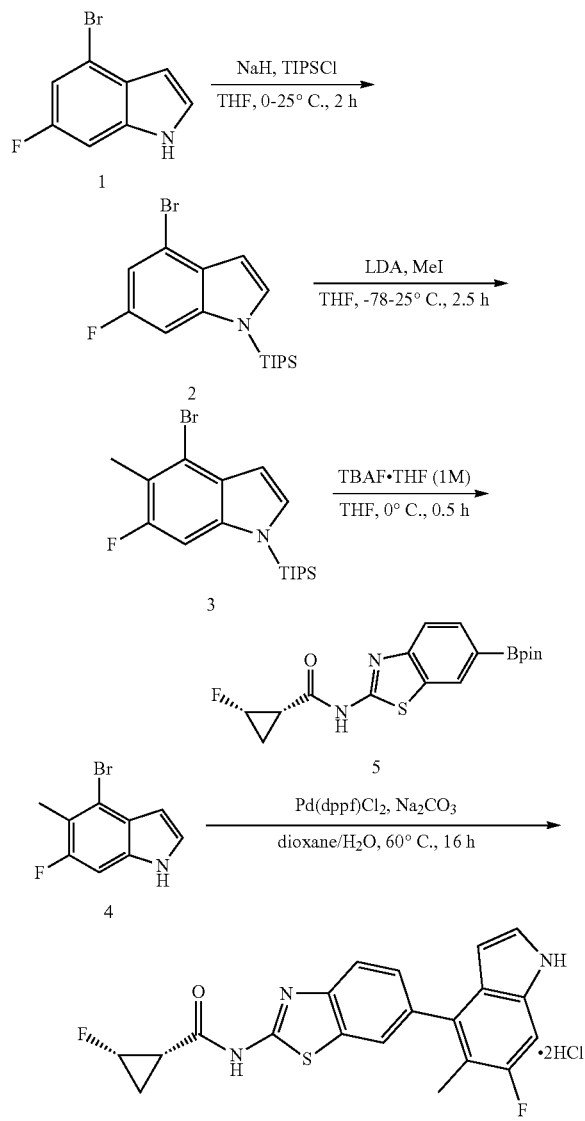

Example 114

Step 1) 4-bromo-6-fluoro-1-(triisopropylsilyl)-1H-indole

To a solution of Compound 1 (900 mg, 4.20 mmol, 1 eq) in THF (9 mL) were added NaH (201.82 mg, 5.05 mmol, 60% purity, 1.2 eq) at 0° C. for 30 min. Then TIPSCl (972.86 mg, 5.05 mmol, 1.08 mL, 1.2 eq) was added to the mixture. The mixture was stirred at 25° C. for 1.5 hr. The reaction mixture was diluted with water 20 mL and extracted with ethyl acetate (20 mL*2). The combined organic layers were washed with brine (20 mL), dried over Na2SO4, filtered and the filtrate was concentrated under reduced pressure to give a residue. The residue was purified by column chromatography (Silical gel, Petroleum ether:Ethyl acetate=1:0 to 100:1). Compound 2 (1.5 g, 4.05 mmol, 96% yield) was obtained as a yellow oil.

$^1$H NMR (400 MHz, CDCl$_3$) δ=7.28-7.26 (m, 1H), 7.19-7.10 (m, 2H), 6.65 (dd, J=0.9, 3.3 Hz, 1H), 1.67 (m, J=7.5 Hz, 3H), 1.15 (d, J=7.6 Hz, 18H).

Step 2) 4-bromo-6-fluoro-5-methyl-1-(triisopropylsilyl)-1H-indole

To a solution of Compound 2 (500 mg, 1.35 mmol, 1 eq) in THF (5 mL) was added LDA (2 M, 1.01 mL, 1.5 eq) at −78° C. for 30 min under N2 atmosphere. Then MeI (287.42 mg, 2.02 mmol, 126.06 μL, 1.5 eq) was added to the mixture. The mixture was stirred at 25° C. for 2 hr. The reaction mixture was quenched by addition with saturated NH4Cl aqueous (3 mL) at 25° C., and then diluted with water 20 mL and extracted with ethyl acetate (20 mL*2). The combined organic layers were washed with brine (40 mL), dried over Na2SO4, filtered and the filtrate was concentrated under reduced pressure to give a crude product. Compound 3 (500 mg, crude) were obtained as a yellow oil, which used into the next step without further purification.

Step 3) 4-bromo-6-fluoro-5-methyl-1H-indole

To a solution of Compound 3 (500 mg, 1.30 mmol, 1 eq) in THF (8 mL) was added TBAF•THF (1 M, 1.30 mL, 1 eq) at 0° C. The mixture was stirred at 0° C. for 0.5 hr. The reaction mixture was concentrated under reduced pressure to remove solvent. The residue was diluted with water 20 mL and extracted with ethyl acetate (20 mL*2). The combined organic layers were washed with brine (30 mL), dried over Na2SO4, filtered and the filtrate was concentrated under reduced pressure to give a residue. The residue was purified by prep-TLC (Silical gel plate, Petroleum ether:Ethyl acetate=5:1) to give a crude product. The crude product was purified by prep-HPLC (column: Phenomenex Synergi C18 150*25*10 um; mobile phase: [water (0.1% TFA)-ACN]; B %: 48%-78%, 10 min). The cut fraction was concentrated under reduced pressure to remove ACN, the residue was washed with saturated NaHCO3 aqueous (10 mL). The mixture was extracted with ethyl acetate (20 mL*2). The combined organic layers were washed with brine (30 mL), dried over Na2SO4, filtered and the filtrate was concentrated under reduced pressure to give a product. Compound 4 (100 mg, 438.48 μmol, 33% yield) was obtained as a yellow solid.

$^1$H NMR (400 MHz, CDCl$_3$) δ=8.21 (s, 1H), 7.20 (dd, J=2.4, 3.2 Hz, 1H), 7.06 (d, J=9.8 Hz, 1H), 6.60-6.52 (m, 1H), 2.44 (d, J=2.6 Hz, 3H).

Step 4) (1S,2S)-2-fluoro-N-(6-(6-fluoro-5-methyl-1H-indol-4-yl)benzo[d]thiazol-2-yl)cyclopropane-1-carboxamide. 2HCl salt To a solution of Compound 4 (100 mg, 438.48 μmol, 1 eq) and Compound 5 (190.59 mg, 526.18 μmol, 1.2 eq) in dioxane (2 mL) and H2O (0.5 mL) was added Pd(dppf)Cl2 (32.08 mg, 43.85 µmol, 0.1 eq) and Na2CO3 (92.95 mg, 876.96 µmol, 2 eq) under N2 atmosphere. The mixture was stirred at 60° C. for 16 hr under N2 atmosphere. The reaction mixture was diluted with water 20 mL and extracted with Ethyl acetate (10 mL*2). The combined organic layers were washed with brine (20 mL), dried over Na2SO4, filtered and the filtrate was concentrated under reduced pressure to give a residue. The residue was purified by prep-HPLC (column: Phenomenex Synergi C18 150*25*10 um; mobile phase: [water (0.05% HCl)-ACN]; B %: 43%-63%, 10 min).

Example 114 (14.4 mg, 27.77 µmol, 6% yield, 88% purity, 2HCl) was obtained as a purple solid.

$^1$H NMR (400 MHz, DMSO-$d_6$) δ=12.75 (s, 1H), 11.14 (s, 1H), 7.98 (d, J=1.4 Hz, 1H), 7.85 (d, J=8.3 Hz, 1H), 7.45-7.40 (m, 1H), 7.29-7.25 (m, 1H), 7.19 (d, J=10.5 Hz, 1H), 6.04-6.00 (m, 1H), 5.16-4.94 (m, 1H), 2.30-2.19 (m, 1H), 2.14 (d, J=2.6 Hz, 3H), 1.84-1.68 (m, 1H), 1.38-1.25 (m, 1H); LCMS (electrospray) m/z 384.10 (M+H)+.

Table 1 below shows the compounds of Examples along with general synthetic methods used to make the compounds and characterization data.

TABLE 1

Compounds of Examples

| Ex # | Structure/Name | $^1$H NMR/MS (M + 1) | Synthetic Method |
|---|---|---|---|
| 1 | 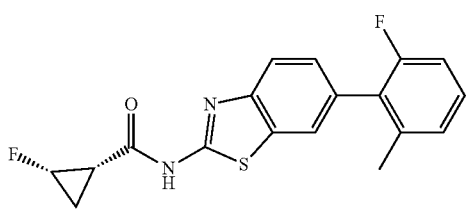<br>(1S,2S)-2-fluoro-N-(6-(2-fluoro-6-methylphenyl)benzo[d]thiazol-2-yl)cyclopropane-1-carboxamide | 1H NMR (400 MHz, DMSO-d6) δ = 12.75 (br s, 1H), 7.92 (s, 1H), 7.81 (d, J = 8.3 Hz, 1H), 7.33 (br d, J = 8.2 Hz, 2H), 7.20-7.11 (m, 2H), 5.16-4.92 (m, 1H), 2.23 (td, J = 6.7, 13.4 Hz, 1H), 2.14 (s, 3H), 1.82-1.68 (m, 1H), 1.37-1.25 (m, 1H); LCMS (electrospray) m/z 345.00 (M + H)+. | A |
| 2 | 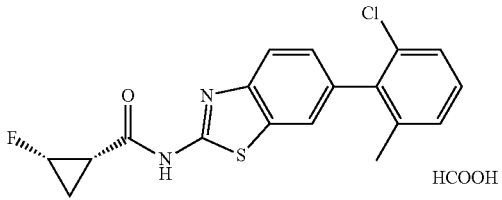<br>(1S,2S)-N-(6-(2-chloro-6-methylphenyl)benzo[d]thiazol-2-yl)-2-fluorocyclopropane-1-carboxamide. FA salt | 1H NMR (400 MHz, CDCl3) δ = 7.85 (d, J = 8.3 Hz, 1H), 7.66 (s, 1H), 7.34 (dd, J = 2.3, 7.0 Hz, 1H), 7.29 (d, J = 1.5 Hz, 1H), 7.23-7.18 (m, 2H), 5.03-4.81 (m, 1H), 2.10 (d, J = 2.0 Hz, 3H), 2.07-1.96 (m, 2H), 1.45-1.37 (m, 1H); LCMS (electrospray) m/z 361.20 (M + H)+. | B |
| 3 | 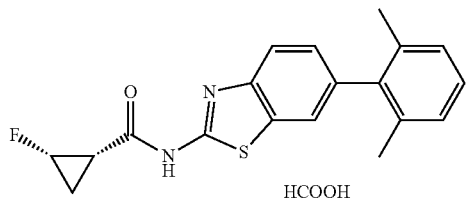<br>(1S,2S)-N-(6-(2,6-dimethylphenyl)benzo[d]thiazol-2-yl)-2-fluorocyclopropane-1-carboxamide. FA salt | 1H NMR (400 MHz, CDCl3) δ = 7.83 (d, J = 8.3 Hz, 1H), 7.60 (d, J = 1.0 Hz, 1H), 7.24 (dd, J = 1.6, 8.3 Hz, 2H), 7.20-7.17 (m, 1H), 7.15-7.11 (m, 2H), 5.03-4.81 (m, 1H), 2.04 (d, J = 2.5 Hz, 6H), 1.97 (d, J = 5.4 Hz, 1H), 1.43-1.35 (m, 1H), 1.26 (br s, 1H); LCMS (electrospray) m/z 341.20 (M + H)+. | B |
| 4 | 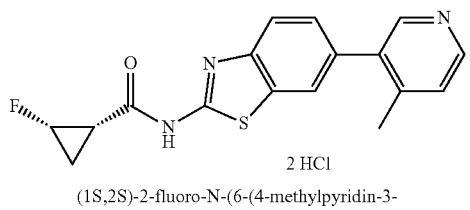<br>(1S,2S)-2-fluoro-N-(6-(4-methylpyridin-3-yl)benzo[d]thiazol-2-yl)cyclopropane-1-carboxamide. 2 HCl salt | 1H NMR (400 MHz, DMSO-d6) δ = 12.81 (br s, 1H), 8.67 (br d, J = 12.7 Hz, 2H), 8.12 (s, 1H), 7.87 (d, J = 8.4 Hz, 1H), 7.53 (br d, J = 8.7 Hz, 1H), 5.16-5.11 (m, 1H), 5.00-4.95 (m, 1H), 2.45 (br s, 3H), 2.29-2.20 (m, 2H), 1.81-1.69 (m, 1H), 1.38-1.28 (m, 1H); LCSM (electrospray) m/z 328.10 (M + H)+. | A |

TABLE 1-continued

Compounds of Examples

| Ex # | Structure/Name | ¹H NMR/MS (M + 1) | Synthetic Method |
|---|---|---|---|
| 5 | 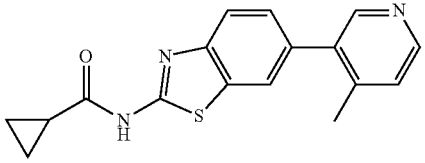<br>N-(6-(4-methylpyridin-3-yl)benzo[d]thiazol-2-yl)cyclopropanecarboxamide | 1H NMR (400 MHz, DMSO-d6); δ 12.69 (s, CONH), 8.44-8.42 (m, 2H), 8.02 (s, 1H), 7.81 (d, J = 8.0 Hz, 1H), 7.44 (d, J = 9.2 Hz, 1H), 7.34 (d, J = 5.4 Hz, 1H), 2.29 (s, 3H), 2.03-2.00 (m, 1H), 0.98-0.96 (m, 4H); LCMS (electrospray) m/z 310.05 (M + H)+. | C |
| 6* | 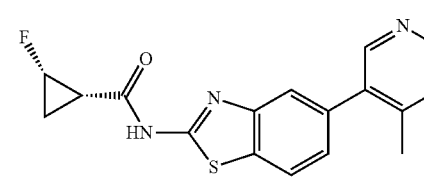<br>(1S,2S)-2-fluoro-N-(5-(4-methylpyridin-3-yl)benzo[d]thiazol-2-yl)cyclopropane-1-carboxamide | 1H NMR (400 MHz, DMSO-d6); δ 12.77 (s, CONH), 8.45 (s, 2H), 8.07 (d, J = 8.0 Hz, 1H), 7.74 (s, 1H), 7.36-7.31 (m, 2H), 5.05 (td, J12 = 3.3 Hz, J13 = 65.7 Hz, 1H), 2.24 (s, 3H), 2.23-2.24 (m, 1H), 1.76 (dd, J12 = 3.6 Hz, J13 = 23.2 Hz, 1H), 1.32 (dd, J12 = 4.4 Hz, J13 = 11.6 Hz, 1H); LCMS (electrospray) m/z 328.10 (M + H)+. | A |
| 7* | 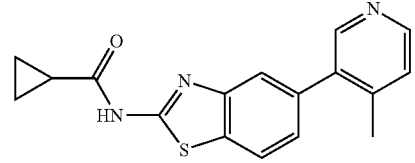<br>N-(5-(4-methylpyridin-3-yl)benzo[d]thiazol-2-yl)cyclopropanecarboxamide | 1H NMR (400 MHz, DMSO-d6); δ 12.71 (s, CONH), 8.45 (s, 2H), 8.05 (d, J = 8.4 Hz, 1H), 7.73 (s, 1H), 7.36-7.30 (m, 2H), 2.29 (s, 3H), 2.01 (t, J = 5.6 Hz 1H), 0.97 (t, J = 3.8 Hz, 4H); LCMS (electrospray) m/z 310.05 (M + H)+. | C |
| 8 | 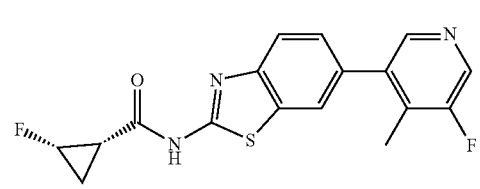<br>(1S,2S)-2-fluoro-N-(6-(5-fluoro-4-methylpyridin-3-yl)benzo[d]thiazol-2-yl)cyclopropane-1-carboxamide | 1H NMR (400 MHz, DMSO-d6); δ 12.78 (s, CONH), 8.50 (s, 1H), 8.35 (s, 1H), 7.84 (d, J = 8.4 Hz, 1H), 7.51-7.47 (m, 1H), 4.08 (s, 1H), 5.05 (td, J12 = 3.8 Hz, J13 = 65.8 Hz, 1H), 2.24 (s, 3H), 2.23-2.24 (m, 1H), 1.75 (dd, J12 = 3.8 Hz, J13 = 23.4 Hz, 1H), 1.32 (dd, J12 = 2.6 Hz, J13 = 7.0 Hz, 1H); LCMS (electrospray) m/z 328.10 (M + H)+. | B |
| 9 | 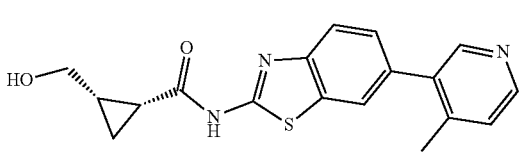<br>(1R,2S)-2-(hydroxymethyl)-N-(6-(4-methylpyridin-3-yl)benzo[d]thiazol-2-yl)cyclopropane-1-carboxamide | 1H NMR (400 MHz, METHANOL-d4) δ = 8.39 (br s, 2H), 8.24 (br s, 1H), 7.92-7.79 (m, 2H), 7.49-7.33 (m, 2H), 3.87 (dd, J = 5.9, 11.5 Hz, 1H), 3.69 (dd, J = 8.5, 11.6 Hz, 1H), 2.36 (s, 3H), 2.12 (dt, J = 5.7, 8.0 Hz, 1H), 1.81-1.66 (m, 1H), 1.29-1.14 (m, 2H); LCMS (electrospray) m/z 340.00 (M + H)+. | K |

TABLE 1-continued

Compounds of Examples

| Ex # | Structure/Name | ¹H NMR/MS (M + 1) | Synthetic Method |
|---|---|---|---|
| 10 | 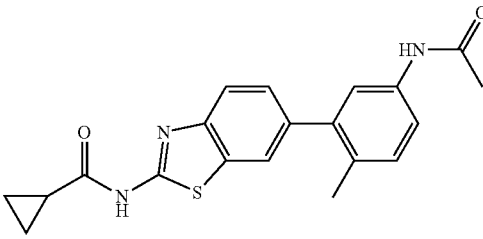<br>N-(6-(5-acetamido-2-methylphenyl)benzo[d]thiazol-2-yl)cyclopropane carboxamide | 1H NMR (400 MHz, DMSO-d6); δ 12.66 (s, CONH), 9.90 (s, CONH), 7.91 (s, 1H), 7.77 (d, J = 8.0 Hz, 1H), 7.50-7.46 (m, 1H), 7.36 (d, J = 8.0 Hz, 1H), 2.18 (s, 3H), 2.02 (s, 3H), 1.98 (m, 1H), 0.96 (t, J = 4.0 Hz, 4H); LCMS (electrospray) m/z 349.00 (M + H)+. | B |
| 11 | 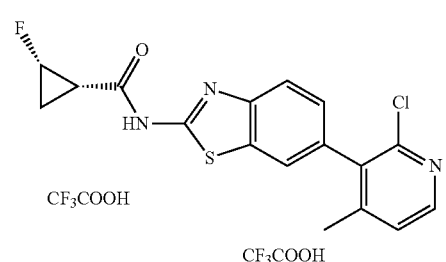<br>(1S,2S)-N-(6-(2-chloro-4-methylpyridin-3-yl)benzo[d]thiazol-2-yl)-2-fluorocyclopropane-1-carboxamide. 2TFA salt | 1H NMR (400 MHz, DMSO-d6) δ = 12.78 (br s, 1H), 8.29 (d, J = 5.0 Hz, 1H), 7.91 (s, 1H), 7.84 (d, J = 8.2 Hz, 1H), 7.41 (d, J = 4.9 Hz, 1H), 7.31 (dd, J = 1.2, 8.3 Hz, 1H), 5.17-4.93 (m, 1H), 2.29-2.21 (m, 1H), 2.10 (s, 3H), 1.83-1.69 (m, 1H), 1.38-1.27 (m, 1H); LCMS (electrospray) m/z 362.10 (M + H)+. | B |
| 12 | 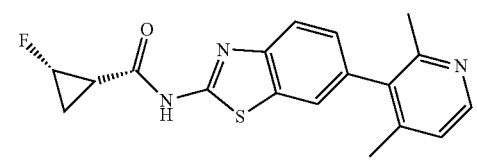<br>(1S,2S)-N-(6-(2,4-dimethylpyridin-3-yl)benzo[d]thiazol-2-yl)-2-fluorocyclopropane-1-carboxamide | 1H NMR (400 MHz, DMSO-d6); δ 12.78 (s, CONH), 8.43 (s, 1H), 7.84-7.84 (m, 2H), 7.40 (d, J = 5.6 Hz, 1H), 7.28 (dd, J12 = 0.8 Hz, J13 = 8.0 Hz, 1H), 5.05 (td, J12 = 3.3 Hz, J13 = 65.7 Hz, 1H), 2.24 (s, 3H), 2.22-2.24 (m, 1H), 1.78-1.73 (m, 1H), 1.31-1.23 (m, 1H); LCMS (electrospray) m/z 342.10 (M + H)+. | A |
| 13* | 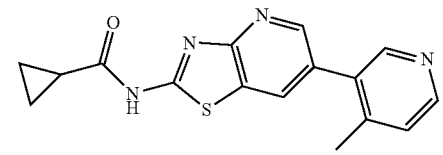<br>N-(6-(4-methylpyridin-3-yl)thiazolo[4,5-b]pyridin-2-yl)cyclopropanecarboxamide | 1H NMR (400 MHz, DMSO); δ 12.98 (brs, 1H), 8.56 (d, J = 2.4 Hz, 1H), 8.53 (d, J = 2.0 Hz, 1H), 8.48(d, J = 4.9 Hz, 1H), 8.46(s, 1H), 7.39(d, J = 4.8 Hz, 1H), 2.31 (s, 3H), 2.05-1.98 (m, 1H), 1.02-0.98 (m, 4H); LCMS (electrospray) m/z 311.0 (M + H)+. | C |
| 14 | 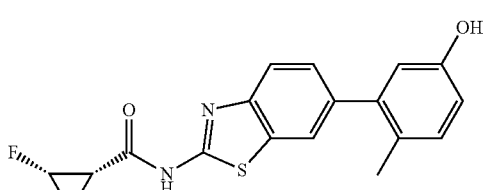<br>(1S,2S)-2-fluoro-N-(6-(5-hydroxy-2-methylphenyl)benzo[d]thiazol-2-yl)cyclopropane-1-carboxamide. TFA salt | ¹H NMR (400 MHz, DMSO-d₆) δ = 12.73 (br s, 1H), 7.92 (d, J = 1.6 Hz, 1H), 7.77 (d, J = 8.3 Hz, 1H), 7.36 (dd, J = 1.8, 8.3 Hz, 1H), 7.08 (d, J = 8.1 Hz, 1H), 6.72-6.64 (m, 2H), 5.17-4.93 (m, 1H), 2.27-2.17 (m, 1H), 2.12 (s, 3H), 1.82-1.68 (m, 1H), 1.31 (tdd, J = 6.3, 8.9, 12.8 Hz, 1H); LCMS (electrospray) m/z 343.2 (M + H)+. | D |

TABLE 1-continued

Compounds of Examples

| Ex # | Structure/Name | ¹H NMR/MS (M + 1) | Synthetic Method |
|---|---|---|---|
| 15 | (1S,2S)-2-fluoro-N-(6-(5-(2-hydroxypropan-2-yl)-2-methylphenyl)benzo[d]thiazol-2-yl)cyclopropane-1-carboxamide | ¹H NMR (400 MHz, DMSO-d$_6$) δ = 1.29 (dq, J = 15.12, 6.42 Hz, 1 H), 1.43 (s, 6 H), 1.66-1.84 (m, 1 H), 2.16-2.22 (m, 1 H), 2.23 (s, 3 H), 4.91-5.14 (m, 1 H), 4.98 (s, 1 H), 7.22 (d, J = 8.53 Hz, 1 H), 7.32-7.36 (m, 2 H), 7.38 (dd, J = 8.28, 1.51 Hz, 1 H), 7.76 (d, J = 8.28 Hz, 1 H), 7.92 (s, 1 H), 12.61 (br s, 1 H); LCMS (electrospray) m/z 385.3 (M + H)+. | E |
| 16 | (1R,2S)-2-(hydroxymethyl)-N-(6-(5-methyl-1H-indol-4-yl)benzo[d]thiazol-2-yl)cyclopropane-1-carboxamide | LCMS (electrospray) m/z 378.46 (M + H)+. | K |
| 17 | (1S,2S)-2-fluoro-N-(6-(2-methyl-5-(prop-1-en-2-yl)phenyl)benzo[d]thiazol-2-yl)cyclopropane-1-carboxamide | ¹H NMR (400 MHz, DMSO-d$_6$) δ = 1.29 (br s, 1 H), 1.64-1.80 (m, 1 H), 2.11 (s, 3 H), 2.18 (br s, 1 H), 2.24 (s, 3 H), 4.93-5.12(m, 1 H), 5.07 (s, 1 H), 5.44 (s, 1 H), 7.29 (d, J = 7.91 Hz, 1 H), 7.35 (s, 1 H), 7.38 (br d, J = 8.53 Hz, 1 H), 7.42 (br d, J = 7.91 Hz, 1 H), 7.74 (br d, J = 8.16 Hz, 1 H), 7.93 (s, 1 H), 11.65-13.53 (m, 1 H); LCMS (electrospray) m/z 367.3 (M + H)+. | E |
| 18* | (1S,2S)-2-fluoro-N-(6-(4-methylpyridin-3-yl)thiazolo[4,5-b]pyridin-2-yl)cyclopropane-1-carboxamide | ¹H NMR (400 MHz, DMSO-d$_6$) δ = 13.06(s, 1H), 8.57-8.55(m, 2H), 8.49-8.47(m, 2H), 7.40-7.38(m, 1H), 5.16-4.99(m, 1H), 2.23(s, 3H), 2.28-2.25(m, 1H), 1.80-1.74(m, 1H), 1.37-1.32(m, 1H); LCMS (electrospray) m/z 329.0 (M + H)+. | F |
| 19 | N-(6-(6-aminopyridin-3-yl)benzo[d]thiazol-2-yl)cyclopropanecarboxamide | ¹H NMR (400 MHz, DMSO-d$_6$) δ = 12.62 (s, 1H), 8.29 (d, J = 6 Hz, 1H), 8.15 (d, J = 3 Hz, 1H), 7.74 (m, 2H), 7.62 (dd, J = 4, 4 Hz, 1H), 6.53 (d, J = 22 Hz, 1H), 6.05 (s, 2H), 2.00 (m, 1H), 0.96 (m, 4H); LCMS (electrospray) m/z 311.38 (M + H)+. | C |

TABLE 1-continued

Compounds of Examples

| Ex # | Structure/Name | $^1$H NMR/MS (M + 1) | Synthetic Method |
|---|---|---|---|
| 20 | 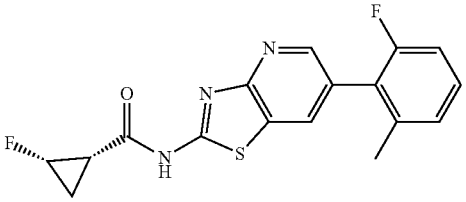<br>(1S,2S)-2-fluoro-N-(6-(2-fluoro-6-methylphenyl)thiazolo[4,5-b]pyridin-2-yl)cyclopropane-1-carboxamide | $^1$H NMR (400 MHz, DMSO-d$_6$) δ = 13.05(s, 1H), 8.45(s, 2H), 7.40-7.35(m, 1H), 7.23-7.15(m, 2H), 5.14-4.98(m, 1H), 2.39-2.26(m, 1H), 2.21(s, 3H), 1.78-1.73(m, 1H), 1.36-1.31(m, 1H); LCMS (electrospray) m/z 346.0 (M + H)+. | F |
| 21* | 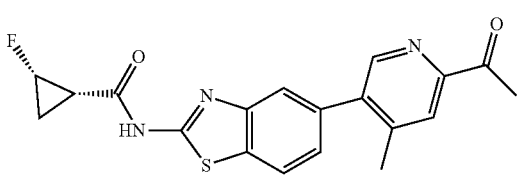<br>(1S,2S)-N-(5-(6-acetyl-4-methylpyridin-3-yl)benzo[d]thiazol-2-yl)-2-fluorocyclopropane-1-carboxamide | $^1$H NMR (400 MHz, CHLOROFORM-d) δ = 1.28-1.44 (m, 1 H), 1.93-2.10 (m, 2 H), 2.39 (s, 3 H), 2.77 (s, 3 H), 4.73-4.97 (m, 1 H), 7.29 (dd, J = 8.22, 1.57 Hz, 1 H), 7.74 (d, J = 1.25 Hz, 1 H), 7.94 (d, J = 8.16 Hz, 1 H), 8.01 (s, 1 H), 8.55 (s, 1 H), 10.23 (br s, 1 H); LCMS (electrospray) m/z 370.3 (M + H)+. | B |
| 22 | 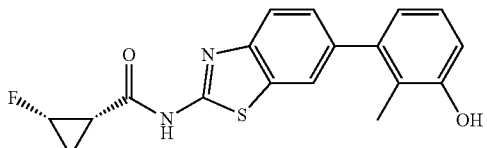<br>CF$_3$COOH<br>(1S,2S)-2-fluoro-N-(6-(3-hydroxy-2-methylphenyl)benzo[d]thiazol-2-yl)cyclopropane-1-carboxamide. TFA salt | $^1$H NMR (400 MHz, DMSO-d$_6$) δ = 12.71 (br s, 1H), 9.43 (br s, 1H), 7.89 (s, 1H), 7.76 (d, J = 8.3 Hz, 1H), 7.35 (dd, J = 1.0, 8.3 Hz, 1H), 7.09-7.01 (m, 1H), 6.82 (d, J = 7.9 Hz, 1H), 6.70 (d, J = 7.5 Hz, 1H), 5.16-4.92 (m, 1H), 2.23 (td, J = 6.8, 13.5 Hz, 1H), 2.04 (s, 3H), 1.82-1.67 (m, 1H), 1.37-1.24 (m, 1H); LCMS (electrospray) m/z 343.2 (M + H)+. | D |
| 23 | 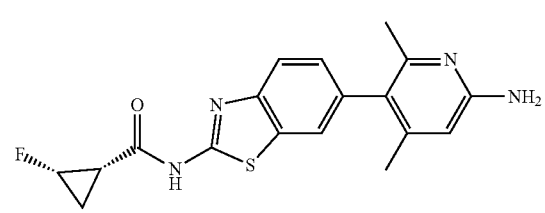<br>(1S,2S)-N-(6-(6-amino-2,4-dimethylpyridin-3-yl)benzo[d]thiazol-2-yl)-2-fluorocyclopropane-1-carboxamide | $^1$H NMR (400 MHz, CHLOROFORM-d) δ = 12.36 (br s, 1H), 7.81 (dd, J = 1.2, 8.3 Hz, 1H), 7.61 (d, J = 1.2 Hz, 1H), 7.21 (dd, J = 1.5, 8.3 Hz, 1H), 6.32 (s, 1H), 4.97-4.70 (m, 1H), 4.57 (br s, 2H), 2.14 (d, J = 2.7 Hz, 3H), 2.11-1.96 (m, 2H), 1.94 (d, J = 3.2 Hz, 3H), 1.37-1.22 (m, 1H); LCMS (electrospray) m/z 357.20 (M + H)+ | B |
| 24 | 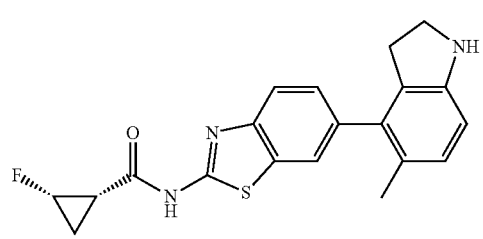<br>(1S,2S)-2-fluoro-N-(6-(5-methylindolin-4-yl)benzo[d]thiazol-2-yl)cyclopropane-1-carboxamide | $^1$H NMR (400 MHz, DMSO-d$_6$) δ = 12.77-12.67 (m, 1H), 7.85 (s, 1H), 7.80 (d, J = 8.3 Hz, 1H), 7.30-7.25 (m, 1H), 7.10 (d, J = 8.3 Hz, 1H), 5.16-4.93 (m, 1H), 3.83 (br t, J = 8.6 Hz, 2H), 2.77 (br s, 2H), 2.23 (td, J = 6.7, 13.5 Hz, 1H), 2.03 (s, 3H), 1.81-1.69 (m, 1H), 1.50 (br s, 9H), 1.35-1.27 (m, 1H); LCMS (electrospray) m/z 468.3 (M + H)+ | B |

TABLE 1-continued

Compounds of Examples

| Ex # | Structure/Name | ¹H NMR/MS (M + 1) | Synthetic Method |
|---|---|---|---|
| 25* | (1S,2S)-2-fluoro-N-(5-(5-methyl-1-((2-(trimethylsilyl)ethoxy)methyl)-1H-indol-4-yl)benzo[d]thiazol-2-yl)cyclopropane-1-carboxamide | ¹H NMR (400 MHz, DMSO-d₆) δ = 12.77 (s, 1H), 8.06 (d, J = 8.1 Hz, 1H), 7.69-7.64 (m, 1H), 7.47 (d, J = 8.4 Hz, 1H), 7.39 (d, J = 3.2 Hz, 1H), 7.31-7.26 (m, 1H), 7.14 (d, J = 8.6 Hz, 1H), 6.04 (d, J = 2.7 Hz, 1H), 5.54 (s, 2H), 5.17-4.93 (m, 1H), 3.51-3.42 (m, 2H), 2.28-2.18 (m, 4H), 1.83-1.69 (m, 1H), 1.37-1.27 (m, 1H), 0.87-0.78 (m, 2H), −0.02--0.11 (m, 9H); LCMS (electrospray) m/z 496.4 (M + H)+ | B |
| 26 | (1S,2S)-2-fluoro-N-(6-(2-fluoro-6-methylphenyl)thiazolo[4,5-c]pyridin-2-yl)cyclopropane-1-carboxamide | ¹H NMR (400 MHz, DMSO-d₆) δ = 12.99(s, 1H), 9.09(s, 1H), 8.12(s, 1H), 7.39-7.33(m, 1H), 7.18-7.11(m, 2H), 4.99-4.98(m, 1H), 2.24-2.23(m, 1H), 2.14(s, 3H), 1.81-1.73(m, 1H), 1.36-1.31(m, 1H); LCMS (electrospray) m/z 346.1 (M + H)+. | A |
| 27* | 6-(4-methylpyridin-3-yl)benzo[d]thiazol-2-amine | ¹H NMR (400 MHz, DMSO-d₆) δ = 8.39-8.37 (m, 2H), 7.70 (s, 1H), 7.55 (br, 2H), 7.40 (d, J = 8.4 Hz, 1H), 7.30 (d, J = 5.2 Hz, 1H), 7.21 (d, J = 8.4 Hz, 1H), 2.28 (s, 3H); LCMS (electrospray) m/z 242.0(M + H)+. | A |
| 28* | (1S,2S)-2-fluoro-N-(5-(6-(1-hydroxyethyl)-4-methylpyridin-3-yl)benzo[d]thiazol-2-yl)cyclopropane-1-carboxamide | ¹H NMR (400 MHz, CHLOROFORM-d) δ = 1.29-1.39 (m, 1 H), 1.58 (d, J = 6.60 Hz, 3 H), 1.94-2.10 (m, 2 H), 2.32 (s, 3 H), 4.33 (br s, 1 H), 4.71-4.92 (m, 1 H), 4.93-5.00 (m, 1 H), 7.24 (s, 1 H), 7.26-7.28 (m, 1 H), 7.72 (d, J = 1.34 Hz, 1H), 7.90 (d, J = 8.07 Hz, 1 H), 8.41 (s, 1 H), 10.63 (br s, 1 H); LCMS (electrospray) m/z 372.2 (M + H)+. | G |
| 29* | (1S,2S)-2-fluoro-N-(5-(6-(hydroxymethyl)-4-methylpyridin-3-yl)benzo[d]thiazol-2-yl)cyclopropane-1-carboxamide | ¹H NMR (400 MHz, DMSO-d₆) δ = 1.31 (dq, J = 15.10, 6.46 Hz, 1 H), 1.69-1.82 (m, 1 H), 2.18-2.26 (m, 1 H), 2.31 (s, 3 H), 4.58 (br d, J = 3.79 Hz, 2 H), 4.91-5.17 (m, 1 H), 5.42 (br s, 1 H), 7.31 (d, J = 8.07 Hz, 1 H), 7.42 (s, 1 H), 7.72 (s, 1 H), 8.06 (d, J = 8.07 Hz, 1 H), 8.33 (s, 1 H), 12.70 (br s, 1 H); LCMS (electrospray) m/z 358.3 (M + H)+. | H |

TABLE 1-continued

Compounds of Examples

| Ex # | Structure/Name | ¹H NMR/MS (M + 1) | Synthetic Method |
|---|---|---|---|
| 30* | 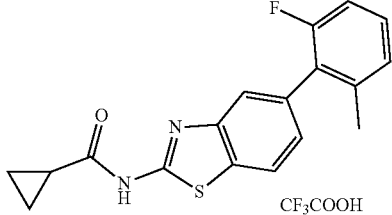<br>N-(5-(2-fluoro-6-methylphenyl)benzo[d]thiazol-2-yl)cyclopropanecarboxamide. TFA salt | ¹H NMR (400 MHz, DMSO-d₆) δ = 12.71 (s, 1H), 8.04 (d, J = 8.1 Hz, 1H), 7.63 (s, 1H), 7.33 (dt, J = 5.9, 7.9 Hz, 1H), 7.22-7.16 (m, 2H), 7.13 (t, J = 8.9 Hz, 1H), 2.14 (s, 3H), 2.05-1.96 (m, 1H), 1.01-0.93 (m, 4 H); LCMS (electrospray) m/z 327.0 (M + H)+. | A |
| 31* | 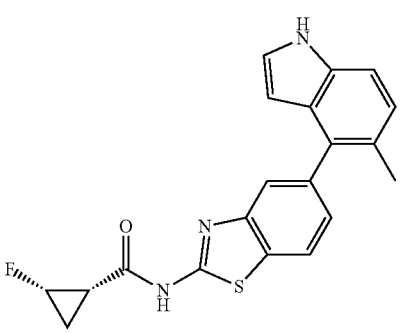<br>(1S,2S)-2-fluoro-N-(5-(5-methyl-1H-indol-4-yl)benzo[d]thiazol-2-yl)cyclopropane-1-carboxamide | ¹H NMR (400 MHz, DMSO-d₆) δ = 12.73 (br s, 1H), 11.06 (br s, 1H), 8.05 (d, J = 8.2 Hz, 1H), 7.67 (d, J = 1.1 Hz, 1H), 7.35-7.22 (m, 3H), 7.05 (d, J = 8.3 Hz, 1H), 6.00 (br s, 1H), 5.18-4.89 (m, 1H), 2.28-2.18 (m, 4H), 1.83-1.70 (m, 1H), 1.31 (tdd, J = 6.3, 9.0, 12.8 Hz, 1H); LCMS (electrospray) m/z 366.2 (M + H)+. | I |
| 32 | 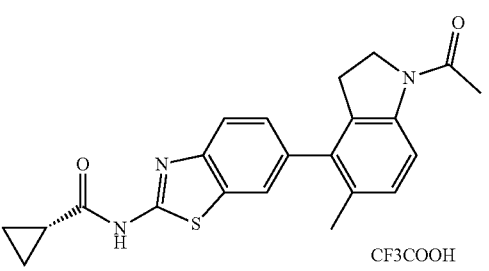<br>(1S,2S)-N-(6-(1-acetyl-5-methylindolin-4-yl)benzo[d]thiazol-2-yl)-2-fluorocyclopropane-1-carboxamide. TFA salt | ¹H NMR (400 MHz, DMSO-d₆) δ = 12.74 (s, 1H), 7.95 (d, J = 8.3 Hz, 1H), 7.88 (d, J = 1.4 Hz, 1H), 7.80 (d, J = 8.3 Hz, 1H), 7.29 (dd, J = 1.7, 8.2 Hz, 1H), 7.10 (d, J = 8.5 Hz, 1H), 5.18-4.91 (m, 1H), 4.02 (br t, J = 8.4 Hz, 2H), 2.85 (br s, 2H), 2.27-2.19 (m, 1H), 2.13 (s, 3H), 2.05 (s, 3H), 1.82-1.67 (m, 1H), 1.37-1.21 (m, 1H); LCMS (electrospray) m/z 410.1 (M + H)+. | J |
| 33* | 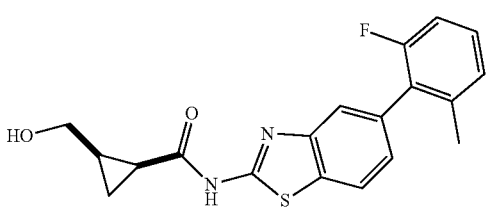<br>(1S,2R)-N-(5-(2-fluoro-6-methylphenyl)benzo[d]thiazol-2-yl)-2-(hydroxymethyl)cyclopropane-1-carboxamide | ¹H NMR (400 MHz, DMSO-d₆) δ = 7.95 (br d, J = 7.9 Hz, 1H), 7.54 (s, 1H), 7.36-7.27 (m, 1H), 7.17 (d, J = 7.6 Hz, 1H), 7.15-7.09 (m, 2H), 3.69 (dd, J = 5.6, 11.3 Hz, 1H), 3.54-3.45 (m, 1H), 2.14 (s, 3H), 2.05-1.95 (m, 1H), 1.60-1.48 (m, 1H), 1.12-0.98 (m, 2H); LCMS (electrospray) m/z 357.1 (M + H)+. | K |

TABLE 1-continued

Compounds of Examples

| Ex # | Structure/Name | ¹H NMR/MS (M + 1) | Synthetic Method |
|---|---|---|---|
| 34 | 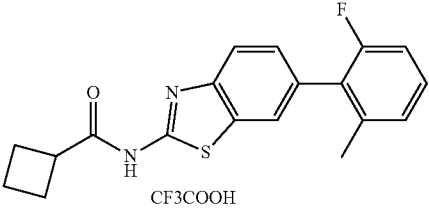<br>N-(6-(2-fluoro-6-methylphenyl)benzo[d]thiazol-2-yl)cyclobutanecarboxamide. TFA salt | ¹H NMR (400 MHz, DMSO-d$_6$) δ = 12.26 (s, 1H), 7.92 (s, 1H), 7.79 (d, J = 8.3 Hz, 1H), 7.36-7.29 (m, 2H), 7.20-7.09 (m, 2H), 3.43 (quin, J = 8.3 Hz, 1H), 2.31-2.11 (m, 7H), 2.03-1.94 (m, 1H), 1.90-1.79 (m, 1H); LCMS (electrospray) m/z 341.1 (M + H)+. | A |
| 35* | <br>N-(6-(5-fluoro-4-methylpyridin-3-yl)thiazolo[4,5-b]pyridin-2-yl)cyclopropanecarboxamide | ¹H NMR (400 MHz, DMSO-d$_6$) δ = 13.02(s, 1H), 8.59-8.56(m, 3H), 8.40(s, 1H), 2.25(s, 3H), 2.04-1.98(m, 1H), 1.02-0.99 (m, 4H); LCMS (electrospray) m/z 329.0(M + H)+. | C |
| 36 | 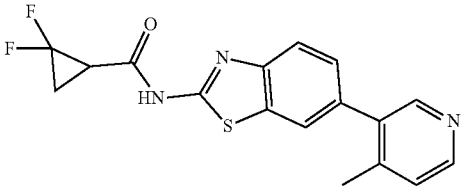<br>2,2-difluoro-N-(6-(4-methylpyridin-3-yl)benzo[d]thiazol-2-yl)cyclopropane-1-carboxamide | ¹H NMR (400 MHz, DMSO-d$_6$) δ = 2.12-2.21 (m, 2 H), 2.31 (s, 3 H), 3.01 (dt, J = 12.99, 9.46 Hz, 1 H), 7.36 (d, J = 5.01 Hz, 1 H), 7.48 (dd, J = 8.31, 1.83 Hz, 1 H), 7.86 (d, J = 8.31 Hz, 1 H), 8.07 (d, J = 1.59 Hz, 1 H), 8.42-8.47 (m, 2 H), 12.88 (br s, 1 H); LCMS (electrospray) m/z 346.0 (M + H)+. | A |
| 37 | 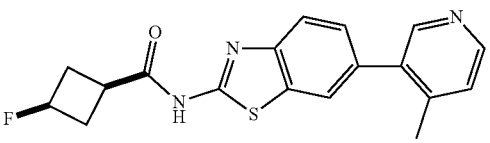<br>(1s,3s)-3-fluoro-N-(6-(4-methylpyridin-3-yl)benzo[d]thiazol-2-yl)cyclobutane-1-carboxamide | ¹H NMR (400 MHz, CHLOROFORM-d) δ = 2.34 (s, 3 H), 2.62-2.75 (m, 5 H), 4.85-5.12 (m, 1 H), 7.24 (d, J = 4.89 Hz, 1 H), 7.42 (dd, J = 8.34, 1.69 Hz, 1H), 7.78-7.85 (m, 2 H), 8.46-8.54 (m, 2 H), 9.63 (br s, 1 H); LCMS (electrospray) m/z 342.3 (M + H)+. | A |
| 38 | 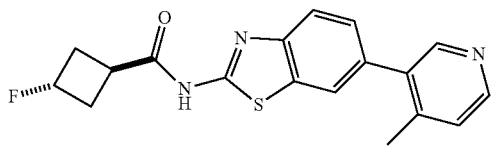<br>(1r,3r)-3-fluoro-N-(6-(4-methylpyridin-3-yl)benzo[d]thiazol-2-yl)cyclobutane-1-carboxamide | ¹H NMR (400 MHz, CHLOROFORM-d) δ = 12.35 (s, 3 H), 2.47-2.87 (m, 4 H), 3.21-3.41 (m, 1 H), 5.24-5.49 (m, 1 H), 7.25 (d, J = 5.02 Hz, 1 H), 7.40-7.48 (m, 1 H), 7.78-7.86 (m, 2 H), 8.47-8.56 (m, 2 H), 10.43 (br s, 1 H); LCMS (electrospray) m/z 342.1 (M + H)+. | A |

TABLE 1-continued

Compounds of Examples

| Ex # | Structure/Name | ¹H NMR/MS (M + 1) | Synthetic Method |
|---|---|---|---|
| 39 | 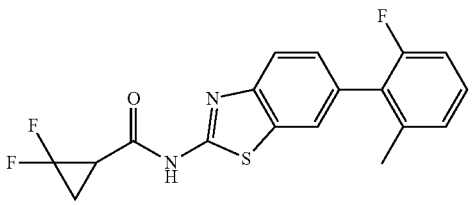<br>2,2-difluoro-N-(6-(2-fluoro-6-methylphenyl)benzo[d]thiazol-2-yl)cyclopropane-1-carboxamide | ¹H NMR (400 MHz, DMSO-$d_6$) δ = 12.91 (br s, 1H), 7.95 (s, 1H), 7.84 (d, J = 8.3 Hz, 1H), 7.38-7.28 (m, 2H), 7.21-7.08 (m, 2H), 3.01 (td, J = 9.5, 12.8 Hz, 1H), 2.22-2.11 (m, 5H); LCMS (electrospray) m/z 363.0 (M + H)+. | A |
| 40 | 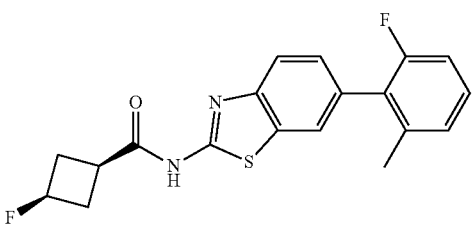<br>(1s,3s)-3-fluoro-N-(6-(2-fluoro-6-methylphenyl)benzo[d]thiazol-2-yl)cyclobutane-1-carboxamide | ¹H NMR (400 MHz, DMSO-$d_6$) δ = 12.47 (s, 1H), 7.94 (s, 1H), 7.80 (d, J = 8.3 Hz, 1H), 7.36-7.29 (m, 2H), 2.96-2.85 (m, 1H), 2.65-2.56 (m, 2H), 2.41-2.35 (m, 2H), 2.14 (s, 3H); LCMS (electrospray) m/z 359.1 (M + H)+. | A |
| 41 | 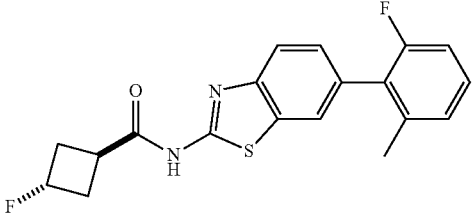<br>(1r,3r)-3-fluoro-N-(6-(2-fluoro-6-methylphenyl)benzo[d]thiazol-2-yl)cyclobutane-1-carboxamide | ¹H NMR (400 MHz, DMSO-$d_6$) δ = 12.46 (br s, 1H), 7.93 (d, J = 1.3 Hz, 1H), 7.80 (d, J = 8.3 Hz, 1H), 7.36-7.29 (m, 2H), 7.20-7.09 (m, 2H), 5.37-5.13 (m, 1H), 3.49-3.39 (m, 1H), 2.66-2.55 (m, 2H), 2.48-2.39 (m, 2H), 2.14 (s, 3H); LCMS (electrospray) m/z 359.1 (M + H)+. | A |
| 42 | 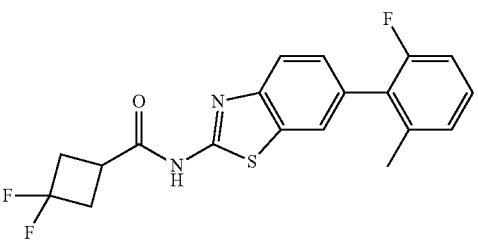<br>3,3-difluoro-N-(6-(2-fluoro-6-methylphenyl)benzo[d]thiazol-2-yl)cyclobutane-1-carboxamide | ¹H NMR (400 MHz, DMSO-$d_6$) δ = 12.59 (br s, 1H), 7.95 (s, 1H), 7.82 (d, J = 8.3 Hz, 1H), 7.37-7.28 (m, 2H), 7.21-7.09 (m, 2H), 3.31 (dquin, J = 2.8, 8.4 Hz, 1H), 2.95-2.81 (m, 4H), 2.14 (s, 3H); LCMS (electrospray) m/z 377.0 (M + H)+. | A |
| 43 | 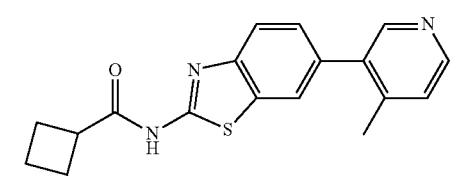<br>N-(6-(4-methylpyridin-3-yl)benzo[d]thiazol-2-yl)cyclobutanecarboxamide | ¹H NMR (400 MHz, METHANOL-$d_4$) δ = 1.91-2.01 (m, 1H), 2.05-2.14 (m, 1 H), 2.25-2.33 (m, 2 H), 2.36 (s, 3 H), 2.37-2.46 (m, 2 H), 3.44 (quin, J = 8.47 Hz, 1 H), 7.37-7.44 (m, 2 H), 7.82 (d, J = 8.28 Hz, 1 H), 7.88 (d, J = 1.63 Hz, 1 H), 8.38 (t, J = 2.51 Hz, 2 H); LCMS (electrospray) m/z 324.1 (M + H)+. | A |

TABLE 1-continued

Compounds of Examples

| Ex # | Structure/Name | ¹H NMR/MS (M + 1) | Synthetic Method |
|---|---|---|---|
| 44 | 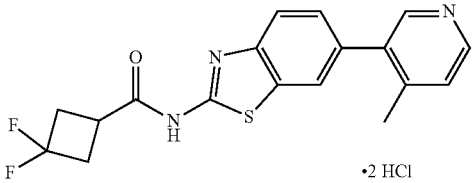<br>3,3-difluoro-N-(6-(4-methylpyridin-3-yl)benzo[d]thiazol-2-yl)cyclobutane-1-carboxamide. 2 HCl salt | ¹H NMR (400 MHz, METHANOL-d₄) δ 2.64 (s, 3 H), 2.85-3.01 (m, 4 H), 3.22-3.29 (m, 1 H), 7.55 (dd, J = 8.38, 1.77 Hz, 1 H), 7.93 (d, J = 8.44 Hz, 1 H), 8.04-8.10 (m, 2 H), 8.72 (d, J = 6.11 Hz, 1 H), 8.77 (s, 1 H); LCMS (electrospray) m/z 360.3 (M + H)+. | A |
| 45* | 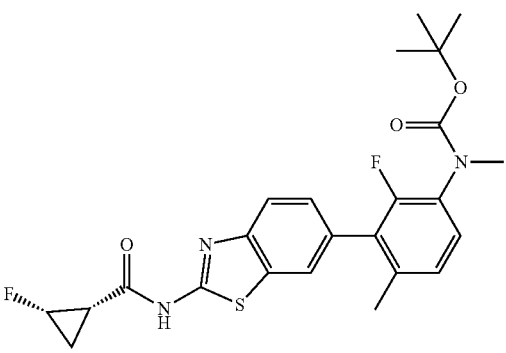<br>tert-butyl (2-fluoro-3-(2-((1S,2S)-2-fluorocyclopropane-1-carboxamido)benzo[d]thiazol-6-yl)-4-methylphenyl)(methyl)carbamate | ¹H NMR (400 MHz, METHANOL-d4) δ = 7.98-7.66 (m, 2H), 7.47-7.03 (m, 3H), 5.20-4.99 (m, 1H), 3.23-3.09 (m, 3H), 2.25-2.02 (m, 4H), 1.97-1.77 (m, 1H), 1.60-1.24 (m, 10H); LCMS (electrospray) m/z 474.7 (M + H)+. | L |
| 46 | 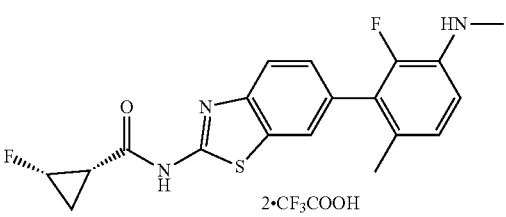<br>(1S,2S)-2-fluoro-N-(6-(2-fluoro-6-methyl-3-(methylamino)phenyl)benzo[d]thiazol-2-yl)cyclopropane-1-carboxamide. 2 TFA salt | ¹H NMR (400 MHz, METHANOL-d4) δ = 7.88-7.80 (m, 1H), 7.68-7.62 (m, 1H), 7.58-7.54 (m, 1H), 7.35 (br d, J = 7.8 Hz, 1H), 7.27-7.19 (m, 1H), 5.14-5.01 (m, 1H), 3.19-2.83 (m, 3H), 2.43-2.06 (m, 4H), 2.01-1.76 (m, 1H), 1.44-1.09 (m, 1H); ); LCMS (electrospray) m/z 374.1 (M + H)+. | L |
| 47 | 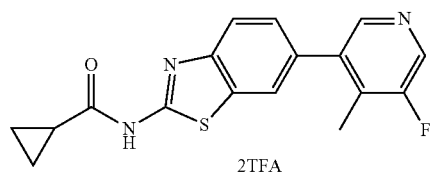<br>N-(6-(5-fluoro-4-methylpyridin-3-yl)benzo[d]thiazol-2-yl)cyclopropanecarboxamide. 2 TFA salt | ¹H NMR (400 MHz, DMSO-d6) δ = 12.73 (s, 1H), 8.51 (s, 1H), 8.36 (s, 1H), 8.07 (d, J = 1.5 Hz, 1H), 7.84 (d, J = 8.3 Hz, 1H), 7.48 (dd, J = 1.8, 8.3 Hz, 1H), 2.24 (d, J = 2.1 Hz, 3H), 2.02 (m, 1H), 1.00-0.94 (m, 4H); LCMS (electrospray) m/z 328.1 (M + H)+. | B |
| 48 | 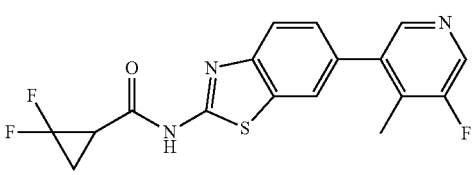<br>2,2-difluoro-N-(6-(5-fluoro-4-methylpyridin-3-yl)benzo[d]thiazol-2-yl)cyclopropane-1-carboxamide | ¹H NMR (400 MHz, CHLOROFORM-d) δ = 10.26 (br s, 1H), 8.42 (s, 1H), 8.36 (s, 1H), 7.89 (d, J = 7.9 Hz, 1H), 7.80 (s, 1H), 7.42 (d, J = 8.3 Hz, 1H), 2.68-2.52 (m, 1H), 2.38 (br dd, J = 6.0, 12.3 Hz, 1H), 2.28 (s, 3H), 1.96 (br s, 1H); LCMS (electrospray) m/z 364.2 (M + H)+. | B |

TABLE 1-continued

Compounds of Examples

| Ex # | Structure/Name | ¹H NMR/MS (M + 1) | Synthetic Method |
|---|---|---|---|
| 49 | 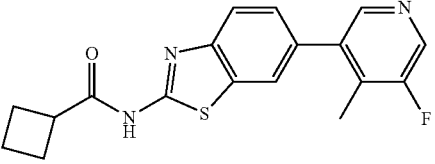<br>N-(6-(5-fluoro-4-methylpyridin-3-yl)benzo[d]thiazol-2-yl)cyclobutanecarboxamide | ¹H NMR (400 MHz, CHLOROFORM-d) δ = 8.85 (br s, 1H), 8.41 (s, 1H), 8.36 (s, 1H), 7.84 (d, J = 7.7 Hz, 1H), 7.78 (s, 1H), 7.39 (d, J = 8.5 Hz, 1H), 3.42-3.21 (m, 1H), 2.58-2.41 (m, 2H), 2.42-2.27 (m, 2H), 2.28 (s, 3H), 2.17-1.95 (m, 2H); LCMS (electrospray) m/z 342.1 (M + H)+. | B |
| 50 | 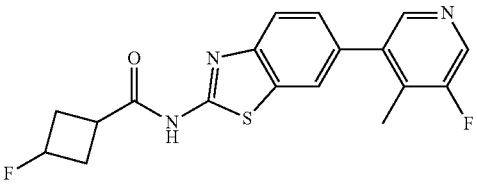<br>3-fluoro-N-(6-(5-fluoro-4-methylpyridin-3-yl)benzo[d]thiazol-2-yl)cyclobutane-1-carboxamide | ¹H NMR (400 MHz, CHLOROFORM-d) δ = 9.73 (br s, 1H), 8.49-8.32 (m, 2H), 7.92-7.75 (m, 2H), 7.42 (td, J = 1.8, 8.3 Hz, 1H), 5.51-5.24 (m, 0.5H), 5.12-4.87 (m, 0.5H), 3.38-3.22 (m, 0.5H), 2.89-2.50 (m, 4.5H), 2.28 (d, J = 2.1 Hz, 3H); LCMS (electrospray) m/z 360.2 (M + H)+. | B |
| 51 | 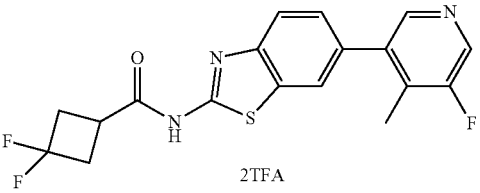<br>3,3-difluoro-N-(6-(5-fluoro-4-methylpyridin-3-yl)benzo[d]thiazol-2-yl)cyclobutane-1-carboxamide. 2 TFA salt | 1H NMR (400 MHz, DMSO-d6) δ = 12.63 (s, 1H), 8.52 (s, 1H), 8.37 (s, 1H), 8.11 (d, J = 1.6 Hz, 1H), 7.85 (d, J = 8.3 Hz, 1H), 7.50 (dd, J = 1.8, 8.3 Hz, 1H), 2.99-2.80 (m, 4H), 2.24 (d, J = 2.0 Hz, 3H); LCMS (electrospray) m/z 378.1 (M + H)+. | B |
| 52* | 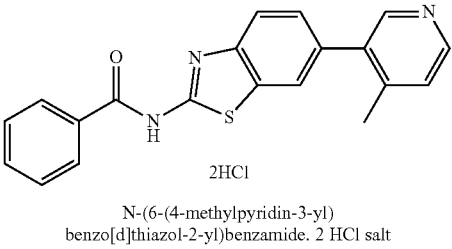 [SMILES: Cc1ccncc1-c1ccc2nc(NC(=O)c3ccccc3)sc2c1]<br>N-(6-(4-methylpyridin-3-yl)benzo[d]thiazol-2-yl)benzamide. 2 HCl salt | ¹H NM (400 MHz, METHANOL-d₄) δ = 2.66 (s, 3 H), 7.56-7.62 (m, 3 H), 7.66-7.71 (m, 1 H), 7.97 (d, J = 8.41 Hz, 1 H), 8.08 (d, J = 5.90 Hz, 4 H), 8.73 (d, J = 6.15 Hz, 1 H), 8.79 (s, 1 H); LCMS (electrospray) m/z 346.3 (M + H)+. | J |
| 53* | 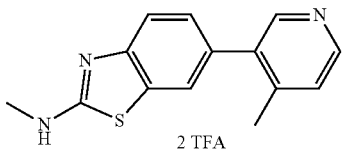<br>N-methyl-6-(4-methylpyridin-3-yl)benzo[d]thiazol-2-amine. 2 TFA salt | ¹H NMR (400 MHz, METHANOL-d₄) δ = 2.62 (s, 3 H), 3.19 (s, 3 H), 7.51 (dd, J = 8.31, 1.71 Hz, 1 H), 7.66 (d, J = 8.31 Hz, 1 H), 7.88 (d, J = 1.47 Hz, 1 H), 8.03 (d, J = 5.87 Hz, 1 H), 8.66-8.78 (m, 2 H); LCMS (electrospray) m/z 256.2 (M + H)+. | M |
| 54* | 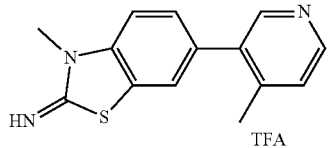<br>3-methyl-6-(4-methylpyridin-3-yl)benzo[d]thiazol-2(3H)-imine. TFA salt | ¹H NMR (400 MHz, METHANOL-d₄) δ 2.57 (s, 3 H), 3.87 (s, 3 H), 7.71 (dd, J = 8.56, 1.71 Hz, 1 H), 7.82 (d, J = 8.56 Hz, 1 H), 7.96-8.03 (m, 2 H), 8.68-8.76 (m, 2 H). | M |

TABLE 1-continued

Compounds of Examples

| Ex # | Structure/Name | ¹H NMR/MS (M + 1) | Synthetic Method |
|---|---|---|---|
| 55 | 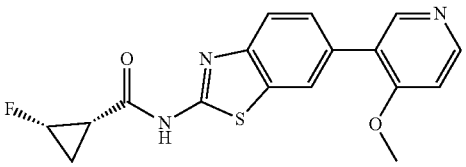<br>(1S,2S)-2-fluoro-N-(6-(4-methoxypyridin-3-yl)benzo[d]thiazol-2-yl)cyclopropane-1-carboxamide | ¹H NMR (400 MHz, CHLOROFORM-d) δ = 1.33-1.44 (m, 1 H), 1.91-2.13 (m, 2 H), 3.94 (s, 3 H), 4.79-5.05 (m, 1 H), 6.96 (d, J = 5.87 Hz, 1 H), 7.63 (dd, J = 8.38, 1.65 Hz, 1 H), 7.87 (d, J = 8.44 Hz, 1 H), 8.02 (d, J = 1.47 Hz, 1 H), 8.51-8.55 (m, 2 H), 10.35 (br s, 1 H); LCMS (electrospray) m/z 344.3 (M + H)+. | N |
| 56 | 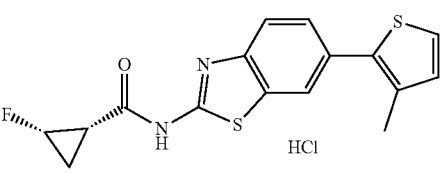<br>(1S,2S)-2-fluoro-N-(6-(3-methylthiophen-2-yl)benzo[d]thiazol-2-yl)cyclopropane-1-carboxamide. HCl salt | ¹H NMR (400 MHz, METHANOL-d₄) δ = 1.27-1.37 (m, 1H), 1.81-1.94 (m, 1 H), 2.14-2.23 (m, 1 H), 2.33 (s, 3 H), 4.98-5.07 (m, 1 H), 6.96 (d, J = 5.14 Hz, 1 H), 7.30 (d, J = 5.14 Hz, 1 H), 7.54 (dd, J = 8.44, 1.71 Hz, 1 H), 7.79 (d, J = 8.44 Hz, 1 H), 7.95 (d, J = 1.59 Hz, 1 H); LCMS (electrospray) m/z 333.0 (M + H)+. | N |
| 57 | 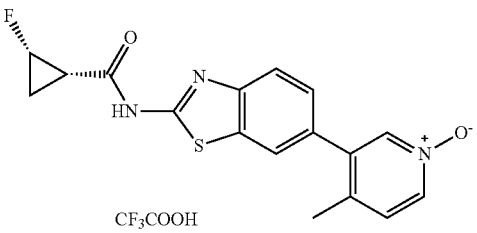<br>3-(2-((1S,2S)-2-fluorocyclopropane-1-carboxamido)benzo[d]thiazol-6-yl)-4-methylpyridine 1-oxide. TFA salt | 1H NMR (400 MHz, DMSO-d6) δ = 12.81 (br s, 1H), 8.29-8.18 (m, 2H), 8.08 (br d, J = 1.3 Hz, 1H), 7.87-7.80 (m, 1H), 7.53-7.41 (m, 2H), 5.18-4.94 (m, 1H), 2.25-2.31 (m, 1H), 2.31 (s, 3H), 1.81-1.71 (m, 1H), 1.38-1.29 (m, 1H); LCMS (electrospray) m/z 344.10 (M + H)+. | N |
| 58 | 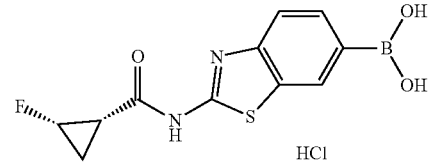<br>(2-((1S,2S)-2-fluorocyclopropane-1-carboxamido)benzo[d]thiazol-6-yl)boronic acid. HCl salt | ¹H NMR (400 MHz, METHANOL-d₄) δ = 1.26-1.39 (m, 1 H), 1.81-1.94 (m, 1 H), 2.19 (dtd, J = 9.19, 6.87, 6.87, 4.34 Hz, 1 H), 4.87-5.18 (m, 1 H), 7.69-7.75 (m, 1 H), 7.81 (br d, J = 7.82 Hz, 1 H), 8.22 (s, 1 H); ; LCMS (electrospray) m/z 281.2 (M + H)+. | O |
| 59 | 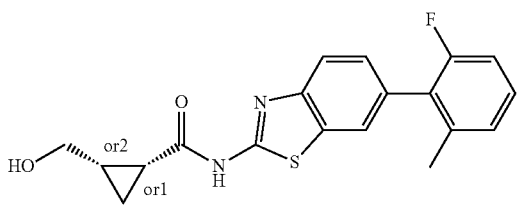<br>(1R,2S)-N-(6-(2-fluoro-6-methylphenyl)benzo[d]thiazol-2-yl)-2-(hydroxymethyl)cyclopropane-1-carboxamide | ¹H NMR (400 MHz, DMSO-d₆) δ = 12.60 (br s, 1H), 7.89 (s, 1H), 7.79 (d, J = 8.2 Hz, 1H), 7.36-7.28 (m, 2H), 7.21-7.07 (m, 2H), 4.56 (br s, 1H), 3.68 (br dd, J = 5.7, 11.2 Hz, 1H), 3.51-3.41 (m, 1H), 2.15-2.06 (m, 4H), 1.67-1.55 (m, 1H), 1.14 (dt, J = 4.0, 8.0 Hz, 1H), 1.05-0.98 (m, 1H); LCMS (electrospray) m/z 357.3 (M + H)+. [a] = (+) 79.105 | K |

TABLE 1-continued

Compounds of Examples

| Ex # | Structure/Name | $^1$H NMR/MS (M + 1) | Synthetic Method |
|---|---|---|---|
| 60 | 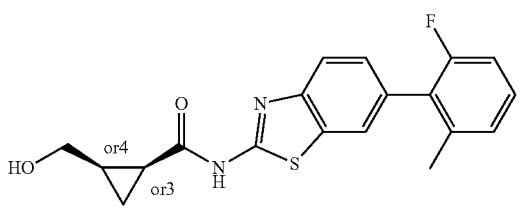<br>(1S,2R)-N-(6-(2-fluoro-6-methylphenyl)benzo[d]thiazol-2-yl)-2-(hydroxymethyl)cyclopropane-1-carboxamide | $^1$H NMR (400 MHz, DMSO-$d_6$) δ = 12.57 (br s, 1H), 7.89 (s, 1H), 7.79 (d, J = 8.3 Hz, 1H), 7.36-7.28 (m, 2H), 7.20-7.08 (m, 2H), 4.59 (br s, 1H), 3.68 (dd, J = 5.8, 11.3 Hz, 1H), 3.46 (br dd, J = 8.5, 11.2 Hz, 1H), 2.16-2.05 (m, 4H), 1.66-1.55 (m, 1H), 1.13 (dt, J = 4.2, 8.1 Hz, 1H), 1.06-0.97 (m, 1H); LCMS (electrospray) m/z 357.2 (M + H)+.<br>[a] = (−) 77.479 | K |
| 61 | 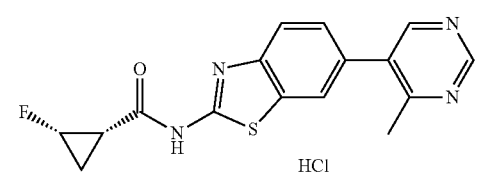<br>(1S,2S)-2-fluoro-N-(6-(4-methylpyrimidin-5-yl)benzo[d]thiazol-2-yl)cyclopropane-1-carboxamide. HCl salt | $^1$H NMR (400 MHz, METHANOL-$d_4$) δ = 1.28-1.39 (m, 1 H), 1.83-1.96 (m 1 H), 2.16-2.26 (m, 1 H), 2.80 (s, 3 H), 5.00-5.08 (m, 1 H), 7.60 (dd, J = 8.38, 1.65 Hz, 1 H), 7.94 (d, J = 8.44 Hz, 1 H), 8.09 (d, J = 1.47 Hz, 1 H), 9.13 (s, 1 H), 9.43 (s, 1 H); LCMS (electrospray) m/z 329.1 (M + H)+. | B |
| 62 | 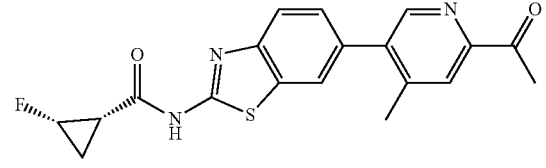<br>(1S,2S)-N-(6-(6-acetyl-4-methylpyridin-3-yl)benzo[d]thiazol-2-yl)-2-fluorocyclopropane-1-carboxamide | $^1$H NMr (400 MHz, DMSO-$d_6$) δ = 1.26-1.37 (m, 1 H), 1.70-1.82 (m, 1 H), 2.24 (dt, J = 13.57, 6.79 Hz, 1 H), 2.40 (s, 3 H), 2.67 (s, 3 H), 4.93-5.18 (m, 1 H), 7.52 (dd, J = 8.38, 1.65 Hz, 1 H), 7.86 (d, J = 8.19 Hz, 1 H), 7.94 (s, 1 H), 8.12 (d, J = 1.34 Hz, 1 H), 8.59 (s, 1 H), 12.79 (br s, 1 H); LCMS (electrospray) m/z 370.3 (M + H)+. | B |
| 63 | 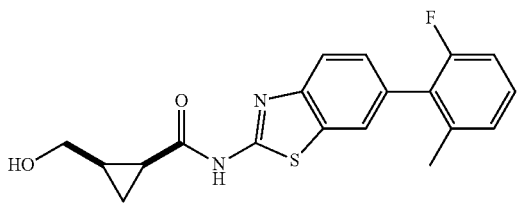<br>(1S,2R)-N-(6-(2-fluoro-6-methylphenyl)benzo[d]thiazol-2-yl)-2-(hydroxymethyl)cyclopropane-1-carboxamide | $^1$H NMR (400 MHz, DMSO-$d_6$) δ = 12.60 (br s, 1H), 7.89 (d, J = 1.2 Hz, 1H), 7.80 (d, J = 8.2 Hz, 1H), 7.36-7.27 (m, 2H), 7.20-7.07 (m, 2H), 4.55 (br s, 1H), 3.68 (dd, J = 5.8, 11.3 Hz, 1H), 3.46 (br dd, J = 8.6, 11.1 Hz, 1H), 2.16-2.08 (m, 4H), 1.67-1.55 (m, 1H), 1.14 (dt, J = 4.2, 8.1 Hz, 1H), 1.06-0.98 (m, 1H); LCMS (electrospray) m/z 357.2 (M + H)+. | K |
| 64 | 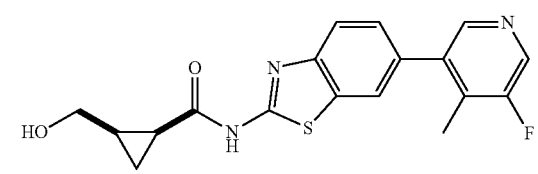<br>(1S,2R)-N-(6-(5-fluoro-4-methylpyridin-3-yl)benzo[d]thiazol-2-yl)-2-(hydroxymethyl)cyclopropane-1-carboxamide | $^1$H NMR (400 MHz, DMSO-$d_6$) δ = 12.98-12.30 (m, 1H), 8.51 (s, 1H), 8.36 (s, 1H), 8.05 (d, J = 1.5 Hz, 1H), 7.82 (d, J = 8.3 Hz, 1H), 7.47 (dd, J = 1.7, 8.3 Hz, 1H), 4.87-4.35 (m, 1H), 3.68 (br dd, J = 5.8, 11.3 Hz, 1H), 3.46 (br dd, J = 8.7, 11.1 Hz, 1H), 2.24 (d, J = 1.8 Hz, 3H), 2.15-2.04 (m, 1H), 1.66-1.55 (m, 1H), 1.14 (dt, J = 4.2, 8.1 Hz, 1H), 1.06-0.98 (m, 1H); LCMS (electrospray) m/z 358.0 (M + H)+. | K |

TABLE 1-continued

Compounds of Examples

| Ex # | Structure/Name | ¹H NMR/MS (M + 1) | Synthetic Method |
|---|---|---|---|
| 65 | 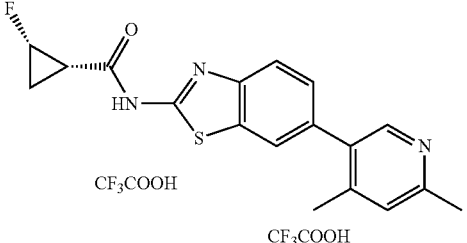<br>(1S,2S)-N-(6-(4,6-dimethylpyridin-3-yl)benzo[d]thiazol-2-yl)-2-fluorocyclopropane-1-carboxamide. 2TFA salt | 1H NMR (400 MHz, DMSO-d6) δ = 12.86 (br s, 1H), 8.71 (s, 1H), 8.13 (d, J = 1.5 Hz, 1H), 7.91-7.87 (m, 2H), 7.54 (dd, J = 1.9, 8.4 Hz, 1H), 5.17-4.95 (m, 1H), 2.70 (s, 3H), 2.49 (s, 3H), 2.29-2.23 (m, 1H), 1.82-1.70 (m, 1H), 1.38-1.29 (m, 1H); LCMS (electrospray) m/z 341.10 (M + H)+. | N |
| 66 | 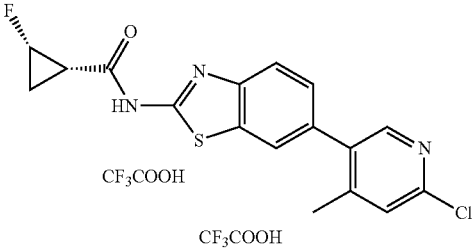<br>(1S,2S)-N-(6-(6-chloro-4-methylpyridin-3-yl)benzo[d]thiazol-2-yl)-2-fluorocyclopropane-1-carboxamide. 2TFA salt | ¹H NMR (400 MHz, DMSO-d₆) δ = 12.77 (s, 1H), 8.27 (s, 1H), 8.05 (s, 1H), 7.83 (d, J = 8.3 Hz, 1H), 7.53 (s, 1H), 7.46 (br d, J = 8.3 Hz, 1H), 5.17-4.93 (m, 1H), 2.31 (s, 3H), 2.28-2.20 (m, 1H), 1.81-1.71 (m, 1H), 1.38-1.26 (m, 1H); LCMS (electrospray) m/z 362.00 (M + H)+. | N |
| 67 | 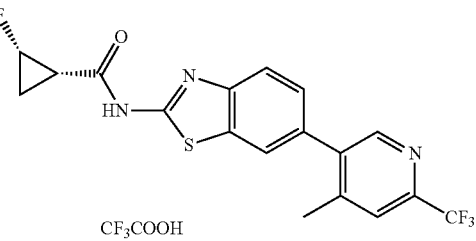<br>(1S,2S)-2-fluoro-N-(6-(4-methyl-6-(trifluoromethyl)pyridin-3-yl)benzo[d]thiazol-2-yl)cyclopropane-1-carboxamide. 2TFA salt | ¹H NMR (400 MHz, DMSO-d₆) δ = 12.79 (s, 1H), 8.62 (s, 1H), 8.11 (d, J = 1.5 Hz, 1H), 7.90 (s, 1H), 7.86 (d, J = 8.3 Hz, 1H), 7.52 (dd, J = 1.7, 8.3 Hz, 1H), 5.15-4.94 (m, 1H), 2.41 (s, 3H), 2.27-2.21 (m, 1H), 1.82-1.70 (m, 1H), 1.31 (tdd, J = 6.4, 8.9, 12.8 Hz, 1H); LCMS (electrospray) m/z 396.10 (M + H)+. | N |
| 68 | 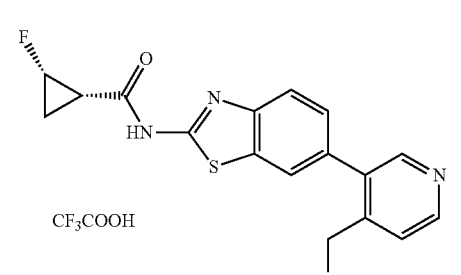<br>(1S,2S)-2-fluoro-N-(6-(4-(hydroxymethyl)pyridin-3-yl)benzo[d]thiazol-2-yl)cyclopropane-1-carboxamide. 2 TFA salt | ¹H NMR (400 MHz, DMSO-d₆) δ = 12.86 (br s, 1H), 8.83 (br d, J = 5.6 Hz, 1H), 8.76 (s, 1H), 8.13 (d, J = 1.6 Hz, 1H), 8.05 (d, J = 5.6 Hz, 1H), 7.88 (d, J = 8.3 Hz, 1H), 7.54 (dd, J = 1.7, 8.3 Hz, 1H), 5.16-4.95 (m, 1H), 4.66 (s, 2H), 2.29-2.23 (m, 1H), 1.81-1.72 (m, 1H), 1.33 (ddd, J = 2.6, 6.3, 12.8 Hz, 1H); LCMS (electrospray) m/z 344.10 (M + H)+ | H |

TABLE 1-continued

Compounds of Examples

| Ex # | Structure/Name | $^1$H NMR/MS (M + 1) | Synthetic Method |
|---|---|---|---|
| 69 | 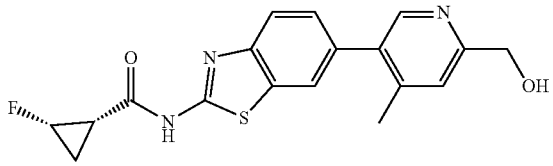<br>(1S,2S)-2-fluoro-N-(6-(6-(hydroxymethyl)-4-methylpyridin-3-yl)benzo[d]thiazol-2-yl)cyclopropane-1-carboxamide | $^1$H NMR (400 MHz, DMSO-d$_6$) δ = 1.32 (ddt, J = 12.79m 8.97, 6.36 Hz, 1H), 1.69-1.82 (m, 1 H), 2.17-2.27 (m, 1 H), 2.31 (s, 3 H), 4.58 (d, J = 5.75 Hz, 2 H), 4.90-5.20 (m, 1 H), 5.41 (t, J = 5.81 Hz, 1 H), 7.41 (s, 1 H), 7.44 (dd, J = 8.31, 1.71 Hz, 1 H), 7.82 (d, J = 8.31 Hz, 1 H), 8.03 (d, J = 1.47 Hz, 1 H), 8.33 (s, 1 H), 12.75 (br s, 1 H); LCMS (electrospray) m/z 358.1 (M + H)+. | H |
| 70 | 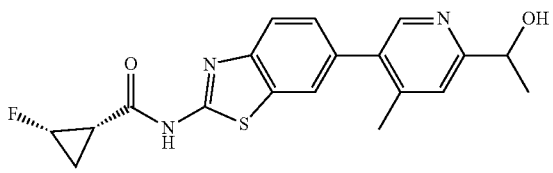<br>(1S,2S)-2-fluoro-N-(6-(6-(1-hydroxyethyl)-4-methylpyridin-3-yl)benzo[d]thiazol-2-yl)cyclopropane-1-carboxamide | $^1$H NMR (400 MHz, DMSO-d$_6$) δ = 1.19-1.33 (m, 1 H), 1.40 (d, J = 6.48 Hz, 3 H), 1.66-1.81 (m, 1 H), 2.12-2.25 (m, 1 H), 2.31 (s, 3 H), 4.74 (q, J = 6.56 Hz, 1 H), 4.90-5.13 (m, 1 H), 5.37 (br s, 1 H), 7.41 (dd, J = 8.31, 1.59 Hz, 1 H), 7.44 (s, 1 H), 7.77 (d, J = 8.31 Hz, 1 H), 7.98 (s, 1 H), 8.32 (s, 1 H); LCMS (electrospray) m/z 372.2 (M + H)+. | G |
| 71* | 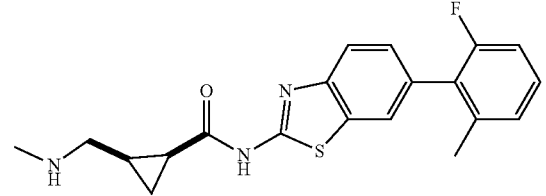<br>N-(6-(2-fluoro-6-methylphenyl)benzo[d]thiazol-2-yl)-2-((methylamino)methyl)cyclopropane-1-carboxamide. 2 HCl salt | $^1$H NMR (400 MHz, METHANOL-d4) δ = 7.74 (s, 1H), 7.87-7.71 (m, 1H), 7.61 (d, J = 8.4 Hz, 1H), 7.49-7.40 (m, 1H), 7.30 (dt, J = 5.7, 7.9 Hz, 1H), 7.14 (d, J = 7.7 Hz, 1H), 7.02 (t, J = 8.9 Hz, 1H), 3.88 (br d, J = 6.5 Hz, 2H), 2.74 (s, 3H), 2.16 (s, 3H), 1.87 (dt, J = 5.7, 8.2 Hz, 1H), 1.71 (qd, J = 7.9, 15.3 Hz, 1H), 1.30-1.06 (m, 2H); LCMS (electrospray) m/z 370.0 (M + H)+. | P |
| 72 | 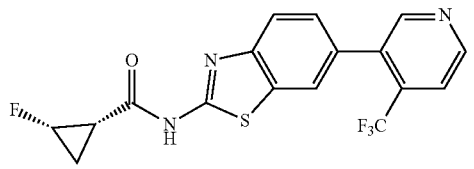<br>(1S,2S)-2-fluoro-N-(6-(4-(trifluoromethyl)pyridin-3-yl)benzo[d]thiazol-2-yl)cyclopropane-1-carboxamide. 2 TFA salt | $^1$H NMR (400 MHz, DMSO-d$_6$) δ = 1.33 (ddt, J = 12.91, 9.00, 6.34, 6.34 Hz, 1H), 1.70-1.82 (m, 1 H), 2.20-2.29 (m, 1 H), 4.93-5.19 (m, 1 H), 7.44 (br d, J = 8.31 Hz, 1 H), 7.85 (d, J = 8.31 Hz, 1 H), 7.88 (d, J = 5.14 Hz, 1 H), 8.06 (d, J = 1.22 Hz, 1 H), 8.77 (s, 1 H), 8.90 (d, J = 5.14 Hz, 1 H), 12.84 (s, 1 H); LCMS (electrospray) m/z 382.2 (M + H)+. | B |
| 73 | 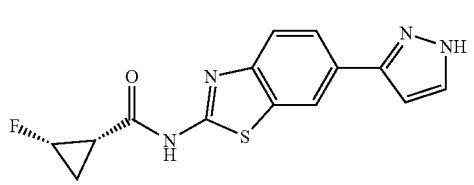<br>(1S,2S)-N-(6-(1H-pyrazol-3-yl)benzo[d]thiazol-2-yl)-2-fluorocyclopropane-1-carboxamide | $^1$H NMR (400 MHz, DMSO-d$_6$) δ = 1.24-1.36 (m, 1 H), 1.68-1.81 (m, 1 H), 2.22 (dt, J = 13.48, 6.77 Hz, 1 H), 4.90-5.16 (m, 1 H), 6.67-6.80 (m, 1 H), 7.72-7.82 (m, 2 H), 7.93 (br d, J = 7.58 Hz, 1 H), 8.29-8.42 (m, 1 H), 12.59-12.93 (m, 2 H); LCMS (electrospray) m/z 303.2 (M + H)+. | C |

TABLE 1-continued

Compounds of Examples

| Ex # | Structure/Name | ¹H NMR/MS (M + 1) | Synthetic Method |
|---|---|---|---|
| 74 | 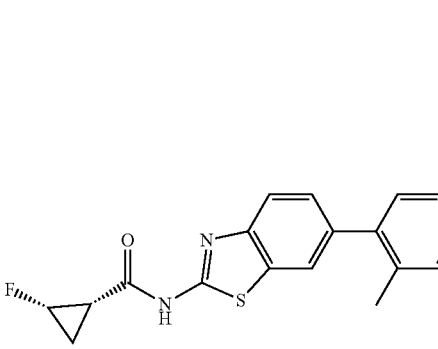<br>(1S,2S)-2-fluoro-N-(6-(2-methyl-5-(pyridin-2-ylethynyl)phenyl)benzo[d]thiazol-2-yl)cyclopropane-1-carboxamide | ¹H NMR (400 MHz, DMSO-d$_6$) δ = 1.32 (ddt, J = 12.76, 9.00, 6.30 Hz, 1 H), 1.69-1.81 (m, 1 H), 2.18-2.26 (m, 1 H), 2.31 (s, 3H), 4.93-5.16 (m, 1 H), 7.38-7.41 (m, 1 H), 7.42-7.44 (m, 1H), 7.46 (dd, J = 8.31, 1.71 Hz, 1 H), 7.49 (d, J = 1.59 Hz, 1 H), 7.51-7.55 (m, 1 H), 7.64 (d, J = 7.82 Hz, 1 H), 8.55-8.64 (m, 1 H), 12.75 (br s, 1 H); LCMS (electrospray) m/z 428.3 (M + H)+. | B |
| 75 | 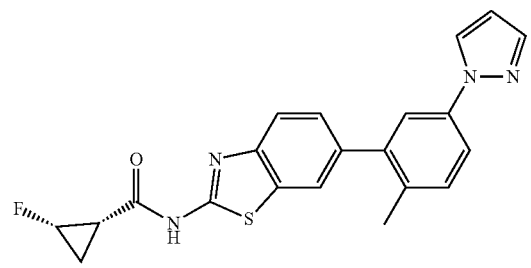<br>(1S,2S)-2-fluoro-N-(6-(2-methyl-5-(1H-pyrazol-1-yl)phenyl)benzo[d]thiazol-2-yl)cyclopropane-1-carboxamide | ¹H NMR (400 MHz, DMSO-d$_6$) 12.75 (s, 1H), 8.54 (d, J = 2.3 Hz, 1H), 8.05 (d, J = 1.5 Hz, 1H), 7.82 (d, J = 8.3 Hz, 1H), 7.79-7.70 (m, 3H), 7.48 (dd, J = 1.7, 8.3 Hz, 1H), 7.43 (d, J = 8.2 Hz, 1H), 6.55-6.49 (m, 1H), 5.18-4.90 (m, 1H), 2.29 (s, 3H), 2.27-2.21 (m, 1H), 1.83-1.69 (m, 1H), 1.32 (tdd, J = 6.3, 8.9, 12.9 Hz, 1H); LCMS (electrospray) m/z 393.3 (M + H)+. | N |
| 76* | 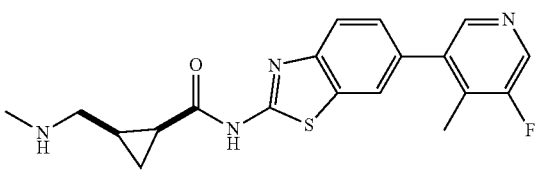<br>3HCl<br>N-(6-(5-fluoro-4-methylpyridin-3-yl)benzo[d]thiazol-2-yl)-2-((methylamino)methyl)cyclopropane-1-carboxamide. 3 HCl salt | ¹H NMR (400 MHz, METHANOL-d4) δ 8.97 (br s, 1H), 8.73 (br s, 1H), 8.12-7.91 (m, 1H), 7.84-7.51 (m, 2H), 4.02-3.79 (m, 2H), 2.75-(s, 3H), 2.61-2.35 (m, 3H), 1.90-1.87 (m, 1H), 1.76-1.70 (m, 1H), 1.38-0.98 (m, 2H); LCMS (electrospray) m/z 371.2 (M + H)+. | P |
| 77 | 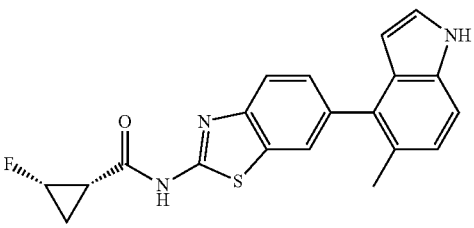<br>(1S,2S)-2-fluoro-N-(6-(5-methyl-1H-indol-4-yl)benzo[d]thiazol-2-yl)cyclopropane-1-carboxamide | ¹H NMR (400 MHz, DMSO-d$_6$) δ = 12.72 (br s, 1H), 11.05 (br s, 1H), 7.94 (d, J = 1.5 Hz, 1H), 7.82 (d, J = 8.2 Hz, 1H), 7.41 (dd, J = 1.7, 8.3 Hz, 1H), 7.30 (d, J = 8.3 Hz, 1H), 7.25 (t, J = 2.8 Hz, 1H), 7.04 (d, J = 8.3 Hz, 1H), 6.01 (br s, 1H), 5.17-4.92 (m, 1H), 2.28-2.18 (m, 4H); LCMS (electrospray) m/z 366.2 (M + H)+. | B |

TABLE 1-continued

Compounds of Examples

| Ex # | Structure/Name | $^1$H NMR/MS (M + 1) | Synthetic Method |
|---|---|---|---|
| 78 | 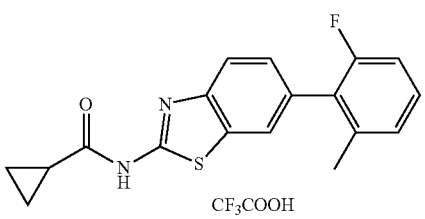<br>N-(6-(2-fluoro-6-methylphenyl)benzo[d]thiazol-2-yl)cyclopropanecarboxamide. TFA salt | $^1$H NMR (400 MHz, DMSO-d$_6$) δ = 12.70 (br s, 1H), 7.89 (s, 1H), 7.79 (d, J = 8.2 Hz, 1H), 7.36-7.28(m, 2H), 7.20-7.09 (m, 2H), 2.13 (s, 3H), 1.99 (br d, J = 6.0 Hz, 1H), 1.01-0.90 (m, 4H); LCMS (electrospray) m/z 327.2 (M + H)+. | A |
| 79 | 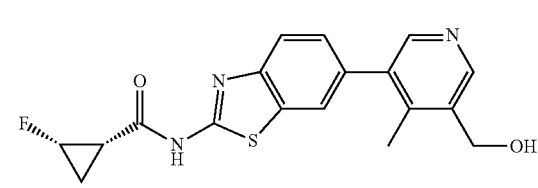<br>(1S,2S)-2-fluoro-N-(6-(5-(hydroxymethyl)-4-methylpyridin-3-yl)benzo[d]thiazol-2-yl)cyclopropane-1-carboxamide | $^1$H HNMR (400 MHz, DMSO-d$_6$) δ = 8.44 (s, 1H), 8.32 (s, 1H), 7.69 (br s, 1H), 7.56 (br s, 1H), 7.19 (br d, J = 7.5 Hz, 1H), 5.25 (br s, 1H), 4.99-4.73 (m, 1H), 4.60 (s, 2H), 2.23 (s, 3H), 1.96 (br s, 1H), 1.71-1.57 (m, 1H), 1.03 (br s, 1H); LCMS (electrospray) m/z 358.3 (M + H)+. | B |
| 80 | 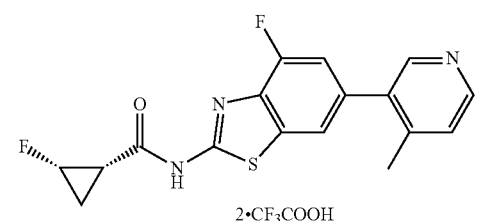<br>(1S,2S)-2-fluoro-N-(4-fluoro-6-(4-methylpyridin-3-yl)benzo[d]thiazol-2-yl)cyclopropane-1-carboxamide. 2 TFA salt | $^1$H NMR (400 MHz, DMSO-d$_6$) δ = 13.07 (s, 1H), 8.64 (br d, J = 7.7 Hz, 2H), 7.95 (br d, J = 1.2 Hz, 1H), 7.68 (br s, 1H), 7.47 (br d, J = 11.5 Hz, 1H), 5.17-4.96 (m, 1H), 2.43 (br s, 3H), 2.23 (td, J = 6.9, 13.5 Hz, 1H), 1.83-1.70 (m, 1H), 1.34 (qd, J = 6.4, 15.1 Hz, 1H); LCMS (electrospray) m/z 346.3 (M + H)+. | Q |
| 81 | 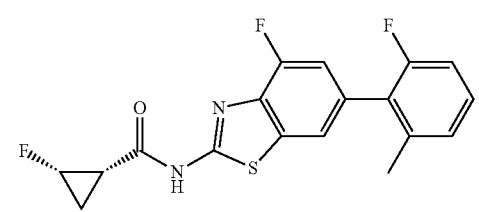<br>(1S,2S)-2-fluoro-N-(4-fluoro-6-(2-fluoro-6-methylphenyl)benzo[d]thiazol-2-yl)cyclopropane-1-carboxamide | $^1$H NMR (400 MHz, DMSO-d$_6$) δ = 12.99 (br s, 1H), 7.69 (s, 1H), 7.38-7.29 (m, 1H), 7.22-7.16 (m, 2H), 7.13 (t, J = 8.9 Hz, 1H), 5.13-4.88 (m, 1H), 2.16 (s, 4H), 1.80-167 (m, 1H), 1.32-1.19 (m, 2H); LCMS (electrospray) m/z 363.2 (M + H)+. | Q |
| 82 | 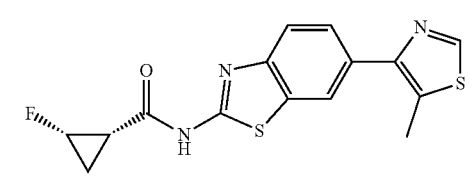<br>(1S,2S)-2-fluoro-N-(6-(5-methylthiazol-4-yl)benzo[d]thiazol-2-yl)cyclopropane-1-carboxamide | $^1$H NMR (400 MHz, DMSO-d$_6$) δ = 12.73 (br s, 1H), 8.96 (s, 1H), 8.26 (d, J = 1.2 Hz, 1H), 7.83-7.72 (m, 2H), 5.15-4.92 (m, 1H), 2.62 (s, 3H), 2.27-2.17 (m, 1H), 1.81-1.68 (m, 1H), 1.29-(tdd, J = 6.3, 9.0, 12.7 Hz, 1H); LCMS (electrospray) m/z 343.2 (M + H)+. | B |

TABLE 1-continued

Compounds of Examples

| Ex # | Structure/Name | ¹H NMR/MS (M + 1) | Synthetic Method |
|---|---|---|---|
| 83 | 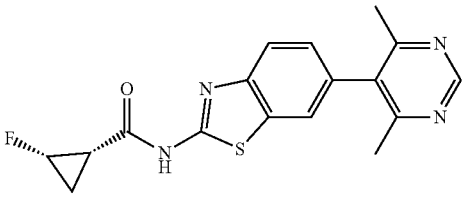<br>(1S,2S)-N-(6-(4,6-dimethylpyrimidin-5-yl)benzo[d]thiazol-2-yl)-2-fluorocyclopropane-1-carboxamide. HCl salt | ¹H NMR (400 MHz, DMSO-$d_6$) δ = 1.26-1.38 (m, 1 H), 1.69-1.83 (m, 1 H), 2.19-2.29 (m, 7 H), 4.92-5.18 (m, 1 H), 7.36 (dd, J = 8.25, 1.77 Hz, 1 H), 7.86 (d, J = 8.31 Hz, 1 H), 7.95 (d, J = 1.47 Hz, 1 H), 8.95 (s, 1 H), 12.81 (br s, 1 H); LCMS (electrospray) m/z 343.2 (M + H)+. | A |
| 84 | 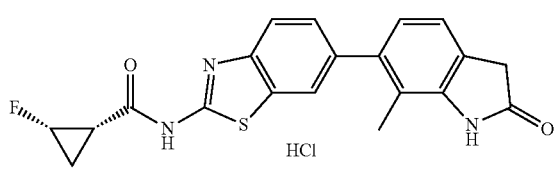<br>(1S,2S)-2-fluoro-N-(6-(7-methyl-2-oxoindolin-6-yl)benzo[d]thiazol-2-yl)cyclopropane-1-carboxamide. HCl salt | ¹H NMR (400 MHz, DMSO-$d_6$) δ = 12.71 (s, 1H), 10.45 (s, 1H), 7.91 (d, J = 1.5 Hz, 1H), 7.77 (d, J = 8.4 Hz, 1H), 7.36 (dd, J = 1.7, 8.3 Hz, 1H), 7.11 (d, J = 7.6 Hz, 1H), 6.86 (d, J = 7.6 Hz, 1H), 5.17-4.92 (m, 1H), 3.54 (s, 2H), 2.23 (td, J = 6.9, 1.36-1.26 (m, 1H); LCMS (electrospray) m/z 382.2 (M + H)+. | N |
| 85 | 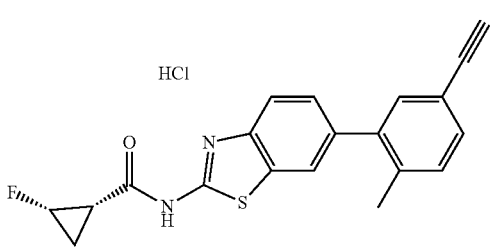<br>(1S,2S)-N-(6-(5-ethynyl-2-methylphenyl)benzo[d]thiazol-2-yl)-2-fluorocyclopropane-1-carboxamide. HCl salt | ¹H NMR (400 MHz, DMSO-$d_6$) δ = 1.24-1.36 (m, 1H), 1.63-1.84 (m, 1H), 2.19-2.25 (m, 1 H), 7.31-7.36 (m, 2H), 2 H), 7.37-7.43 (m, 2 H), 7.79 (d, J = 8.31 Hz, 1 H), 7.98 (d, J = 1.47 Hz, 1 H), 12.74 (s, 1 H); LCMS (electrospray) m/z 351.1 (M + H)+. | B |
| 86 | 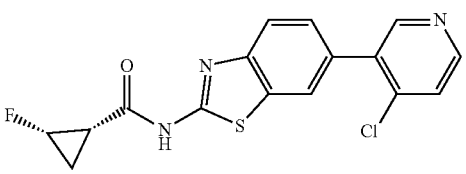<br>(1S,2S)-N-(6-(4-chloropyridin-3-yl)benzo[d]thiazol-2-yl)-2-fluorocyclopropane-1-carboxamide | ¹H NMR (400 MHz, DMSO-$d_6$) δ = 1.33 (ddt, J = 12.79, 8.97, 6.36, 6.36 Hz, 1 H), 1.70-1.83 (m, 1 H), 2.20-2.29 (m, 1 H), 4.94-5.18 (m, 1H), 7.56 (dd, J = 8.38, 1.77 Hz, 1 H), 7.70 (d, J = 5.26 Hz, 1 H), 7.86 (d, J = 8.31 Hz, 1 H), 8.15 (d, J = 1.59 Hz, 1 H), 8.56 (d, J = 5.26 Hz, 1 H), 8.66 (s, 1 H), 12.81 (br s, 1 H).; LCMS (electrospray) m/z 347.9 (M + H)+. | N |
| 87 | 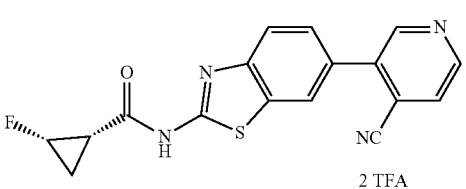<br>(1S,2S)-N-(6-(4-cyanopyridin-3-yl)benzo[d]thiazol-2-yl)-2-fluorocyclopropane-1-carboxamide. 2 TFA salt | ¹H NMR (400 MHz, DMSO-$d_6$) δ = 1.33 (dq, J = 15.30, 6.39 Hz, 1 H), 1.70-1.84 (m, 1 H), 2.25 (dt, J = 13.48, 6.89 Hz, 1 H), 4.90-5.18 (m, 1 H), 7.73 (dd, J = 8.44, 1.83 Hz, 1 H), 7.93 (d, J = 8.31 Hz, 1 H), 8.00 (d, J = 5.14 Hz, 1 H), 8.33 (d, J = 1.47 Hz, 1 H), 8.83 (d, J = 5.01 Hz, 1 H), 8.98 (s, 1 H), 12.86 (br s, 1 H); LCMS (electrospray) m/z 339.1 (M + H)+. | B |

TABLE 1-continued

Compounds of Examples

| Ex # | Structure/Name | ¹H NMR/MS (M + 1) | Synthetic Method |
|---|---|---|---|
| 88 | 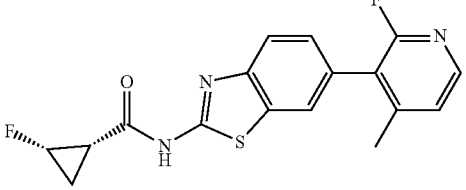<br>(1S,2S)-2-fluoro-N-(6-(2-fluoro-4-methylpyridin-3-yl)benzo[d]thiazol-2-yl)cyclopropane-1-carboxamide | ¹H NMR (400 MHz, DMSO-$d_6$) δ = 1.28 (br d, J = 8.68 Hz, 1 H), 1.66-1.81 (m, 1 H), 2.23 (s, 4 H), 4.87-5.18 (m, 1 H), 7.33-7.43 (m, 2 H), 7.81 (br d, J = 7.95 Hz, 1 H), 7.98 (s, 1 H), 8.12 (br d, J = 4.77 Hz, 1 H), 12.69 (br s, 1 H); LCMS (electrospray) m/z 346.10 (M + H)+. | N |
| 89 | <br>(1S,2S)-2-fluoro-N-(6-(4-(trifluoromethyl)pyrimidin-5-yl)benzo[d]thiazol-2-yl)cyclopropane-1-carboxamide | ¹H NMR (400 MHz, DMSO-$d_6$) δ = 1.28-1.38 (m, 1 H), 1.70-1.82 (m, 1 H), 2.24 (br s, 1 H), 4.91-5.18 (m, 1 H), 7.50 (br d, J = 8.07 Hz, 1 H), 7.87 (d, J = 8.31 Hz, 1 H), 8.11 (s, 1 H), 9.14 (s, 1 H), 9.47 (s, 1 H), 12.82 (br s, 1 H); LCMS (electrospray) m/z 383.2 (M + H)+. | N |
| 90 | 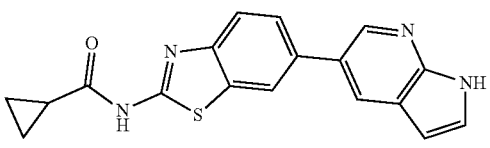<br>N-(6-(1H-pyrrolo[2,3-b]pyridin-5-yl)benzo[d]thiazol-2-yl)cyclopropanecarboxamide | ¹H NMR (400 MHz, DMSO-$d_6$) δ = 12.66 (s, 1H), 11.70 (s, 1H), 8.57 (d, J = 5 Hz, 1H), 8.31 (d, J = 3 Hz, 1H), 8.25 (d, J = 4 Hz, 1H), 7.81 (t, J = 21 Hz, 1H), 7.77 (dd, J = 5, 4 Hz, 1H), 7.52 (t, J = 7 Hz, 1H), 6.51 (q, J = 5 Hz, 1H), 2.02 (m, 1H), 0.97 (m, 4H); LCMS (electrospray) m/z 335.2 (M + H)+. | C |
| 91 | 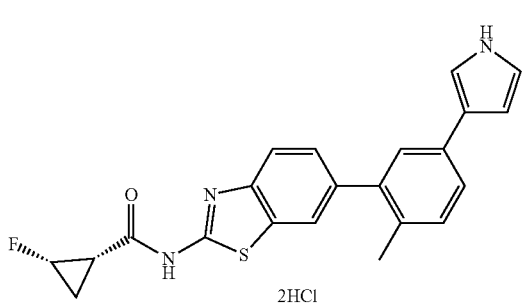<br>(1S,2S)-2-fluoro-N-(6-(2-methyl-5-(1H-pyrrol-3-yl)phenyl)benzo[d]thiazol-2-yl)cyclopropane-1-carboxamide. 2 HCl salt | 1H NMR (400 MHz, DMSO-d6) Shift = 12.70 (s, 1H), 10.87 (br s, 1H), 7.98 (d, J = 1.6 Hz, 1H), 7.79 (d, J = 8.3 Hz, 1H), 7.48-7.36 (m, 3H), 7.27-7.18 (m, 2H), 6.77 (q, J = 2.3 Hz, 1H), 6.43 (d, J = 1.7 Hz, 1H), 5.17-4.91 (m, 1H), 2.27-2.23 (m, 1H), 2.21 (s, 3H), 1.83-1.67 (m, 1H), 1.31 (tdd, J = 6.4, 9.0, 12.8 Hz, 1H); LCMS (electrospray) m/z 392.1 (M + H)+. | R |

TABLE 1-continued

Compounds of Examples

| Ex # | Structure/Name | ¹H NMR/MS (M + 1) | Synthetic Method |
|---|---|---|---|
| 92 | 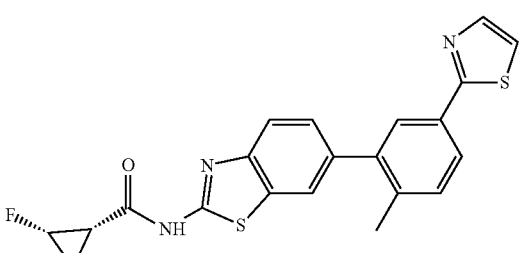<br>(1S,2S)-2-fluoro-N-(6-(2-methyl-5-(thiazol-2-yl)phenyl)benzo[d]thiazol-2-yl)cyclopropane-1-carboxamide, 2HCl salt | 1H NMR (400 MHz, DMSO-d6) Shift = 12.88 (br s, 1H), 8.16 (d, J = 1.3 Hz, 1H), 8.02 (d, J = 3.2 Hz, 1H), 7.98 (dd, J = 1.8, 7.9 Hz, 1H), 7.95-7.90 (m, 2H), 7.88 (d, J = 3.2 Hz, 1H), 7.63-7.53 (m, 2H), 5.33-5.01 (m, 1H), 2.42 (s, 3H), 2.40-2.33 (m, 1H), 1.96-1.77 (m, 1H), 1.53-1.36 (m, 1H); LCMS (electrospray) m/z 410.2 (M + H)+. | S |
| 93 | 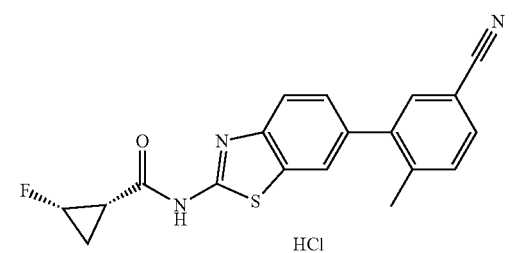<br>(1S,2S)-N-(6-(5-cyano-2-methylphenyl)benzo[d]thiazol-2-yl)-2-fluorocyclopropane-1-carboxamide, HCl salt | ¹H NMR (400 MHz, DMSO-d₆) δ = 1.32 (ddt, J = 12.84, 9.02, 6.31, 6.31 Hz, 1 H), 1.69-1.81 (m, 1 H), 2.20-2.28 (m, 1 H), 2.34 (s, 3 H), 4.93-5.17 (m, 1 H), 7.45 (dd, J = 8.38, 1.77 Hz, 1 H), 7.54 (d, J = 7.83 Hz, 1 H), 7.71-7.77 (m, 2 H), 7.81 (d, J = 8.31 Hz, 1 H), 8.03 (d, J = 1.47 Hz, 1 H), 12.79 (s, 1 H); LCMS (electrospray) m/z 352.2 (M + H)+. | N |
| 94 | 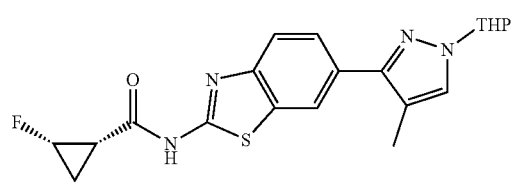<br>(1S,2S)-2-fluoro-N-(6-(4-methyl-1-(tetrahydro-2H-pyran-2-yl)-1H-pyrazol-3-yl)benzo[d]thiazol-2-yl)cyclopropane-1-carboxamide | ¹H NMR (400 MHz, DMSO-d₆) δ = 12.72 (br s, 1H), 8.22 (s, 1H), 7.81-7.71 (m, 3H), 5.36 (dd, J = 2.1, 10.0 Hz, 1H), 5.16-4.92 (m, 1H), 3.94 (br d, J = 11.9 Hz, 1H), 3.68-3.58 (m, 1H), 2.28-2.19 (m, 4H), 2.16-2.05 (m, 1H), 2.02-1.89 (m, 2H), 1.81-1.65 (m, 2H), 1.60-1.50 (m, 2H), 1.31 (tdd, J = 6.4, 8.9, 12.8 Hz, 1H); LCMS (electrospray) m/z 401.1 (M + H)+. | T |
| 95 | 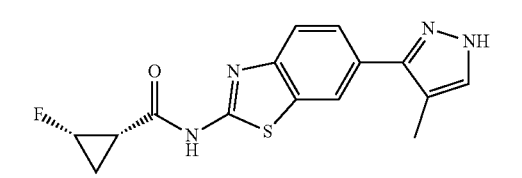<br>(1S,2S)-2-fluoro-N-(6-(4-methyl-1H-pyrazol-3-yl)benzo[d]thiazol-2-yl)cyclopropane-1-carboxamide | ¹H NMR (400 MHz, DMSO-d₆) δ = 12.46 (br s, 2H), 8.15 (s, 1H), 7.80-7.75 (m, 1H), 7.74-7.66 (m, 1H), 7.47 (br s, 1H), 5.12-4.88 (m, 1H), 2.30-2.19 (m, 4H), 1.85-1.70 (m, 1H), 1.36-1.22 (m, 1H); LCMS (electrospray) m/z 317.2 (M + H)+. | T |

TABLE 1-continued

Compounds of Examples

| Ex # | Structure/Name | ¹H NMR/MS (M + 1) | Synthetic Method |
|---|---|---|---|
| 96 | 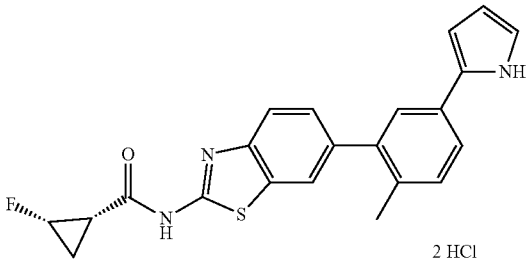<br>(1S,2S)-2-fluoro-N-(6-(2-methyl-5-(1H-pyrrol-2-yl)phenyl)benzo[d]thiazol-2-yl)cyclopropane-1-carboxamide. 2HCl salt | ¹H NMR (400 MHz, DMSO-$d_6$) δ = 1.26-1.38 (m, 1 H), 1.67-1.82 (m, 1 H), 2.20-2.28 (m, 4 H), 4.92-5.17 (m, 1 H), 6.06-6.12 (m, 1 H), 6.49 (br s, 1 H), 6.80 (br d, J = 1.34 Hz, 1 H), 7.27 (d, J = 7.70 Hz, 1 H), 7.45 (dd, J = 8.31, 1.71 Hz, 1 H), 7.50-7.56 (m, 2 H), 7.81 (d, J = 8.31 Hz, 1 H), 8.00 (d, J = 1.34 Hz, 1 H), 11.23 (br s, 1 H), 12.71 (s, 1H) ); LCMS (electrospray) m/z 392.1 (M + H)+. | R |
| 97 | 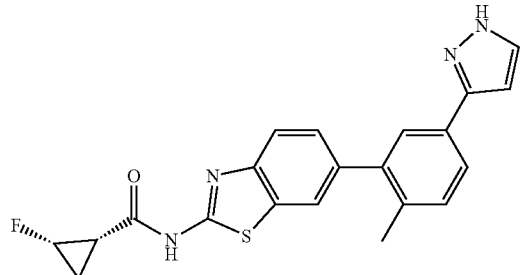<br>(1S,2S)-2-fluoro-N-(6-(2-methyl-5-(1H-pyrazol-3-yl)phenyl)benzo[d]thiazol-2-yl)cyclopropane-1-carboxamide. 2 TFA salt | ¹H NMR (400 MHz, DMSO-$d_6$) δ = 1.32 (ddt, J = 12.64, 9.00, 6.30, 6.30 Hz, 1 H), 1.68-1.83 (m, 1 H), 2.19-2.29 (m, 4 H), 4.92-5.18 (m, 1 H), 6.72 (d, J = 2.08 Hz, 1 H), 7.35 (d, J = 8.68 Hz, 1 H), 7.45 (dd, J = 8.31, 1.83 Hz, 1 H), 7.66-7.74 (m, 3 H), 7.81 (d, J = 8.31 Hz, 1 H), 8.01 (d, J = 1.47 Hz, 1 H), 12.72 (br s, 1H); LCMS (electrospray) m/z 393.2 (M + H)+. | R |
| 98 | 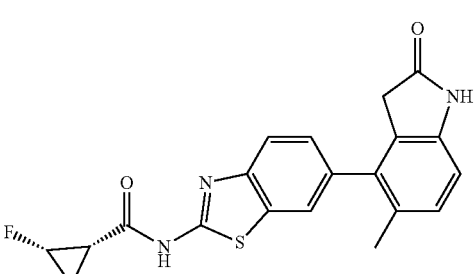<br>(1S,2S)-2-fluoro-N-(6-(5-methyl-2-oxoindolin-4-yl)benzo[d]thiazol-2-yl)cyclopropane-1-carboxamide. TFA salt | ¹H NMR (400 MHz, DMSO-$d_6$) δ = 1.31 (ddt, J = 12.78, 8.99, 6.30, 6.30 Hz, 1H), 1.68-1.82 (m, 1 H), 2.08 (s, 3H), 2.19-2.26 (m, 1 H), 3.25 (s, 2H), 4.90-5.19 (m, 1 H), 6.74 (d, J = 7.82 Hz, 1 H), 7.13 (d, J = 7.95 Hz, 1 H), 7.35 (dd, J = 8.25, 1.65 Hz, 1 H), 7.79 (d, J = 8.31 Hz, 1 H), 7.93 (d, J = 1.47 Hz, 1 H), 10.33 (s, 1 H), 12.72 (s, 1 H); LCMS (electrospray) m/z 382.1 (M + H)+. | N |
| 99 | 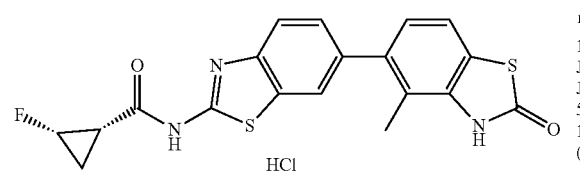<br>(1S,2S)-2-fluoro-N-(4-methyl-2-oxo-2,3-dihydro-[5,6'-bibenzo[d]thiazol]-2'-yl)cyclopropane-1-carboxamide. HCl salt | ¹H NMR (400 MHz, DMSO-d6) δ = 12.75-12.70 (m, 1H), 11.78-11.74 (m, 1H), 7.95 (d, J = 1.5 Hz, 1H), 7.79 (d, J = 8.3 Hz, 1H), 7.47 (d, J = 8.1 Hz, 1H), 7.41-7.37 (m, 1H), 7.08 (s, 1H), 5.17-4.94 (m, 1H), 2.29-2.18 (m, 4H), 1.81-1.71 (m, 1H), 1.36-1.28 (m, 1H); LCMS (electrospray) m/z 400.1 (M + H)+. | U |

TABLE 1-continued

Compounds of Examples

| Ex # | Structure/Name | ¹H NMR/MS (M + 1) | Synthetic Method |
|---|---|---|---|
| 100 | N-(6-(3-methyl-1H-pyrrolo[2,3-b]pyridin-5-yl)benzo[d]thiazol-2-yl)cyclopropanecarboxamide | ¹H NMR (400 MHz, DMSO-$d_6$) δ = 12.66(s, 1H), 11.35(s, 1H), 8.55 (d, J = 4 Hz, 1H), 8.33(d, J = 5 Hz, 1H), 8.22(d, J = 6 Hz, 1H), 7.81(s, 2H), 7.27(s, 1H), 2.31(s, 3H), 2.05-1.99(m, 1H), 0.98-0.96(m, 4H); LCMS (electrospray) m/z 349.1 (M + H)+. | C |
| 101 | (1S,2S)-N-(6-(1H-pyrrolo[2,3-b]pyridin-5-yl)benzo[d]thiazol-2-yl)-2-fluorocyclopropane-1-carboxamide | ¹H NMR (400 MHz, DMSO-$d_6$) δ = 12.72(s, 1H), 11.71(s, 1H), 8.57 (d, J = 6 Hz, 1H), 8.33(d, J = 4 Hz, 1H), 8.26(d, J = 4 Hz, 1H), 7.84-7.77(m, 2H), 7.52(t, J = 8 Hz, 1H), 6.51(q, J = 6 Hz, 1H), 5.15-5.11 (m, 0.5H), 4.98-4.94(m, 0.5H), 2.67-2.20(m, 1H), 1.81-1.70(m, 1H), 1.36-1.27(m, 1H); LCMS (electrospray) m/z 353.0 (M + H)+. | A |
| 102 | N-(6-(1H-pyrazolo[3,4-b]pyridin-5-yl)benzo[d]thiazol-2-yl)cyclopropanecarboxamide | ¹H NMR (400 MHz, DMSO-$d_6$) δ = 13.72(s, 1H), 8.89(d, J = 4 Hz, 1H), 8.52(d, J = 6 Hz, 1H), 8.37(d, J = 2 Hz, 1H), 8.20(s, 1H), 7.85-7.80(m, 2H), 2.06-2.00(m, 1H), 0.99-0.96(m, 4H); LCMS (electrospray) m/z 336.0 (M + H)+. | C |
| 103 | N-(6-(2-oxo-2,3-dihydro-1H-pyrrolo[2,3-b]pyridin-5-yl)benzo[d]thiazol-2-yl)cyclopropanecarboxamide | ¹H NMR (400 MHz, DMSO-$d_6$) δ = 12.67(s, 1H), 11.07(s, 1H), 8.41(d, J = 6 Hz, 1H), 8.25(d, J = 4 Hz, 1H), 7.92(s, 1H), 7.79(d, J = 21 Hz, 1H), 7.71-7.69(m, 1H), 3.62(s, 2H), 2.04-1.98 (m, 1H), 0.99-0.95(m, 4H); LCMS (electrospray) m/z 351.1 (M + H)+. | C |

TABLE 1-continued

Compounds of Examples

| Ex # | Structure/Name | ¹H NMR/MS (M + 1) | Synthetic Method |
|---|---|---|---|
| 104 | N-(6-(2,3-dihydro-1H-pyrrolo[2,3-b]pyridin-5-yl)benzo[d]thiazol-2-yl)cyclopropanecarboxamide | ¹H NMR (400 MHz, DMSO-$d_6$) δ = 12.61(s, 1H), 8.13(d, J = 4 Hz, 1H), 8.05(d, J = 6 Hz, 1H), 7.72(d, J = 21 Hz, 1H), 7.62-7.59(m, 2H), 6.51(s, 1H), 3.52(t, J = 21 Hz, 1H), 3.03(t, J = 21 Hz, 1H), 2.03-1.97(m, 1H), 0.98-0.93(m, 4H); LCMS (electrospray) m/z 337.1 (M + H)+. | C |
| 105 | (1S,2S)-2-fluoro-N-(6-(3-methylisothiazol-5-yl)benzo[d]thiazol-2-yl)cyclopropane-1-carboxamide. 2 HCl salt | ¹H NMR (400 MHz, DMSO-$d_6$) δ = 12.86 (br s, 1H), 8.39 (s, 1H), 7.83-7.78 (m, 1H), 7.77-7.71 (m, 1H), 7.61 (s, 1H), 5.17-4.93 (m, 1H), 2.46 (s, 3H), 2.29-2.22 (m, 1H), 1.82-1.68 (m, 1H), 1.39-1.26 (m, 1H); LCMS (electrospray) m/z 334.0 (M + H)+. | N |
| 106 | (1S,2S)-N-(6-(4-chloro-3-methylisothiazol-5-yl)benzo[d]thiazol-2-yl)-2-fluorocyclopropane-1-carboxamide. 2 HCl Salt. | ¹H NMR (400 MHz, METHANOL-$d_4$) δ = 8.24 (s, 1H), 7.87 (d, J = 8.3 Hz, 1H), 7.73 (br d, J = 8.7 Hz, 1H), 5.02 (br d, J = 3.8 Hz, 1H), 2.51 (s, 3H), 2.18 (br s, 1H), 1.95-1.81 (m, 1H), 1.30 (br d, J = 6.2 Hz, 1H); LCMS (electrospray) m/z 368.1 (M + H)+. | N |
| 107 | (1S,2S)-2-fluoro-N-(6-(7-methyl-1H-indazol-4-yl)benzo[d]thiazol-2-yl)cyclopropane-1-carboxamide | ¹H NMR (400 MHz, DMSO-$d_6$) δ = 13.30 (br s, 1H), 12.74 (br s, 1H), 8.35-8.20 (m, 2H), 7.90-7.83 (m, 1H), 7.81-7.74 (m, 1H), 7.21 (br s, 2H), 5.17-4.93 (m, 1H), 2.57 (s, 3H), 2.24 (br s, 1H), 1.83-1.69 (m, 1H), 1.31 (br s, 1H); LCMS (electrospray) m/z 367.0 (M + H)+. | V |
| 108 | (1S,2S)-2-fluoro-N-(6-(7-methyl-1H-indazol-6-yl)-benzo[d]thiazol-2-yl)cyclopropane-1-carboxamide. 2HCl salt | ¹H NMR (400 MHz, METHANOL-$d_4$) δ = 8.31 (s, 1H), 7.90 (s, 1H), 7.84 (d, J = 8.3 Hz, 1H), 7.73 (d, J = 8.4 Hz, 1H), 7.48 (d, J = 8.3 Hz, 1H), 7.22 (d, J = 8.3 Hz, 1H), 5.09-4.97 (m, 1H), 5.09-4.94 (m, 1H), 2.51 (s, 3H), 2.26-2.16 (m, 1H), 1.95-1.82 (m, 1H), 1.39-1.27 (m, 1H); LCMS (electrospray) m/z 367.1 (M + H)+. | V |

TABLE 1-continued

Compounds of Examples

| Ex # | Structure/Name | ¹H NMR/MS (M + 1) | Synthetic Method |
|---|---|---|---|
| 109 | (1S,2S)-N-(6-(3,4-dimethylisothiazol-5-yl)benzo[d]thiazol-2-yl)-2-fluorocyclopropane-1-carboxamide | ¹H NMR (400 MHz, DMSO-d6) δ 12.81 (s, 1H), 8.16 (d, J = 1.6 Hz, 1H), 7.86 (d, J = 8.3 Hz, 1H), 7.52 (dd, J = 1.8, 8.4 Hz, 1H), 5.18-4.93 (m, 1H), 2.42 (s, 3H), 2.25 (m, 4H), 1.84-1.68 (m, 1H), 1.39-1.25 (m, 1H); LCMS (electrospray) m/z 348.2 (M + H)+. | N |
| 110 | (1S,2S)-N-(6-(5-(1H-imidazol-2-yl)-2-methylphenyl)benzo[d]thiazol-2-yl)-2-fluorocyclopropane-1-carboxamide. 2TFA salt | ¹H NMR (400 MHz, DMSO-d₆) δ = 1.27-1.39 (m, 1H), 1.69-1.82 (m, 1 H), 2.21-2.27 (m, 1 H), 2.38 (s, 3H), 4.94-5.18 (m, 1 H), 7.51 (dd, J = 8.31, 1.71 Hz, 1H), 7.61 (d, J = 8.19 Hz, 1H), 7.81 (s, 2 H), 7.86 (d, J = 8.31 Hz, 1 H), 7.90-7.95 (m, 1 H), 7.99 (d, J = 1.71 Hz, 1H), 8.06 (d, J = 1.47 Hz, 1 H), 12.78 (s, 1 H), 14.63 (br s, 1 H); LCMS (electrospray) m/z 393.3 (M + H)+. | R |
| 111 | (1S,2S)-2-fluoro-N-(6'-methyl-[6,7'-bibenzo[d]thiazol]-2-yl)cyclopropane-1-carboxamide. 2 HCl salt | ¹H NMR (400 MHz, MEHANOL-d₄) δ = 9.60 (s, 1H), 8.02 (d, J = 8.4 Hz, 1H), 7.99 (d, J = 1.3 Hz, 1H), 7.94 (d, J = 8.3 Hz, 1H), 7.69 (d, J = 8.4 Hz, 1H), 7.52 (dd, J = 1.7, 8.3 Hz, 1H), 5.05 (dt, J = 3.9, 6.2 Hz, 1H), 2.39 (s, 3H), 2.22 (dtd, J = 4.3, 6.9, 9.1 Hz, 1H), 1.96-1.83 (m, 1H), 1.39-1.28 (m, 1H); LCMS (electrospray) m/z 384.0 (M + H)+. | W |
| 112* | (1S,2S)-2-fluoro-N-methyl-N-(6-(4-methylpyridin-3-yl)benzo[d]thiazol-2-yl)cyclopropane-1-carboxamide | ¹H NMR (400 MHz, DMSO-d₆) δ = 8.44-8.41 (m, 2H), 8.04 (d, J = 1.6 Hz, 1H), 7.89 (d, J = 8.4 Hz, 1H), 7.47 (dd, J12 =1.6 Hz, J13 = 8.4 Hz, 1H), 7.35 (t, J = 7.35 Hz, 1H), 5.21 (J12 = 2.9 Hz, J13 = 66.27 Hz, 1H), 3.95 (s, N—CH3, 3H), 2.66-2.62 (m, 1H), 2.29 (s, Me, 3H), 1.83-1.79 (m, 1H), 1.35-1.31 (m, 1H); LCMS (electrospray) m/z 342.1 (M + H)+. | X |
| 113 | (1S,2S)-2-fluoro-N-(6-(6-(fluoromethyl)-4-methylpyridin-3-yl)benzo[d]thiazol-2-yl)cyclopropane-1-carboxamide. 2TFA salt | 1H NMR (400 MHz, DMSO-d6) δ = 1.32 (ddt, J = 12.84, 8.99, 6.33 Hz, 1 H), 1.69-1.82 (m, 1 H), 2.20-2.28 (m, 1 H), 2.36 (s, 3 H), 4.93-5.17 (m, 1 H), 5.46 (s, 1 H), 5.57 (s, 1 H), 7.48 (dd, J = 8.31, 1.83 Hz, 1 H), 7.53 (s, 1 H), 7.84 (d, J = 8.31 Hz, 1 H), 8.07 (d, J = 1.59 Hz, 1 H), 8.48 (s, 1 H), 12.77 (br s, 1 H); LCMS (electrospray) m/z 360.00 (M + H)+. | Y |

TABLE 1-continued

Compounds of Examples

| Ex # | Structure/Name | ¹H NMR/MS (M + 1) | Synthetic Method |
|---|---|---|---|
| 114 | 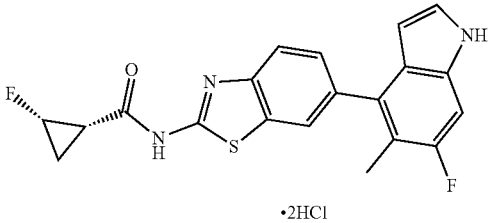<br>•2HCl<br>(1S,2S)-2-fluoro-N-(6-(6-fluoro-5-methyl-1H-indol-4-yl)benzo[d]thiazol-2-yl)cyclopropane-1-carboxamide. 2HCl salt | 1H NMR (400 MHz, DMSO-d6) δ = 12.75 (s, 1H), 11.14 (s, 1H), 7.98 (d, J = 1.4 Hz, 1H), 7.85 (d, J = 8.3 Hz, 1H), 7.45-7.40 (m, 1H), 7.29-7.25 (m, 1H), 7.19 (d, J = 10.5 Hz, 1H), 6.04-6.00 (m, 1H), 5.16-4.94 (m, 1H), 2.30-2.19 (m, 1H), 2.14 (d, J = 2.6 Hz, 3H), 1.84-1.68 (m, 1H), 1.38-1.25 (m, 1H); LCMS (electrospray) m/z 384.10 (M + H)+. | Z |
| 115 | 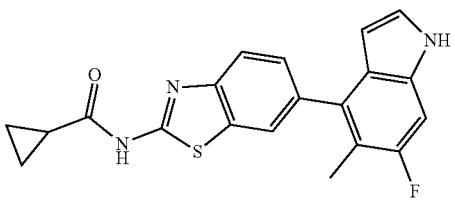<br>N-(6-(6-fluoro-5-methyl-1H-indol-4-yl)benzo[d]thiazol-2-yl)cyclopropanecarboxamide | LCMS (electrospray) m/z 366.43 (M + H)+. | Z |
| 116 | 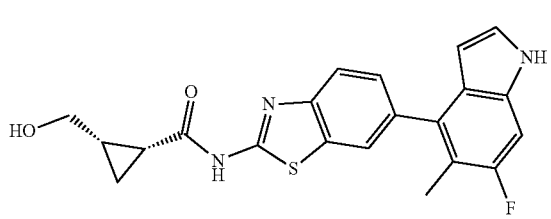<br>(1R,2S)-N-(6-(6-fluoro-5-methyl-1H-indol-4-yl)benzo[d]thiazol-2-yl)-2-(hydroxymethyl)cyclopropane-1-carboxamide | LCMS (electrospray) m/z 396.45 (M + H)+. | K |
| 117 | 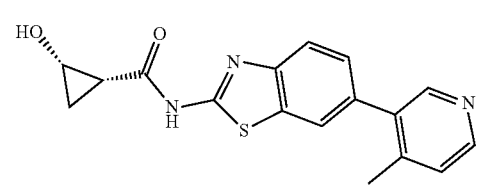<br>(1R,2S)-2-hydroxy-N-(6-(4-methylpyridin-3-yl)benzo[d]thiazol-2-yl)cyclopropane-1-carboxamide | LCMS (electrospray) m/z 325.39 (M + H)+. | |
| 118 | 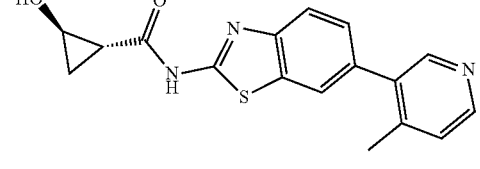<br>(1R,2R)-2-hydroxy-N-(6-(4-methylpyridin-3-yl)benzo[d]thiazol-2-yl)cyclopropane-1-carboxamide | LCMS (electrospray) m/z 325.39 (M + H)+. | |

TABLE 1-continued

Compounds of Examples

| Ex # | Structure/Name | ¹H NMR/MS (M + 1) | Synthetic Method |
|---|---|---|---|
| 119 | 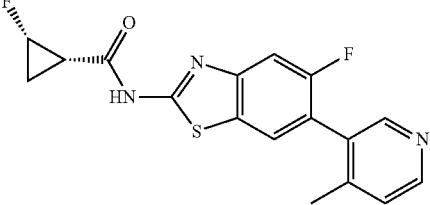<br>(1S,2S)-2-fluoro-N-(5-fluoro-6-(4-methylpyridin-3-yl)benzo[d]thiazol-2-yl)cyclopropane-1-carboxamide | LCMS (electrospray) m/z 346.10 (M + H)+. | Q |
| 120 | 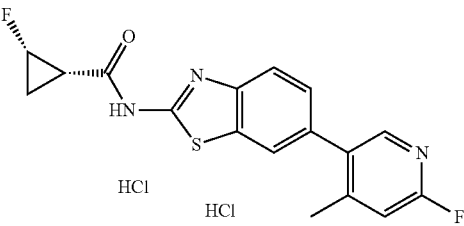<br>(1S,2S)-2-fluoro-N-(6-(6-fluoro-4-methylpyridin-3-yl)benzo[d]thiazol-2-yl)cyclopropane-1-carboxamide. 2HCl salt | 1H NMR (400 MHz, DMSO-d6) δ = 12.87-12.68 (m, 1H), 8.14-8.10 (m, 1H), 8.07-8.02 (m, 1H), 7.86-7.81 (m, 1H), 7.49-7.43 (m, 1H), 7.21-7.18 (m, 1H), 5.18-4.94 (m, 1H), 2.34-2.33 (m, 3H), 2.23 (br s, 1H), 1.82-1.70 (m, 1H), 1.37-1.26 (m, 1H); LCMS (electrospray) m/z 346.10 (M + H)+. | N |
| 121 | 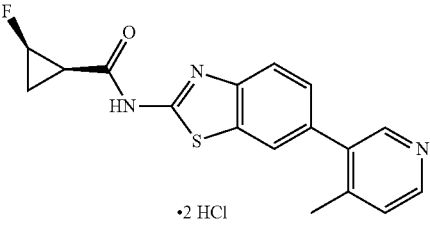<br>(1R,2R)-2-fluoro-N-(6-(4-methylpyridin-3-yl)benzo[d]thiazol-2-yl)cyclopropane-1-carboxamide. 2HCl salt | 1H NMR (400 MHz, DMSO-d6) δ = 8.76 (s, 1H), 8.71 (dd, J = 0.7, 6.1 Hz, 1H), 8.07 (d, J = 6.0 Hz, 1H), 8.03 (d, J = 1.3 Hz, 1H), 7.92 (d, J = 8.4 Hz, 1H), 7.54 (dd, J = 1.8, 8.4 Hz, 1H), 5.03 (dt, J = 3.8, 6.2 Hz, 1H), 2.64 (s, 3H), 2.19 (dtd, J = 4.3, 6.8, 9.2 Hz, 1H), 1.95-1.80 (m, 1H), 1.40-1.27 (m, 1H); LCMS (electrospray) m/z 328.20 (M + H)+. | A |
| 122 | 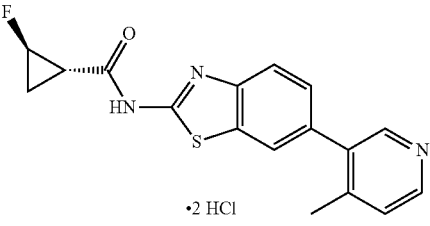<br>(1S,2R)-2-fluoro-N-(6-(4-methylpyridin-3-yl)benzo[d]thiazol-2-yl)cyclopropane-1-carboxamide. 2HCl salt | 1H NMR (400 MHz, METHANOL-d4) δ = 8.77 (s, 1H), 8.72 (d, J = 6.1 Hz, 1H), 8.07 (d, J = 6.1 Hz, 1H), 8.03 (d, J = 1.6 Hz, 1H), 7.93 (d, J = 8.3 Hz, 1H), 7.55 (dd, J = 1.8, 8.4 Hz, 1H), 5.02 (ddd, J = 1.6, 3.5, 6.1 Hz, 1H), 2.70-2.57 (m, 3H), 2.46 (dddd, J = 1.5, 6.6, 10.4, 17.0 Hz, 1H), 1.65 (tddd, J = 3.5, 6.9, 10.6, 17.9 Hz, 1H), 1.48 (qd, J = 6.5, 13.1 Hz, 1H); LCMS (electrospray) m/z 328.20 (M + H)+. | A |
| 123 | 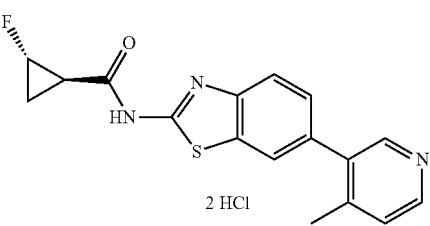<br>(1R,2S)-2-fluoro-N-(6-(4-methylpyridin-3-yl)benzo[d]thiazol-2-yl)cyclopropane-1-carboxamide. 2HCl salt | 1H NMR (400 MHz,METHANOL-d4) δ = 8.76 (s, 1H), 8.72 (d, J = 6.1 Hz, 1H), 8.07 (d, J = 6.0 Hz, 1H), 8.03 (d, J = 1.5 Hz, 1H), 7.93 (d, J = 8.4 Hz, 1H), 7.55 (dd, J = 1.8, 8.4 Hz, 1H), 5.02 (ddd, J = 1.6, 3.5, 6.1 Hz, 1H), 2.72-2.59 (m, 3H), 2.46 (dddd, J = 1.5, 6.6, 10.4, 17.0 Hz, 1H), 1.65 (tddd, J = 3.4, 6.9, 10.6, 17.9 Hz, 1H), 1.48 (qd, J = 6.5, 13.0 Hz, 1H); LCMS (electrospray) m/z 328.20 (M + H)+. | A |

*denotes a compound used for a comparison study.

Evaluation of Compounds
c-abl Kinase Assay

ADP-Glo assay kit was purchased from Promega. Magnesium chloride ($MgCl_2$), bovine serum albumin (BSA), ethylene glycol-bis(β-aminoethyl ether)-N,N,N',N'-tetraacetic acid (EGTA), tween-20, 1,4-dithiothreitol (DTT) and dimethyl sulfoxide (DMSO) were purchased from Sigma-Aldrich. HEPES buffer was purchased from Gibco. ABL1 kinase and Abltide were purchased from Signalchem.

c-abl kinase activity was measured by Promega's ADP-Glo™ Assay. In this assay, His-tagged recombinant human ABL1 (0.25 ng/μl) is incubated with 5 μL of compounds (0.5% DMSO), 5 μL of Abltide (0.01 μg/μl) and 5 μL of ATP (25 μM) in buffer (50 mM HEPES, 7.5; 10 mM $MgCl_2$; 1 mM EGTA; 0.05% BSA; 0.01% Tween-20; 2 mM DTT.). The assay was started by incubating the reaction mixture in a 96-well plate at 30° C. for 30-min. After the incubation, 25 μL ADP-Glo reagent was added and the reaction was incubated at room temperature for 40-min to stop the reaction and degrade residual ATP. The ADP product was then converted to ATP by adding 50 μL per well of detection reagent. Luminescence was detected after 30-min room temperature incubation with the Molecular device I3X plate reader. The $IC_{50}$ values were calculated from a series of percent inhibition values determined at a range of inhibitor concentration using software routines as implemented in the GraphPad Prism 7 software or SigmaPlot 13.0.

Table 2 shows $IC_{50}$ values for the compounds of Examples.

TABLE 2

| In vitro activity against c-abl data. | |
|---|---|
| Example | c-abl - $IC_{50}$ (nM) |
| 1 | 18.4 |
| 2 | 29.8 |
| 3 | 11.9 |
| 4 | 4.1 |
| 5 | 9.0 |
| 6 | >10,000 |
| 7 | >10,000 |
| 8 | 2.7 |
| 9 | 34.6 |
| 10 | 22.6 |
| 11 | 8.3 |
| 12 | 32.3 |
| 13 | 9500 |
| 14 | 1.3 |
| 15 | 116.0 |
| 16 | ND |
| 17 | 7.8 |
| 18 | >2,000 |
| 19 | 7.4 |
| 20 | 729.0 |
| 21 | >2000 |
| 22 | 0.6 |
| 23 | 4.0 |
| 24 | 2.3 |
| 25 | >2000 |
| 26 | 422.6 |
| 27 | >2000 |
| 28 | >2000 |
| 29 | >2000 |
| 30 | >2000 |
| 31 | >2000 |
| 32 | 47.2 |
| 33 | >2000 |
| 34 | 364.2 |
| 35 | 1155.7 |
| 36 | 11.4 |
| 37 | 76.2 |
| 38 | 102.7 |
| 39 | 27.5 |
| 40 | 215.0 |
| 41 | 339.3 |
| 42 | 875.5 |
| 43 | 56.4 |
| 44 | 161.4 |
| 45 | 5311.2 |
| 46 | 16.8 |
| 47 | 2.5 |
| 48 | 7.9 |
| 49 | 11.6 |
| 50 | 24.4 |
| 51 | 35.7 |
| 52 | 5773.5 |
| 53 | >10,000 |
| 54 | >10,000 |
| 55 | 5.9 |
| 56 | 7.9 |
| 57 | 74.2 |
| 58 | 130.8 |
| 59 | 38.8 |
| 60 | 127.5 |
| 61 | 50.1 |
| 62 | 19.9 |
| 63 | 58.2 |
| 64 | 17.0 |
| 65 | 21.3 |
| 66 | 20.3 |
| 67 | 454.7 |
| 68 | 17.8 |
| 69 | 25.4 |
| 70 | 24.6 |
| 71 | >2,000 |
| 72 | 63.5 |
| 73 | 57.6 |
| 74 | 171.5 |
| 75 | 8.3 |
| 76 | 1663.8 |
| 77 | 1.6 |
| 78 | 4.2 |
| 79 | 20.0 |
| 80 | 39.3 |
| 81 | 141.9 |
| 82 | 40.4 |
| 83 | 90.6 |
| 84 | 18.8 |
| 85 | 3.6 |
| 86 | 7.4 |
| 87 | 50.9 |
| 88 | 5.1 |
| 89 | 119.9 |
| 90 | 1.6 |
| 91 | 9.9 |
| 92 | 9.3 |
| 93 | 7.1 |
| 94 | 757.9 |
| 95 | 21.1 |
| 96 | 10.1 |
| 97 | 1.2 |
| 98 | 2.1 |
| 99 | 102.8 |
| 100 | 2.5 |
| 101 | 3.2 |
| 102 | 5.1 |
| 103 | 20.3 |
| 104 | 21.0 |
| 105 | 11.5 |
| 106 | 116.1 |
| 107 | 14.8 |
| 108 | 3.8 |
| 109 | 13.7 |
| 110 | 7.7 |
| 111 | 3.0 |
| 112 | >10,000 |
| 113 | 21.2 |
| 114 | ND |

TABLE 2-continued

In vitro activity against c-abl data.

| Example | c-abl - IC$_{50}$ (nM) |
|---|---|
| 115 | ND |
| 116 | ND |
| 117 | ND |
| 118 | ND |
| 119 | ND |
| 120 | 13.3 |
| 121 | 12.7 |
| 122 | 23.7 |
| 123 | ND |

ND = not determined c-KIT Kinase Assay

ADP-Glo assay kit was purchased from Promega. Magnesium chloride (MgCl$_2$), Manganese(II) chloride (MnCl$_2$), Bovine serum albumin (BSA) and dimethylsulfoxide (DMSO) were purchased from Sigma-Aldrich. Tris-HCl buffer was purchased from Biosesang. c-Kit kinase and Poly (4:1 Glu, Tyr) Peptide were purchased from Signalchem.

c-Kit kinase activity was measured by Promega's ADP-Glo™ Assay. In this assay, Recombinant human c-Kit (100 ng) is incubated with 5 µL of compounds (0.5% DMSO), 5 µL of Poly (4:1 Glu, Tyr) (250 ng/µl) and 5 µL of ATP (250 µM) in buffer (40 mM Tris, 7.5; 20 mM MgCl$_2$; 0.1 mg/ml BSA; 2 mM MnCl$_2$; 50 µM DTT.). The assay was started by incubating the reaction mixture in a 96-well plate at 30° C. for 2 hr. After the incubation, 25 µL ADP-Glo reagent was added and the reaction was incubated at 30° C. for 45 min to stop the reaction and degrade residual ATP. The ADP product was then converted to ATP by adding 50 µL per well of detection reagent. Luminescence was detected after 30 min room temperature incubation with the Molecular device I3X plate reader. The IC$_{50}$ values were calculated from a series of percent inhibition values determined at a range of inhibitor concentration using software routines as implemented in the GraphPad Prism 7 software or SigmaPlot 13.0.

PDGFRα Kinase Assay

ADP-Glo assay kit was purchased from Promega. Magnesium chloride (MgCl$_2$), Bovine serum albumin (BSA) and dimethylsulfoxide (DMSO) were purchased from Sigma-Aldrich. Tris-HCl buffer was purchased from Biosesang. PDGFRα kinase and Poly (4:1 Glu, Tyr) Peptide were purchased from Signalchem.

PDGFRα kinase activity was measured by Promega's ADP-Glo™ Assay. In this assay, Recombinant human PDGFRα (40 ng) is incubated with 5 µL of compounds (0.5% DMSO), 5 µL of Poly (4:1 Glu, Tyr) (0.5 µg/µl) and 5 µL of ATP (125 µM) in buffer (40 mM Tris, 7.5; 20 mM MgCl$_2$; 0.1 mg/ml BSA; 50 µM DTT.). The assay was started by incubating the reaction mixture in a 96-well plate at 30° C. for 1 hr. After the incubation, 25 µL ADP-Glo reagent was added and the reaction was incubated at room temperature for 45 min to stop the reaction and degrade residual ATP. The ADP product was then converted to ATP by adding 50 µL per well of detection reagent. Luminescence was detected after 30-min room temperature incubation with the Molecular device I3X plate reader. The IC$_{50}$ values were calculated from a series of percent inhibition values determined at a range of inhibitor concentration using software routines as implemented in the GraphPad Prism 7 software or SigmaPlot 13.0.

In Table 3, IC$_{50}$ values present against c-abl, c-Kit and PDGFRa Kinases, and the following designations are used ND=not determined.

TABLE 3

Biochemical activities to test kinase selectivity

| Example | c-abl IC50 (nM) | c-Kit IC$_{50}$ (nM) | PDGFRa IC$_{50}$ (nM) |
|---|---|---|---|
| 1 | 18.4 | >10,000 | >3099 |
| 2 | 29.8 | 4,022 | >10,000 |
| 3 | 11.9 | 3,853 | 8,384 |
| 4 | 4.1 | >10,000 | 1,966 |
| 5 | 9.0 | ND | 1,614 |
| 8 | 2.7 | 3,129 | 391 |
| 9 | 34.6 | ND | ND |
| 10 | 22.6 | ND | ND |
| 11 | 8.3 | ND | ND |
| 12 | 32.3 | >10,000 | >10,000 |
| 14 | 1.8 | 1,338 | 143 |
| 17 | 7.8 | >10,000 | 1,300 |
| 22 | 0.6 | 1,018 | 177 |
| 24 | 2.3 | >10,000 | 1,156 |
| 36 | 11.4 | >10,000 | 5,760 |

Kinase Inhibition Assay

The kinase inhibition profiles of the compounds (Examples 1, 4, 8 and 17) were tested using SelectScreen Kinase Profiling service (93 kinase panel or 485 kinase panel) by ThermoFisher SCIENTIFIC. We tested percentage of inhibition against diverse human kinases activity. Using these panel, the compounds were screened at a final concentration of 100-fold to IC$_{50}$ of c-abl kinase or 500 nM. The assay protocols of each kinase are published on the ThermoFisher SCIENTIFIC.

This kinase screening assay is a competition binding assay that profiled the selectivity of the compounds. The compounds showed c-abl kinase inhibition more than 80%, but PI3K, c-kit and PDGFR kinase activity less than 20%.

The compounds showed a percentage of inhibition less than 40% against AAK1, ACVR1 (ALK2), ACVR1B (ALK4), ACVR2A, ADCK3, ADRBK1 (GRK2), ADRBK2 (GRK3), AKT1 (PKB alpha), AKT2 (PKB beta), AKT3 (PKB gamma), ALK, ALK C1156Y, ALK F1174L, ALK L1196M, ALK R1275Q, ALK T1151_L1152insT, AMPK (A1/B1/G2), AMPK (A1/B1/G3), AMPK (A1/B2/G1), AMPK (A1/B2/G2), AMPK (A1/B2/G3), AMPK (A2/B1/G2), AMPK (A2/B1/G3), AMPK (A2/B2/G1), AMPK (A2/B2/G2), AMPK (A2/B2/G3), AMPK A1/B1/G1, AMPK A2/B1/G1, AURKA (Aurora A), AURKB (Aurora B), AURKC (Aurora C), AXL, AXL R499C, BLK, BMPR1A (ALK3), BMPR1B (ALK6), BMPR2, BMX, BRAF (lantha), BRAF (Z-LYTE), BRAF V599E (lantha), BRAF V599E (Z-LYTE), BRSK1 (SAD1), BRSK2, BTK, CAMK1 (CaMK1), CAMK1D (CaMKI delta), CAMK1G (CAMKI gamma), CAMK2A (CaMKII alpha), CAMK2B (CaMKII beta), CAMK2D (CaMKII delta), CAMK2G (CaMKII gamma), CAMK4 (CaMKIV), CAMKK1 (CAMKKA), CAMKK2 (CaMKK beta), CASK, CDC42 BPA (MRCKA), CDC42 BPB (MRCKB), CDC42 BPG (MRCKG), CDC7/DBF4, CDK1/cyclin B, CDK11 (Inactive), CDK11/cyclin C, CDK13/cyclin K, CDK14 (PFTK1)/cyclin Y, CDK16 (PCTK1)/cyclin Y, CDK17/cyclin Y, CDK18/cyclin Y, CDK2/cyclin A, CDK2/cyclin A1, CDK2/cyclin E1, CDK2/cyclin O, CDK3/cyclin E1, CDK4/Cyclin D1, CDK4/cyclin D3, CDK5 (Inactive), CDK5/p25, CDK5/p35, CDK6/Cyclin D1, CDK7/cyclin H/MNAT1, CDK8/cyclin C, CDK9 (Inactive), CDK9/cyclin K, CDK9/cyclin T1, CDKL5, CHEK1 (CHK1), CHEK2 (CHK2), CHUK (IKK alpha), CLK1, CLK2, CLK4, CSK, CSNK1A1 (CK1 alpha 1), CSNK1A1L, CSNK1D (CK1 delta), CSNK1E (CK1 epsilon) R178C, CSNK1G1 (CK1 gamma 1), CSNK1G2 (CK1 gamma 2), CSNK1G3 (CK1 gamma 3), CSNK2A1 (CK2 alpha 1), CSNK2A2 (CK2 alpha 2), DAPK1, DAPK2, DAPK3 (ZIPK), DCAMKL1 (DCLK1), DCAMKL2 (DCK2), DDR1, DDR2, DDR2 T654M, DMPK, DYRK1A, DYRK1B, DYRK2, DYRK3, DYRK4, EEF2K, EGFR (ErbB1), EGFR (ErbB1) C797S, EGFR (ErbB1) d746-750, EGFR (ErbB1) d747-749 A750P, EGFR (ErbB1) G719C, EGFR (ErbB1) G719S, EGFR (ErbB1) L858R, EGFR (ErbB1) L861Q, EGFR (ErbB1) T790M, EGFR (ErbB1) T790M C797S L858R, EGFR (ErbB1) T790M L858R, EIF2AK2 (PKR), EPHA1, EPHA6, EPHA7, EPHB1, EPHB3, EPHB4, ERBB2 (HER2), ERBB4 (HER4), ERN1, ERN2, FER, FES (FPS), FGFR1, FGFR1 V561M, FGFR2, FGFR2 N549H, FGFR3, FGFR3 G697C, FGFR3 K650E, FGFR3 K650M, FGFR3 V555M, FGFR4, FLT1 (VEGFR1), FLT3, FLT3 D835Y, FLT3 ITD, FLT4 (VEGFR3), FRAP1 (mTOR), FRK (PTK5), FYN A, GAK, GRK1, GRK4, GRK5, GRK6, GRK7, GSG2 (Haspin), GSK3A (GSK3 alpha), GSK3B (GSK3 beta), HCK, HIPK1 (Myak), HIPK2, HIPK3 (YAK1), HIPK4, HUNK, ICK, IGF1R, IKBKB (IKK beta), IKBKE (IKK epsilon), INSR, INSRR (IRR), IRAK4, ITK, JAK1, JAK2, JAK2 JH1 JH2, JAK2 JH1 JH2 V617F, JAK3, KDR (VEGFR2), KIT, KIT A829P, KIT D816H, KIT D816V, KIT D820E, KIT N822K, KIT T670E, KIT T670I, KIT V559D, KIT V559D T670I, KIT V559D V654A, KIT V560G, KIT V654A, KIT Y823D, KSR2, LATS1, LATS2, LIMK1, LIMK2, LRRK2 I2020T, LRRK2 R1441C, LTK (TYK1), MAP2K1 (MEK1) (lantha), MAP2K1 (MEK1) (Z-LYTE), MAP2K1 (MEK1) S218D S222D, MAP2K2 (MEK2) (lantha), MAP2K2 (MEK2) (Z-LYTE), MAP2K4 (MEK4), MAP2K5 (MEK5), MAP2K6 (MKK6) (lantha), MAP2K6 (MKK6) (Z-LYTE), MAP2K6 (MKK6) S207E T211E, MAP3K10 (MLK2), MAP3K11 (MLK3), MAP3K14 (NIK), MAP3K19 (YSK4), MAP3K2 (MEKK2), MAP3K3 (MEKK3), MAP3K5 (ASK1), MAP3K7/MAP3K7IP1 (TAK1-TAB1), MAP3K8 (COT), MAP3K9 (MLK1), MAP4K2 (GCK), MAP4K3 (GLK), MAP4K5 (KHS1), MAPK1 (ERK2), MAPK10 (JNK3) (lantha), MAPK10 (JNK3) (Z-LYTE), MAPK11 (p38 beta), MAPK12 (p38 gamma), MAPK13 (p38 delta), MAPK14 (p38 alpha), MAPK14 (p38 alpha) Direct, MAPK15 (ERK7), MAPK3 (ERK1), MAPK7 (ERK5), MAPK8 (JNK1) (lantha), MAPK8 (JNK1) (Z-LYTE), MAPK9 (JNK2) (lantha), MAPK9 (JNK2) (Z-LYTE), MAPKAPK2, MAPKAPK3, MAPKAPK5 (PRAK), MARK1 (MARK), MARK2, MARK3, MARK4, MASTL, MATK (HYL), MELK, MERTK (cMER), MERTK (cMER) A708S, MET (cMet), MET (cMET) Y1235D, MET M1250T, MKNK1 (MNK1), MKNK2 (MNK2), MLK4, MST1R (RON), MST4, MUSK, MYLK (MLCK), MYLK4, MYO3A (MYO3 alpha), NEK1, NEK2, NEK4, NEK6, NEK7, NEK8, NEK9, NIM1K, NLK, NUAK1 (ARK5), NUAK2, PAK1, PAK2 (PAK65), PAK3, PAK4, PAK6, PAK7 (KIAA1264), PASK, PDGFRA (PDGFR alpha), PDGFRA D842V, PDGFRA T674I, PDGFRB (PDGFR beta), PDK1, PDK1 Direct, PHKG1, PHKG2, PI4K2A (PI4K2 alpha), PI4K2B (PI4K2 beta), PI4KA (PI4K alpha), PI4KB (PI4K beta), PIM1, PIM2, PIM3, PIP4K2A, PIP5K1A, PIP5K1B, PIP5K1C, PKMYT1, PKN1 (PRK1), $PKN_2$ (PRK2), PLK1, PLK2, PLK3, PLK4, PRKACA (PKA), PRKACB (PRKAC beta), PRKACG (PRKAC gamma), PRKCA (PKC alpha), PRKCB1 (PKC beta I), PRKCB2 (PKC beta II), PRKCD (PKC delta), PRKCE (PKC epsilon), PRKCG (PKC gamma), PRKCH (PKC eta), PRKCI (PKC iota), PRKCN (PKD3), PRKCQ (PKC theta), PRKCZ (PKC zeta), PRKD2 (PKD2), PRKG1, PRKG2 (PKG2), PRKX, PTK2 (FAK), PTK2B (FAK2), PTK6 (Brk), RAF1 (cRAF) Y340D Y341D (lantha), RAF1 (cRAF) Y340D Y341D (Z-LYTE), RET, RET A883F, RET G691S, RET M918T, RET S891A, RET V804E, RET V804L, RET V804M, RET Y791F, ROCK1, ROCK2, ROS1, RPS6KA1 (RSK1), RPS6KA2 (RSK3), RPS6KA3 (RSK2), RPS6KA4 (MSK2), RPS6KA5 (MSK1), RPS6KA6 (RSK4), RPS6KB1 (p70S6K), RPS6KB2 (p70S6Kb), SBK1, SGK (SGK1), SGK2, SGKL (SGK3), SIK1, SIK3, SLK, SNF1LK2, SPHK1, SPHK2, SRMS (Srm), SRPK1, SRPK2, STK16 (PKL12), STK17A (DRAK1), STK17B (DRAK2), STK22B (TSSK2), STK22D (TSSK1), STK23 (MSSK1), STK24 (MST3), STK25 (YSK1), STK3 (MST2), STK32B (YANK2), STK32C (YANK3), STK33, STK38 (NDR), STK38L (NDR2), STK39 (STLK3), STK4 (MST1), TAOK1, TAOK3 (JIK), TBK1, TEC, TEK (TIE2) R849W, TEK (TIE2) Y1108F, TEK (TIE2) Y897S, TESK1, TESK2, TGFBR1 (ALK5), TGFBR2, TLK1, TLK2, TNK1, TNK2 (ACK), TTK, TXK, TYK2, TYRO3 (RSE), ULK1, ULK2, ULK3, VRK2, WEE1, WNK1, WNK2, WNK3, ZAK, ZAP70.

Oral Dose Pharmacokinetic Study in Mice

Oral dose pharmacokinetic parameters of Examples 1, 4, 5, 6, 8 and nilotinib were evaluated in mice.

Male ICR mice fasted for 15 h before beginning pharmacokinetic experiment and received single oral doses of compounds dissolved in 20% dimethyl sulfoxide (DMSO)/1% Tween-20/79% NS solution at a dose of 5 mg/kg. To observe pharmacokinetics of compounds, blood from each mouse was collected from retro-orbital plexus at specific time points (5, 15, 30 and 60 min., 1.5, 2, 3, 4, 6, 8, 10 and 24 hr, n=3 for each time point) after administration using sodium heparinized capillary tube. The plasma samples were separated by centrifugation at 10,000 rpm for 5 min. and stored at −80° C. until analysis. To observe exposure of compounds, mice brains were collected at 30 and 60 min., 2, 4 and 24 hr (n=1 for each time point) after treatment of compounds with 5 mg/kg and also collected matched plasma samples and then stored at −80° C. until analysis. Freshly thawed brain samples were weighted and homogenized in 3 volumes of PBS.

Plasma and homogenized brain were treated with acetonitrile to precipitate proteins. After shaking and centrifugation, the supernatant was diluted 3-fold with distilled water and analyzed using ExionLC ultra-high-performance liquid chromatograph (SCIEX, USA) coupled with an SCIEX 6500+ triple-quadrupole mass spectrometry (SCIEX, USA) (LC-MS/MS). Ten microliters of each sample were injected onto a CORTECS® C18+ 2.1 mm×50 mm I.D., 2.7 um column (Water, USA) and separated by gradient conditions using mobile phase (A: 0.1% formic acid in water, B: 0.1% formic acid in ACN) at a flow rate of 0.3 mL/min. Peak integrations and areas were determined using Analyst software (SIEX, USA) and non-compartmental pharmacokinetic analysis with mean concentration was performed using Pheonix WinNonlin® software version 8.0 (Pharsight Corp, USA).

The plasma $AUC_{INF}$ (min*ng/mL) and brain/plasma concentration ratio (BP ratio) following oral dosing at dose of 5 mg/kg were shown in Table 4. All examples exhibit better brain exposure than nilotinib.

TABLE 4

Pharmacokinetic parameters of Examples 1, 4, 5, 6, 8 and nilotinib.

| Example | Matrix | Route | Dose (mg/kg) | AUC$_{INF}$ (min*ng/mL) | BP ratio$^a$ |
|---|---|---|---|---|---|
| 1 | Plasma | PO | 5 | 61506.8 | — |
|  | Brain | PO | 5 | 152143.0 | 2.03 |
| 4 | Plasma | PO | 5 | 682041.7 | — |
|  | Brain | PO | 5 | 248386.8 | 0.41 |
| 5 | Plasma | PO | 5 | 509093.6 | — |
|  | Brain | PO | 5 | 118802.8 | 0.16 |
| 6 | Plasma | PO | 5 | 291672.8 | — |
|  | Brain | PO | 5 | 236835.9 | 0.50 |
| 8 | Plasma | PO | 5 | 871230.0 | — |
|  | Brain | PO | 5 | 1202940.1 | 0.94 |
| Nilotinib | Plasma | PO | 5 | 631652.5 | — |
|  | Brain | PO | 5 | 11778.6 | 0.01 |

$^a$BP ratios were calculated based on AUC$_{INF}$ value from brain and matched plasma.

Validation of In Vitro Efficacy c-abl is active in Parkinson's disease and recent studies show that c-abl is activated by treatment of α-synuclein preformed fibrils (PFF) in a time-dependent manner and α-synuclein PFF was significantly decreased in the neurons with treatment of c-abl inhibitor, nilotinib. (Zui-Hua Zhou et at. *Neurol Sci.* 2016)

However, nilotinib has been known to cause cardiovascular adverse events such as QTc prolongation and irregular heartbeat which may lead to sudden death. These adverse events (black box warning) could be due to its hERG activity. Nilotinib, ponatinib, and dasatinib have hERG IC$_{50}$ of 0.13, 2.33 and 14.3 µM, respectively. Moreover, nilotinib neither shows c-abl kinase selectivity nor high BBB penetration. It may mean that nilotinib is not suitable for usage in chronic neurodegenerative disease.

Examples 4 and 8 showed little hERG activity (23.87% and 12.61% inhibition at 10 µM, respectively) and it indicated the compounds are unlikely to cause cardiovascular adverse events. Example 4 decreased the α-synuclein PFF-induced pathologic aggregation (Lewy body-like pathology) and Examples 4 and 8 also inhibited PFF-induced neuronal toxicity in a dose dependent manner (dose: 0.5, 1, 5, 10, 100 nM).

Examples 4 and 8 have good PK profiles in mice and better brain exposure than nilotinib.

TABLE 5

Comparison of nilotinib and Examples 4 and 8

| Drug | Dose (mg/kg) | Route | T$_{max}$ (min) | C$_{max}$ (ng/mL) | AUC$_{INF}$ (min * ng/mL) | Brain/plasma ratio (AUC) Total/Free |
|---|---|---|---|---|---|---|
| Nilotinib | 5 | PO | 60 | 4409.1 | 631652.5 | 0.01/0.002 |
| Example 4 | 5 | PO | 30 | 3585.9 | 682041.7 | 0.42/0.27 |
| Example 8 | 5 | PO | 60 | 4165.6 | 1514891.9 | 0.71/0.21 |

Validation of In Vivo Efficacy in AD and PD Model

The pharmacology activity of Examples 4 and 8 was estimated in the Aβ$_{25-35}$ induced Alzheimer's disease (AD) and α-synuclein pre-formed fibrils (PFF) induced Parkinson's disease (PD) mice model.

In Vivo Efficacy in PD Model

Phosphorylation of α-synuclein at ser129 was increased in α-synuclein PFF induced PD model and it was statistically reduced by oral administration of Example 4 (3 and 10 mg/kg, q.d.) about 50% and 80%, respectively. However, nilotinib (3 and 10 mg/kg, q.d.) was not effective on phosphorylation of α-synuclein statistically. It means that Example 4 is potent candidate to ameliorate Lewy body pathogenesis.

In α-synuclein PFF induced PD mice, Example 4 (0.3, 1, 3 and 10 mg/kg) and nilotinib (3, 10 and 30 mg/kg) was administered orally once daily for 5 months and pole test was performed to evaluate the movement disorder of α-synuclein PFF induced PD mice. Increased pole climb down time (sec) by α-synuclein PFF injection was recovered by treatment of Example 4 in a dose-dependent manner. 0.3 mg/kg of Example 4 resulted in 50% improvement of pole climb down time and 10 mg/kg completely recovered. However, nilotinib showed just a slight improvement at 10 mg/kg.

It indicates that the compounds confer behavioral recovery of mice from motor dysfunction induced by α-synuclein PFF in a dose dependent way and the compounds are disease modifying agents for neurodegenerative disorders including Parkinson's disease and potentially dementia with Lewy body.

In Vivo Efficacy in AD Model

Example 4 (1, 3 and 10 mg/kg), Example 8 (1 and 3 mg/kg) and nilotinib (3 mg/kg) was administered orally once daily to the Aβ$_{25-35}$ induced AD mice for 10 days and spontaneous alternation performance in the Y-maze, an index of spatial working memory and step-through passive avoidance (STPA) test were performed. Y-maze test as a behavioral test was used to assess memory function and the willingness of rodents to explore new environments ICV injection of oligomeric Aβ$_{25-35}$ peptide triggered neurotoxic effects and behavioral deficit in Y-maze test evaluating short term memory, by measurement of spontaneous alternation, while any change of motor symptom was not observed by measurement of locomotion.

Figure 7:
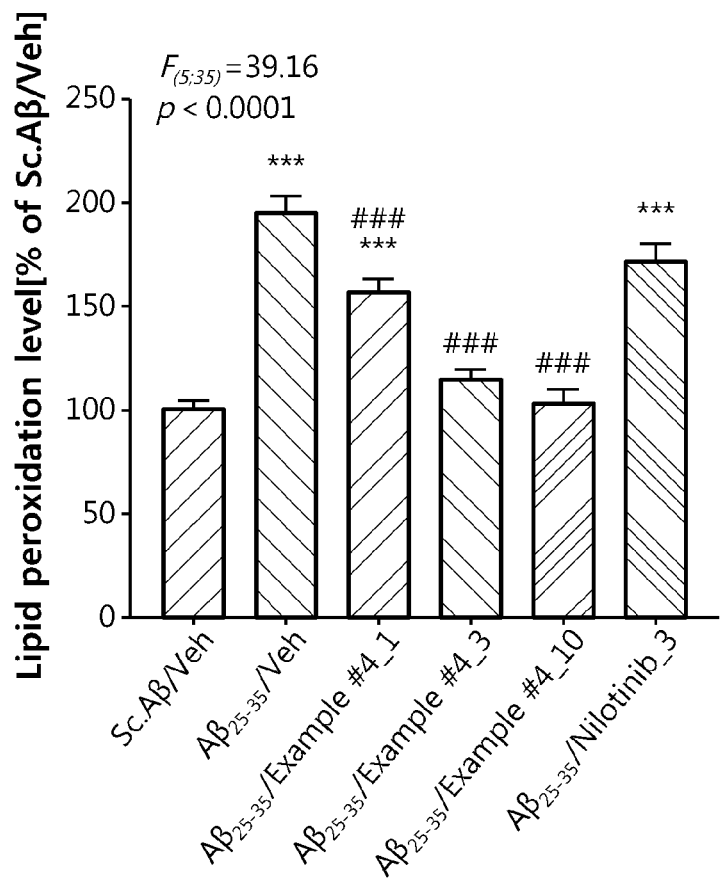
FIG. 7 shows that once daily oral dosing of 3 mg/kg and 10 mg/kg of Example 4 completely inhibited lipid peroxidation, meaning the reduction of oxidative stress.

10 Days after ICV injection of oligomeric Aβ$_{25-35}$ peptide, the hippocampus was dissected out. And lipid peroxidation level was quantified in the hippocampus homogenates. ICV injection of oligomeric Aβ$_{25-35}$ peptide induced lipid peroxidation, a marker for oxidative stress. Once daily oral dosing of 3 mg/kg and 10 mg/kg of Example 4 completely inhibited lipid peroxidation, meaning the reduction of oxidative stress. (FIG. 7)

Oxidative stress is considered to be a major mechanism of neuronal toxicity induced by Aβ$_{25-35}$ peptide through mitochondrial dysfunction (Ref: Meunier et al. *Eur J. Pharm* 2012), which is successfully inhibited by Example 4.

This indicates that Example 4 very significantly and fully alleviated deficits of alternation behavior and contextual long-term memory in a dose-response manner, while nilotinib partially alleviated spatial working memory deficits or showed no significant effect on contextual long-term memory deficits.

The results are shown in FIGS. 1 to 7. The result indicates that the compounds have high neuroprotective activity and low cardiovascular events and thus can be useful to treat or inhibit neurodegenerative disease such as Parkinson's disease, Alzheimer's disease and/or ALS.

What is claimed is:

1. A method for treating neurodegenerative disease in a subject, comprising:
administering to the subject in need thereof a therapeutically effective amount of a compound of Formula (I) or a pharmaceutically acceptable salt thereof:

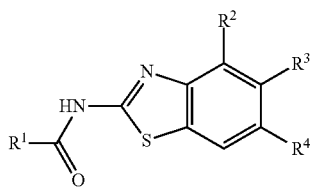

(I)

wherein:
$R^1$ is cyclopropyl, wherein $R^1$ is substituted with one or more groups selected from the group consisting of halo, alkyl, hydroxyalkyl and haloalkyl,
$R^2$ and $R^3$ are independently —H, halo, alkyl, alkoxy, —$CF_3$, or —$OCF_3$,
$R^4$ is aryl, monocyclic heteroaryl, cycloalkyl, or heterocyclyl, wherein $R^4$ is optionally substituted with one or more groups selected from the group consisting of halo, hydroxyl, alkyl, alkenyl, alkynyl, haloalkyl, hydroxyalkyl, trimethylsilylethoxymethyl, —$NO_2$, —$NR_aR_b$, —$NR_aC(=O)R_b$, —$NR_aC(=O)NR_aR_b$, —$NR_aC(=O)OR_b$, —$OR_a$, —CN, —$C(=O)R_a$, —$C(=O)OR_a$, —$C(=O)NR_aR_b$, —$OC(=O)R_a$, —$OC(=O)OR_a$, —$OC(=O)NR_aR_b$, —$SR_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl, and
$R_a$ and $R_b$ are independently —H, halo, amino, alkyl, or haloalkyl, and
wherein the neurodegenerative disease is α-synucleinopathy, Parkinson's disease, dementia with Lewy body, multiple system atrophy (MSA), Alzheimer's disease or amyotrophic lateral sclerosis (ALS).

2. The method of claim 1, wherein the subject is a human.

3. The method of claim 1, wherein
$R^1$ is cyclopropyl, wherein $R^1$ is substituted with one or more groups selected from the group consisting of halo, $C_1$-$C_3$ alkyl, $C_1$-$C_3$ hydroxyalkyl and $C_1$-$C_3$ haloalkyl;
$R^2$ and $R^3$ are independently —H, halo, $C_1$-$C_3$ alkyl, $C_1$-$C_3$ alkoxy, —$CF_3$, or —$OCF_3$;
$R^4$ is aryl, heteroaryl, cycloalkyl, or heterocyclyl, wherein $R^4$ is optionally substituted with one or more groups selected from the group consisting of halo, hydroxyl, $C_1$-$C_3$alkyl, $C_2$-$C_3$ alkenyl, $C_2$-$C_3$ alkynyl, $C_1$-$C_3$ haloalkyl, mono-$C_1$-$C_3$ alkylamino, di-$C_1$-$C_3$ alkylamino, —$NO_2$, —$NR_aR_b$, —$NR_aC(=O)R_b$, —$NR_aC(=O)NR_aR_b$, —$NR_aC(=O)OR_b$, —$OR_a$, —CN, —$C(=O)R_a$, —$C(=O)OR_a$, —$C(=O)NR_aR_b$, —$OC(=O)R_a$, —$OC(=O)OR_a$, —$OC(=O)NR_aR_b$, —$SR_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl, and
$R_a$ and $R_b$ are independently —H, halo, amino, $C_1$-$C_3$ alkyl, or $C_1$-$C_3$ haloalkyl.

4. The method of claim 1, wherein
$R^1$ is cyclopropyl substituted with one or more selected from the group consisting of fluoro, $C_1$-$C_3$ alkyl, $C_1$-$C_3$ hydroxyalkyl and $C_1$-$C_3$ fluoroalkyl,
$R^2$ and $R^3$ are independently —H, —F, —Br, —Cl, $C_1$-$C_3$ alkyl, or —$CF_3$,
$R^4$ is phenyl, pyridinyl, thiophenyl, pyrazolyl, imidazolyl, isothiazolyl, thiazolyl, pyrimidinyl, pyrazinyl, oxazolyl, isoxazolyl, pyrrolyl, or pyridazinyl, wherein $R^4$ is optionally substituted with one or more groups selected from the group consisting of halo, hydroxyl, $C_1$-$C_3$ alkyl, $C_1$-$C_3$ haloalkyl, mono($C_1$-$C_3$)alkylamino, di($C_1$-$C_3$)alkylamino, —$NR_aR_b$, —$OR_a$, —CN, —$C(=O)R_a$, —$C(=O)OR_a$, —$OC(=O)R_a$, —$OC(=O)OR_a$, —$SR_a$, pyrazolyl, imidazolyl, isothiazolyl, thiazolyl, pyridinyl, pyridazinyl, pyrimidinyl, pyrazinyl and pyrrolyl,
$R_a$ and $R_b$ are independently —H, halo, amino, $C_1$-$C_3$ alkyl, or $C_1$-$C_3$ haloalkyl.

5. The method of claim 1, wherein $R^1$ is cyclopropyl substituted with one or more groups selected from the group consisting of fluoro, methyl, ethyl, hydroxymethyl, and hydroxyethyl.

6. The method of claim 1, wherein $R^1$ is fluorocyclopropyl, hydroxymethylcyclopropyl, or difluorocyclopropyl; and $R^2$ and $R^3$ are independently —H, methyl, or fluoro.

7. The method of claim 1, wherein $R^4$ is fluoro-methylphenyl, chloro-methylphenyl, dimethylphenyl, acetamidomethylphenyl, hydroxy-methylphenyl, hydroxypropanylmethylphenyl, methyl-propenylphenyl, methylpyrrolylphenyl, methyl-thiazolylphenyl, imidazolylmethylphenyl, cyano-methylphenyl, methylpyrazolylphenyl, ethynyl-methylphenyl, methylpyridinyl, fluoro-methyl-methylaminophenyl, dimethylpyridinyl, fluoro-methylpyridinyl, fluoromethyl-methylpyridinyl, cyanopyridinyl, trifluoromethyl-methylpyridinyl, hydroxymethylpyridinyl, hydroxymethyl-methylpyridinyl, hydroxyethyl-methylpyridinyl, chloro-methylpyridinyl, aminopyridinyl, acetyl-methylpyridinyl, amino-dimethylpyridinyl, hydroxyethyl-methylpyridinyl, methylpyrimidinyl, dimethylpyrimidinyl, trifluoromethylpyrimidinyl, pyrazolyl, methylthiazolyl, methyl-tetrahydropyranyl, methylpyrazolyl, methylisothiazolyl, chloro-methylisothiazolyl, or dimethylisothiazolyl.

8. The method of claim 1, wherein $R^4$ is fluoro-methylphenyl, chloro-methylphenyl, bimethylphenyl, acetamidomethylphenyl, hydroxyl-methylphenyl, methyl-propenylphenyl, ethynyl-methylphenyl, fluoro-methylmethylaminophenyl, methyl-pyrrolylphenyl, methylthiazolylphenyl, cyano-methylphenyl, imidazolylmethylphenyl, methylpyridinyl, chloro-methylpyridinyl, fluoro-methylpyridinyl, fluoromethyl-methylpyridinyl, bimethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethylmethylpyridinyl, cyanopyridinyl, trifluoromethylpyridinyl, methylthiophenyl, methylpyrimidinyl, dimethylpyrimidinyl, pyrazolyl, methylpyrazolyl, methylpyrrolyl, or methylisothiazolyl, dimethylisothiazolyl.

9. The method of claim 1, wherein $R^4$ is selected from the group consisting of phenyl, pyridinyl, pyrimidinyl, pyrazolyl, thiazolyl, pyrrolyl, thiophenyl, and isothiazolyl, wherein $R^4$ is optionally substituted with one or more groups selected from the group consisting of halo, alkyl, alkynyl, hydroxyalkyl, amino, cyano, acetyl, hydroxy, and haloalkyl.

10. The method of claim 1, wherein $R^4$ is selected from the group consisting of:

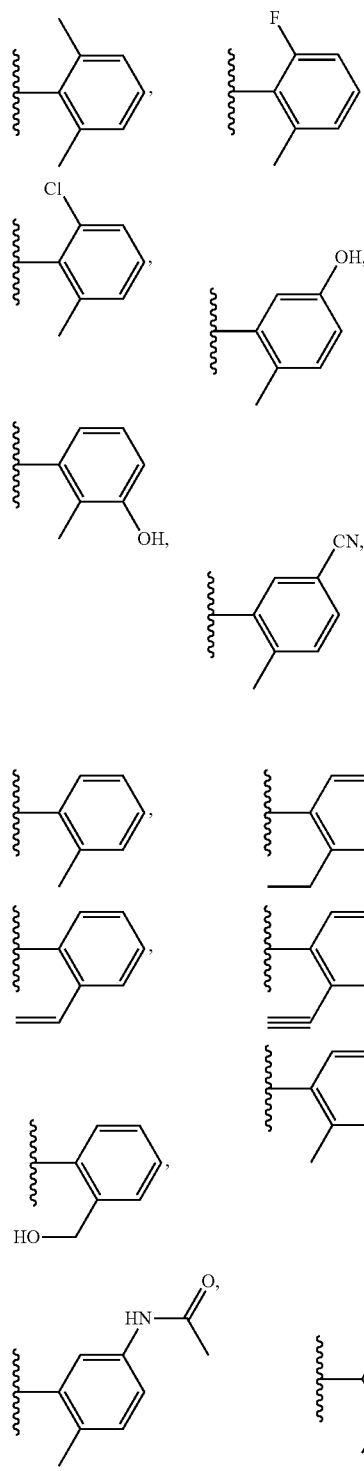

-continued

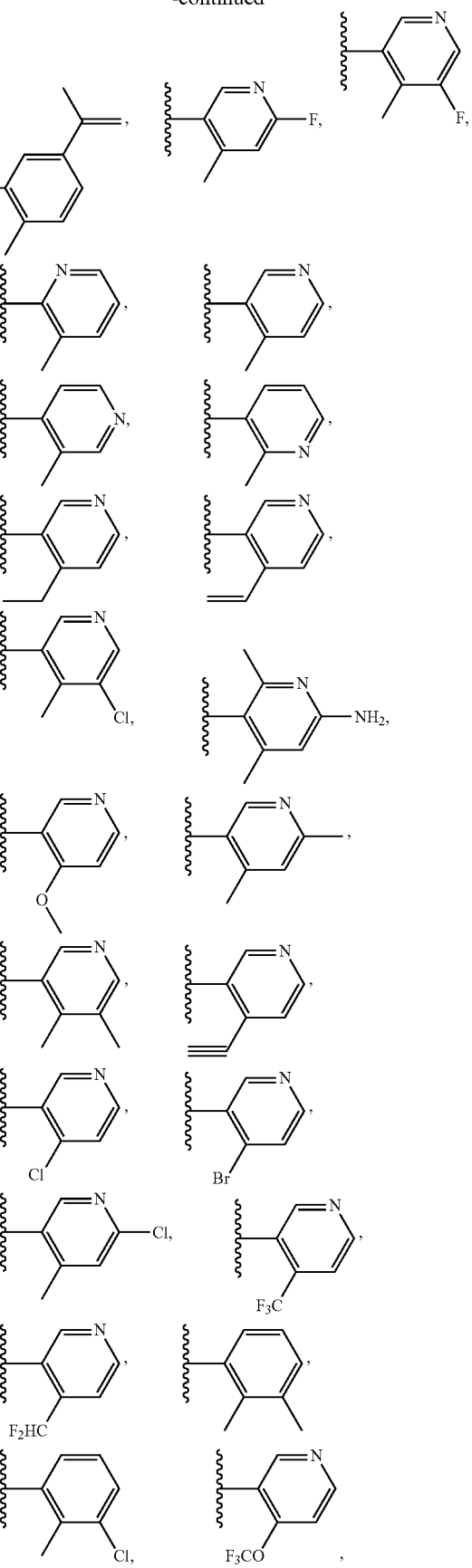

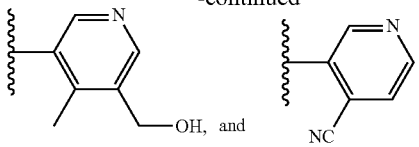

11. The method of claim 1, wherein R¹ is fluorocyclopropyl.

12. The method of claim 1, wherein R¹ is hydroxymethylcyclopropyl.

13. The method of claim 12, wherein the compound is selected from the group consisting of:
   2-(hydroxymethyl)-N-(6-(4-methylpyridin-3-yl)benzo[d]thiazol-2-yl)cyclopropane-1-carboxamide;
   N-(6-(2-fluoro-6-methylphenyl)benzo[d]thiazol-2-yl)-2-(hydroxymethyl)cyclopropane-1-carboxamide; and
   N-(6-(5-fluoro-4-methylpyridin-3-yl)benzo[d]thiazol-2-yl)-2-(hydroxymethyl)cyclopropane-1-carboxamide.

14. The method of claim 1, wherein R¹ is hydroxycyclopropyl or difluorocyclopropyl.

15. The method of claim 14, wherein the compound is selected from the group consisting of:
   2-hydroxy-N-(6-(4-methylpyridin-3-yl)benzo[d]thiazol-2-yl)cyclopropane-1-carboxamide;
   2,2-difluoro-N-(6-(4-methylpyridin-3-yl)benzo[d]thiazol-2-yl)cyclopropane-1-carboxamide;
   2,2-difluoro-N-(6-(2-fluoro-6-methylphenyl)benzo[d]thiazol-2-yl)cyclopropane-1-carboxamide; and
   2,2-difluoro-N-(6-(5-fluoro-4-methylpyridin-3-yl)benzo[d]thiazol-2-yl)cyclopropane-1-carboxamide.

16. The method of claim 1, wherein the compound is selected from the group consisting of:
   (1S,2S)-2-fluoro-N-(6-(2-fluoro-6-methylphenyl)benzo[d]thiazol-2-yl)cyclopropane-1-carboxamide;
   (1S,2S)-2-fluoro-N-(6-(4-methylpyridin-3-yl)benzo[d]thiazol-2-yl)cyclopropane-1-carboxamide; and
   (1S,2S)-2-fluoro-N-(6-(5-fluoro-4-methylpyridin-3-yl)benzo[d]thiazol-2-yl)cyclopropane-1-carboxamide.

17. The method of claim 1, wherein the compound is a compound of Formula (II):

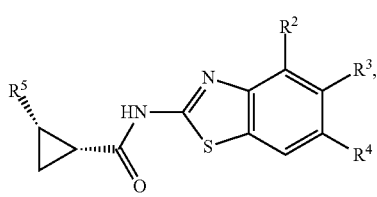

(II)

or pharmaceutically acceptable salt thereof,
wherein R⁵ is selected from the group consisting of halo, $C_1$-$C_3$ alkyl, $C_1$-$C_3$ hydroxyalkyl and $C_1$-$C_3$ haloalkyl.

18. The method of claim 17, wherein R⁴ is fluoromethylphenyl, chloro-methylphenyl, bimethylphenyl, acetamido-methylphenyl, hydroxyl-methylphenyl, methyl-propenylphenyl, ethynyl-methylphenyl, fluoro-methyl-methylaminophenyl, methyl-pyrrolylphenyl, methyl-thiazolylphenyl, cyano-methylphenyl, imidazolyl-methylphenyl, methylpyridinyl, chloro-methylpyridinyl, fluoro-methylpyridinyl, fluoromethyl-methylpyridinyl, bimethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethyl-methylpyridinyl, cyanopyridinyl, trifluoromethylpyridinyl, methylthiophenyl, methylpyrimidinyl, dimethylpyrimidinyl, pyrazolyl, methylpyrazolyl, methylpyrrolyl, methylisothiazolyl, or dimethylisothiazolyl.

19. The method of claim 17, wherein the compound is selected from the group consisting of:
   (1S,2S)-2-fluoro-N-(6-(2-fluoro-6-methylphenyl)benzo[d]thiazol-2-yl)cyclopropane-1-carboxamide;
   (1S,2S)-N-(6-(2-chloro-6-methylphenyl)benzo[d]thiazol-2-yl)-2-fluorocyclopropane-1-carboxamide;
   (1S,2S)-N-(6-(2,6-dimethylphenyl)benzo[d]thiazol-2-yl)-2-fluorocyclopropane-1-carboxamide;
   (1S,2S)-2-fluoro-N-(6-(4-methylpyridin-3-yl)benzo[d]thiazol-2-yl)cyclopropane-1-carboxamide;
   (1S,2S)-2-fluoro-N-(6-(5-fluoro-4-methylpyridin-3-yl)benzo[d]thiazol-2-yl)cyclopropane-1-carboxamide;
   (1S,2S)-2-fluoro-N-(6-(2-methyl-5-(prop-1-en-2-yl)phenyl)benzo[d]thiazol-2-yl)cyclopropane-1-carboxamide;
   (1S,2S)-N-(6-(2-chloro-4-methylpyridin-3-yl)benzo[d]thiazol-2-yl)-2-fluorocyclopropane-1-carboxamide;
   (1S,2S)-N-(6-(2,4-dimethylpyridin-3-yl)benzo[d]thiazol-2-yl)-2-fluorocyclopropane-1-carboxamide;
   (1S,2S)-2-fluoro-N-(6-(5-hydroxy-2-methylphenyl)benzo[d]thiazol-2-yl)cyclopropane-1-carboxamide;
   (1S,2S)-2-fluoro-N-(6-(5-(2-hydroxypropan-2-yl)-2-methylphenyl)benzo[d]thiazol-2-yl)cyclopropane-1-carboxamide;
   (1S,2S)-2-fluoro-N-(6-(3-hydroxy-2-methylphenyl)benzo[d]thiazol-2-yl)cyclopropane-1-carboxamide;
   (1S,2S)-N-(6-(6-amino-2,4-dimethylpyridin-3-yl)benzo[d]thiazol-2-yl)-2-fluorocyclopropane-1-carboxamide;
   (1S,2S)-2-fluoro-N-(6-(4-methoxypyridin-3-yl)benzo[d]thiazol-2-yl)cyclopropane-1-carboxamide;
   (1S,2S)-2-fluoro-N-(6-(3-methylthiophen-2-yl)benzo[d]thiazol-2-yl)cyclopropane-1-carboxamide;
   (1S,2S)-2-fluoro-N-(6-(4-methylpyrimidin-5-yl)benzo[d]thiazol-2-yl)cyclopropane-1-carboxamide;
   (1S,2S)-N-(6-(6-acetyl-4-methylpyridin-3-yl)benzo[d]thiazol-2-yl)-2-fluorocyclopropane-1-carboxamide;
   (1S,2S)-N-(6-(4,6-dimethylpyridin-3-yl)benzo[d]thiazol-2-yl)-2-fluorocyclopropane-1-carboxamide;
   (1S,2S)-N-(6-(6-chloro-4-methylpyridin-3-yl)benzo[d]thiazol-2-yl)-2-fluorocyclopropane-1-carboxamide;
   (1S,2S)-2-fluoro-N-(6-(4-methyl-6-(trifluoromethyl)pyridin-3-yl)benzo[d]thiazol-2-yl)cyclopropane-1-carboxamide;
   (1S,2S)-2-fluoro-N-(6-(4-(hydroxymethyl)pyridin-3-yl)benzo[d]thiazol-2-yl)cyclopropane-1-carboxamide;
   (1S,2S)-2-fluoro-N-(6-(6-(hydroxymethyl)-4-methylpyridin-3-yl)benzo[d]thiazol-2-yl)cyclopropane-1-carboxamide;
   (1S,2S)-2-fluoro-N-(6-(6-(1-hydroxyethyl)-4-methylpyridin-3-yl)benzo[d]thiazol-2-yl)cyclopropane-1-carboxamide;
   (1S,2S)-2-fluoro-N-(6-(4-(trifluoromethyl)pyridin-3-yl)benzo[d]thiazol-2-yl)cyclopropane-1-carboxamide;
   (1S,2S)-N-(6-(1H-pyrazol-3-yl)benzo[d]thiazol-2-yl)-2-fluorocyclopropane-1-carboxamide;
   (1S,2S)-2-fluoro-N-(6-(2-methyl-5-(1H-pyrazol-1-yl)phenyl)benzo[d]thiazol-2-yl)cyclopropane-1-carboxamide;
   (1S,2S)-2-fluoro-N-(6-(5-(hydroxymethyl)-4-methylpyridin-3-yl)benzo[d]thiazol-2-yl)cyclopropane-1-carboxamide;
   (1S,2S)-2-fluoro-N-(4-fluoro-6-(4-methylpyridin-3-yl)benzo[d]thiazol-2-yl)cyclopropane-1-carboxamide;

(1S,2S)-2-fluoro-N-(4-fluoro-6-(2-fluoro-6-methylphenyl)benzo[d]thiazol-2-yl)cyclopropane-1-carboxamide;
(1S,2S)-2-fluoro-N-(6-(5-methylthiazol-4-yl)benzo[d]thiazol-2-yl)cyclopropane-1-carboxamide;
(1S,2S)-N-(6-(4,6-dimethylpyrimidin-5-yl)benzo[d]thiazol-2-yl)-2-fluorocyclopropane-1-carboxamide;
(1S,2S)-N-(6-(5-ethynyl-2-methylphenyl)benzo[d]thiazol-2-yl)-2-fluorocyclopropane-1-carboxamide;
(1S,2S)-N-(6-(4-chloropyridin-3-yl)benzo[d]thiazol-2-yl)-2-fluorocyclopropane-1-carboxamide;
(1S,2S)-N-(6-(4-cyanopyridin-3-yl)benzo[d]thiazol-2-yl)-2-fluorocyclopropane-1-carboxamide;
(1S,2S)-2-fluoro-N-(6-(2-fluoro-4-methylpyridin-3-yl)benzo[d]thiazol-2-yl)cyclopropane-1-carboxamide;
(1S,2S)-2-fluoro-N-(6-(4-(trifluoromethyl)pyrimidin-5-yl)benzo[d]thiazol-2-yl)cyclopropane-1-carboxamide;
(1S,2S)-2-fluoro-N-(6-(2-methyl-5-(1H-pyrrol-3-yl)phenyl)benzo[d]thiazol-2-yl)cyclopropane-1-carboxamide;
(1S,2S)-2-fluoro-N-(6-(2-methyl-5-(thiazol-2-yl)phenyl)benzo[d]thiazol-2-yl)cyclopropane-1-carboxamide;
(1S,2S)-N-(6-(5-cyano-2-methylphenyl)benzo[d]thiazol-2-yl)-2-fluorocyclopropane-1-carboxamide;
(1S,2S)-2-fluoro-N-(6-(4-methyl-1-(tetrahydro-2H-pyran-2-yl)-1H-pyrazol-3-yl)benzo[d]thiazol-2-yl)cyclopropane-1-carboxamide;
(1S,2S)-2-fluoro-N-(6-(4-methyl-1H-pyrazol-3-yl)benzo[d]thiazol-2-yl)cyclopropane-1-carboxamide;
(1S,2S)-2-fluoro-N-(6-(2-methyl-5-(1H-pyrrol-2-yl)phenyl)benzo[d]thiazol-2-yl)cyclopropane-1-carboxamide;
(1S,2S)-2-fluoro-N-(6-(2-methyl-5-(1H-pyrazol-3-yl)phenyl)benzo[d]thiazol-2-yl)cyclopropane-1-carboxamide;
(1S,2S)-2-fluoro-N-(6-(3-methylisothiazol-5-yl)benzo[d]thiazol-2-yl)cyclopropane-1-carboxamide;
(1S,2S)-N-(6-(4-chloro-3-methylisothiazol-5-yl)benzo[d]thiazol-2-yl)-2-fluorocyclopropane-1-carboxamide;
(1S,2S)-N-(6-(3,4-dimethylisothiazol-5-yl)benzo[d]thiazol-2-yl)-2-fluorocyclopropane-1-carboxamide;
(1S,2S)-N-(6-(5-(1H-imidazol-2-yl)-2-methylphenyl)benzo[d]thiazol-2-yl)-2-fluorocyclopropane-1-carboxamide;
(1S,2S)-2-fluoro-N-(6-(6-(fluoromethyl)-4-methylpyridin-3-yl)benzo[d]thiazol-2-yl)cyclopropane-1-carboxamide;
(1S,2S)-2-fluoro-N-(5-fluoro-6-(4-methylpyridin-3-yl)benzo[d]thiazol-2-yl)cyclopropane-1-carboxamide; and
(1S,2S)-2-fluoro-N-(6-(6-fluoro-4-methylpyridin-3-yl)benzo[d]thiazol-2-yl)cyclopropane-1-carboxamide.

20. The method of claim 1, wherein the salt is hydrochloric acid salt, formic acid salt, or trifluoroacetic acid salt.

* * * * *